US008821894B2

(12) United States Patent
Schneewind et al.

(10) Patent No.: US 8,821,894 B2
(45) **Date of Patent: *Sep. 2, 2014**

(54) COMPOSITIONS AND METHODS RELATED TO PROTEIN A (SPA) VARIANTS

(75) Inventors: Olaf Schneewind, Chicago, IL (US); Alice G. Cheng, Chicago, IL (US); Dominique M. Missiakas, Chicago, IL (US); Hwan Keun Kim, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/807,598

(22) PCT Filed: Jul. 1, 2011

(86) PCT No.: PCT/US2011/042845

§ 371 (c)(1), (2), (4) Date: Mar. 19, 2013

(87) PCT Pub. No.: WO2012/003474

PCT Pub. Date: Jan. 5, 2012

(65) Prior Publication Data

US 2013/0171183 A1 Jul. 4, 2013

Related U.S. Application Data

(60) Provisional application No. 61/361,218, filed on Jul. 2, 2010, provisional application No. 61/370,725, filed on Aug. 4, 2010.

(51) Int. Cl.
*A61K 39/085* (2006.01)
*C07K 14/31* (2006.01)

(52) U.S. Cl.
USPC .................. 424/243.1; 424/190.1; 424/235.1; 530/324

(58) Field of Classification Search
None
See application file for complete search history.

(56) References Cited

U.S. PATENT DOCUMENTS

| | | | | |
|---|---|---|---|---|
| 5,294,177 | A | 3/1994 | Rasnick et al. | 297/270.1 |
| 5,648,240 | A | 7/1997 | Hook | 435/69.3 |
| 5,801,234 | A | 9/1998 | Hodgson | 536/23.7 |
| 5,840,846 | A | 11/1998 | Hook | 530/350 |
| 6,008,341 | A | 12/1999 | Foster | 536/23.7 |
| 6,288,214 | B1 | 9/2001 | Hook | 530/387.1 |
| 6,403,337 | B1 | 6/2002 | Bailey et al. | 435/69.7 |
| 6,593,114 | B1 | 7/2003 | Kunsch et al. | 435/91.41 |
| 6,703,492 | B1 | 3/2004 | Kimmerly | 536/23.1 |
| 6,737,248 | B2 | 5/2004 | Kunsch et al. | 435/69.1 |
| 6,753,149 | B2 | 6/2004 | Bailey et al. | 435/6.15 |
| 6,833,253 | B2 | 12/2004 | Choi | 435/69.1 |
| 2002/0169288 | A1 | 11/2002 | Hook | 424/190.1 |
| 2004/0043037 | A1 | 3/2004 | Kunsch et al. | 424/190.1 |
| 2004/0265962 | A1 | 12/2004 | Bailey et al. | 435/69.1 |
| 2005/0106597 | A1 | 5/2005 | Choi | 435/6.16 |
| 2005/0255478 | A1 | 11/2005 | Kimmerly | 435/6.15 |
| 2006/0205016 | A1 | 9/2006 | Silverman | 435/6 |
| 2007/0020746 | A1 | 1/2007 | Kunsch et al. | 435/252.3 |
| 2008/0311146 | A1 | 12/2008 | Castado | 424/243.1 |
| 2009/0317421 | A1 | 12/2009 | Missiakas | 424/184.1 |
| 2010/0272743 | A1 | 10/2010 | Kimmerly | 424/190.1 |
| 2011/0027265 | A1 | 2/2011 | Bubeck-Wardenburg | 424/184.1 |
| 2011/0206676 | A1 | 8/2011 | Missiakas | 424/184.1 |
| 2011/0262477 | A1 | 10/2011 | Cheng | 424/190.1 |
| 2012/0114686 | A1 | 5/2012 | Schneewind | 424/190.1 |
| 2012/0282247 | A1 | 11/2012 | Schneewind | 424/150.1 |
| 2013/0136746 | A1 | 5/2013 | Schneewind | 424/150.1 |
| 2013/0189249 | A1 | 7/2013 | Bubeck-Wardenburg | 424/184.1 |
| 2013/0230550 | A1 | 9/2013 | Schneewind | 424/190.1 |
| 2013/0236419 | A1 | 9/2013 | Schneewind | 424/165.15 |

FOREIGN PATENT DOCUMENTS

| | | |
|---|---|---|
| EP | 0786519 | 7/1997 |
| EP | 0594610 | 9/1998 |
| WO | WO 98/57994 | 12/1998 |
| WO | WO 00/02523 | 1/2000 |
| WO | WO 00/12132 | 3/2000 |
| WO | WO 00/12689 | 3/2000 |
| WO | WO 00/15238 | 3/2000 |
| WO | WO 01/34809 | 5/2001 |
| WO | WO 01/60852 | 8/2001 |
| WO | WO 01/98499 | 12/2001 |
| WO | WO 02/059148 | 8/2002 |
| WO | WO 02/094868 | 11/2002 |
| WO | WO 2006/032472 | 3/2006 |
| WO | WO 2006/032475 | 3/2006 |
| WO | WO 2006/032500 | 3/2006 |
| WO | WO 2007/113222 | 10/2007 |
| WO | WO 2007/113223 | 10/2007 |
| WO | WO 2012/122533 | 9/2012 |

OTHER PUBLICATIONS

Abdallah et al., "A specific secretion system mediates PPE41 transport in pathogenic mycobacteria", *Mol. Microbiol.*, 62, 667-679, 2006.

Abdallah et al., "Type VII secretion—mycobacteria show the way", *Nat. Rev. Microbiol.*, 5:883-891, 2007.

(Continued)

*Primary Examiner* — Padma V Baskar

(74) *Attorney, Agent, or Firm* — Fulbright & Jaworski LLP

(57) ABSTRACT

The present invention concerns methods and compositions for treating or preventing a bacterial infection, particularly infection by a *Staphylococcus* bacterium. The invention provides methods and compositions for stimulating an immune response against the bacteria. In certain embodiments, the methods and compositions involve a non-toxigenic Protein A (SpA) variant.

11 Claims, 12 Drawing Sheets

(56) References Cited

OTHER PUBLICATIONS

Andersen et al., "Recall of Long-Lived Immunity to *Mycobacterium tuberculosis* Infection in Mice", *J. Immunol.*, 154:3359-3372, 1995.
Archer, "*Staphylococcus aureus*: A Well-Armed Pathogen", *Clin. Infect. Dis.*, 26:1179-1181, 1998.
Baba et al., "Genome Sequence of *Staphylococcus aureus* Strain Newman and comparative analysis of Staphylococcal Genomes: Polymorphism and Evolution of Two Major Pathogenicity Islands", *J. Bacteriol.* 190(1):300-310, 2007.
Bae et al., "*Staphylococcus aureus* virulence genes identified by bursa aurealis mutagenesis and nematode killing", *Proc. Natl. Acad. Sci. USA*, 101(33):12312-12317, 2004.
Bjerketorp et al., "The von Willebrand factor-binding protein (vWbp) of *Stphylococcus aureus* is a coagulase", *FEMS Microbiol. Lett.*, 234:309-314, 2004.
Brown et al., "Determining Protein—Protein Interactions by Oxidative Cross-Linking of a Glycine-Glycine-Histidine Fusion Protein", *Biochemistry*, 37:4397-4406, 1998.
Burts et al., "EsxA and EsxB are secreted by an ESAT-6-like system that is required for the pathogenesis of *Staphylococcus aureus* infections", *Proc. Natl. Acad. Sci. USA*, 102(4):1169-1174, 2005.
Burts et al., "EsaC substrate for the ESAT-6 Secretion Pathway and its role in persistent infections of *S. aureus", Mol. Microbiol.*, 69(3):736-746, 2008.
Cedergren et al., "Mutational analysis of the interaction between staphylococcal protein A and human IgG1", *Protein Eng.*, 6(4):441-448, 1993.
Cespedes et al., "The Clonality of *Staphylococcus aureus* Nasal Carriage", *J. Infect. Dis.*, 191(3):444-452, 2005.
Cheng et al., "Genetic requirements for *Staphylococcus aureus* abscess formaton and persistance in host tissues", *FASEB J.*, 23:3393-3404, 2009.
Dalbey and Wickner, "Leader Peptidase Catalyzes the Release of Exported Proteins from the Outer Surface of the *Escherichia coli* Plasma Membrane", *J. Biol. Chem.*, 260(29):15925-15931, 1985.
DeDent et al., "Distribution of Protein A on the Surface of *Staphylococcus aureus", J. Bacteriol.* 189:4473-4484, 2007.
DeDent et al., "Signal peptides direct surface proteins to two distinct envelope locations of *Staphylococcus aureus", EMBO J.* 27:2656-2668, 2008.
Deisenhofer et al., "Crystallizaton, Crystal Structure Analysis and Atomic Model of the Complex Formed by a Human Fc Fragment and Fragment B of Protein A from *Staphylococcus aureus", Hoppe-Seyh Zeitsch. Physiol. Chem.* 359:975-985, 1978.
Deisenhofer, "Crystallographic Refinement and Atomic Models of a Human Fc Fragment and Its Complex with Fragment B of Protein A from *Staphylococcus aureus* at 2.9- and 2.8-A Resolution", *Biochemistry* 20(9):2361-2370, 1981.
Dinges et al., "Exotoxins of *Staphylococcus aureus", Clin. Microbiol. Rev.*, 13(1):16-34, 2000.
Duthie and Lorenz, "Staphylococcal coagulase: Mode of action and Antigenicity", *J. Gen. Microbiol.*, 6:95-107, 1952.
Ekstedt and Yotis, "Effect of Coagulase on the Virulence of Coagulase Negative Strains", *Ann. N. Y. Acad. Sci.*, 80:496-500, 1960.
Field and Smith, "The Coagulase Test for *Staphylococci", J. Comp. Pathol.*, 55:63-69, 1945.
Fortune et al., "Mutually dependent secretion of proteins required for mycobacterial virulence", *Proc Natl. Acad. Sci. USA*, 102(30):10676-10681, 2005.
Foster, "Immune Evasion by *Staphylococci", Nat. Rev. Microbiol.*, 3:948-958, 2005.
Fournier et al., "Purification and Characterization of *Staphylococcus aureus* Type 8 Capsular Polysaccharide", *Infect. Immun.*, 45(1):87-93, 1984.
Galan and Collmer, "Type III Secretion Machines: Bacterial Devices for Protein Delivery into Host Cells", *Science*, 284:1322-1328, 1999.
Gomez et al., "*Staphylococcus aureus* protein A induces airway epithelial inflammatory responses by activating TNFR1", *Nature Med.* 10(8):842-848, 2004.
Gomez et al., "Mechanisms of Signal Transduction: *Staphylococcus aureus* Protein A Activates TNFR1 Signaling through Conserved IgG Binding Domains", *J. Biol. Chem.* 281(29):20190-20196, 2006.
Gomez et al., "*Staphylococcus aureus* protein A activates TACE through EGFR-dependent signaling", *EMBO J.* 26:701-709, 2007.
Goodyear and Silverman, "Staphylococcal toxin induced preferential and prolonged in vivo deletion of innate-like B lymphocytes", *Proc. Nat. Acad. Sci. USA*, 101(31):11392-11397, 2004.
Goodyear and Silverman, "Death by a B Cell Superantigen: In Vivo VH-targeted Apoptotic Supraclonal B Cell Deletion by a Staphylococcal Toxin", *J. Exp. Med.*, 197(9):1125-1139, 2003.
Gouda et al., "Three-Dimensional Solution Structure of the B Domain of Staphylococcal Protein A: Comparisons of the Solution and Crystal Structures", *Biochemistry*, 31(40):9665-72, 1992.
Graille et al., "Crystal structure of a *Staphylococcus aureus* protein A domain complexed with the Fab fragment of a human IgM antibody: Structural basis for recognition of B-cell receptors and superantigen activity", *Proc. Nat. Acad. Sci. USA* 97(10):5399-5404, 2000.
Guss et al., "Region X, the cell-wall-attachment part of staphylococcal protein A", *Eur. J. Biochem.* 138:413-420, 1984.
Hartleib et al., "Protein A is the von Willebrand factor binding protein on *Staphylococcus aureus", Blood* 96:2149-2156, 2000.
Hsu et al., "The primary mechanism of attenuation of bacillus Calmette-Guerin is a loss of secreted lytic function required for invasion of lung interstitial tissue", *Proc. Natl. Acad. Sci. USA*, 100(21):12420-12425, 2003.
Jansson et al., "All individual domains of staphylococcal protein A show Fab binding", *FEMS Immunol. Med. Microbiol.* 20:69-78, 1998.
Jensen, "A Normally Occurring *Staphylococcus* Antibody in Human Serum", *Acta Path. Microbiol. Scandin.* 44:421-428, 1958.
Jonsson et al., "Virulence of *Staphylococcus aureus* in a Mouse Mastitis Model: Studies of Alpha Hemolysin, Coagulase, and Protein A as Possible Virulence Determinants with Protoplast Fusion and Gene Cloning", *Infection and Immunity*, 49(3):765-769, 1985.
Kennedy et al., "Epidemic community-associated methicillin-resistant *Staphylococcus aureus*: Recent clonal expansion and diversification", *Proc. Natl. Acad. Sci. USA* 105(4):1327-1332, 2008.
Kuklin et al., "A Novel *Staphylococcus aureus* Vaccine: Iron Surface Determinant B Induces Rapid Antibody Responses in Rhesus Macaques and Specific Increased Survival in a Murine *S. aureus* Sepsis Model", *Infect. Immun.*, 74(4):2215-23, 2006.
Lagergard et al., "Determination of Neutralizing Antibodies and Specific Immunoglobulin Isotype Levels in Infants after Vaccination against Diphtheria", *Eur. J. Clin. Microbiol. Infect. Dis.*, 11(4):341-345, 1992.
Lam et al., "Abscess-Forming Factor(s) Produced by *Staphylococcus aureus", J. Bacteriol.*, 86:87-91, 1963.
Lee, "The prospects for developing a vaccine against *Staphylococcus aureus", Trends Microbiol.* 4(4):162-166, 1996.
Lowy, "*Staphylococcus aureus* Infections", *New Engl. J. Med.*, 339(8):520-532, 1998.
MacGurn et al., "A non-RD1 gene cluster is required for Snm secretion in *Mycobacterium tuberculosis", Mol. Microbiol.*, 57(6):1653-1663, 2005.
Mazmanian et al., "*Staphylococcus aureus* Sortase, an Enzyme that Anchors Surface Proteins to the Cell Wall", *Science*, 285(5428):760-3, 1999.
Mazmanian et al., "*Staphylococcus aureus* sortase mutants defective in the display of surface proteins and in the pathogenesis of animal infections", *Proc. Natl. Acad. Sci. USA*, 97(10):5510-5515, 2000.
Mazmanian et al., "Sortase-catalysed anchoring of surface proteins to the cell wall of *Staphylococcus aureus", Mol. Microbiol.*, 40(5):1049-1057, 2001.
McLaughlin et al., "A *Mycobacterium* ESX-1-Secreted Virulence Factor with Unique Requirements for Export", *PLoS Pathog.*, 3(8):1051-1061, 2007.
Moreau et al., "Structure of the type 5 capsular polysaccharide of *Staphylococcus aureus", Carbohydrate Res.*, 201(2):285-297, 1990.
Moreillon et al. "Role of *Staphylococcus aureus* Coagulase and Clumping Factor in Pathogenesis of Experimental Endocarditis", *Infect. Immun.*, 63(12):4738-4743, 1995.

(56) References Cited

OTHER PUBLICATIONS

Novick, "Autoinduction and signal transduction in the regulation of staphylococcal virulence", *Mol. Microbiol.*, 48(6):1429-1449, 2003.
O'Brien et al., "Multiple mechanisms for the activation of human platelet aggregation by *Staphylococcus aureus*: roles for the clumping factors ClfA and ClfB, the serine-aspartate repeat protein SdrE and protein A", *Mol. Microbiol.* 44(4):1033-1044, 2002.
O'Seaghdha et al., "*Staphylococcus aureus* protein A binding to von Willebrand factor A1 domain is mediated by conserved IgG binding regions", *FEBS J.* 273:4831-4841, 2006.
Pallen, "The ESAT-6/WXG100 superfamily—and a new Gram-positive secretion system?", *Trends Microbiol.*, 10(5):209-212, 2002.
Palmqvist et al., "Bacterial cell wall-expressed protein A triggers supraclonal B-cell responses upon in vivo infection with *Staphylococcus aureus", Microbes. Infect.*, 7:1501-1511, 2005.
Panizzi et al., "Fibrinogen Sustrate Recognition by Staphylocoagulase-(Pro) thrombin Complexes", *J. Biol. Chem.*, 281(2):1179-1187, 2006.
Phonimdaeng et al., "The coagulase of *Staphylococcus aureus* 8325-4. Sequence analysis and virulence of site-specific coagulase-deficient mutants", *Mol. Microbiol.*, 4(3):393-404, 1990.
Pym et al., "Loss of RD1 contributed to the attenuation of the live tuberculosis vaccines *Mycobacterium bovis* BCG and *Mycobacterium microti", Molecular Microbiology*, 46(3):709-717, 2002.
Roben et al., "VH3 Family Antibodies Bind Domain D of Staphylococcal Protein A1", *J. Immunol.* 154:6437-6445, 1995.
Said-Salim et al., "Community-Acquired Methicillin-Resistant *Staphylococcus aureus*: An Emerging Pathogen", *Infect. Control Hosp. Epidemiol.* 24(6):451-455, 2003.
Schneewind et al., "Sorting of Protein A to the Staphylococcal Cell Wall", *Cell* 70:267-281, 1992.
Search Report and Written Opinion in PCT/US11/42845 mailed Feb. 10, 2012.
Shaw et al., "The role and regulation of the extracellular proteases of *Staphylococcus aureus", Microbiology*, 150:217-228, 2004.
Sheagren, "*Staphylococcus aureus*: The Persistent Pathogen", *N. Engl. J. Med.* 310(21):1368-1373, 1984.
Sibbald et al., "Mapping the Pathways to Staphylococcal Pathogenesis by Comparative Secrtomics", *Microbiol. Mol Biol. Rev.*, 70(3):755-788, 2006.
Sjodahl, "Repetitive Sequences in Protein A from *Staphylococcus aureus", Eur. J. Biochem.* 73:343-351, 1977.
Sjoquist et al., "Protein A Isolated from *Staphylococcus aureus* after Digestion with Lysostaphin", Eur. J. Biochem. 29 :572-578, 1972.
Smith et al., "The Role of Coagulase in Staphylococcal Infections", *Brit. J. Exp. Pathol.*, 28:57-67, 1947.
Stanley et al., "Acute infection and macrophage subversion by *Mycobacterium tuberculosis* require a specialized secretion system", *Proc. Natl. Acad. Sci. USA*, 100(22):13001-13006, 2003.
Stranger-Jones et al., "Vaccine assembly from surface proteins of *Staphylococcus aureus", Proc. Nat. Acad. Sci. USA*, 103(45):16942-16947, 2006.
Ton-That et al., "Purificaton and characterizaton of sortase, the transpeptidase that cleaves surface proteins of *Staphylococcus aureus* at the LPXTG motif", *Proc. Natl. Acad. Sci. USA*, 96(22):12424-12429, 1999.
Uhlen et al., "Complete Sequence of the Staphylococcal Gene Encoding Protein A: A gene evolved through multiple duplications", *J. Biol. Chem.* 259(3):1695-1702, 1984.
van Wely et al., "Translocation of proteins across the cell envelope of Gram-positive bacteria", *FEMS Microbiol. Rev.*, 25:437-454, 2001.
Weiss et al., "Effect of srtA and srtB gene expression on the virulence of *Staphylococcus aureus* in animal models of infection", *J. Antimicrob. Chemother.*, 53:480-486, 2004.
Xu et al., "A unique *Mycobacterium* ESX-1 protein co-secretes with CFP-10/ESAT-6 and is necessary for inhibiting phagosome maturation", *Mol. Microbiol.*, 66(3):787-800, 2007.

COMPOSITIONS AND METHODS RELATED TO PROTEIN A (SPA) VARIANTS

The present application is a national phase application under 35 U.S.C. §371 of International Patent Application No. PCT/US2011/042845 filed Jul. 1, 2011, which claims the benefit of priority to U.S. Provisional Patent Application Ser. No. 61/361,218 filed Jul. 2, 2010, and 61/370,725 filed Aug. 4, 2010, hereby incorporated by reference in their entirety.

This invention was made with government support under AI057153, AI052474, and GM007281 awarded by the National Institutes of Health. The government has certain rights in the invention.

BACKGROUND OF THE INVENTION

I. Field of the Invention

The present invention relates generally to the fields of immunology, microbiology, and pathology. More particularly, it concerns methods and compositions involving bacterial Protein A variants, which can be used to invoke an immune response against the bacteria.

II. Background

The number of both community acquired and hospital acquired infections have increased over recent years with the increased use of intravascular devices. Hospital acquired (nosocomial) infections are a major cause of morbidity and mortality, more particularly in the United States, where it affects more than 2 million patients annually. The most frequent infections are urinary tract infections (33% of the infections), followed by pneumonia (15.5%), surgical site infections (14.8%) and primary bloodstream infections (13%) (Emorl and Gaynes, 1993).

The major nosocomial pathogens include *Staphylococcus aureus*, coagulase-negative Staphylococci (mostly *Staphylococcus epidermidis*), *enterococcus* spp., *Escherichia coli* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens.

Staphylococci can cause a wide variety of diseases in humans and other animals through either toxin production or invasion. Staphylococcal toxins are also a common cause of food poisoning, as the bacteria can grow in improperly-stored food.

*Staphylococcus epidermidis* is a normal skin commensal which is also an important opportunistic pathogen responsible for infections of impaired medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*Staphylococcus aureus* is the most common cause of nosocomial infections with a significant morbidity and mortality. It is the cause of some cases of osteomyelitis, endocarditis, septic arthritis, pneumonia, abscesses, and toxic shock syndrome. *S. aureus* can survive on dry surfaces, increasing the chance of transmission. Any *S. aureus* infection can cause the staphylococcal scalded skin syndrome, a cutaneous reaction to exotoxin absorbed into the bloodstream. It can also cause a type of septicemia called pyaemia that can be life-threatening. Problematically, Methicillin-resistant *Staphylococcus aureus* (MRSA) has become a major cause of hospital-acquired infections.

*S. aureus* and *S. epidermidis* infections are typically treated with antibiotics, with penicillin being the drug of choice, whereas vancomycin is used for methicillin resistant isolates. The percentage of staphylococcal strains exhibiting wide-spectrum resistance to antibiotics has become increasingly prevalent, posing a threat for effective antimicrobial therapy. In addition, the recent emergence of vancomycin resistant *S. aureus* strain has aroused fear that MRSA strains are emerging and spreading for which no effective therapy is available.

An alternative to antibiotic treatment for staphylococcal infections is under investigation that uses antibodies directed against staphylococcal antigens. This therapy involves administration of polyclonal antisera (WO00/15238, WO00/12132) or treatment with monoclonal antibodies against lipoteichoic acid (WO98/57994).

An alternative approach would be the use of active vaccination to generate an immune response against staphylococci. The *S. aureus* genome has been sequenced and many of the coding sequences have been identified (WO02/094868, EP0786519), which can lead to the identification of potential antigens. The same is true for *S. epidermidis* (WO01/34809). As a refinement of this approach, others have identified proteins that are recognized by hyperimmune sera from patients who have suffered staphylococcal infection (WO01/98499, WO02/059148).

*S. aureus* secretes a plethora of virulence factors into the extracellular milieu (Archer, 1998; Dinges et al., 2000; Foster, 2005; Shaw et al., 2004; Sibbald et al., 2006). Like most secreted proteins, these virulence factors are translocated by the Sec machinery across the plasma membrane. Proteins secreted by the Sec machinery bear an N-terminal leader peptide that is removed by leader peptidase once the pre-protein is engaged in the Sec translocon (Dalbey and Wickner, 1985; van Wely et al., 2001). Recent genome analysis suggests that Actinobacteria and members of the Firmicutes encode an additional secretion system that recognizes a subset of proteins in a Sec-independent manner (Pallen, 2002). ESAT-6 (early secreted antigen target 6 kDa) and CFP-10 (culture filtrate antigen 10 kDa) of *Mycobacterium tuberculosis* represent the first substrates of this novel secretion system termed ESX-1 or 5 nm in *M. tuberculosis* (Andersen et al., 1995; Hsu et al., 2003; Pym et al., 2003; Stanley et al., 2003). In *S. aureus*, two ESAT-6 like factors designated EsxA and EsxB are secreted by the Ess pathway (ESAT-6 secretion system) (Burts et al., 2005).

The first generation of vaccines targeted against *S. aureus* or against the exoproteins it produces have met with limited success (Lee, 1996). There remains a need to develop effective vaccines against staphylococcal infections. Additional compositions for treating staphylococcal infections are also needed.

SUMMARY OF THE INVENTION

Protein A (SpA) (SEQ ID NO:33), a cell wall anchored surface protein of *Staphylococcus aureus*, provides for bacterial evasion from innate and adaptive immune responses. Protein A binds immunoglobulins at their Fc portion, interacts with the VH3 domain of B cell receptors inappropriately stimulating B cell proliferation and apotosis, binds to von Willebrand factor A1 domains to activate intracellular clotting, and also binds to the TNF Receptor-1 to contribute to the pathogenesis of staphylococcal pneumonia. Due to the fact that Protein A captures immunoglobulin and displays toxic attributes, the possibility that this surface molecule may function as a vaccine in humans has not been rigorously pursued. Here the inventors demonstrate that Protein A variants no longer able to bind to immunoglobulins, which are thereby removed of their toxigenic potential, i.e., are non-toxigenic, stimulate humoral immune responses that protect against staphylococcal disease.

In certain embodiments the SpA variant is a full length SpA variant comprising a variant A, B, C, D, and/or E domain. In certain aspects, the SpA variant comprises or consists of the amino acid sequence that is 80, 90, 95, 98, 99, or 100% identical to the amino acid sequence of SEQ ID NO:34 In other embodiments the SpA variant comprises a segment of SpA. The SpA segment can comprise at least or at most 1, 2, 3, 4, 5 or more IgG binding domains. The IgG domains can be at least or at most 1, 2, 3, 4, 5 or more variant A, B, C, D, or E domains. In certain aspects the SpA variant comprises at least or at most 1, 2, 3, 4, 5, or more variant A domains. In a further aspect the SpA variant comprises at least or at most 1, 2, 3, 4, 5, or more variant B domains. In still a further aspect the SpA variant comprises at least or at most 1, 2, 3, 4, 5, or more variant C domains. In yet a further aspect the SpA variant comprises at least or at most 1, 2, 3, 4, 5, or more variant D domains. In certain aspects the SpA variant comprises at least or at most 1, 2, 3, 4, 5, or more variant E domains. In a further aspect the SpA variant comprises a combination of A, B, C, D, and E domains in various combinations and permutations. The combinations can include all or part of a SpA signal peptide segment, a SpA region X segment, and/or a SpA sorting signal segment. In other aspects the SpA variant does not include a SpA signal peptide segment, a SpA region X segment, and/or a SpA sorting signal segment. In certain aspects a variant A domain comprises a substitution at position(s) 7, 8, 34, and/or 35 of SEQ ID NO:4. In another aspect a variant B domain comprises a substitution at position(s) 7, 8, 34, and/or 35 of SEQ ID NO:6. In still another aspect a variant C domain comprises a substitution at position(s) 7, 8, 34, and/or 35 of SEQ ID NO:5. In certain aspects a variant D domain comprises a substitution at position(s) 9, 10, 36, and/or 37 of SEQ ID NO:2. In a further aspect a variant E domain comprises a substitution at position(s) 6, 7, 33, and/or 34 of SEQ ID NO:3.

In certain aspects, an SpA domain D variant or its equivalent can comprise a mutation at position 9 and 36; 9 and 37; 9 and 10; 36 and 37; 10 and 36; 10 and 37; 9, 36, and 37; 10, 36, and 37, 9, 10 and 36; or 9,10 and 37 of SEQ ID NO:2. In a further aspect, analogous mutations can be included in one or more of domains A, B, C, or E.

In further aspects, the amino acid glutamine (Q) at position 9 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 9 can be substituted with an arginine (R). In a further aspect, the glutamine at position 9 of SEQ ID NO:2, or its equivalent, can be substituted with a lysine or a glycine. Any 1, 2, 3, 4, 5, 6, 7, 8, 9, 10, or more of the substitutions can be explicitly excluded.

In another aspect, the amino acid glutamine (Q) at position 10 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 10 can be substituted with an arginine (R). In a further aspect, the glutamine at position 10 of SEQ ID NO:2, or its equivalent, can be substituted with a lysine or a glycine. Any 1, 2, 3, 4, 5, 6, 7, 8, 9, 10, or more of the substitutions can be explicitly excluded.

In certain aspects, the aspartic acid (D) at position 36 of SEQ ID NO:2 (or its analogous amino acid in other SpA domains) can be replaced with an alanine (A), an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 36 can be substituted with a glutamic acid (E). In certain aspects, an aspartic acid at position 36 of SEQ ID NO:2, or its equivalent, can be substituted with an alanine or a serine. Any 1, 2, 3, 4, 5, 6, 7, 8, 9, 10, or more of the substitutions can be explicitly excluded.

In another aspect, the aspartic acid (D) at position 37 of SEQ ID NO:2 (or its analogous amino acid in other SpA domains) can be replaced with an alanine (A), a an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 37 can be substituted with a glutamic acid (E). In certain aspects, an aspartic acid at position 37 of SEQ ID NO:2, or its equivalent, can be substituted with an alanine or a serine. Any 1, 2, 3, 4, 5, 6, 7, 8, 9, 10, or more of the substitutions can be explicitly excluded.

In a particular embodiment the amino at position 9 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 9 of SEQ ID NO:2 is replaced by a glycine. In a further aspect the amino acid at position 9 of SEQ ID NO:2 is replaced by a lysine.

In a particular embodiment the amino at position 10 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 10 of SEQ ID NO:2 is replaced by a glycine. In a further aspect the amino acid at position 10 of SEQ ID NO:2 is replaced by a lysine.

In a particular embodiment the amino at position 36 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 36 of SEQ ID NO:2 is replaced by a serine. In a further aspect the amino acid at position 36 of SEQ ID NO:2 is replaced by an alanine.

In a particular embodiment the amino at position 37 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 37 of SEQ ID NO:2 is replaced by a serine. In a further aspect the amino acid at position 37 of SEQ ID NO:2 is replaced by an alanine.

In certain aspects the SpA variant includes a substitution of (a) one or more amino acid substitution in an IgG Fc binding sub-domain of SpA domain A, B, C, D, and/or E that disrupts or decreases binding to IgG Fc, and (b) one or more amino acid substitution in a $V_H3$ binding sub-domain of SpA domain A, B, C, D, and/or E that disrupts or decreases binding to $V_H3$. In still further aspects the amino acid sequence of a SpA variant comprises an amino acid sequence that is at least 50%, 60%, 70%, 80%, 90%, 95%, or 100% identical, including all values and ranges there between, to the amino acid sequence of SEQ ID NOs:2-6.

In a further aspect the SpA variant includes (a) one or more amino acid substitution in an IgG Fc binding sub-domain of SpA domain D, or at a corresponding amino acid position in other IgG domains, that disrupts or decreases binding to IgG Fc, and (b) one or more amino acid substitution in a $V_H3$ binding sub-domain of SpA domain D, or at a corresponding amino acid position in other IgG domains, that disrupts or decreases binding to $V_H3$. In certain aspects amino acid residue F5, Q9, Q10, S11, F13, Y14, L17, N28, I31, and/or K35 (SEQ ID NO:2, QQNNFNKDQQSAFYEILNMPNLNEAQRNGFIQSLKDDPSQSTNVLGEAKKLNES) of the IgG Fc binding sub-domain of domain D are modified or substituted. In certain aspects amino acid residue Q26, G29, F30, S33, D36, D37, Q40, N43, and/or E47 (SEQ ID NO:2) of the $V_H3$ binding sub-domain of domain D are modified or substituted such that binding to Fc or $V_H3$ is attenuated. In further aspects corresponding modifications or substitutions can be engineered in corresponding positions of the domain A, B, C, and/or E. Corresponding positions are defined by alignment of the domain D amino acid sequence with one or more of the amino acid sequences from other IgG binding domains of SpA, for example see FIG. 2A. In certain aspects the amino acid substitution can be any of the other 20 amino acids. In a further aspect conservative amino acid substitutions can be specifically excluded from possible amino acid substitutions. In other aspects only non-conservative substitutions are included. In any event, any substitution or combination of substitutions that reduces the binding of the domain such that SpA toxicity is significantly reduced is contemplated. The significance of the reduction in binding refers to a variant that produces minimal to no toxicity when introduced into a subject and can be assessed using in vitro methods described herein.

In certain embodiments, a variant SpA comprises at least or at most 1, 2, 3, 4, 5, 6, 7, 8, 9, 10, or more variant SpA domain D peptides. In certain aspects 1, 2, 3, 4, 5, 6, 7, 8, 9, 10, 11, 12, 13, 14, 15, 16, 17, 18, or 19 or more amino acid residues of the variant SpA are substituted or modified—including but not limited to amino acids F5, Q9, Q10, S11, F13, Y14, L17, N28, I31, and/or K35 (SEQ ID NO:2) of the IgG Fc binding sub-domain of domain D and amino acid residue Q26, G29, F30, S33, D36, D37, Q40, N43, and/or E47 (SEQ ID NO:2) of the $V_H3$ binding sub-domain of domain D. In one aspect of the invention glutamine residues at position 9 and/or 10 of SEQ ID NO:2 (or corresponding positions in other domains) are mutated. In another aspect, aspartic acid residues 36 and/or 37 of SEQ ID NO:2 (or corresponding positions in other domains) are mutated. In a further aspect, glutamine 9 and 10, and aspartic acid residues 36 and 37 are mutated. Purified non-toxigenic SpA or SpA-D mutants/variants described herein are no longer able to significantly bind (i.e., demonstrate attenuated or disrupted binding affinity) Fcγ or $F(ab)_2$ $V_H3$ and also do not stimulate B cell apoptosis. These non-toxigenic Protein A variants can be used as subunit vaccines and raise humoral immune responses and confer protective immunity against *S. aureus* challenge. Compared to wild-type full-length Protein A or the wild-type SpA-domain D, immunization with SpA-D variants resulted in an increase in Protein A specific antibody. Using a mouse model of staphylococcal challenge and abscess formation, it was observed that immunization with the non-toxigenic Protein A variants generated significant protection from staphylococcal infection and abscess formation. As virtually all *S. aureus* strains express Protein A, immunization of humans with the non-toxigenic Protein A variants can neutralize this virulence factor and thereby establish protective immunity. In certain aspects the protective immunity protects or ameliorates infection by drug resistant strains of *Staphylococcus*, such as USA300 and other MRSA strains.

Embodiments include the use of Protein A variants in methods and compositions for the treatment of bacterial and/or staphylococcal infection. This application also provides an immunogenic composition comprising a Protein A variant or immunogenic fragment thereof. In certain aspects, the immunogenic fragment is a Protein A domain D segment. Furthermore, the present invention provides methods and compositions that can be used to treat (e.g., limiting staphylococcal abscess formation and/or persistence in a subject) or prevent bacterial infection. In some cases, methods for stimulating an immune response involve administering to the subject an effective amount of a composition including or encoding all or part of a Protein A variant polypeptide or antigen, and in certain aspects other bacterial proteins. Other bacterial proteins include, but are not limited to (i) a secreted virulence factor, and/or a cell surface protein or peptide, or (ii) a recombinant nucleic acid molecule encoding a secreted virulence factor, and/or a cell surface protein or peptide.

In other aspects, the subject can be administered all or part of a Protein A variant, such as a variant Protein A domain D segment. The polypeptide of the invention can be formulated in a pharmaceutically acceptable composition. The composition can further comprise one or more of at least or at most 1, 2, 3, 4, 5, 6, 7, 8, 9, 10, 11, 12, 13, 14, 15, 16, 17, 18, or 19 additional staphylococcal antigen or immunogenic fragment thereof (e.g., Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, or vWh). Additional staphylococcal antigens that can be used in combination with a Protein A variant include, but are not limited to 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). The staphylococcal antigen or immunogenic fragment can be administered concurrently with the Protein A variant. The staphylococcal antigen or immunogenic fragment and the Protein A variant can be administered in the same composition. The Protein A variant can also be a recombinant nucleic acid molecule encoding a Protein A variant. A recombinant nucleic acid molecule can encode the Protein A variant and at least one staphylococcal antigen or immunogenic fragment thereof. As used herein, the term “modulate” or “modulation” encompasses the meanings of the words “enhance,” or “inhibit.” “Modulation” of activity may be either an increase or a decrease in activity. As used herein, the term “modulator” refers to compounds that effect the function of a moiety, including up-regulation, induction, stimulation, potentiation, inhibition, down-regulation, or suppression of a protein, nucleic acid, gene, organism or the like.

In certain embodiments the methods and compositions use or include or encode all or part of the Protein A variant or antigen. In other aspects, the Protein A variant may be used in combination with secreted factors or surface antigens including, but not limited to one or more of an isolated Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, or vWh polypeptide or immunogenic segment thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In certain embodiments, 1, 2, 3, 4, 5, 6, 7, 8, 9, 10 or more of Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. can be specifically excluded from a formulation of the invention.

The following table lists the various combinations of SpA variants and various other Staphyloccal antigens

TABLE 1

SpA and staphylococcal antigen combinations.

| | | | | | | | | | | | | | | | | | | | | | |
|---|---|---|---|---|---|---|---|---|---|---|---|---|---|---|---|---|---|---|---|---|---|
| Eap | + | + | + | + | + | + | + | + | + | + | + | + | + | + | + | + | + | + | + | + | + |
| Ebh | | + | + | + | + | + | + | + | + | + | + | + | + | + | + | + | + | + | + | + | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |
| IsdB | | | | | | | | | | | | + | + | + | + | + | + | + | + | + | + |
| ClfA | | | | | | | | | | | | | + | + | + | + | + | + | + | + | + |
| ClfB | | | | | | | | | | | | | | + | + | + | + | + | + | + | + |
| Coa | | | | | | | | | | | | | | | + | + | + | + | + | + | + |
| Hla | | | | | | | | | | | | | | | | + | + | + | + | + | + |
| $Hla_{H35A}$ | | | | | | | | | | | | | | | | | + | + | + | + | + |
| IsdC | | | | | | | | | | | | | | | | | | + | + | + | + |
| SasF | | | | | | | | | | | | | | | | | | | + | + | + |
| vWbp | | | | | | | | | | | | | | | | | | | | + | + |
| vWh | | | | | | | | | | | | | | | | | | | | | + |
| Ebh | | + | + | + | + | + | + | + | + | + | + | + | + | + | + | + | + | + | + | + | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |
| IsdB | | | | | | | | | | | | + | + | + | + | + | + | + | + | + | + |
| ClfA | | | | | | | | | | | | | + | + | + | + | + | + | + | + | + |
| ClfB | | | | | | | | | | | | | | + | + | + | + | + | + | + | + |
| Coa | | | | | | | | | | | | | | | + | + | + | + | + | + | + |
| Hla | | | | | | | | | | | | | | | | + | + | + | + | + | + |
| $Hla_{H35A}$ | | | | | | | | | | | | | | | | | + | + | + | + | + |
| IsdC | | | | | | | | | | | | | | | | | | + | + | + | + |
| SasF | | | | | | | | | | | | | | | | | | | + | + | + |
| vWbp | | | | | | | | | | | | | | | | | | | | + | + |
| vWh | | | | | | | | | | | | | | | | | | | | | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |

TABLE 1-continued

SpA and staphylococcal antigen combinations.

| | | | | | | | | | | | | | | | | | | |
|---|---|---|---|---|---|---|---|---|---|---|---|---|---|---|---|---|---|---|
| SdrC | | | | | + | + | + | + | + | + | + | + | + | + | + | + | + | + |
| SdrD | | | | | | + | + | + | + | + | + | + | + | + | + | + | + | + |
| SdrE | | | | | | | + | + | + | + | + | + | + | + | + | + | + | + |
| IsdA | | | | | | | | + | + | + | + | + | + | + | + | + | + | + |
| IsdB | | | | | | | | | + | + | + | + | + | + | + | + | + | + |
| ClfA | | | | | | | | | | + | + | + | + | + | + | + | + | + |
| ClfB | | | | | | | | | | | + | + | + | + | + | + | + | + |
| Coa | | | | | | | | | | | | + | + | + | + | + | + | + |
| Hla | | | | | | | | | | | | | + | + | + | + | + | + |
| $Hla_{H35A}$ | | | | | | | | | | | | | | + | + | + | + | + |
| IsdC | | | | | | | | | | | | | | | + | + | + | + |
| SasF | | | | | | | | | | | | | | | | + | + | + |
| vWbp | | | | | | | | | | | | | | | | | + | + |
| vWh | | | | | | | | | | | | | | | | | | + |
| EsaB | + | + | + | + | + | + | + | + | + | + | + | + | + | + | + | + | + | + |
| EsaC | | + | + | + | + | + | + | + | + | + | + | + | + | + | + | + | + | + |
| EsxA | | | + | + | + | + | + | + | + | + | + | + | + | + | + | + | + | + |
| EsxB | | | | + | + | + | + | + | + | + | + | + | + | + | + | + | + | + |
| SdrC | | | | | + | + | + | + | + | + | + | + | + | + | + | + | + | + |
| SdrD | | | | | | + | + | + | + | + | + | + | + | + | + | + | + | + |
| SdrE | | | | | | | + | + | + | + | + | + | + | + | + | + | + | + |
| IsdA | | | | | | | | + | + | + | + | + | + | + | + | + | + | + |
| IsdB | | | | | | | | | + | + | + | + | + | + | + | + | + | + |
| ClfA | | | | | | | | | | + | + | + | + | + | + | + | + | + |
| ClfB | | | | | | | | | | | + | + | + | + | + | + | + | + |
| Coa | | | | | | | | | | | | + | + | + | + | + | + | + |
| Hla | | | | | | | | | | | | | + | + | + | + | + | + |
| $Hla_{H35A}$ | | | | | | | | | | | | | | + | + | + | + | + |
| IsdC | | | | | | | | | | | | | | | + | + | + | + |
| SasF | | | | | | | | | | | | | | | | + | + | + |
| vWbp | | | | | | | | | | | | | | | | | + | + |
| vWh | | | | | | | | | | | | | | | | | | + |
| EsaC | | + | + | + | + | + | + | + | + | + | + | + | + | + | + | + | + | + |
| EsxA | | | + | + | + | + | + | + | + | + | + | + | + | + | + | + | + | + |
| EsxB | | | | + | + | + | + | + | + | + | + | + | + | + | + | + | + | + |
| SdrC | | | | | + | + | + | + | + | + | + | + | + | + | + | + | + | + |
| SdrD | | | | | | + | + | + | + | + | + | + | + | + | + | + | + | + |
| SdrE | | | | | | | + | + | + | + | + | + | + | + | + | + | + | + |
| IsdA | | | | | | | | + | + | + | + | + | + | + | + | + | + | + |
| IsdB | | | | | | | | | + | + | + | + | + | + | + | + | + | + |
| ClfA | | | | | | | | | | + | + | + | + | + | + | + | + | + |
| ClfB | | | | | | | | | | | + | + | + | + | + | + | + | + |
| Coa | | | | | | | | | | | | + | + | + | + | + | + | + |
| Hla | | | | | | | | | | | | | + | + | + | + | + | + |
| $Hla_{H35A}$ | | | | | | | | | | | | | | + | + | + | + | + |
| IsdC | | | | | | | | | | | | | | | + | + | + | + |
| SasF | | | | | | | | | | | | | | | | + | + | + |
| vWbp | | | | | | | | | | | | | | | | | + | + |
| vWh | | | | | | | | | | | | | | | | | | + |
| EsxA | | | + | + | + | + | + | + | + | + | + | + | + | + | + | + | + | + |
| EsxB | | | | + | + | + | + | + | + | + | + | + | + | + | + | + | + | + |
| SdrC | | | | | + | + | + | + | + | + | + | + | + | + | + | + | + | + |
| SdrD | | | | | | + | + | + | + | + | + | + | + | + | + | + | + | + |
| SdrE | | | | | | | + | + | + | + | + | + | + | + | + | + | + | + |
| IsdA | | | | | | | | + | + | + | + | + | + | + | + | + | + | + |
| IsdB | | | | | | | | | + | + | + | + | + | + | + | + | + | + |
| ClfA | | | | | | | | | | + | + | + | + | + | + | + | + | + |
| ClfB | | | | | | | | | | | + | + | + | + | + | + | + | + |
| Coa | | | | | | | | | | | | + | + | + | + | + | + | + |
| Hla | | | | | | | | | | | | | + | + | + | + | + | + |
| $Hla_{H35A}$ | | | | | | | | | | | | | | + | + | + | + | + |
| IsdC | | | | | | | | | | | | | | | + | + | + | + |
| SasF | | | | | | | | | | | | | | | | + | + | + |
| vWbp | | | | | | | | | | | | | | | | | + | + |
| vWh | | | | | | | | | | | | | | | | | | + |
| EsxB | | | | + | + | + | + | + | + | + | + | + | + | + | + | + | + | + |
| SdrC | | | | | + | + | + | + | + | + | + | + | + | + | + | + | + | + |
| SdrD | | | | | | + | + | + | + | + | + | + | + | + | + | + | + | + |
| SdrE | | | | | | | + | + | + | + | + | + | + | + | + | + | + | + |
| IsdA | | | | | | | | + | + | + | + | + | + | + | + | + | + | + |
| IsdB | | | | | | | | | + | + | + | + | + | + | + | + | + | + |
| ClfA | | | | | | | | | | + | + | + | + | + | + | + | + | + |
| ClfB | | | | | | | | | | | + | + | + | + | + | + | + | + |
| Coa | | | | | | | | | | | | + | + | + | + | + | + | + |
| Hla | | | | | | | | | | | | | + | + | + | + | + | + |
| $Hla_{H35A}$ | | | | | | | | | | | | | | + | + | + | + | + |
| IsdC | | | | | | | | | | | | | | | + | + | + | + |
| SasF | | | | | | | | | | | | | | | | + | + | + |

TABLE 1-continued

SpA and staphylococcal antigen combinations.

| | | | | | | | | | | | | | | |
|---|---|---|---|---|---|---|---|---|---|---|---|---|---|---|
| vWbp | | | | | | | | | | | | | + | + |
| vWh | | | | | | | | | | | | | | + |
| SdrC | + | + | + | + | + | + | + | + | + | + | + | + | + | + |
| SdrD | | + | + | + | + | + | + | + | + | + | + | + | + | + |
| SdrE | | | + | + | + | + | + | + | + | + | + | + | + | + |
| IsdA | | | | + | + | + | + | + | + | + | + | + | + | + |
| IsdB | | | | | + | + | + | + | + | + | + | + | + | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| SdrD | | + | + | + | + | + | + | + | + | + | + | + | + | + |
| SdrE | | | + | + | + | + | + | + | + | + | + | + | + | + |
| IsdA | | | | + | + | + | + | + | + | + | + | + | + | + |
| IsdB | | | | | + | + | + | + | + | + | + | + | + | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| SdrE | | | + | + | + | + | + | + | + | + | + | + | + | + |
| IsdA | | | | + | + | + | + | + | + | + | + | + | + | + |
| IsdB | | | | | + | + | + | + | + | + | + | + | + | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| IsdA | | | | + | + | + | + | + | + | + | + | + | + | + |
| IsdB | | | | | + | + | + | + | + | + | + | + | + | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| IsdB | | | | | + | + | + | + | + | + | + | + | + | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| ClfA | | | | | | + | + | + | + | + | + | + | + | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |
| vWh | | | | | | | | | | | | | | + |
| ClfB | | | | | | | + | + | + | + | + | + | + | + |
| Coa | | | | | | | | + | + | + | + | + | + | + |
| Hla | | | | | | | | | + | + | + | + | + | + |
| $Hla_{H35A}$ | | | | | | | | | | + | + | + | + | + |
| IsdC | | | | | | | | | | | + | + | + | + |
| SasF | | | | | | | | | | | | + | + | + |
| vWbp | | | | | | | | | | | | | + | + |

TABLE 1-continued

SpA and staphylococcal antigen combinations.

| | | | | | | | |
|---|---|---|---|---|---|---|---|
| vWh | | | | | | | + |
| Coa | + | + | + | + | + | + | + |
| Hla | | + | + | + | + | + | + |
| $Hla_{H35A}$ | | | + | + | + | + | + |
| IsdC | | | | + | + | + | + |
| SasF | | | | | + | + | + |
| vWbp | | | | | | + | + |
| vWh | | | | | | | + |
| Hla | | + | + | + | + | + | + |
| $Hla_{H35A}$ | | | + | + | + | + | + |
| IsdC | | | | + | + | + | + |
| SasF | | | | | + | + | + |
| vWbp | | | | | | + | + |
| vWh | | | | | | | + |
| $Hla_{H35A}$ | | | + | + | + | + | + |
| IsdC | | | | + | + | + | + |
| SasF | | | | | + | + | + |
| vWbp | | | | | | + | + |
| vWh | | | | | | | + |
| IsdC | | | | + | + | + | + |
| SasF | | | | | + | + | + |
| vWbp | | | | | | + | + |
| vWh | | | | | | | + |
| SasF | | | | | + | + | + |
| vWbp | | | | | | + | + |
| vWh | | | | | | | + |
| vWbp | | | | | | + | + |
| vWh | | | | | | | + |
| vWh | | | | | | | + |

In still further aspects, the isolated Protein A variant is multimerized, e.g., dimerized or a linear fusion of two or more polypeptides or peptide segments. In certain aspects of the invention, a composition comprises multimers or concatamers of 1, 2, 3, 4, 5, 6, 7, 8, 9, 10, 11, 12, 13, 14, 15, 16, 17, 18, 19, 20 or more isolated cell surface proteins or segments thereof. Concatamers are linear polypeptides having one or more repeating peptide units. SpA polypeptides or fragments can be consecutive or separated by a spacer or other peptide sequences, e.g., one or more additional bacterial peptide. In a further aspect, the other polypeptides or peptides contained in the multimer or concatamer can include, but are not limited to 1, 2, 3, 4, 5, 6, 7, 8, 9, 10, 11, 12, 13, 14, 15, 16, 17, 18, 19 of Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, vWh or immunogenic fragments thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein.

The term "Protein A variant" or "SpA variant" refers to polypeptides that include a SpA IgG domain having two or more amino acid substitutions that disrupt binding to Fc and $V_H3$. In certain aspect, a SpA variant includes a variant domain D peptide, as well as variants of SpA polypeptides and segments thereof that are non-toxigenic and stimulate an immune response against *staphylococcus* bacteria Protein A and/or bacteria expressing such.

Embodiments of the present invention include methods for eliciting an immune response against a *staphylococcus* bacterium or staphylococci in a subject comprising providing to the subject an effective amount of a Protein A variant or a segment thereof. In certain aspects, the methods for eliciting an immune response against a *staphylococcus* bacterium or staphylococci in a subject comprising providing to the subject an effective amount of 1, 2, 3, 4, 5, 6, 7, 8, 9, 10, 11, 12, 13, 14, 15, 16, 17, 18, 19 or more secreted proteins and/or cell surface proteins or segments/fragments thereof. A secreted protein or cell surface protein includes, but is not limited to Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, and/or vWh proteins and immunogenic fragments thereof. Additional staphylococcal antigens that can be used in combination with a Protein A variant include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein.

Embodiments of the invention include compositions that include a polypeptide, peptide, or protein that is or is at least 70%, 75%, 80%, 85%, 90%, 95%, 96%, 97%, 98%, or 99% identical or similar to Protein A, or a second protein or peptide that is a secreted bacterial protein or a bacterial cell surface protein. In a further embodiment of the invention a composition may include a polypeptide, peptide, or protein that is or is at least 70%, 75%, 80%, 85%, 90%, 95%, 96%, 97%, 98%, or 99% identical or similar to a Protein A domain D polypeptide (SEQ ID NO:2), domain E (SEQ ID NO:3), domain A (SEQ ID NO:4), domain C (SEQ ID NO:5), domain B (SEQ ID NO:6), or a nucleic acid sequence encoding a Protein A domain D, domain E, domain A, domain C, or domain B polypeptide. In certain aspects a Protein A polypeptide segment will have an amino acid sequence of SEQ ID NO:8. Similarity or identity, with identity being preferred, is known in the art and a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith & Waterman (1981), by the sequence identity alignment algorithm of Needleman & Wunsch (1970), by the search for similarity method of Pearson & Lipman (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art. Percent identity is essentially the number of identical amino acids divided by the total number of amino acids compared times one hundred.

Still further embodiments include methods for stimulating in a subject a protective or therapeutic immune response against a *staphylococcus* bacterium comprising administering to the subject an effective amount of a composition including (i) a SpA variant, e.g., a variant SpA domain D polypeptide or peptide thereof; or, (ii) a nucleic acid molecule encoding such a SpA variant polypeptide or peptide thereof, or (iii) administering a SpA variant domain D polypeptide with any combination or permutation of bacterial proteins described herein. In a preferred embodiment the composition is not a *staphylococcus* bacterium. In certain aspects the subject is a human or a cow. In a further aspect the composition is formulated in a pharmaceutically acceptable formulation. The staphylococci may be *Staphylococcus aureus*.

Yet still further embodiments include vaccines comprising a pharmaceutically acceptable composition having an isolated SpA variant polypeptide, or any other combination or permutation of protein(s) or peptide(s) described herein, wherein the composition is capable of stimulating an immune response against a *staphylococcus* bacterium. The vaccine may comprise an isolated SpA variant polypeptide, or any other combination or permutation of protein(s) or peptide(s) described. In certain aspects of the invention the isolated SpA variant polypeptide, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated non-SpA polypeptide. Typically the vaccine comprises an adjuvant. In certain aspects a protein or peptide of the invention is linked (covalently or non-covalently) to the adjuvant, preferably the adjuvant is chemically conjugated to the protein.

In still yet further embodiments, a vaccine composition is a pharmaceutically acceptable composition having a recombinant nucleic acid encoding all or part of a SpA variant polypeptide, or any other combination or permutation of protein(s) or peptide(s) described herein, wherein the composition is capable of stimulating an immune response against a *staphylococcus* bacteria. The vaccine composition may comprise a recombinant nucleic acid encoding all or part of a SpA variant polypeptide, or any other combination or permutation of protein(s) or peptide(s) described herein. In certain embodiments the recombinant nucleic acid contains a heterologous promoter. Preferably the recombinant nucleic acid is a vector. More preferably the vector is a plasmid or a viral vector. In some aspects the vaccine includes a recombinant, non-staphylococcus bacterium containing the nucleic acid. The recombinant non-staphylococci may be *Salmonella* or another gram-positive bacteria. The vaccine may comprise a pharmaceutically acceptable excipient, more preferably an adjuvant.

Still further embodiments include methods for stimulating in a subject a protective or therapeutic immune response against a *staphylococcus* bacterium comprising administering to the subject an effective amount of a composition of a SpA variant polypeptide or segment/fragment thereof and further comprising one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, or vWh protein or peptide thereof. In a preferred embodiment the composition comprises a non-staphylococcus bacterium. In a further aspect the composition is formulated in a pharmaceutically acceptable formulation. The staphylococci for which a subject is being treated may be *Staphylococcus aureus*. Methods of the invention also include SpA variant compositions that contain 1, 2, 3, 4, 5, 6, 7, 8, 9, 10, 11, 12, 13, 14, 15, 16, 17, 18, 19 or more secreted virulence factors and/or cell surface proteins, such as Eap, Ebh, Emp, EsaC, EsxA, EsxB, SdrC, SdrD, SdrE, IsdA, IsdB, ClfA, ClfB, Coa, Hla, IsdC, SasF, vWbp, or vWh in various combinations. In certain aspects a vaccine formulation includes Eap, Ebh, Emp, EsaC, EsxA, EsxB, SdrC, SdrD, SdrE, IsdA, IsdB, ClfA, ClfB, Coa, Hla, IsdC, SasF, vWbp, and vWh. In certain aspects an antigen combination can include (1) a SpA variant and IsdA; (2) SpA variant and ClfB; (3) SpA variant and SdrD; (4) SpA variant and Hla or Hla variant; (5) SpA variant and ClfB, SdrD, and Hla or Hla variant; (6) SpA variant, IsdA, SdrD, and Hla or Hla variant; (7) SpA variant, IsdA, ClfB, and Hla or Hla variant; (8) SpA variant, IsdA, ClfB, and SdrD; (9) SpA variant, IsdA, ClfB, SdrD and Hla or Hla variant; (10) SpA variant, IsdA, ClfB, and SdrD; (11) SpA variant, IsdA, SdrD, and Hla or Hla variant; (12) SpA variant, IsdA, and Hla or Hla variant; (13) SpA variant, IsdA, ClfB, and Hla or Hla variant; (14) SpA variant, ClfB, and SdrD; (15) SpA variant, ClfB, and Hla or Hla variant; or (16) SpA variant, SdrD, and Hla or Hla variant.

In certain aspects, a bacterium delivering a composition of the invention will be limited or attenuated with respect to prolonged or persistent growth or abscess formation. In yet a further aspect, SpA variant(s) can be overexpressed in an attenuated bacterium to further enhance or supplement an immune response or vaccine formulation.

The term "EsxA protein" refers to a protein that includes isolated wild-type EsxA polypeptides from *staphylococcus* bacteria and segments thereof, as well as variants that stimulate an immune response against *staphylococcus* bacteria EsxA proteins.

The term "EsxB protein" refers to a protein that includes isolated wild-type EsxB polypeptides from *staphylococcus* bacteria and segments thereof, as well as variants that stimulate an immune response against *staphylococcus* bacteria EsxB proteins.

The term "SdrD protein" refers to a protein that includes isolated wild-type SdrD polypeptides from *staphylococcus* bacteria and segments thereof, as well as variants that stimulate an immune response against *staphylococcus* bacteria SdrD proteins.

The term "SdrE protein" refers to a protein that includes isolated wild-type SdrE polypeptides from *staphylococcus* bacteria and segments thereof, as well as variants that stimulate an immune response against *staphylococcus* bacteria SdrE proteins.

The term "IsdA protein" refers to a protein that includes isolated wild-type IsdA polypeptides from *staphylococcus* bacteria and segments thereof, as well as variants that stimulate an immune response against *staphylococcus* bacteria IsdA proteins.

The term "IsdB protein" refers to a protein that includes isolated wild-type IsdB polypeptides from *staphylococcus* bacteria and segments thereof, as well as variants that stimulate an immune response against *staphylococcus* bacteria IsdB proteins.

The term "Eap protein" refers to a protein that includes isolated wild-type Eap polypeptides from *staphylococcus* bacteria and segments thereof, as well as variants that stimulate an immune response against *staphylococcus* bacteria Eap proteins.

The term "Ebh protein" refers to a protein that includes isolated wild-type Ebh polypeptides from *staphylococcus* bacteria and segments thereof, as well as variants that stimulate an immune response against *staphylococcus* bacteria Ebh proteins.

The term "Emp protein" refers to a protein that includes isolated wild-type Emp polypeptides from *staphylococcus* bacteria and segments thereof, as well as variants that stimulate an immune response against *staphylococcus* bacteria Emp proteins.

The term "EsaB protein" refers to a protein that includes isolated wild-type EsaB polypeptides from *staphylococcus* bacteria and segments thereof, as well as variants that stimulate an immune response against *staphylococcus* bacteria EsaB proteins.

The term "EsaC protein" refers to a protein that includes isolated wild-type EsaC polypeptides from *staphylococcus* bacteria and segments thereof, as well as variants that stimulate an immune response against *staphylococcus* bacteria EsaC proteins.

The term "SdrC protein" refers to a protein that includes isolated wild-type SdrC polypeptides from *staphylococcus* bacteria and segments thereof, as well as variants that stimulate an immune response against *staphylococcus* bacteria SdrC proteins.

The term "ClfA protein" refers to a protein that includes isolated wild-type ClfA polypeptides from *staphylococcus* bacteria and segments thereof, as well as variants that stimulate an immune response against *staphylococcus* bacteria ClfA proteins.

The term "ClfB protein" refers to a protein that includes isolated wild-type ClfB polypeptides from *staphylococcus* bacteria and segments thereof, as well as variants that stimulate an immune response against *staphylococcus* bacteria ClfB proteins.

The term "Coa protein" refers to a protein that includes isolated wild-type Coa polypeptides from *staphylococcus* bacteria and segments thereof, as well as variants that stimulate an immune response against *staphylococcus* bacteria Coa proteins.

The term "Hla protein" refers to a protein that includes isolated wild-type Hla polypeptides from *staphylococcus* bacteria and segments thereof, as well as variants that stimulate an immune response against *staphylococcus* bacteria Hla proteins.

The term "IsdC protein" refers to a protein that includes isolated wild-type IsdC polypeptides from *staphylococcus* bacteria and segments thereof, as well as variants that stimulate an immune response against *staphylococcus* bacteria IsdC proteins.

The term "SasF protein" refers to a protein that includes isolated wild-type SasF polypeptides from *staphylococcus* bacteria and segments thereof, as well as variants that stimulate an immune response against *staphylococcus* bacteria SasF proteins.

The term "vWbp protein" refers to a protein that includes isolated wild-type vWbp (von Willebrand factor binding protein) polypeptides from *staphylococcus* bacteria and segments thereof, as well as variants that stimulate an immune response against *staphylococcus* bacteria vWbp proteins.

The term "vWh protein" refers to a protein that includes isolated wild-type vWh (von Willebrand factor binding protein homolog) polypeptides from *staphylococcus* bacteria and segments thereof, as well as variants that stimulate an immune response against *staphylococcus* bacteria vWh proteins.

An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In still further embodiments of the invention a composition may include a polypeptide, peptide, or protein that is or is at least 70%, 75%, 80%, 85%, 90%, 95%, 96%, 97%, 98%, or 99% identical or similar to an EsxA protein. In certain aspects the EsxA protein will have all or part of the amino acid sequence of SEQ ID NO:11.

In still further embodiments of the invention a composition may include a polypeptide, peptide, or protein that is or is at least 70%, 75%, 80%, 85%, 90%, 95%, 96%, 97%, 98%, or 99% identical or similar to an EsxB protein. In certain aspects the EsxB protein will have all or part of the amino acid sequence of SEQ ID NO:12.

In yet still further embodiments of the invention a composition may include a polypeptide, peptide, or protein that is or is at least 70%, 75%, 80%, 85%, 90%, 95%, 96%, 97%, 98%, or 99% identical or similar to an SdrD protein. In certain aspects the SdrD protein will have all or part of the amino acid sequence of SEQ ID NO:13.

In further embodiments of the invention a composition may include a polypeptide, peptide, or protein that is or is at least 70%, 75%, 80%, 85%, 90%, 95%, 96%, 97%, 98%, or 99% identical or similar to an SdrE protein. In certain aspects the SdrE protein will have all or part of the amino acid sequence of SEQ ID NO:14.

In still further embodiments of the invention a composition may include a polypeptide, peptide, or protein that is or is at least 70%, 75%, 80%, 85%, 90%, 95%, 96%, 97%, 98%, or 99% identical or similar to an IsdA protein. In certain aspects the IsdA protein will have all or part of the amino acid sequence of SEQ ID NO:15.

In yet still further embodiments of the invention a composition may include a polypeptide, peptide, or protein that is or is at least 70%, 75%, 80%, 85%, 90%, 95%, 96%, 97%, 98%, or 99% identical or similar to an IsdB protein. In certain aspects the IsdB protein will have all or part of the amino acid sequence of SEQ ID NO:16.

Embodiments of the invention include compositions that include a polypeptide, peptide, or protein that is or is at least 70%, 75%, 80%, 85%, 90%, 95%, 96%, 97%, 98%, or 99% identical or similar to a EsaB protein. In certain aspects the EsaB protein will have all or part of the amino acid sequence of SEQ ID NO:17.

In a further embodiments of the invention a composition may include a polypeptide, peptide, or protein that is or is at least 70%, 75%, 80%, 85%, 90%, 95%, 96%, 97%, 98%, or 99% identical or similar to a ClfB protein. In certain aspects the ClfB protein will have all or part of the amino acid sequence of SEQ ID NO:18.

In still further embodiments of the invention a composition may include a polypeptide, peptide, or protein that is or is at least 70%, 75%, 80%, 85%, 90%, 95%, 96%, 97%, 98%, or 99% identical or similar to an IsdC protein. In certain aspects the IsdC protein will have all or part of the amino acid sequence of SEQ ID NO:19.

In yet further embodiments of the invention a composition may include a polypeptide, peptide, or protein that is or is at least 70%, 75%, 80%, 85%, 90%, 95%, 96%, 97%, 98%, or 99% identical or similar to a SasF protein. In certain aspects the SasF protein will have all or part of the amino acid sequence of SEQ ID NO:20.

In yet still further embodiments of the invention a composition may include a polypeptide, peptide, or protein that is or is at least 70%, 75%, 80%, 85%, 90%, 95%, 96%, 97%, 98%, or 99% identical or similar to a SdrC protein. In certain aspects the SdrC protein will have all or part of the amino acid sequence of SEQ ID NO:21.

In yet still further embodiments of the invention a composition may include a polypeptide, peptide, or protein that is or is at least 70%, 75%, 80%, 85%, 90%, 95%, 96%, 97%, 98%, or 99% identical or similar to a ClfA protein. In certain aspects the ClfA protein will have all or part of the amino acid sequence of SEQ ID NO:22.

In yet still further embodiments of the invention a composition may include a polypeptide, peptide, or protein that is or is at least 70%, 75%, 80%, 85%, 90%, 95%, 96%, 97%, 98%, or 99% identical or similar to an Eap protein. In certain aspects the Eap protein will have all or part of the amino acid sequence of SEQ ID NO:23.

In yet still further embodiments of the invention a composition may include a polypeptide, peptide, or protein that is or is at least 70%, 75%, 80%, 85%, 90%, 95%, 96%, 97%, 98%, or 99% identical or similar to an Ebh protein. In certain aspects the Ebh protein will have all or part of the amino acid sequence of SEQ ID NO:24.

In yet still further embodiments of the invention a composition may include a polypeptide, peptide, or protein that is or is at least 70%, 75%, 80%, 85%, 90%, 95%, 96%, 97%, 98%, or 99% identical or similar to an Emp protein. In certain aspects the Emp protein will have all or part of the amino acid sequence of SEQ ID NO:25.

In yet still further embodiments of the invention a composition may include a polypeptide, peptide, or protein that is or is at least 70%, 75%, 80%, 85%, 90%, 95%, 96%, 97%, 98%, or 99% identical or similar to an EsaC protein. In certain aspects the EsaC protein will have all or part of the amino acid sequence of SEQ ID NO:26. Sequence of EsaC polypeptides can be found in the protein databases and include, but are not limited to accession numbers ZP_02760162 (GI:168727885), NP_645081.1 (GI:21281993), and NP_370813.1 (GI:15923279), each of which is incorporated herein by reference as of the priority date of this application.

In yet still further embodiments of the invention a composition may include a polypeptide, peptide, or protein that is or is at least 70%, 75%, 80%, 85%, 90%, 95%, 96%, 97%, 98%, or 99% identical or similar to a Coa protein. In certain aspects the Coa protein will have all or part of the amino acid sequence of SEQ ID NO:27.

In yet still further embodiments of the invention a composition may include a polypeptide, peptide, or protein that is or is at least 70%, 75%, 80%, 85%, 90%, 95%, 96%, 97%, 98%, or 99% identical or similar to a Hla protein. In certain aspects the Hla protein will have all or part of the amino acid sequence of SEQ ID NO:28.

In yet still further embodiments of the invention a composition may include a polypeptide, peptide, or protein that is or is at least 70%, 75%, 80%, 85%, 90%, 95%, 96%, 97%, 98%, or 99% identical or similar to a vWa protein. In certain aspects the vWa protein will have all or part of the amino acid sequence of SEQ ID NO:29.

In yet still further embodiments of the invention a composition may include a polypeptide, peptide, or protein that is or is at least 70%, 75%, 80%, 85%, 90%, 95%, 96%, 97%, 98%, or 99% identical or similar to a vWbp protein. In certain aspects the vWbp protein will have all or part of the amino acid sequence of SEQ ID NO:32.

In certain aspects, a polypeptide or segment/fragment can have a sequence that is at least 85%, at least 90%, at least 95%, at least 98%, or at least 99% or more identical to the amino acid sequence of the reference polypeptide. The term "similarity" refers to a polypeptide that has a sequence that has a certain percentage of amino acids that are either identical with the reference polypeptide or constitute conservative substitutions with the reference polypeptides.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:32-34.

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:33-34.

The compositions may be formulated in a pharmaceutically acceptable composition. In certain aspects of the invention the *staphylococcus* bacterium is an *S. aureus* bacterium.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the invention is a vector, in still other aspects the vector is a plasmid. In certain embodiments the vector is a viral vector. In certain aspects a composition includes a recombinant, non-*staphylococcus* bacterium containing or expressing a polypeptide described herein. In particular aspects the recombinant non-staphylococcus bacteria is *Salmonella* or another gram-positive bacteria. A composition is typically administered to mammals, such as human subjects, but administration to other animals that are capable of eliciting an immune response is contemplated. In further aspects the *staphylococcus* bacterium containing or expressing the polypeptide is *Staphylococcus aureus*. In further embodiments the immune response is a protective immune response.

In further embodiments a composition comprises a recombinant nucleic acid molecule encoding all or part of one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, SpA, vWbp, or vWh protein or peptide or variant thereof. Additional staphylococcal antigens that can be used in combination with the polypeptides described herein include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In particular aspects, a bacteria is a recombinant non-staphylococcus bacteria, such as a *Salmonella* or other gram-positive bacteria.

Compositions of the invention are typically administered to human subjects, but administration to other animals that are capable of eliciting an immune response to a *staphylococcus* bacterium is contemplated, particularly cattle, horses, goats, sheep and other domestic animals, i.e., mammals.

In certain aspects the *staphylococcus* bacterium is a *Staphylococcus aureus*. In further embodiments the immune response is a protective immune response. In still further aspects, the methods and compositions of the invention can be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Any embodiment discussed with respect to one aspect of the invention applies to other aspects of the invention as well. In particular, any embodiment discussed in the context of a SpA variant polypeptide or peptide or nucleic acid may be implemented with respect to other antigens, such as Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (or nucleic acids), and vice versa. It is also understood that any one or more of Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein can be specifically excluded from a claimed composition.

Embodiments of the invention include compositions that contain or do not contain a bacterium. A composition may or may not include an attenuated or viable or intact staphylococcal bacterium. In certain aspects, the composition comprises a bacterium that is not a staphylococcal bacterium or does not contain staphylococcal bacteria. In certain embodiments a bacterial composition comprises an isolated or recombinantly expressed staphylococcal Protein A variant or a nucleotide encoding the same. The composition may be or include a recombinantly engineered *staphylococcus* bacterium that has been altered in a way that comprises specifically altering the bacterium with respect to a secreted virulence factor or cell surface protein. For example, the bacteria may be recombinantly modified to express more of the virulence factor or cell surface protein than it would express if unmodified.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject will have (e.g., are diagnosed with a staphylococcal infection), will be suspected of having, or will be at risk of developing a staphylococcal infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

(FIG. 1A) Primary structure of the Protein A precursor with an N-terminal YSIRK motif signal peptide, five immunoglobulin binding domains as tandem repeats designated E, D, A, B, C, region X, and the LPXTG sorting signal. (FIG. 1B) Following synthesis of the Protein A precursor, staphylococci secrete this product via the Sec pathway, and sortase A cleaves the LPXTG sorting signal between the T and G residues. Nucleophilic attack of the amino group within lipid II at the sortase-Protein A thioester-linked intermediate forms the amide bond that links Protein A to the cell wall envelope and enables its display on the bacterial surface.

DETAILED DESCRIPTION

Figures 1A, 1B:
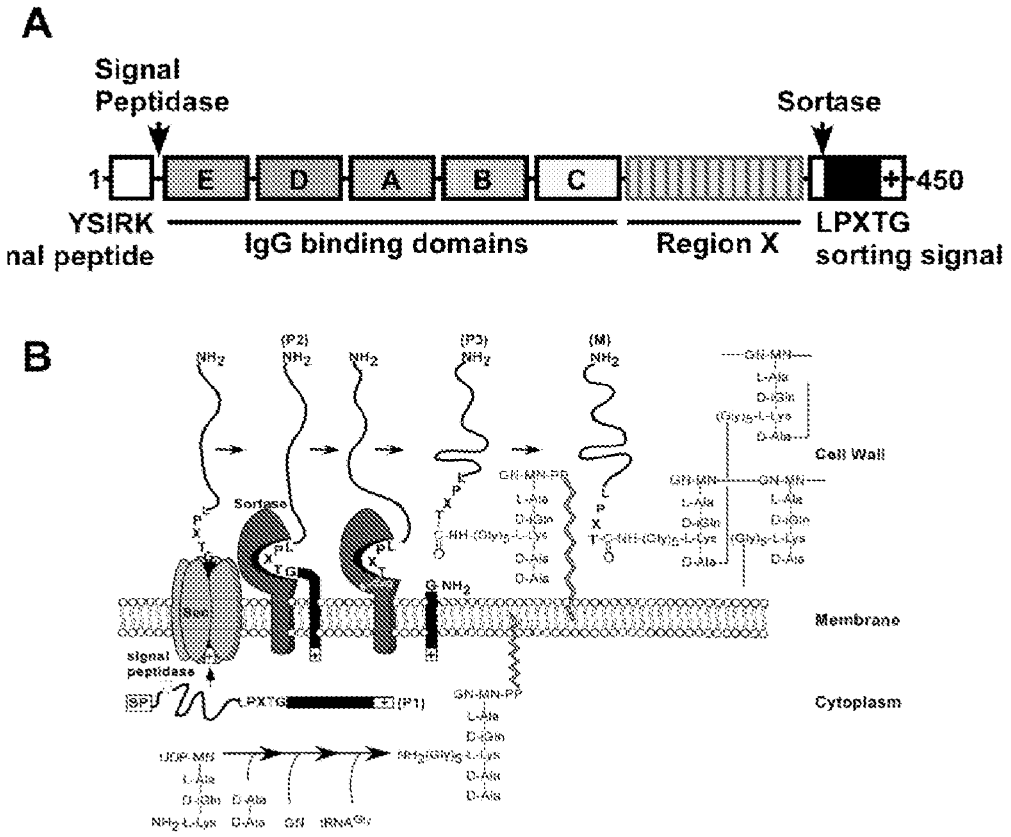
FIGS. 1A-1B.
Figure 2:
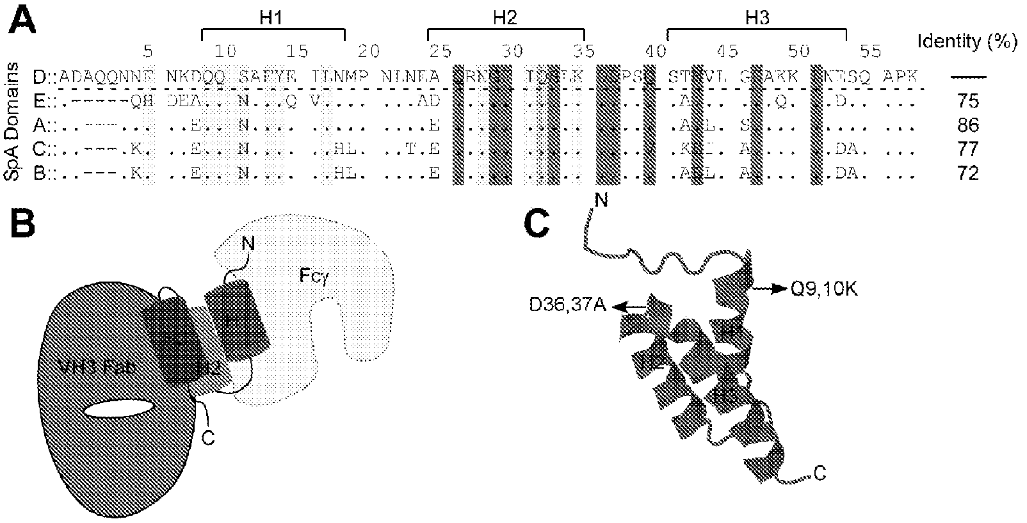
FIG. 2. Three dimensional model of the molecular interactions between the SpA-domain D of Protein A, the VH3 Fab domain of the B cell receptor, and of the Fcγ domain of immunoglobulin. The model is derived from two crystal structures (Graille et al., 2000 and Gouda et al., 1992) that revealed side chain residues involved in the formation of ionic bonds that enable these complexes. Gln-9 and Gln-10 of SpA-D promote binding to Fcγ, whereas Asp-36 and Asp-37 enable complex formation with VH3 Fab.

*Staphylococcus aureus* is a commensal of the human skin and nares, and the leading cause of bloodstream, skin and soft tissue infections (Klevens et al., 2007). Recent dramatic increases in the mortality of staphylococcal diseases are attributed to the spread of methicillin-resistant *S. aureus* (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents *S. aureus* diseases is not available.

The inventors describe here the use of Protein A, a cell wall anchored surface protein of staphylococci, for the generation of variants that can serve as subunit vaccines. The pathogenesis of staphylococcal infections is initiated as bacteria invade the skin or blood stream via trauma, surgical wounds, or medical devices (Lowy, 1998). Although the invading pathogen may be phagocytosed and killed, staphylococci can also escape innate immune defenses and seed infections in organ tissues, inducing inflammatory responses that attract macrophages, neutrophils, and other phagocytes (Lowy, 1998). The responsive invasion of immune cells to the site of infection is accompanied by liquefaction necrosis as the host seeks to prevent staphylococcal spread and allow for removal of necrotic tissue debris (Lam et al., 1963). Such lesions can be observed by microscopy as hypercellular areas containing necrotic tissue, leukocytes, and a central nidus of bacteria (Lam et al., 1963). Unless staphylococcal abscesses are surgically drained and treated with antibiotics, disseminated infection and septicemia produce a lethal outcome (Sheagren, 1984).

II. STAPHYLOCOCCAL ANTIGENS

A. Staphylcoccal Protein A (SpA)

All *Staphylococcus aureus* strains express the structural gene for Protein A (spa) (Jensen, 1958; Said-Salim et al., 2003), a well characterized virulence factor whose cell wall anchored surface protein product (SpA) encompasses five highly homologous immunoglobulin binding domains designated E, D, A, B, and C (Sjodahl, 1977). These domains display ~80% identity at the amino acid level, are 56 to 61 residues in length, and are organized as tandem repeats (Uhlen et al., 1984). SpA is synthesized as a precursor protein with an N-terminal YSIRK/GS signal peptide and a C-terminal LPXTG motif sorting signal (DeDent et al., 2008; Schneewind et al., 1992). Cell wall anchored Protein A is displayed in great abundance on the staphylococcal surface (DeDent et al., 2007; Sjoquist et al., 1972). Each of its immunoglobulin binding domains is composed of anti-parallel α-helices that assemble into a three helix bundle and bind the Fc domain of immunoglobulin G (IgG) (Deisenhofer, 1981; Deisenhofer et al., 1978), the VH3 heavy chain (Fab) of IgM (i.e., the B cell receptor) (Graille et al., 2000), the von Willebrand factor at its A1 domain [vWF AI is a ligand for platelets] (O'Seaghdha et al., 2006) and the tumor necrosis factor α (TNF-α) receptor I (TNFRI) (Gomez et al., 2006), which is displayed on surfaces of airway epithelia (Gomez et al., 2004; Gomez et al., 2007).

SpA impedes neutrophil phagocytosis of staphylococci through its attribute of binding the Fc component of IgG (Jensen, 1958; Uhlen et al., 1984). Moreover, SpA is able to activate intravascular clotting via its binding to von Willebrand factor AI domains (Hartleib et al., 2000). Plasma proteins such as fibrinogen and fibronectin act as bridges between staphylococci (CIfA and CIFB) and the platelet integrin GPIIb/IIIa (O'Brien et al., 2002), an activity that is supplemented through Protein A association with vWF AI, which allows staphylococci to capture platelets via the GPIb-α platelet receptor (Foster, 2005; O'Seaghdha et al., 2006). SpA also binds TNFRI and this interaction contributes to the pathogenesis of staphylococcal pneumonia (Gomez et al., 2004). SpA activates proinflammatory signaling through TNFR1 mediated activation of TRAF2, the p38/c-Jun kinase, mitogen activate protein kinase (MAPK) and the Rel-transcription factor NF-KB. SpA binding further induces TNFR1 shedding, an activity that appears to require the TNF-converting enzyme (TACE) (Gomez et al., 2007). All of the aforementioned SpA activities are mediated through its five IgG binding domains and can be perturbed by the same amino acid substitutions, initially defined by their requirement for the interaction between Protein A and human IgG1 (Cedergren et al., 1993.

SpA also functions as a B cell superantigen by capturing the Fab region of VH3 bearing IgM, the B cell receptor (Gomez et al., 2007; Goodyear et al., 2003; Goodyear and Silverman, 2004; Roben et al., 1995). Following intravenous challenge, staphylococcal Protein A (SpA) mutations show a reduction in staphylococcal load in organ tissues and dramatically diminished ability to form abscesses (described herein). During infection with wildtype *S. aureus*, abscesses are formed within forty-eight hours and are detectable by light microscopy of hematoxylin-eosin stained, thin-sectioned kidney tissue, initially marked by an influx of polymorphonuclear leukocytes (PMNs). On day 5 of infection, abscesses increase in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. The inventors also observed a rim of necrotic PMNs at the periphery of abscess lesions, bordering the eosinophilic pseudocapsule that separated healthy renal tissue from the infectious lesion. Staphylococcal variants lacking Protein A are unable to establish the histopathology features of abscesses and are cleared during infection.

In previous studies, Cedergren et al. (1993) engineered five individual substitutions in the Fc fragment binding sub-domain of the B domain of SpA, L17D, N28A, I31A and K35A. These authors created these proteins to test data gathered from a three dimensional structure of a complex between one domain of SpA and $Fc_1$. Cedergren et al. determined the effects of these mutations on stability and binding, but did not contemplate use of such substitutions for the production of a vaccine antigen.

Brown et al. (1998) describe studies designed to engineer new proteins based on SpA that allow the use of more favorable elution conditions when used as affinity ligands. The mutations studied included single mutations of Q13A, Q14H, N15A, N15H, F17H, Y18F, L21H, N32H, or K39H. Brown et al. report that Q13A, N15A, N15H, and N32H substitutions made little difference to the dissociation constant values and that the Y18F substitution resulted in a 2 fold decrease in binding affinity as compared to wild type SpA. Brown et al. also report that L21H and F17H substitutions decrease the binding affinity by five-fold and a hundred-fold respectively. The authors also studied analogous substitutions in two tandem domains. Thus, the Brown et al. studies were directed to generating a SpA with a more favorable elution profile, hence the use of His substitutions to provide a pH sensitive alteration in the binding affinity. Brown et al. is silent on the use of SpA as a vaccine antigen.

Graille et al. (2000) describe a crystal structure of domain D of SpA and the Fab fragment of a human IgM antibody. Graille et al. define by analysis of a crystal structure the D domain amino acid residues that interact with the Fab fragment as residues Q26, G29, F30, Q32, S33, D36, D37, Q40, N43, E47, or L51, as well as the amino acid residues that form the interface between the domain D sub-domains. Graille et al. define the molecular interactions of these two proteins, but is silent in regard to any use of substitutions in the interacting residues in producing a vaccine antigen.

O'Seaghdha et al. (2006) describe studies directed at elucidating which sub-domain of domain D binds vWF. The authors generated single mutations in either the Fc or VH3 binding sub-domains, i.e., amino acid residues F5A, Q9A, Q10A, F13A, Y14A, L17A, N28A, I31A, K35A, G29A, F30A, S33A, D36A, D37A, Q40A, E47A, or Q32A. The authors discovered that vWF binds the same sub-domain that binds Fc. O'Seaghda et al. define the sub-domain of domain D responsible for binding vWF, but is silent in regard to any use of substitutions in the interacting residues in producing a vaccine antigen.

Gomez et al. (2006) describe the identification of residues responsible for activation of the TNFR1 by using single mutations of F5A, F13A, Y14A, L17A, N21A, I31A, Q32A, and K35A. Gomez et al. is silent in regard to any use of substitutions in the interacting residues in producing a vaccine antigen.

Recombinant affinity tagged Protein A, a polypeptide encompassing the five IgG domains (EDCAB) (Sjodahl, 1977) but lacking the C-terminal Region X (Guss et al., 1984), was purified from recombinant *E. coli* and used as a vaccine antigen (Stranger-Jones et al., 2006). Because of the attributes of SpA in binding the Fc portion of IgG, a specific humoral immune response to Protein A could not be measured (Stranger-Jones et al., 2006). The inventors have overcome this obstacle through the generation of SpA-DQ9,10K; D36,37A. BALB/c mice immunized with recombinant Protein A (SpA) displayed significant protection against intravenous challenge with *S. aureus* strains: a 2.951 log reduction in staphylococcal load as compared to the wild-type (P>0.005; Student's t-test) (Stranger-Jones et al., 2006). SpA specific antibodies may cause phagocytic clearance prior to abscess formation and/or impact the formation of the aforementioned eosinophilic barrier in abscesses that separate staphylococcal communities from immune cells since these do not form during infection with Protein A mutant strains. Each of the five SpA domains (i.e., domains formed from three helix bundles designated E, D, A, B, and C) exerts similar binding properties (Jansson et al., 1998). The solution and crystal structure of the domain D has been solved both with and without the Fc and VH3 (Fab) ligands, which bind Protein A in a non-competitive manner at distinct sites (Graille et al., 2000). Mutations in residues known to be involved in IgG binding (FS, Q9, Q10, S11, F13, Y14, L17, N28, I31 and K35) are also required for vWF AI and TNFR1 binding (Cedergren et al., 1993; Gomez et al., 2006; O'Seaghdha et al., 2006), whereas residues important for the VH3 interaction (Q26, G29, F30, S33, D36, D37, Q40, N43, E47) appear to have no impact on the other binding activities (Graille et al., 2000; Jansson et al., 1998). SpA specifically targets a subset of B cells that express VH3 family related IgM on their surface, i.e., VH3 type B cell receptors (Roben et al., 1995). Upon interaction with SpA, these B cells proliferate and commit to apoptosis, leading to preferential and prolonged deletion of innate-like B lymphocytes (i.e., marginal zone B cells and follicular B2 cells) (Goodyear et al., 2003; Goodyear et al., 2004).

Molecular Basis of Protein a Surface Display and Function.

Protein A is synthesized as a precursor in the bacterial cytoplasm and secreted via its YSIRK signal peptide at the cross wall, i.e. the cell division septum of staphylococci (FIG. 1) (DeDent et al., 2007; DeDent et al., 2008). Following cleavage of the C-terminal LPXTG sorting signal, Protein A is anchored to bacterial peptidoglycan crossbridges by sortase A (Mazmanian et al., 1999; Schneewind et al., 1995; Mazmanian et al., 2000). Protein A is the most abundant surface protein of staphylococci; the molecule is expressed by virtually all *S. aureus* strains (Cespedes et al., 2005; Kennedy et al., 2008; Said-Salim et al., 2003). Staphylococci turn over 15-20% of their cell wall per division cycle (Navarre and Schneewind, 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen, 1958; Goodyear et al., 2004). Interestingly, region X of Protein A (Guss et al., 1984), a repeat domain that tethers the IgG binding domains to the LPXTG sorting signal /cell wall anchor, is perhaps the most variable portion of the staphylococcal genome (Said-Salim, 2003; Schneewind et al., 1992). Each of the five immunoglobulin binding domains of Protein A (SpA), formed from three helix bundles and designated E, D, A, B, and C, exerts similar structural and functional properties (Sjodahl, 1977; Jansson et al., 1998). The solution and crystal structure of the domain D has been solved both with and without the Fc and $V_H3$ (Fab) ligands, which bind Protein A in a non-competitive manner at distinct sites (Graille 2000).

In the crystal structure complex, the Fab interacts with helix II and helix III of domain D via a surface composed of four VH region β-strands (Graille 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II, Asp-37 and Gln-40 in the loop between helix II and helix III and several other residues (Graille 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, the inventors mutated these residues.

The SpA-D sites responsible for Fab binding are structurally separate from the domain surface that mediates Fcγ binding. The interaction of Fcγ with domain D primarily involves residues in helix I with lesser involvement of helix II (Gouda et al., 1992; Deisenhofer, 1981). With the exception of the Gln-32, a minor contact in both complexes, none of the residues that mediate the Fcγ interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), an SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFR1 (O'Seaghdha et al., 2006). Mutations in residues essential for IgG Fc binding (F5, Q9, Q10, S11, F13, Y14, L17, N28, I31 and K35) are also required for vWF A1 and TNFR1 binding (O'Seaghdha et al., 2006; Cedergren et al., 1993; Gomez et al., 2006), whereas residues critical for the VH3 interaction (Q26, G29, F30, S33, D36, D37, Q40, N43, E47) have no impact on the binding activities of IgG Fc, vWF A1 or TNFR1 (Jansson et al., 1998; Graille et al., 2000). The Protein A immunoglobulin Fab binding activity targets a subset of B cells that express $V_H3$ family related IgM on their surface, i.e., these molecules function as VH3type B cell receptors (Roben et al., 1995). Upon interaction with SpA, these B cells rapidly proliferate and then commit to apoptosis, leading to preferential and prolonged deletion of innate-like B lymphocytes (i.e., marginal zone B cells and follicular B2 cells) (Goodyear and Silverman, 2004; Goodyear and Silverman, 2003). More than 40% of circulating B cells are targeted by the Protein A interaction and the $V_H3$ family represents the largest family of human B cell receptors to impart protective humoral responses against pathogens (Goodyear and Silverman, 2004; Goodyear and Silverman, 2003). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

In sum, Protein A domains can viewed as displaying two different interfaces for binding with host molecules and any development of Protein A based vaccines must consider the generation of variants that do not perturb host cell signaling, platelet aggregation, sequestration of immunoglobulins or the induction of B cell proliferation and apoptosis. Such Protein A variants should also be useful in analyzing vaccines for the ability of raising antibodies that block the aforementioned SpA activities and occupy the five repeat domains at their dual binding interfaces. This goal is articulated and pursued here for the first time and methods are described in detail for the generation of Protein A variants that can be used as a safe vaccine for humans. To perturb IgG Fcγ, vWF AI and TNFR1 binding, glutamine (Q) 9 and 10 [numbering derived from the SpA domain D as described in Uhlen et al., 1984] were mutated, and generated lysine substitutions for both glutamines with the expectation that these abolish the ligand attributes at the first binding interface. To perturb IgM Fab VH3 binding, aspartate (D) 36 and 37 were mutated, each of which is required for the association with the B cell receptor. D36 and D37 were both substituted with alanine. Q9,10K and D36,37A mutations are here combined in the recombinant molecule SpA-DQ9,10K;D36,37A and tested for the binding attributes of Protein A. Further, SpA-D and SpA-DQ9,10K; D36,37A are subjected to immunization studies in mice and rabbits and analyzed for [1] the production of specific antibodies (SpA-D Ab); [2] the ability of SpA-D Ab to block the association between Protein A and its four different ligands; and, [3] the attributes of SpA-D Ab to generate protective immunity against staphylococcal infections. (See Examples section below).

B. Staphylococcal Coagulases

Coagulases are enzymes produced by *Staphylococcus* bacteria that convert fibrinogen to fibrin. Coa and $vW_h$ activate prothrombin without proteolysis (Friedrich et al., 2003). The coagulase.prothrombin complex recognizes fibrinogen as a specific substrate, converting it directly into fibrin. The crystal structure of the active complex revealed binding of the D1 and D2 domains to prothrombin and insertion of its Ile1-$Val^2$ N-terminus into the $Ile^{16}$ pocket, inducing a functional active site in the zymogen through conformational change (Friedrich et al., 2003). Exosite I of α-thrombin, the fibrinogen recognition site, and proexosite I on prothrombin are blocked by the D2 of Coa (Friedrich et al., 2003). Nevertheless, association of the tetrameric $(\text{Coa.prothrombin})_2$ complex binds fibrinogen at a new site with high affinity (Panizzi et al., 2006). This model explains the coagulant properties and efficient fibrinogen conversion by coagulase (Panizzi et al., 2006).

Fibrinogen is a large glycoprotein (Mr ~340,000), formed by three pairs of Aα-, Bβ-, and γ-chains covalently linked to form a "dimer of trimers," where A and B designate the fibrinopeptides released by thrombin cleavage (Panizzi et al., 2006). The elongated molecule folds into three separate domains, a central fragment E that contains the N-termini of all six chains and two flanking fragments D formed mainly by the C-termini of the Bβ- and γ-chains. These globular domains are connected by long triple-helical structures. Coagulase-prothrombin complexes, which convert human fibrinogen to the self-polymerizing fibrin, are not targeted by circulating thrombin inhibitors (Panizzi et al., 2006). Thus, staphylococcal coagulases bypass the physiological blood coagulation pathway.

All *S. aureus* strains secrete coagulase and vWbp (Bjerketorp et al., 2004; Field and Smith, 1945). Although early work reported important contributions of coagulase to the pathogenesis of staphylococcal infections (Ekstedt and Yotis, 1960; Smith et al., 1947), more recent investigations with molecular genetics tools challenged this view by observing no virulence phenotypes with endocarditis, skin abscess and mastitis models in mice (Moreillon et al., 1995; Phonimdaeng et al., 1990). Generating isogenic variants of *S. aureus* Newman, a fully virulent clinical isolate (Duthie et al., 1952), it is described herein that coa mutants indeed display virulence defects in a lethal bacteremia and renal abscess model in mice. In the inventors experience, *S. aureus* 8325-4 is not fully virulent and it is presumed that mutational lesions in this strain may not be able to reveal virulence defects in vivo. Moreover, antibodies raised against Coa or vWbp perturb the pathogenesis of *S. aureus* Newman infections to a degree mirroring the impact of gene deletions. Coa and vWbp contribute to staphylococcal abscess formation and lethal bacteremia and may also function as protective antigens in subunit vaccines.

Biochemical studies document the biological value of antibodies against Coa and vWbp. By binding to antigen and blocking its association with clotting factors, the antibodies prevent the formation of Coa.prothrombin and vWbp.prothrombin complexes. Passive transfer studies revealed protection of experimental animals against staphylococcal abscess formation and lethal challenge by Coa and vWbp antibodies. Thus, Coa and vWbp neutralizing antibodies generate immune protection against staphylococcal disease.

Earlier studies revealed a requirement of coagulase for resisting phagocytosis in blood (Smith et al., 1947) and the inventors observed a similar phenotype for Δcoa mutants in lepirudin-treated mouse blood (see Example 3 below). As vWbp displays higher affinity for human prothrombin than the mouse counterpart, it is suspected the same may be true for ΔvWbp variants in human blood. Further, expression of Coa and vWbp in abscess lesions as well as their striking distribution in the eosinophilic pseudocapsule surrounding (staphylococcal abscess communities (SACs) or the peripheral fibrin wall, suggest that secreted coagulases contribute to the establishment of these lesions. This hypothesis was tested and, indeed, Δcoa mutants were defective in the establishment of abscesses. A corresponding test, blocking Coa function with specific antibodies, produced the same effect. Consequently, it is proposed that the clotting of fibrin is a critical event in the establishment of staphylococcal abscesses that can be targeted for the development of protective vaccines. Due to their overlapping function on human prothrombin, both Coa and vWbp are considered excellent candidates for vaccine development.

C. Other Staphylococcal Antigens

Research over the past several decades identified *S. aureus* exotoxins, surface proteins and regulatory molecules as important virulence factors (Foster, 2005; Mazmanian et al., 2001; Novick, 2003). Much progress has been achieved regarding the regulation of these genes. For example, staphylococci perform a bacterial census via the secretion of autoinducing peptides that bind to a cognate receptor at threshold concentration, thereby activating phospho-relay reactions and transcriptional activation of many of the exotoxin genes (Novick, 2003). The pathogenesis of staphylococcal infections relies on these virulence factors (secreted exotoxins, exopolysaccharides, and surface adhesins). The development of staphylococcal vaccines is hindered by the multifaceted nature of staphylococcal invasion mechanisms. It is well established that live attenuated microorganisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. Embodiments of the invention are directed to compositions and methods including variant SpA polypeptides and peptides, as well as other immunogenic extracellular proteins, polypeptides, and peptides (including both secreted and cell surface proteins or peptides) of gram positive bacteria for the use in mitigating or immunizing against infection. In particular embodiments the bacteria is a *staphylococcus* bacteria. Extracellular proteins, polypeptides, or peptides include, but are not limited to secreted and cell surface proteins of the targeted bacteria.

The human pathogen *S. aureus* secretes EsxA and EsxB, two ESAT-6 like proteins, across the bacterial envelope (Burts et al., 2005, which is incorporated herein by reference). Staphylococcal esxA and esxB are clustered with six other genes in the order of transcription: esxA esaA essA esaB essB essC esaC esxB. The acronyms esa, ess, and esx stand for ESAT-6 secretion accessory, system, and extracellular, respectively, depending whether the encoded proteins play an accessory (esa) or direct (ess) role for secretion, or are secreted (esx) in the extracellular milieu. The entire cluster of eight genes is herein referred to as the Ess cluster. EsxA, esxB, essA, essB, and essC are all required for synthesis or secretion of EsxA and EsxB. Mutants that fail to produce EsxA, EsxB, and EssC display defects in the pathogenesis of *S. aureus* murine abscesses, suggesting that this specialized secretion system may be a general strategy of human bacterial pathogenesis. Secretion of non-WXG100 substrates by the ESX-1 pathway has been reported for several antigens including EspA, EspB, Rv3483c, and Rv3615c (Fortune et al., 2005; MacGurn et al., 2005; McLaughlin et al., 2007; Xu et al., 2007). The alternate ESX-5 pathway has also been shown to secrete both WXG100 and non-WXG100 proteins in pathogenic mycobacteria (Abdallah et al., 2007; Abdallah et al., 2006).

The *Staphylococcus aureus* Ess pathway can be viewed as a secretion module equipped with specialized transport components (Ess), accessory factors (Esa) and cognate secretion substrates (Esx). EssA, EssB and EssC are required for EsxA and EsxB secretion. Because EssA, EssB and EssC are predicted to be transmembrane proteins, it is contemplated that these proteins form a secretion apparatus. Some of the proteins in the ess gene cluster may actively transport secreted substrates (acting as motor) while others may regulate transport (regulator). Regulation may be achieved, but need not be limited to, transcriptional or post-translational mechanisms for secreted polypeptides, sorting of specific substrates to defined locations (e.g., extracellular medium or host cells), or timing of secretion events during infection. At this point, it is unclear whether all secreted Esx proteins function as toxins or contribute indirectly to pathogenesis.

Staphylococci rely on surface protein mediated-adhesion to host cells or invasion of tissues as a strategy for escape from immune defenses. Furthermore, *S. aureus* utilize surface proteins to sequester iron from the host during infection. The majority of surface proteins involved in staphylococcal pathogenesis carry C-terminal sorting signals, i.e., they are covalently linked to the cell wall envelope by sortase. Further, staphylococcal strains lacking the genes required for surface protein anchoring, i.e., sortase A and B, display a dramatic defect in the virulence in several different mouse models of disease. Thus, surface protein antigens represent a validated vaccine target as the corresponding genes are essential for the development of staphylococcal disease and can be exploited in various embodiments of the invention. The sortase enzyme superfamily are Gram-positive transpeptidases responsible for anchoring surface protein virulence factors to the peptidoglycan cell wall layer. Two sortase isoforms have been identified in *Staphylococcus aureus*, SrtA and SrtB. These enzymes have been shown to recognize a LPXTG motif in substrate proteins. The SrtB isoform appears to be important in heme iron acquisition and iron homeostasis, whereas the SrtA isoform plays a critical role in the pathogenesis of Gram-positive bacteria by modulating the ability of the bacterium to adhere to host tissue via the covalent anchoring of adhesins and other proteins to the cell wall peptidoglycan. In certain embodiments the SpA variants described herein can be used in combination with other staphylococcal proteins such as Coa, Eap, Ebh, Emp, EsaC, EsaB, EsxA, EsxB, Hla, SdrC, SdrD, SdrE, IsdA, IsdB, ClfA, ClfB, IsdC, SasF, vWbp, and/or vWh proteins.

Certain aspects of the invention include methods and compositions concerning proteinaceous compositions including polypeptides, peptides, or nucleic acid encoding SpA variant(s) and other staphylococcal antigens such as other proteins transported by the Ess pathway, or sortase substrates. These proteins may be modified by deletion, insertion, and/or substitution.

The Esx polypeptides include the amino acid sequence of Esx proteins from bacteria in the *Staphylococcus* genus. The Esx sequence may be from a particular *staphylococcus* species, such as *Staphylococcus aureus*, and may be from a particular strain, such as Newman. In certain embodiments, the EsxA sequence is SAV0282 from strain Mu50 (which is the same amino acid sequence for Newman) and can be accessed using Genbank Accession Number Q99WU4 (gi|68565539), which is hereby incorporated by reference. In other embodiments, the EsxB sequence is SAV0290 from strain Mu50 (which is the same amino acid sequence for Newman) and can be accessed using Genbank Accession Number Q99WT7 (gi|68565532), which is hereby incorporated by reference. In further embodiments, other polypeptides transported by the Ess pathway may be used, the sequences of which may be identified by one of skill in the art using databases and internet accessible resources.

The sortase substrate polypeptides include, but are not limited to the amino acid sequence of SdrC, SdrD, SdrE, IsdA, IsdB, ClfA, ClfB, IsdC or SasF proteins from bacteria in the *Staphylococcus* genus. The sortase substrate polypeptide sequence may be from a particular *staphylococcus* species, such as *Staphylococcus aureus*, and may be from a particular strain, such as Newman. In certain embodiments, the SdrD sequence is from strain N315 and can be accessed using Genbank Accession Number NP_373773.1 (gi|15926240), which is incorporated by reference. In other embodiments, the SdrE sequence is from strain N315 and can be accessed using Genbank Accession Number NP_373774.1 (gi|15926241), which is incorporated by reference. In other embodiments, the IsdA sequence is SAV1130 from strain Mu50 (which is the same amino acid sequence for Newman) and can be accessed using Genbank Accession Number NP_371654.1 (gi|15924120), which is incorporated by reference. In other embodiments, the IsdB sequence is SAV1129 from strain Mu50 (which is the same amino acid sequence for Newman) and can be accessed using Genbank Accession Number NP_371653.1 (gi|15924119), which is incorporated by reference. In further embodiments, other polypeptides transported by the Ess pathway or processed by sortase may be used, the sequences of which may be identified by one of skill in the art using databases and internet accessible resources.

Examples of various proteins that can be used in the context of the present invention can be identified by analysis of database submissions of bacterial genomes, including but not limited to accession numbers NC_002951 (GI:57650036 and GenBank CP000046), NC_002758 (GI:57634611 and GenBank BA000017), NC_002745 (GI:29165615 and GenBank BA000018), NC_003923 (GI:21281729 and GenBank BA000033), NC_002952 (GI:49482253 and GenBank BX571856), NC_002953 (GI:49484912 and GenBank BX571857), NC_007793 (GI:87125858 and GenBank CP000255), NC_007795 (GI:87201381 and GenBank CP000253) each of which are incorporated by reference.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of SpA, coagulases and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., SEQ ID NO:2-8 or SEQ ID NO:11-30, A variant can include 2, 3, 4, 5, 6, 7, 8, 9, 10, 11, 12, 13, 14, 15, 16, 17, 18, 19, 20, or more substitute amino acids. A polypeptide processed or secreted by the Ess pathway or other surface proteins (see Table 1) or sortase substrates from any *staphylococcus* species and strain are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a non-polar or uncharged amino acid, and vice versa.

TABLE 2

| Exemplary surface proteins of *S. aureus* strains. | | | | | | | | |
|---|---|---|---|---|---|---|---|---|
| SAV # | SA# | Surface | MW2 | Mu50 | N315 | Newman | MRSA252* | MSSA476* |
| SAV0111 | SA0107 | Spa | 492 | 450 | 450 | 520 | 516 | 492 |
| SAV2503 | SA2291 | FnBPA | 1015 | 1038 | 1038 | 741 | — | 1015 |
| SAV2502 | SA2290 | FnBPB | 943 | 961 | 961 | 677 | 965 | 957 |
| SAV0811 | SA0742 | ClfA | 946 | 935 | 989 | 933 | 1029 | 928 |
| SAV2630 | SA2423 | ClfB | 907 | 877 | 877 | 913 | 873 | 905 |
| Np | Np | Cna | 1183 | — | — | — | 1183 | 1183 |
| SAV0561 | SA0519 | SdrC | 955 | 953 | 953 | 947 | 906 | 957 |
| SAV0562 | SA0520 | SdrD | 1347 | 1385 | 1385 | 1315 | — | 1365 |
| SAV0563 | SA0521 | SdrE | 1141 | 1141 | 1141 | 1166 | 1137 | 1141 |
| Np | Np | Pls | — | — | — | — | — | — |
| SAV2654 | SA2447 | SasA | 2275 | 2271 | 2271 | 2271 | 1351 | 2275 |
| SAV2160 | SA1964 | SasB | 686 | 2481 | 2481 | 2481 | 2222 | 685 |
| | SA1577 | SasC | 2186 | 213 | 2186 | 2186 | 2189 | 2186 |
| SAV0134 | SA0129 | SasD | 241 | 241 | 241 | 241 | 221 | 241 |
| SAV1130 | SA0977 | SasE/IsdA | 350 | 350 | 350 | 350 | 354 | 350 |
| SAV2646 | SA2439 | SasF | 635 | 635 | 635 | 635 | 627 | 635 |
| SAV2496 | | SasG | 1371 | 525 | 927 | — | — | 1371 |
| SAV0023 | SA0022 | SasH | 772 | — | 772 | 772 | 786 | 786 |
| SAV1731 | SA1552 | SasI | 895 | 891 | 891 | 891 | 534 | 895 |
| SAV1129 | SA0976 | SasJ/IsdB | 645 | 645 | 645 | 645 | 652 | 645 |
| | SA2381 | SasK | 198 | 211 | 211 | — | — | 197 |
| | Np | SasL | — | 232 | — | — | — | — |
| SAV1131 | SA0978 | IsdC | 227 | 227 | 227 | 227 | 227 | 227 |

Proteins of the invention may be recombinant, or synthesized in vitro. Alternatively, a non-recombinant or recombinant protein may be isolated from bacteria. It is also contemplated that a bacteria containing such a variant may be implemented in compositions and methods of the invention. Consequently, a protein need not be isolated.

The term “functionally equivalent codon” is used herein to refer to codons that encode the same amino acid, such as the six codons for arginine or serine, and also refers to codons that encode biologically equivalent amino acids (see Table 2, below).

TABLE 3

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |

TABLE 3-continued

| Codon Table | | | |
|---|---|---|---|
| Amino Acids | | | Codons |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein’s functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an SpA variant or a coagulase, and may be used in combination with other peptides or polypeptides, such as other bacterial peptides and/or antigens.

The present invention contemplates the administration of variant SpA polypeptides or peptides to effect a preventative therapy or therapeutic effect against the development of a disease or condition associated with infection by a *staphylococcus* pathogen.

In certain aspects, combinations of staphylococcal antigens are used in the production of an immunogenic composition that is effective at treating or preventing staphylococcal infection. Staphylococcal infections progress through several different stages. For example, the staphylococcal life cycle involves commensal colonization, initiation of infection by accessing adjoining tissues or the bloodstream, and/or anaerobic multiplication in the blood. The interplay between *S. aureus* virulence determinants and the host defense mechanisms can induce complications such as endocarditis, metastatic abscess formation, and sepsis syndrome. Different molecules on the surface of the bacterium are involved in different steps of the infection cycle. Combinations of certain antigens can elicit an immune response which protects against multiple stages of staphylococcal infection. The effectiveness of the immune response can be measured either in animal model assays and/or using an opsonophagocytic assay.

D. Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also include fragments that when administered at an effective dose, (either alone or as a hapten bound to a carrier), elicit a protective or therapeutic immune response against Staphylococcal infection, in certain aspects it is protective against *S. aureus* and/or *S. epidermidis* infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the invention are fusion proteins composed of one or more Staphylococcal proteins, or immunogenic fragments of staphylococcal proteins. Such fusion proteins may be made recombinantly and may comprise one portion of at least 1, 2, 3, 4, 5, or 6 staphylococcal proteins or segments. Alternatively, a fusion protein may comprise multiple portions of at least 1, 2, 3, 4 or 5 staphylococcal proteins. These may combine different Staphylococcal proteins and/or multiples of the same protein or proten fragment, or immunogenic fragments in the same protein (forming a multimer or a concatamer). Alternatively, the invention also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

II. NUCLEIC ACIDS

In certain embodiments, the present invention concerns recombinant polynucleotides encoding the proteins, polypeptides, peptides of the invention. The nucleic acid sequences for SpA, coagulases and other bacterial proteins are included, all of which are incorporated by reference, and can be used to prepare peptides or polypeptides.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein (see Table 3 above).

In particular embodiments, the invention concerns isolated nucleic acid segments and recombinant vectors incorporating nucleic acid sequences that encode a variant SpA or coagulase. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a variant SpA or coagulase polypeptide or peptide to generate an immune response in a subject. In various embodiments the nucleic acids of the invention may be used in genetic vaccines.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the invention concerns isolated nucleic acid segments and recombinant vectors that include within their sequence a contiguous nucleic acid sequence from SEQ ID NO:1 (SpA domain D) or SEQ ID NO:3 (SpA) or any other nucleic acid sequences encoding coagulases or other secreted virulence factors and/or surface proteins including proteins transported by the Ess pathway, processed by sortase, or proteins incorporated herein by reference.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters).

The invention also contemplates the use of polynucleotides which are complementary to all the above described polynucleotides.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a variant SpA polypeptide the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon—poly(rI)x/poly(rc) (Tavernier et al., 1983); Adenovirus 5 E2-ElA (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MHC Class I Gene H-2κb—Interferon (Blanar et al., 1989); HSP70—ElA/SV40

Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone a Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of a variant SpA for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. POLYSACCHARIDES

The immunogenic compositions of the invention may further comprise capsular polysaccharides including one or more of PIA (also known as PNAG) and/or *S. aureus* Type V and/or type VIII capsular polysaccharide and/or *S. epidermidis* Type I, and/or Type II and/or Type III capsular polysaccharide.

A. PIA (PNAG)

It is now clear that the various forms of staphylococcal surface polysaccharides identified as PS/A, PIA and SAA are the same chemical entity—PNAG (Maira-Litran et al., 2004). Therefore the term PIA or PNAG encompasses all these polysaccharides or oligosaccharides derived from them.

PIA is a polysaccharide intercellular adhesin and is composed of a polymer of β-(1→6)-linked glucosamine substituted with N-acetyl and O-succinyl constituents. This polysaccharide is present in both *S. aureus* and *S. epidermidis* and can be isolated from either source (Joyce et al., 2003; Maira-Litran et al., 2002). For example, PNAG may be isolated from *S. aureus* strain MN8m (WO04/43407). PIA isolated from *S. epidermidis* is a integral constituent of biofilm. It is responsible for mediating cell-cell adhesion and probably also functions to shield the growing colony from the host's immune response. The polysaccharide previously known as poly-N-succinyl-β-(1→6)-glucosamine (PNSG) was recently shown not to have the expected structure since the identification of N-succinylation was incorrect (Maira-Litran et al., 2002). Therefore the polysaccharide formally known as PNSG and now found to be PNAG is also encompassed by the term PIA.

PIA (or PNAG) may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PIA polysaccharide or oligosaccharide may be use in an immunogenic composition of the invention, in one aspect the polysaccharide is over 40 kDa. Sizing may be achieved by any method known in the art, for instance by microfluidization, ultrasonic irradiation or by chemical cleavage (WO 03/53462, EP497524, EP497525). In certain aspects PIA (PNAG) is at least or at most 40-400 kDa, 40-300 kDa, 50-350 kDa, 60-300 kDa, 50-250 kDa and 60-200 kDa.

PIA (PNAG) can have different degree of acetylation due to substitution on the amino groups by acetate. PIA produced in vitro is almost fully substituted on amino groups (95-100%). Alternatively, a deacetylated PIA (PNAG) can be used having less than 60%, 50%, 40%, 30%, 20%, 10% acetylation. Use of a deacetylated PIA (PNAG) is preferred since non-acetylated epitopes of PNAG are efficient at mediating opsonic killing of Gram positive bacteria, preferably *S. aureus* and/or *S. epidermidis*. In certain aspects, the PIA (PNAG) has a size between 40 kDa and 300 kDa and is deacetylated so that less than 60%, 50%, 40%, 30% or 20% of amino groups are acetylated.

The term deacetylated PNAG (dPNAG) refers to a PNAG polysaccharide or oligosaccharide in which less than 60%, 50%, 40%, 30%, 20% or 10% of the amino agroups are acetylated. In certain aspects, PNAG is deaceylated to form dPNAG by chemically treating the native polysaccharide. For example, the native PNAG is treated with a basic solution such that the pH rises to above 10. For instance the PNAG is treated with 0.1-5 M, 0.2-4 M, 0.3-3 M, 0.5-2 M, 0.75-1.5 M or 1 M NaOH, KOH or $NH_4OH$. Treatment is for at least 10 to 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

The polysaccharide(s) can be conjugated or unconjugated to a carrier protein.

B. Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al., (1990) and Fournier et al., (1984). Both have FucNAcp in their repeat unit as well as ManNAcA which can be used to introduce a sulfhydryl group. The structures are:

Type 5

→4)-β-D-ManNAcA(3OAc)-(1→4)-α-L-FucNAc (1→3)-β-D-FucNAc-(1→

Type 8

→3)-β-D-ManNAcA(4OAc)-(1→3)-α-L-FucNAc (1→3)-β-D-FucNAc-(1→

Recently (Jones, 2005) NMR spectroscopy revised the structures to:

Type 5

→4)-β-D-ManNAcA-(1→4)-α-L-FucNAc(3OAc)-(1→3)-β-D-FucNAc-(1→

Type 8

→3)-β-D-ManNAcA(4OAc)-(1→3)-α-L-FucNAc (1→3)-α-D-FucNAc(1→

Polysaccharides may be extracted from the appropriate strain of *S. aureus* using method well known to of skill in the art, See U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation, or by chemical treatment. The invention also covers oligosaccharides derived from the type 5 and 8 polysaccharides from *S. aureus*. The type 5 and 8 polysaccharides included in the immunogenic composition of the invention are preferably conjugated to a carrier protein as described below or are alternatively unconjugated. The immunogenic compositions of the invention alternatively contains either type 5 or type 8 polysaccharide.

C. *S. aureus* 336 Antigen

In an embodiment, the immunogenic composition of the invention comprises the *S. aureus* 336 antigen described in U.S. Pat. No. 6,294,177. The 336 antigen comprises β-linked hexosamine, contains no O-acetyl groups, and specifically binds to antibodies to *S. aureus* Type 336 deposited under ATCC 55804. In an embodiment, the 336 antigen is a polysaccharide which is of native size or alternatively may be sized, for instance by microfluidisation, ultrasonic irradiation, or by chemical treatment. The invention also covers oligosaccharides derived from the 336 antigen. The 336 antigen can be unconjugated or conjugated to a carrier protein.

D. Type I, II and III Polysaccharides from *S. epidermidis*

Amongst the problems associated with the use of polysaccharides in vaccination, is the fact that polysaccharides per se are poor immunogens. It is preferred that the polysaccharides utilized in the invention are linked to a protein carrier which provide bystander T-cell help to improve immunogenicity. Examples of such carriers which may be conjugated to polysaccharide immunogens include the Diphtheria and Tetanus toxoids (DT, DT CRM197 and TT respectively), Keyhole Limpet Haemocyanin (KLH), and the purified protein derivative of Tuberculin (PPD), *Pseudomonas aeruginosa* exoprotein A (rEPA), protein D from *Haemophilus influenzae*, pneumolysin or fragments of any of the above. Fragments suitable for use include fragments encompassing T-helper epitopes. In particular the protein D fragment from *H. influenza* will preferably contain the N-terminal 1/3 of the protein. Protein D is an IgD-binding protein from *Haemophilus influenzae* (EP 0 594 610 B1) and is a potential immunogen. In addition, staphylococcal proteins may be used as a carrier protein in the polysaccharide conjugates of the invention.

A carrier protein that would be particularly advantageous to use in the context of a staphylococcal vaccine is staphylococcal alpha toxoid. The native form may be conjugated to a polysaccharide since the process of conjugation reduces toxicity. Preferably genetically detoxified alpha toxins such as the His35Leu or His35Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

The polysaccharides may be linked to the carrier protein(s) by any known method (for example those methods described in U.S. Pat. Nos. 4,372,945, 4,474,757, and 4,356,170). Preferably, CDAP conjugation chemistry is carried out (see WO95/08348). In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

Conjugation preferably involves producing a direct linkage between the carrier protein and polysaccharide. Optionally a spacer (such as adipic dihydride (ADH)) may be introduced between the carrier protein and the polysaccharide.

IV. IMMUNE RESPONSE AND ASSAYS

As discussed above, the invention concerns evoking or inducing an immune response in a subject against a variant SpA or coagulase peptide. In one embodiment, the immune response can protect against or treat a subject having, suspected of having, or at risk of developing an infection or related disease, particularly those related to staphylococci. One use of the immunogenic compositions of the invention is to prevent nosocomial infections by inoculating a subject prior to undergoing procedures in a hospital or other environment having an increased risk of infection.

A. Immunoassays

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Bacterial Infection

In addition to the use of proteins, polypeptides, and/or peptides, as well as antibodies binding these polypeptides, proteins, and/or peptides, to treat or prevent infection as described above, the present invention contemplates the use of these polypeptides, proteins, peptides, and/or antibodies in a variety of ways, including the detection of the presence of Staphylococci to diagnose an infection, whether in a patient or on medical equipment which may also become infected. In accordance with the invention, a preferred method of detecting the presence of infections involves the steps of obtaining a sample suspected of being infected by one or more staphylococcal bacteria species or strains, such as a sample taken from an individual, for example, from one's blood, saliva, tissues, bone, muscle, cartilage, or skin. Following isolation of the sample, diagnostic assays utilizing the polypeptides, proteins, peptides, and/or antibodies of the present invention may be carried out to detect the presence of staphylococci, and such assay techniques for determining such presence in a sample are well known to those skilled in the art and include methods such as radioimmunoassay, western blot analysis and ELISA assays. In general, in accordance with the invention, a method of diagnosing an infection is contemplated wherein a sample suspected of being infected with staphylococci has added to it the polypeptide, protein, peptide, antibody, or monoclonal antibody in accordance with the present invention, and staphylococci are indicated by antibody binding to the polypeptides, proteins, and/or peptides, or polypeptides, proteins, and/or peptides binding to the antibodies in the sample.

Accordingly, antibodies in accordance with the invention may be used for the prevention of infection from staphylococcal bacteria (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present invention. While according to one aspect, a polypeptide is derived from an immunogen designed to induce an active immune response in a recipient, according to another aspect of the invention, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge with the antigenic composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the invention are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

D. Treatment Methods

A method of the present invention includes treatment for a disease or condition caused by a *staphylococcus* pathogen. An immunogenic polypeptide of the invention can be given to induce an immune response in a person infected with *staphylococcus* or suspected of having been exposed to *staphylococcus*. Methods may be employed with respect to individuals who have tested positive for exposure to *staphylococcus* or who are deemed to be at risk for infection based on possible exposure.

In particular, the invention encompasses a method of treatment for staphylococcal infection, particularly hospital acquired nosocomial infections. The immunogenic compositions and vaccines of the invention are particularly advantageous to use in cases of elective surgery. Such patients will know the date of surgery in advance and could be inoculated in advance. The immunogenic compositions and vaccines of the invention are also advantageous to use to inoculate health care workers.

In some embodiments, the treatment is administered in the presence of adjuvants or carriers or other staphylococcal antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

V. VACCINE AND OTHER PHARMACEUTICAL COMPOSITIONS AND ADMINISTRATION

A. Vaccines

The present invention includes methods for preventing or ameliorating staphylococcal infections, particularly hospital acquired nosocomial infections. As such, the invention contemplates vaccines for use in both active and passive immunization embodiments. Immunogenic compositions, proposed to be suitable for use as a vaccine, may be prepared from immunogenic SpA polypeptide(s), such as a SpA domain D variant, or immunogenic coagulases. In other embodiments SpA or coagulases can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a variant SpA polypeptide or coagulase, or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide mono-oleate (Aracel A)); or emulsion with a 20% solution of a perfluorocarbon (Fluosol-DA®) used as a block substitute may also be employed to produce an adjuvant effect.

Examples of and often preferred adjuvants include complete Freund's adjuvant (a non-specific stimulator of the immune response containing killed *Mycobacterium tuberculosis*), incomplete Freund's adjuvants, and aluminum hydroxide.

In some aspects, it is preferred that the adjuvant be selected to be a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ T cell clones by Mosmann and Coffman (Mosmann, and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/$m^2$) (Johnson/Mead, NJ) and cytokines such as γ-interferon, IL-2, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of a secreted virulence factor or surface protein, including a variant SpA polypeptide or peptide, and/or other bacterial peptides or proteins to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a polypeptide vaccine and/or therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic molecule given as part of an immune therapy regime, such as an antigen, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the immunogenic compositions of the present invention to a patient/subject will follow general protocols for the administration of such compounds, taking into account the toxicity, if any, of the SpA composition, or other compositions described herein. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, staphylococcal antigens, members of the Ess pathway, including polypeptides or peptides of the Esa or Esx class, and/or members of sortase substrates may be administered to the patient to protect against infection by one or more *staphylococcus* pathogens. Alternatively, an expression vector encoding one or more such polypeptides or peptides may be given to a patient as a preventative treatment. Additionally, such compounds can be administered in combination with an antibiotic or an antibacterial. Such compositions will generally be dissolved or dispersed in a pharmaceutically acceptable carrier or aqueous medium.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds of the present invention can be formulated for parenteral administration, e.g., formulated for injection via the intravenous, intramuscular, subcutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present invention, the compositions may be administered either in vitro, ex vivo, or in vivo. In certain in vitro embodiments, autologous B-lymphocyte cell lines are incubated with a virus vector of the instant invention for 24 to 48 hours or with a variant SpA and/or cogaulase and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

F. Antibodies and Passive Immunization

Another aspect of the invention is a method of preparing an immunoglobulin for use in prevention or treatment of staphylococcal infection comprising the steps of immunizing a recipient or donor with the vaccine of the invention and isolating immunoglobulin from the recipient or donor. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane, 1988). Antibodies can include antiserum preparations from a variety of commonly used animals, e.g. goats, primates, donkeys, swine, horses, guinea pigs, rats or man.

An immunoglobulin produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex.

A vaccine of the present invention can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals, or where treatment is required and there is no time for the individual to produce antibodies in response to vaccination.

An additional aspect of the invention is a pharmaceutical composition comprising two of more monoclonal antibodies (or fragments thereof; preferably human or humanised) reactive against at least two constituents of the immunogenic composition of the invention, which could be used to treat or prevent infection by Gram positive bacteria, preferably staphylococci, more preferably *S. aureus* or *S. epidermidis*. Such pharmaceutical compositions comprise monoclonal antibodies that can be whole immunoglobulins of any class, chimeric antibodies, or hybrid antibodies with specificity to two or more antigens of the invention. They may also be fragments (e.g., F(ab')2, Fab', Fab, Fv and the like) including hybrid fragments.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Non-Toxigenic Protein a Variants as Subunit Vaccines to Prevent *Staphylococcus aureus* Infections A. Results An animal model for *S. aureus* infection BALB/c mice were infected by intravenous injection with $1\times10^7$ CFU of the human clinical isolate *S. aureus* Newman (Baba et al., 2007). Within 6 hours following infection, 99.999% of staphylococci disappeared from the blood stream and were distributed via the vasculature. Staphylococcal dissemination to peripheral tissues occurred rapidly, as the bacterial load in kidney and other peripheral organ tissues reached $1\times10^5$ CFU $g^{-1}$ within the first three hours. The staphylococcal load in kidney tissues increased by 1.5 log CFU within twenty-four hours. Forty-eight hours following infection, mice developed disseminated abscesses in multiple organs, detectable by light microscopy of hematoxylin-eosin stained, thin-sectioned kidney tissue. The initial abscess diameter was 524 μM (±65

μM); lesions were initially marked by an influx of polymorphonuclear leukocytes (PMNs) and harbored no discernable organization of staphylococci, most of which appeared to reside within PMNs. On day 5 of infection, abscesses increased in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. A rim of necrotic PMNs were observed at the periphery of abscess lesions, bordering eosinophilic, amorphous material that separates healthy renal tissue from lesions. Abscesses eventually reached a diameter of ≥1,524 μM on day 15 or 36. At later time intervals, the staphylococcal load was increased to $10^4$-$10^6$ CFU $g^{-1}$ and growing abscess lesions migrated towards the organ capsule. Peripheral lesions were prone to rupture, thereby releasing necrotic material and staphylococci into the peritoneal cavity or the retroperitoneal space. These events resulted in bacteremia as well as a secondary wave of abscesses, eventually precipitating a lethal outcome.

To enumerate staphylococcal load in renal tissue, animals were killed, their kidneys excised and tissue homogenate spread on agar media for colony formation. On day 5 of infection, a mean of $1\times10^6$ CFU $g^{-1}$ renal tissue for *S. aureus* Newman was observed. To quantify abscess formation, kidneys were visually inspected, and each individual organ was given a score of one or zero. The final sum was divided by the total number of kidneys to calculate percent surface abscesses (Table 4). In addition, randomly chosen kidneys were fixed in formalin, embedded, thin sectioned, and stained with hematoxylin-eosin. For each kidney, four sagittal sections at 200 μM intervals were viewed by microscopy. The numbers of lesions were counted for each section and averaged to quantify the number of abscesses within the kidneys. *S. aureus* Newman caused 4.364±0.889 abscesses per kidney, and surface abscesses were observed on 14 out of 20 kidneys (70%) (Table 4).

When examined by scanning electron microscopy, *S. aureus* Newman was located in tightly associated lawns at the center of abscesses. Staphylococci were contained by an amorphous pseudocapsule that separated bacteria from the cuff of abscesses leukocytes. No immune cells were observed in these central nests of staphylococci, however occasional red blood cells were located among the bacteria. Bacterial populations at the abscess center, designated staphylococcal abscess communities (SAC), appeared homogenous and coated by an electron-dense, granular material. The kinetics of the appearance of infectious lesions and the morphological attributes of abscesses formed by *S. aureus* Newman were similar to those observed following mouse infection with *S. aureus* USA300 (LAC), the current epidemic community-acquired methicillin-resistant *S. aureus* (CA-MRSA) clone in the United States (Diep et al., 2006).

TABLE 4

Genetic requirements for *S. aureus* Newman abscess formation in mice

| | Staphylococcal load in kidney tissue | | | Abscess formation in kidney tissue | | |
|---|---|---|---|---|---|---|
| Genotype | [a]$\log_{10}$ CFU $g^{-1}$ tissue | [b]Significance (P-value) | [c]Reduction ($\log_{10}$ CFU $g^{-1}$) | [d]Surface abscesses (%) | [e]Number of abscesses per kidney | [f]Significance (P-value) |
| wild-type | 6.141 ± 0.192 | — | — | 70 | 4.364 ± 0.889 | — |
| ΔsrtA | 4.095 ± 0.347 | $6.7\times10^{-6}$ | 2.046 | 0 | 0.000 ± 0.000 | 0.0216 |
| spa | 5.137 ± 0.374 | 0.0144 | 1.004 | 13 | 0.375 ± 0.374 | 0.0356 |

[a]Means of staphylococcal load calculated as $\log_{10}$ CFU $g^{-1}$ in homogenized renal tissues 5 days following infection in cohorts of fifteen BALB/c mice per challenge strain. Standard error of the means (±SEM) is indicated.
[b]Statistical significance was calculated with the Students t-test and P-values recorded; P-values < 0.05 were deemed significant.
[c]Reduction in bacterial load calculated as $\log_{10}$ CFU $g^{-1}$.
[d]Abscess formation in kidney tissues five days following infection was measured by macroscopic inspection (% positive)
[e]Histopathology of hematoxylin-eosin stained, thin sectioned kidneys from eight to ten animals; the average number of abscesses per kidney was recorded and averaged again for the final mean (±SEM).
[f]Statistical significance was calculated with the Students t-test and P-values recorded; P-values < 0.05 were deemed significant.

*S. aureus* Protein A (Spa) Mutants are Avirulent and Cannot Form Abscesses

Sortase A is a transpeptidase that immobilizes nineteen surface proteins in the envelope of *S. aureus* strain Newman (Mazmanian et al., 1999; Mazmanian et al., 2000). Earlier work identified sortase A as a virulence factor in multiple animal model systems, however the contributions of this enzyme and its anchored surface proteins to abscess formation or persistence have not yet been revealed (Jonsson et al., 2002; Weiss et al., 2004). Compared to the wild-type parent (Baba et al., 2007), an isogenic srtA variant (ΔsrtA) failed to form abscess lesions on either macroscopic or histopathology examination on days 2, 5, or 15. In mice infected with the strA mutant, only $1\times10^4$ CFU $g^{-1}$ was recovered from kidney tissue on day 5 of infection, which is a 2.046 $\log_{10}$ CFU $g^{-1}$ reduction compared to the wild-type parent strain (P=$6.73\times10^{-6}$). A similar defect was observed for the srtA mutant of MRSA strain USA300 (data not shown). Scanning electron microscopy showed that srtA mutants were highly dispersed and often associated with leukocytes in otherwise healthy renal tissue. On day fifteen following infection, srtA mutants were cleared from renal tissues, a ≥3.5 $\log_{10}$ CFU $g^{-1}$ reduction compared to the wild-type (Table 3). Thus, sortase A anchored surface proteins enable the formation of abscess lesions and the persistence of bacteria in host tissues, wherein staphylococci replicate as communities embedded in an extracellular matrix and shielded from surrounding leukocytes by an amorphous pseudocapsule.

Sortase A anchors a large spectrum of proteins with LPXTG motif sorting signals to the cell wall envelope, thereby providing for the surface display of many virulence factors (Mazmanian et al., 2002). To identify surface proteins required for staphylococcal abscess formation, bursa aurealis insertions were introduced in 5' coding sequences of genes that encode polypeptides with LPXTG motif proteins (Bae et al., 2004) and these mutations were transduced into *S. aureus* Newman. Mutations in the structural gene for Protein A (spa)

reduced the staphylococcal load in infected mouse kidney tissues by 1.004 $\log_{10}$ (P=0.0144). When analyzed for their ability to form abscesses in kidney tissues by histopathology, we observed that the spa mutants were unable to form abscesses as compared with the wild-type parent strain *S. aureus* Newman (wild-type *S. aureus* Newman 4.364±0.889 abscesses per kidney vs. the isogenic spa mutant with 0.375±0.374 lesions; P=0.0356).

Protein A Blocks Innate and Adaptive Immune Responses.

Studies identified Protein A as a critical virulence factor during the pathogenesis of *S. aureus* infections. Earlier work demonstrated that Protein A impedes phagocytosis of staphylococci by binding the Fc component of immunoglobulin (Jensen 1958; Uhlén et al., 1984), activates platelet aggregation via the von Willebrand factor (Hartleib et al., 2000), functions as a B cell superantigen by capturing the $F(ab)_2$ region of VH3 bearing IgM (Roben et al., 1995), and, through its activation of TNFR1, can initiate staphylococcal pneumonia (Gomez et al., 2004). Due to the fact that Protein A captures immunoglobulin and displays toxic attributes, the possibility that this surface molecule may function as a vaccine in humans has not been rigorously pursued. The inventors demonstrate for the first time that Protein A variants no longer able to bind to immunoglobulins, vWF and TNFR-1 are removed of their toxigenic potential and are able to stimulate humoral immune responses that protect against staphylococcal disease.

Molecular Basis of Protein A Surface Display and Function.

Protein A is synthesized as a precursor in the bacterial cytoplasm and secreted via its YSIRK signal peptide at the cross wall, i.e., the cell division septum of staphylococci (FIG. 1). (DeDent et al., 2007; DeDent et al., 2008). Following cleavage of the C-terminal LPXTG sorting signal, Protein A is anchored to bacterial peptidoglycan crossbridges by sortase A (Schneewind et al., 1995; Mazmanian et al., 1999; Mazmanian et al., 2000). Protein A is the most abundant surface protein of staphylococci; the molecule is expressed by virtually all *S. aureus* strains (Said-Salim et al., 2003; Cespedes et al., 2005; Kennedy et al., 2008). Staphylococci turn over 15-20% of their cell wall per division cycle (Navarre and Schneewind 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen 1958; Goodyear and Silverman 2004). Interestingly, region X of Protein A (Guss et al., 1984), a repeat domain that tethers the IgG binding domains to the LPXTG sorting signal/cell wall anchor, is perhaps the most variable portion of the staphylococcal genome (Schneewind et al., 1992; Said-Salim et al., 2003). Each of the five immunoglobulin binding domains of Protein A (SpA), formed from three helix bundles and designated E, D, A, B, and C, exerts similar structural and functional properties (Sjödahl 1977; Jansson et al., 1998). The solution and crystal structure of domain D has been solved both with and without the Fc and $V_H3$ (Fab) ligands, which bind Protein A in a non-competitive manner at distinct sites (Graille et al., 2000).

In the crystal structure complex, the Fab interacts with helix II and helix III of domain D via a surface composed of four VH region β-strands (Graille et al., 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II as well as Asp-37 and Gln-40 in the loop between helix II and helix III, in addition to several other residues with SpA-D (Graille et al., 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, these residues were selected for mutagenesis.

The SpA-D sites responsible for Fab binding are structurally separate from the domain surface that mediates Fcγ binding. The interaction of Fcγ with domain B primarily involves residues in helix I with lesser involvement of helix II (Deisenhofer 1981; Gouda et al., 1992). With the exception of the Gln-32, a minor contact in both complexes, none of the residues that mediate the Fcγ interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), a SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFR1 (O'Seaghdha et al., 2006). Mutations in residues essential for IgG Fc binding (F5, Q9, Q10, S11, F13, Y14, L17, N28, I31 and K35) are also required for vWF A1 and TNFR1 binding (Cedergren et al., 1993; Gomez et al., 2006; O'Seaghdha et al. 2006), whereas residues critical for the $V_H3$ interaction (Q26, G29, F30, S33, D36, D37, Q40, N43, E47) have no impact on the binding activities of IgG Fc, vWF A1 or TNFR1 (Jansson et al., 1998; Graille et al., 2000). The Protein A immunoglobulin Fab binding activity targets a subset of B cells that express VH3 family related IgM on their surface, i.e. these molecules function as VH3 type B cell receptors (Roben et al., 1995). Upon interaction with SpA, these B cells rapidly proliferate and then commit to apoptosis, leading to preferential and prolonged deletion of innate-like B lymphocytes (i.e. marginal zone B cells and follicular B2 cells) (Goodyear and Silverman 2003; Goodyear and Silverman 2004). It is important to note that more than 40% of circulating B cells are targeted by the Protein A interaction and the VH3 family represents the largest family of human B cell receptors to impart protective humoral responses against pathogens (Goodyear and Silverman 2003; Goodyear and Silverman 2004). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

Non-Toxigenic Variant of Protein A.

The inventors have developed a non-toxigenic variant of staphylococcal Protein A and, with this reagent in hand, aimed for the first time to measure the immune response of animals to Protein A immunization. Further, the inventors address whether immunization of animals with a non-toxigenic variant of Protein A could generate immune responses that raise protective immunity against staphylococcal infection.

To perturb the IgG Fc, vWF A1 and TNFR1 binding activities of Protein A, glutamine (Q) residues 9 and 10 [the numbering here is derived from that established for the SpA domain D] were modified generating lysine or glycine substitutions for both glutamines with the expectation that these substitutions abolish the ion bonds formed between wild-type Protein A and its ligands. The added effect of the dual lysine substitutions may be that these positively charged residues institute a repellent charge for immunoglobulins. To perturb IgM Fab VH3 binding, the inventors selected the aspartate (D) residues 36 and 37 of SpA-D, each of which is required for the association of Protein A with the B cell receptor. D36 and D37 were both substituted with alanine. The Q9,10K and D36,37A mutations were combined in the recombinant molecule SpA-$D_{Q9,10K;D36,37A}$ and examined for the binding attributes of Protein A.

In brief, the Protein A (spa) genomic sequence of *Staphylococcus aureus* N315 was PCR amplified with the primers (GCTGCACATATGGCGCAACACGATGAAGCTCAAC [5' primer](SEQ ID NO:35) and AGTGGATCCTTATGCTTTGTTAGCATCTGC [3' primer] (SEQ ID NO:36)), cloned into the pET15b vector (pYSJ1, codons 48-486) (Stranger-Jones, et al., 2006) and recombinant plasmid transformed into *E. coli* BL21(DE3) (Studier et al., 1990). The Protein A product derived from pYSJ1 harbors SpA residues 36-265 fused to the N-terminal His tag (MGSSHHHHHHSSGLVPRGS (SEQ ID NO:37)). Following IPTG inducible expression, recombinant N-terminal $His_6$-tagged SpA was purified by affinity chromatography on Ni-NTA resin (Stranger-Jones et al., 2006). The domain D of SpA (SpA-D) was PCR amplified with a pair of specific primers (AACATATGTTCAACAAAGATCAACAAAGC [5' primer] (SEQ ID NO:38) and AAGGATCCAGATTCGTTTAATTTTTTAGC [3' primer] (SEQ ID NO:39)), sub-cloned into the pET15b vector (pHAN1, spa codons 212-261) and recombinant plasmid transformed into *E. coli* BL21(DE3) to express and purify recombinant N-terminal $His_6$-tagged protein. To generate mutations in the SpA-D coding sequence, sets of two pairs of primers were synthesized (for D to A substitutions: CTTCATTCAAAGTCTTAAAGCCGCCCCAAGCCAAAGCACTAAC [5' primer] (SEQ ID NO:40) and GTTAGTGCTTTGGCTTGGGGCGGCTTTAAGACTTTGAATGAAG [3' primer] (SEQ ID NO:41); for Q to K substitutions CATATGTTCAACAAAGATAAAAAAAGCGCCTTCTATGAAATC [5' primer] (SEQ ID NO:42) and GATTTCATAGAAGGCGCTTTTTTTATCTTTGTTGAACATATG [3' primer] (SEQ ID NO:43); for Q to G substitutions CATATGTTCAACAAAGATGGAGGAAGCGCCTTCTATGAAATC [5' primer] (SEQ ID NO:44) and GATTTCATAGAAGGCGCTTCCTCCATCTTTGTTGAACATATG' [3' primer] (SEQ ID NO:45). Primers were used for quick-change mutagenesis protocols. Following mutagenesis, DNA sequences were confirmed for each of the recombinant proteins: SpA, SpA-D and SpA-$D_{Q9,10G;D36,37A}$ and SpA-$D_{Q9,10K;D36,37A}$. All proteins were purified from lysates of recombinant *E. coli* using Ni-NTA chromatography and subsequently dialyzed against PBS and stored at 4° C.

Figure 3:
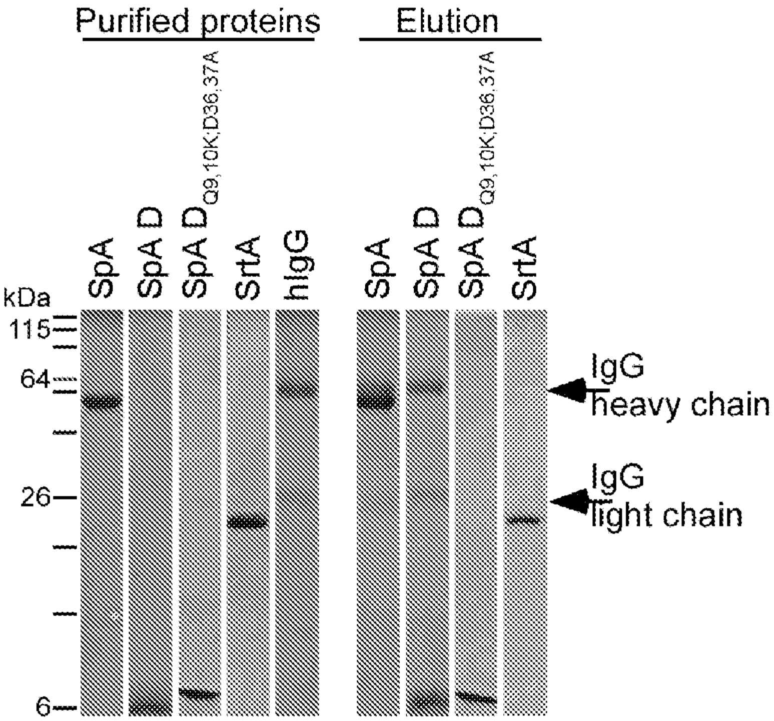
FIG. 3. Left panel—Coomassie Blue stained SDS-PAGE reveals the migrational position of purified His-tagged SpA, SpA-D, SPA-$D_{Q9,10K;D36,37A}$, human IgG, and sortase A (SrtA), a control protein. Right panel—Coomassie Blue stained SDS-PAGE to reveal the elution of Protein A immunoglobulin complexes eluted following affinity chromatography of human IgG on Ni-NTA columns pre-charged with His-tagged SpA, SpA-D, SpA-$D_{Q9,10K;D36,37A}$ or SrtA.

To measure binding of immunoglobulin to Protein A and its variants, 200 μg of purified protein was diluted into a 1 ml volume using column buffer (50 mM Tris-HCl, 150 mM NaCl, pH7.5) and then loaded onto a pre-equilibrated Ni-NTA column (1 ml bed volume). Columns were washed with 10 ml of column buffer. 200 μg of purified human IgG was diluted in a total volume of 1 ml column buffer and then applied to each of the columns charged with Protein A and its variants. The columns were subsequently washed with 5 ml wash buffer (10 mM imidazole in column buffer) and 5 ml column buffer. Protein samples were eluted with 2 ml elution buffer (500 mM imidazole in column buffer), fractions collected and aliquots subjected to SDS-PAGE gel electrophoresis, followed by Coomassie-Blue staining. As shown in FIG. 3, wild-type Protein A (SpA) and its SpA-domain D both retained immunogobulin during chromatography. In contrast, the SpA-$D_{Q9,10K;D36,37A}$ variant did not bind to immunoglobulin.

Figure 4:
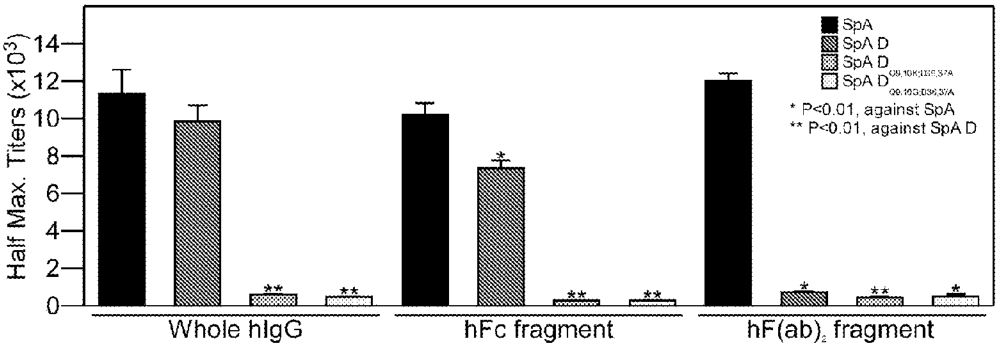
FIG. 4. ELISA assays to quantify human immunoglobulin (hIgG), human $F(ab)_2$ IgG fragments and human Fc fragments of immunoglobulin (hFc). Plates were coated with equal amounts of His-tagged SpA, SpA-D, SpA-$D_{Q9,10K;D36,37A}$ or SrtA. hIgG-HRP, $F(ab)_2$-HRP and hFc-HRP were added onto the plates and incubated for an hour. Absorbance at 450 nm was recorded and plotted to determine the half maximal titers.
Figure 5:
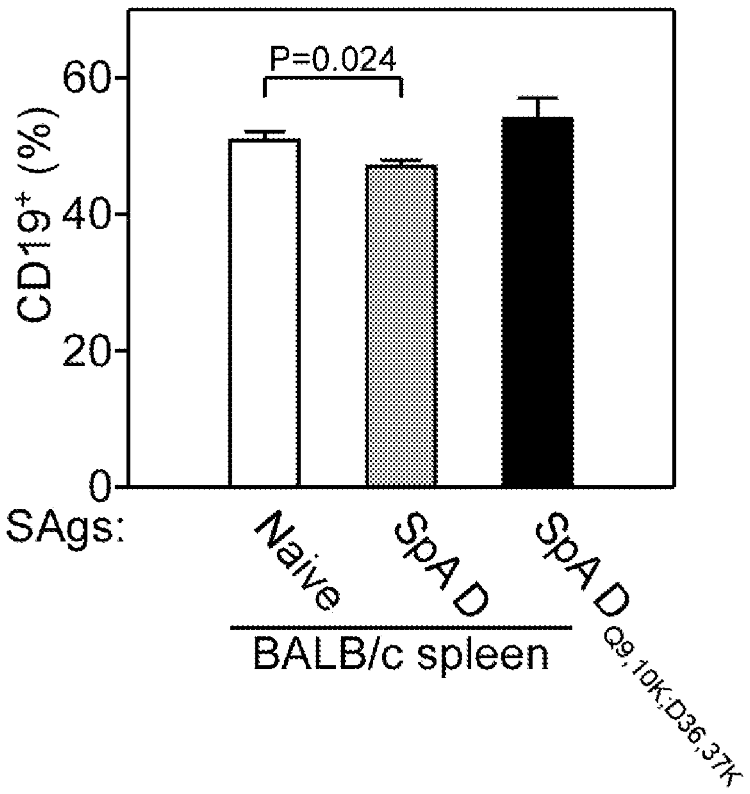
FIG. 5. Purified SpA-D, SpA-$D_{Q9,10K;D36,37A}$ or a PBS mock control were injected into the peritoneum of mice and analyzed for their ability to reduce the B cell population in the spleen of experimental BALB/c mice. Animals were killed 4 hours following injection, their spleen removed, tissue homogenized and stained with CD 19 antibodies directed against B cells. The number of B cells was quantified by FACS sorting.

To quantify the binding of Protein A and its variants to the Fc portion of immunoglobulin and the VH3 domain of Fab, HRP conjugated human immunoglobulin G [hIgG], the Fc portion of human IgG [hFc] and the $F(ab)_2$ portion of human IgG [$hF(ab)_2$] as well as ELISA assays were used to quantify the relative amount binding to Protein A and its variants. The data in FIG. 4 demonstrate the binding of SpA and SpA-D to hIgG and hFc, whereas SPA-$D_{Q9,10G;D36,37A}$ and SpA-$D_{Q9,10K;D36,37A}$ displayed only background binding activities. SpA bound similar amounts of hFc and $hF(ab)_2$, however the binding of SpA-D to $hF(ab)_2$ was reduced compared to full length SpA. This result suggests that the presence of multiple IgG binding domains may cooperatively increase the ability of Protein A to bind to the B cell receptor. When compared with the reduced binding power of SpA-D for $hF(ab)_2$, of the two variants only SpA-$D_{Q9,10K;D36,37A}$ displayed a significant reduction in the ability to bind the VH3 domain of immunoglobulin. To examine the toxigenic attributes of SpA-D and its variants, purified proteins were injected into mice, which were sacrificed after 4 hours to remove their spleens. Organ tissue was homogenized, capsular material removed and B cells stained with fluorescent CD19 antibodies. Following FACS analysis to quantify the abundance of B cells in splenic tissues, it was observed that SpA-D caused a 5% drop in the B cell count compared to a mock (PBS) control (FIG. 5). In contrast, SpA-$D_{Q9,10K;D36,37A}$ did not cause a reduction in B-cell counts, indicating that the mutant molecule had lost its toxigenic attributes of stimulating B cell proliferation and death (FIG. 5). In summary, amino acid substitutions in the SpA-D residues Q9, Q10, D36, and D37 abolished the ability of Protein A domains to bind immunoglobulins or exert toxigenic functions in human and animal tissues.

Non-Toxigenic Protein A Variants Elicit Vaccine Protection.

To test whether or not Protein A and its variants can function as vaccine antigens, SpA, SpA-D, SpA-$D_{Q9,10K;D36,37A}$, and SpA-$D_{Q9,10K;D36,37A}$ were emulsified with complete or incomplete Freund's adjuvant and immunized 4 week old BALB/c mice on day 1 and day 11 with 50 μg of purified protein. Cohort of animals (n=5) were analyzed for humoral immune responses to immunization by bleeding the animals before (day 0) and after the immunization schedule (day 21). Table 5 indicates that immunized mice generated only a modest humoral immune response directed at wild-type Protein A or its SpA-D module, whereas the amount of antibody raised following immunization with SpA-$D_{Q9,10K;D36,37A}$ or SpA-$D_{Q9,10K;D36,37A}$ was increased four to five fold. Following intravenous challenge with $1\times10^7$ CFU *S. aureus* Newman, animals were killed on day 4, their kidneys removed and either analyzed for staphylococcal load (by plating tissue homogenate on agar plates and enumerating colony forming units, CFU) or histopathology. As expected, mock (PBS) immunized mice (n=19) harbored 6.46 $\log_{10}$ (±0.25) CFU in kidney tissue and infectious lesions were organized into 3.7 (±1.2) abscesses per organ (n=10) (Table 5). Immunization of animals with SpA led to a 2.51 $\log_{10}$ CFU reduction on day 5 (P=0.0003) with 2.1 (±1.2) abscesses per organ. The latter data indicate that there was no significant reduction in abscess formation (P=0.35). Immunization with SpA-D generated similar results: a 2.03 $\log_{10}$ CFU reduction on day 5 (P=0.0001) with 1.5 (±0.8) abscesses per organ (P=0.15). In contrast, immunization with SpA-$D_{Q9,10K;D36,37A}$ or SpA-$D_{Q9,10G;D36,37A}$ created increased protection, with 3.07 $\log_{10}$ and 3.03 $\log_{10}$ CFU reduction on day 4, respectively (statistical significance P<0.0001 for both observations). Further, immunization with both SpA-$D_{Q9,10K;D36,37A}$ and SpA-$D_{Q9,10G;D36,37A}$ generated significant protection from staphylococcal abscess formation, as only 0.5 (±0.4) and 0.8 (±0.5) infectious lesions per organ (P=0.02 and P=0.04) were identified. Thus, immunization with non-toxigenic Protein A variants generates increased humoral immune responses for Protein A and provides protective immunity against staphylococcal challenge. These data indicate that Protein A is an ideal candidate for a human vaccine that prevents *S. aureus* disease.

These exciting results have several implications for the design of a human vaccine. First, the generation of substitution mutations that affect the ability of the immunoglobulin binding domains of Protein A, either alone or in combination of two or more domains, can generate non-toxigenic variants suitable for vaccine development. It seems likely that a combination of mutant IgG binding domains closely resembling the structure of Protein A can generate even better humoral immune responses as is reported here for the SpA-domain D alone. Further, a likely attribute of Protein A specific antibodies may be that the interaction of antigen binding sites with the microbial surface can neutralize the ability of staphylococci to capture immunoglobulins via their Fc portion or to stimulate the B cell receptor via the VH3 binding activities.

TABLE 5

Non-toxigenic Protein A variants as vaccine antigens that prevent *S. aureus* disease

| Antigen | Bacterial load in kidney (n = number of mice) [a]$\log_{10}$ CFU $g^{-1}$ | [b]Reduction | [c]P value | IgG titer | Abscess formation in mice (n = number of mice) [d]Surface abscess | Reduction | [e]Histopathology | Reduction | [f]P value |
|---|---|---|---|---|---|---|---|---|---|
| Mock | 6.46 ± 0.25 (n = 19) | — | — | <100 | 14/19 (70%) | — | 3.7 ± 1.2 (n = 10) | — | — |
| SpA | 3.95 ± 0.56 (n = 20) | 2.51 | 0.0003 | 1706 ± 370 | 10/20 (50%) | 32% | 2.1 ± 1.2 (n = 10) | 2.2 | 0.35 |
| SpA-D | 4.43 ± 0.41 (n = 18) | 2.03 | 0.0001 | 381 ± 27 | 10/18 (55%) | 25% | 1.5 ± 0.8 (n = 10) | 2.2 | 0.15 |
| SpA-D1 | 3.39 ± 0.50 (n = 19) | 3.07 | <0.0001 | 5600 ± 801 | 6/20 (30%) | 59% | 0.5 ± 0.4 (n = 10) | 3.2 | 0.02 |
| SpA-D2 | 3.43 ± 0.46 (n = 19) | 3.03 | <0.0001 | 3980 ± 676 | 6/19 (32%) | 57% | 0.8 ± 0.5 (n = 10) | 2.9 | 0.04 |

[a]Means of staphylococcal load calculated as $\log_{10}$ CFU $g^{-1}$ in homogenized renal tissues 4 days following infection in cohorts of 18 to 20 BALB/c mice. Standard error of the means (±SEM) is indicated.
[c]Statistical significance was calculated with the Students t-test and P-values recorded; P-values < 0.05 were deemed significant.
[b]Reduction in bacterial load calculated as $\log_{10}$ CFU $g^{-1}$.
[d]Abscess formation in kidney tissues four days following infection was measured by macroscopic inspection (% positive)
[e]Histopathology of hematoxylin-eosin stained, thin sectioned kidneys from ten animals; the number of abscesses per kidney was recorded and averaged for the final mean (±SEM).
[f]Statistical significance was calculated with the Students t-test and P-values recorded; P-values < 0.05 were deemed significant.
SpA-D1 and SpA-D2 represent SpA-$D_{Q9,10K;D36,37A}$ and SpA-$D_{Q9,10G;D36,37A}$, respectively.

Vaccine Protection in Murine Abscess, Murine Lethal Infection, and Murine Pneumonia Models.

Three animal models have been established for the study of *S. aureus* infectious disease. These models are used here to examine the level of protective immunity provided via the generation of Protein A specific antibodies.

Murine Abscess—

BALB/c mice (24-day-old female, 8-10 mice per group, Charles River Laboratories, Wilmington, Mass.) are immunized by intramuscular injection into the hind leg with purified protein (Chang et al., 2003; Schneewind et al., 1992). Purified SpA, SpA-D or SpA-DQ9,10K;D36,37A (50 μg protein) is administered on days 0 (emulsified 1:1 with complete Freund's adjuvant) and 11 (emulsified 1:1 with incomplete Freund's adjuvant). Blood samples are drawn by retroorbital bleeding on days 0, 11, and 20. Sera are examined by ELISA for IgG titers for specific SpA-D and SpA-DQ9,10K;D36,37A binding activity. Immunized animals are challenged on day 21 by retroorbital injection of 100 μl of *S. aureus* Newman or *S. aureus* USA300 suspension ($1\times10^7$ cfu). For this, overnight cultures of *S. aureus* Newman are diluted 1:100 into fresh tryptic soy broth and grown for 3 h at 37° C. Staphylococci are centrifuged, washed twice, and diluted in PBS to yield an $A_{600}$ of 0.4 ($1\times10^8$ cfu per ml). Dilutions are verified experimentally by agar plating and colony formation. Mice are anesthetized by intraperitoneal injection of 80-120 mg of ketamine and 3-6 mg of xylazine per kilogram of body weight and infected by retroorbital injection. On day 5 or 15 following challenge, mice are euthanized by compressed $CO_2$ inhalation. Kidneys are removed and homogenized in 1% Triton X-100. Aliquots are diluted and plated on agar medium for triplicate determination of cfu. For histology, kidney tissue is incubated at room temperature in 10% formalin for 24 h. Tissues are embedded in paraffin, thin-sectioned, stained with hematoxylinleosin, and examined by microscopy.

Murine Lethal Infection—

BALB/c mice (24-day-old female, 8-10 mice per group, Charles River Laboratories, Wilmington, Mass.) are immunized by intramuscular injection into the hind leg with purified SpA, SpA-D or SpA-$D_{Q9,10K;D36,37A}$ (50 μg protein). Vaccine is administered on days 0 (emulsified 1:1 with complete Freund's adjuvant) and 11 (emulsified 1:1 with incomplete Freund's adjuvant). Blood samples are drawn by retroorbital bleeding on days 0, 11, and 20. Sera are examined by ELISA for IgG titers with specific SpA-D and SpA-$D_{Q9,10K;D36,37A}$ binding activity. Immunized animals are challenged on day 21 by retroorbital injection of 100 μl of *S. aureus* Newman or *S. aureus* USA300 suspension ($15\times10^7$ cfu) (34). For this, overnight cultures of *S. aureus* Newman are diluted 1:100 into fresh tryptic soy broth and grown for 3 h at 37° C. Staphylococci are centrifuged, washed twice, diluted in PBS to yield an $A_{600}$ of 0.4 ($1\times10^8$ cfu per ml) and concentrated. Dilutions are verified experimentally by agar plating and colony formation. Mice are anesthetized by intraperitoneal injection of 80-120 mg of ketamine and 3-6 mg of xylazine per kilogram of body weight. Immunized animals are challenged on day 21 by intraperitoneal inject with $2\times10^{10}$ cfu of *S. aureus* Newman or 3-$10\times10^9$ cfu of clinical *S. aureus* isolates. Animals are monitored for 14 days, and lethal disease is recorded.

Murine Pneumonia Model—

*S. aureus* strains Newman or USA300 (LAC) are grown at 37° C. in tryptic soy broth/agar to $OD_{660}$ 0.5. 50-ml culture aliquots are centrifuged, washed in PBS, and suspended in 750 μl PBS for mortality studies (3-$4\times10^8$ CFU per 30-μl volume), or 1,250 μl PBS ($2\times10^8$ CFU per 30 μl volume) for bacterial load and histopathology experiments (2, 3). For lung infection, 7-wk-old C57BL/6J mice (The Jackson Laboratory) are anesthetized before inoculation of 30 μl of *S. aureus* suspension into the left nare. Animals are placed into the cage in a supine position for recovery and observed for 14 days. For active immunization, 4-wk-old mice receive 20 μg SpA-D or SpA-$D_{Q9,10K;D36,37A}$ in CFA on day 0 via the i.m. route, followed by a boost with 20 μg SpA-D or SpA-$D_{Q9,10K;D36,37A}$ in incomplete Freund's adjuvant (IFA) on day 10. Animals are challenged with *S. aureus* on day 21. Sera are collected before immunization and on day 20 to assess specific antibody production. For passive immunization studies, 7-wk-old mice receive 100 μl of either NRS (normal rabbit serum) or SpA-D-specific rabbit antisera via i.p. injection 24 h before challenge. To assess the pathological correlates of pneumonia, infected animals are killed via forced $CO_2$ inhalation before removal of both lungs. The right lung is homogenized for enumeration of lung bacterial load. The left lung is placed in 1% formalin and paraffin embedded, thin sectioned, stained with hematoxylin-eosin, and analyzed by microscopy.

Rabbit Antibodies—

Purified 200 μg SpA-D or SpA-$D_{Q9,10K;D36,37A}$ is used as an immunogen for the production of rabbit antisera. 200 μg protein is emulsified with CFA for injection at day 0, followed by booster injections with 200 μg protein emulsified with IFA on days 21 and 42. Rabbit antibody titers are determined by ELISA. Purified antibodies are obtained by affinity chromatography of rabbit serum on SpA-D or SpA-$D_{Q9,10K;D36,37A}$ sepharose. The concentration of eluted antibodies is measured by absorbance at $A_{280}$ and specific antibody titers are determined by ELISA.

Active Immunization with SpA-Domain D Variants.—

To determine vaccine efficacy, animals are actively immunized with purified SpA-D or $SpAD_{Q9,10K;D36,37A}$. As a control, animals are immunized with adjuvant alone. Antibody titers against Protein A preparations are determined using SpA-D or SpA-$D_{Q9,10K;D36,37A}$ as antigens; note that the SpA-$D_{Q9,10K;D36,37A}$ variant cannot bind the Fc or Fab portion of IgG. Using infectious disease models described above, any reduction in bacterial load (murine abscess and pneumonia), histopathology evidence of staphylococcal disease (murine abscess and pneumonia) and protection from lethal disease (murine lethal challenge and pneumonia) is measured.

Passive Immunization with Affinity Purified Rabbit Polyclonal Antibodies Generated Against SpA-Domain D Variants.

To determine protective immunity of Protein A specific rabbit antibodies, mice are passively immunized with 5 mg/kg of purified SpA-D or SpA-$D_{Q9,10K;D36,37A}$ derived rabbit antibodies. Both of these antibody preparations are purified by affinity chromatography using immobilized SpA-D or SpA-$D_{Q9,10K;D36,37A}$. As a control, animals are passively immunized with rV10 antibodies (a plague protective antigen that has no impact on the outcome of staphylococcal infections). Antibody titers against all Protein A preparations are determined using SpA-$D_{Q9,10K;D36,37A}$ as an antigen, as this variant cannot bind the Fc or Fab portion of IgG. Using the infectious disease models described above, the reduction in bacterial load (murine abscess and pneumonia), histopathology evidence of staphylococcal disease (murine abscess and pneumonia), and the protection from lethal disease (murine lethal challenge and pneumonia) is measured.

Example 2

Figure 6:
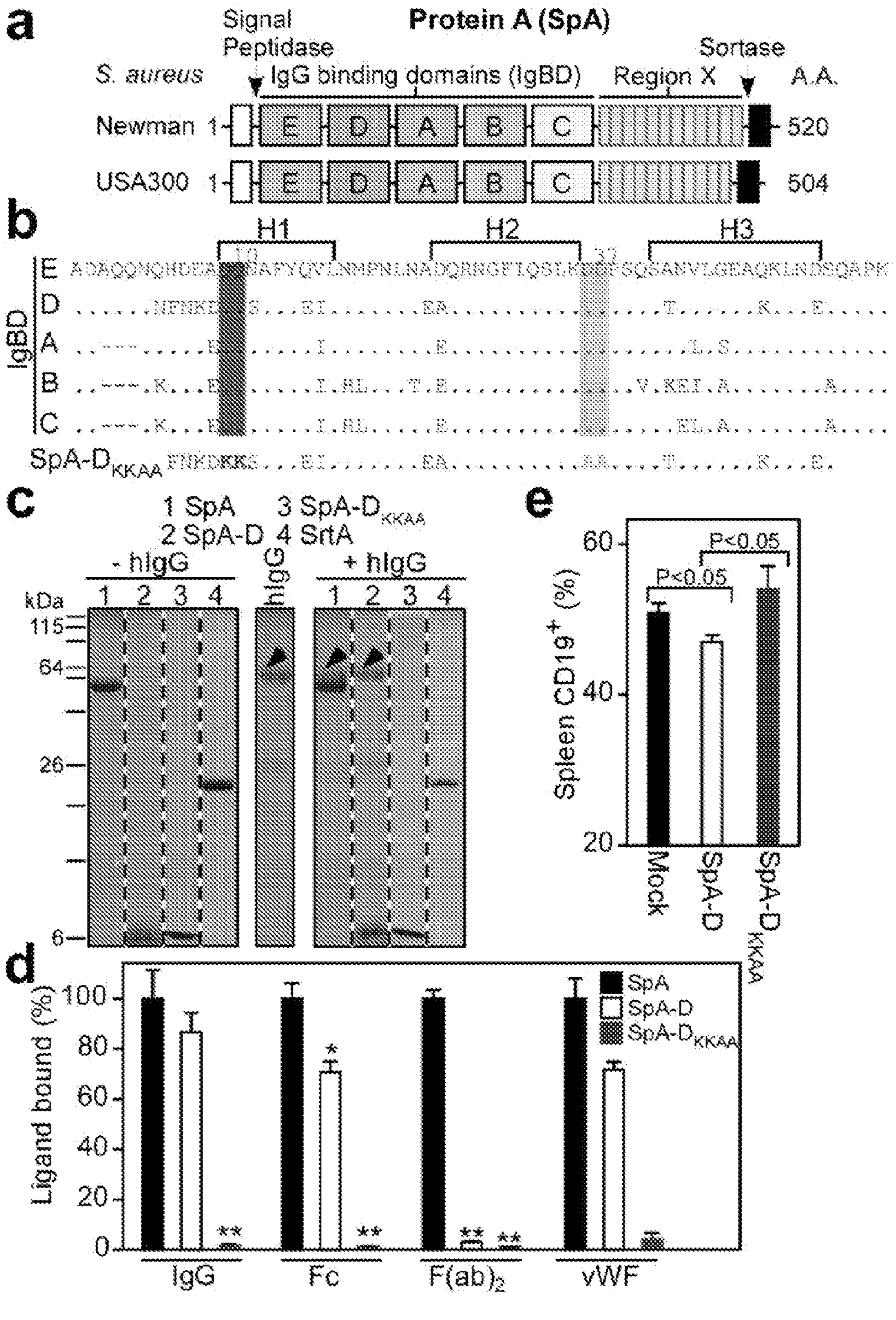
FIG. 6 Generation of a non-toxigenic protein A vaccine. a, Translational protein A (SpA) product of *S. aureus* Newman and USA300 LAC with an N-terminal signal peptide (white box), five immunoglobulin binding domains (IgBDs designated E, D, A, B and C), variable region X and C-terminal sorting signal (black box). b, Amino acid sequence of the five IgBDs as well as nontoxigenic SpA-$D_{KKAA}$, with the positions of triple α-helical bundles (H1, H2 and H3) as well as glutamine (Q) 9, 10 and aspartate (D) 36, 37 indicated. c, Coomassie Blue-stained SDS-PAGE of SpA, SpA-D, SpA-$D_{KKAA}$ or SrtA purified on Ni-NTA sepharose in the presence or absence of human immunoglobulin (hIgG). d, ELISA examining the association of immobilized SpA, SpA-D or SpA-$D_{KKAA}$ with human IgG as well as its Fc or $F(ab)_2$ fragments and von Willebrand factor (vWF). e, CD19+ B lymphocytes in splenic tissue of BALB/c mice that had been mock immunized or treated with SpA-D or SpA-$D_{KKAA}$ were quantified by FACS.

Non-Toxigenic Protein a Vaccine for Methicillin-Resistant *Staphylococcus aureus* Infection Clinical isolates of *S. aureus* express protein A (Shopsin et al., 1999, whose primary translational product is comprised of an N-terminal signal peptide (DeDent et al., 2008), five Ig-BDs (designated E, D, A, B and C) (Sjodahl, 1977), region X with variable repeats of an eight residue peptide (Guss et al., 1984), and C-terminal sorting signal for the cell wall anchoring of SpA (Schneewind et al., 1992; Schneewind et al., 1995) (FIG. 6). Guided by amino acid homology (Uhlen et al., 1984), the triple α-helical bundle structure of IgBDs (Deisenhofer et al., 1978; Deisenhofer et al., 1981) and their atomic interactions with Fab $V_H3$ (Graille et al., 2000) or Fcγ (Gouda et al., 1998), glutamine 9 and 10 were selected as well as aspartate 36 and 37 as critical for the association of SpA with antibodies or B cell receptor, respectively. Substitutions Gln9Lys, Gln10Lys, Asp36Ala and Asp37Ala were introduced into the D domain to generate SpA-$D_{KKAA}$ (FIG. 6). The ability of isolated SpA-D or SpA-$D_{KKAA}$ to bind human IgG was analyzed by affinity chromatography (FIG. 6). Polyhistidine tagged SpA-D as well as full-length SpA retained human IgG on Ni-NTA, whereas SpA-$D_{KKAA}$ and a negative control (SrtA) did not (FIG. 6). A similar result was observed with von Willebrand factor (Hartleib et al., 2000), which, along with tumor necrosis factor receptor 1 (TNFR1) (Gomez et al., 2004), can also bind protein A via glutamine 9 and 10 (FIG. 6). Human immunoglobulin encompasses 60-70% $V_H3$-type IgG. The inventors distinguish between Fc domain and B cell receptor activation of Igs and measured association of human Fcγ and $F(ab)_2$ fragments, both of which bound to full-length SpA or SpA-D, but not to SpA-$D_{KKAA}$ (FIG. 6). Injection of SpA-D into the peritoneal cavity of mice resulted in B cell expansion followed by apoptotic collapse of CD19+ lymphocytes in spleen tissue of BALB/c mice (Goodyear and Silverman, 2003) (FIG. 6). B cell superantigen activity was not observed following injection with SpA-$D_{KKAA}$, and TUNEL-staining of splenic tissue failed to detect the increase in apoptotic cells that follows injection of SpA or SpA-D (FIG. 6).

Figure 7:
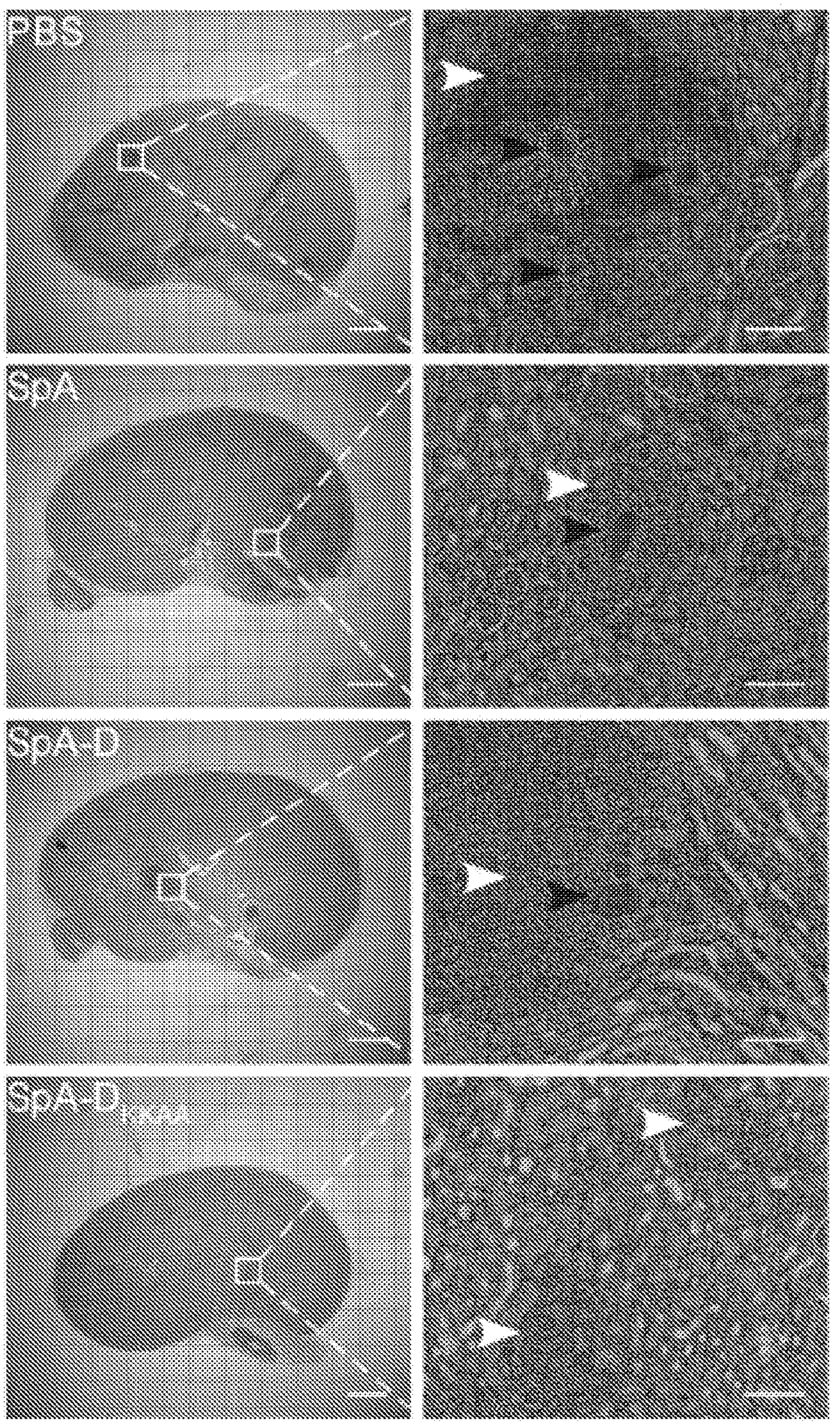
FIG. 7 Non-toxigenic protein A vaccine prevents abscess formation. Histopathology of renal tissue isolated during necropsy of BALB/c mice that had been mock immunized (PBS) or vaccinated with SpA, SpA-D as well as SpA-$D_{KKAA}$ and challenged with *S. aureus* Newman. Thin sectioned tissues were stained with hematoxylin-eosin. White arrows identify polymorphonuclear leukocyte (PMN) infiltrates. Dark arrows identify staphylococcal abscess communities.

Naive six week old BALB/c mice were injected with 50 μg each of purified SpA, SpA-D or SpA-$D_{KKAA}$ emulsified in CFA and boosted with the same antigen emulsified in IFA. In agreement with the hypothesis that SpA-D promotes the apoptotic collapse of activated clonal B cell populations, the inventors observed a ten-fold higher titer of SpA-$D_{KKAA}$ specific antibodies following immunization of mice with the non-toxigenic variant as compared to the B cell superantigen (Spa-D vs. SpA-$D_{KKAA}$ P<0.0001, Table 6). Antibody titers raised by immunization with full-length SpA were higher than those elicited by SpA-D (P=0.0022), which is likely due to the larger size and reiterative domain structure of this antigen (Table 6). Nevertheless, even SpA elicited lower antibody titers than SpA-$D_{KKAA}$ (P=0.0003), which encompasses only 50 amino acids of protein A (520 residues, SEQ ID NO:33). Immunized mice were challenged by intravenous inoculation with *S. aureus* Newman and the ability of staphylococci to seed abscesses in renal tissues was examined by necropsy four days after challenge. In homogenized renal tissue of mock (PBS/adjuvant) immunized mice, an average staphylococcal load of 6.46 $\log_{10}$ CFU $g^{-1}$ was enumerated (Table 6). Immunization of mice with SpA or SpA-D led to a reduction in staphylococcal load, however SpA-$D_{KKAA}$ vaccinated animals displayed an even greater, 3.07 $\log_{10}$ CFU $g^{-1}$ reduction of *S. aureus* Newman in renal tissues (P<0.0001, Table 6). Abscess formation in kidneys was analyzed by histopathology (FIG. 7). Mock immunized animals harbored an average of 3.7 (±1.2) abscesses per kidney (Table 6). Vaccination with SpA-$D_{KKAA}$ reduced the average number of abscesses to 0.5 (±0.4) (P=0.0204), whereas immunization with SpA or SpA-D did not cause a significant reduction in the number of abscess lesions (Table 6). Lesions from SpA-$D_{KKAA}$ vaccinated animals were smaller in size, with fewer infiltrating PMNs and characteristically lacked staphylococcal abscess communities (Cheng et al., 2009) (FIG. 7). Abscesses in animals that had been immunized with SpA or SpA-D displayed the same overall structure of lesions in mock immunized animals (FIG. 7).

The inventors examined whether SpA-$D_{KKAA}$ immunization can protect mice against MRSA strains and selected the USA300 LAC isolate for animal challenge (Diep et al., 2006). This highly virulent CA-MRSA strain spread rapidly throughout the United States, causing significant human morbidity and mortality (Kennedy et al., 2008). Compared to adjuvant control mice, SpA-$D_{KKAA}$ immunized animals harbored a 1.07 $\log_{10}$ CFU $g^{-1}$ reduction in bacterial load of infected kidney tissues. Histopathology examination of renal tissue following *S. aureus* USA300 challenge revealed that the average number of abscesses was reduced from 4.04 (±0.8) to 1.6 (±0.6) (P=0.02774). In contrast, SpA or SpA-D immunization did not cause a significant reduction in bacterial load or abscess formation (Table 6).

Figure 8:
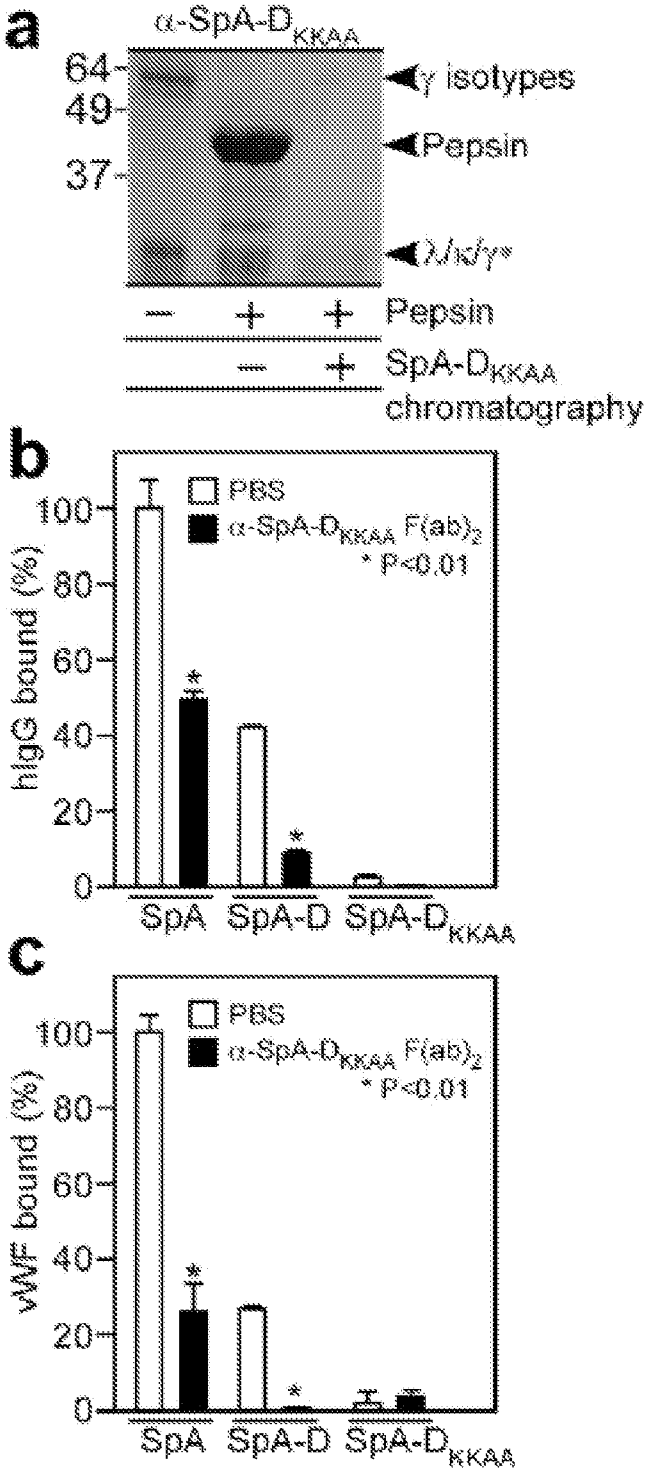
FIG. 8 Antibodies raised by the non-toxigenic protein A vaccine block the B cell superantigen function of SpA. a, Rabbit antibodies raised against SpA-$D_{KKAA}$ were purified on a matrix with immobilized antigen and analyzed by Coomassie Blue-stained SDS-PAGE. Antibodies were cleaved with pepsin and F(ab)2 fragments were purified by a second round of affinity chromatography on SpA-$D_{KKAA}$ matrix. b, SpA-$D_{KKAA}$ specific F(ab)2 interfere with the binding of SpA or SpA-D to human immunoglobulin (hIgG) or, c, to von Willebrand Factor (vWF).

Rabbits were immunized with SpA-$D_{KKAA}$ and specific antibodies were purified on SpA-$D_{KKAA}$ affinity column followed by SDS-PAGE (FIG. 8). SpA-$D_{KKAA}$ specific IgG was cleaved with pepsin to generate Fcγ and $F(ab)_2$ fragments, the latter of which were purified by chromatography on SpA-$D_{KKAA}$ column (FIG. 8). Binding of human IgG or vWF to SpA or SpA-D was perturbed by SpA-$D_{KKAA}$ specific $F(ab)_2$, indicating that SpA-$D_{KKAA}$ derived antibodies neutralize the B cell superantigen function of protein A as well as its interactions with Ig (FIG. 8).

Figure 9:
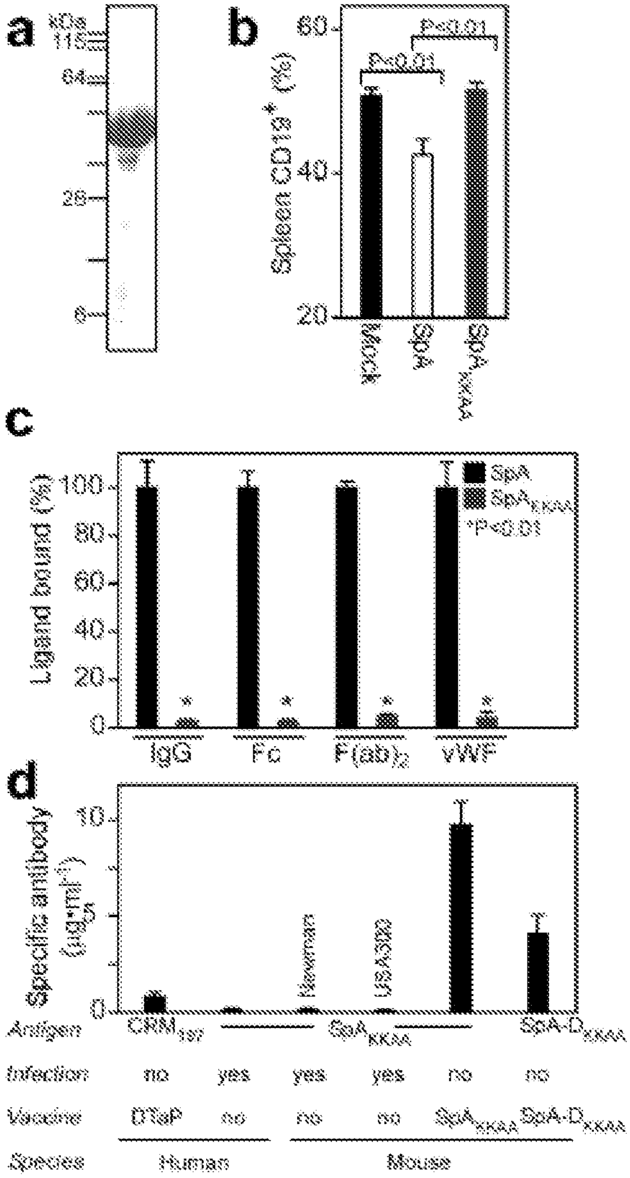
FIG. 9 Full-length non-toxigenic protein A generates improved immune responses. a, Full-length $SpA_{KKAA}$ was purified on Ni-NTA sepharose and analyzed by Coomassie-Blue stained SDS-PAGE. b, CD 19+ B lymphocytes in splenic tissue of BALB/c mice that had been mock immunized or treated with SpA or $SpA_{KKAA}$ were quantified by FACS. c, ELISA examining the association of immobilized SpA or $SpA_{KKAA}$ with human IgG as well as its Fc or F(ab)2 fragments or von Willebrand factor (vWF). d, Human or mouse serum antibody titers to diphtheria toxoid (CRM197) and non-toxigenic $SpA_{KKAA}$ or SpA-$D_{KKAA}$. Human volunteers with a history of DTaP immunization and staphylococcal infection (n=16) as well as mice (n=20) that had been infected with *S. aureus* Newman or USA 300 LAC or immunized with $SpA_{KKAA}$ or SpA-$D_{KKAA}$ were examined by quantitative dot blot.

To further improve the vaccine properties for non-toxigenic protein A, the inventors generated $SpA_{KKAA}$, which includes all five IgBDs with four amino acid substitutions—substitutions corresponding to Gln9Lys, Gln10Lys, Asp36Ala and Asp37Ala of domain D—in each of its five domains (E, D, A, B and C). Polyhistidine tagged $SpA_{KKAA}$ was purified by affinity chromatography and analyzed by Coomassie Blue-stained SDS-PAGE (FIG. 9). Unlike full-length SpA, $SpA_{KKAA}$ did not bind human IgG, Fc and $F(ab)_2$ or vWF (FIG. 9). $SpA_{KKAA}$ failed to display B cell superantigen activity, as injection of the variant into BALB/c mice did not cause a depletion of CD19+ B cells in splenic tissue (FIG. 9). $SpA_{KKAA}$ vaccination generated higher specific antibody titers than SpA-$D_{KKAA}$ immunization and provided mice with elevated protection against *S. aureus* USA300 challenge (Table 6). Four days following challenge, $SpA_{KKAA}$ vaccinated animals harbored 3.54 $\log_{10}$ CFU $g^{-1}$ fewer staphylococci in renal tissues (P=0.0001) and also caused a greater reduction in the number of abscess lesions (P=0.0109) (Table 6).

$SpA_{KKAA}$ was used to immunize rabbits. Rabbit antibodies specific for SpA-$D_{KKAA}$ or $SpA_{KKAA}$ were affinity purified on matrices with immobilized cognate antigen and injected at a concentration of 5 mg $kg^{-1}$ body weight into the peritoneal cavity of BALB/c mice (Table 7). Twenty-four hours later, specific antibody titers were determined in serum and animals challenged by intravenous inoculation with *S. aureus* Newman. Passive transfer reduced the staphylococcal load in kidney tissues for SpA-$D_{KKAA}$ (P=0.0016) or $SpA_{KKAA}$ (P=0.0005) specific antibodies. On histopathology examination, both antibodies reduced the abundance of abscess lesions in the kidneys of mice challenged with *S. aureus* Newman (Table 7). Together these data reveal that vaccine protection following immunization with SpA-$D_{KKAA}$ or $SpA_{KKAA}$ is conferred by antibodies that neutralize protein A.

TABLE 6

Immunization of mice with protein A vaccines.

| | Staphylococcal load and abscess formation in renal tissue | | | | | |
|---|---|---|---|---|---|---|
| Antigen | [a]$\log_{10}$ CFU $g^{-1}$ | [b]P-value | [c]Reduction ($\log_{10}$ CFU $g^{-1}$) | [d]IgG Titer | [e]Number of abscesses | [e]P-value |
| *S. aureus* Newman challenge | | | | | | |
| Mock | 6.46 ± 0.25 | — | — | <100 | 3.7 ± 1.2 | — |
| SpA | 3.95 ± 0.56 | 0.0003 | 2.51 | 1706 ± 370 | 2.1 ± 1.2 | 0.3581 |
| SpA-D | 4.43 ± 0.41 | 0.0001 | 2.03 | 381 ± 27 | 1.5 ± 0.8 | 0.1480 |
| SpA-$D_{KKAA}$ | 3.39 ± 0.50 | <0.0001 | 3.07 | 5600 ± 801 | 0.5 ± 0.4 | 0.0204 |

TABLE 6-continued

Immunization of mice with protein A vaccines.

| Antigen | Staphylococcal load and abscess formation in renal tissue | | | | | |
|---|---|---|---|---|---|---|
| | [a]$\log_{10}$ CFU $g^{-1}$ | [b]P-value | [c]Reduction ($\log_{10}$ CFU $g^{-1}$) | [d]IgG Titer | [e]Number of abscesses | [e]P-value |
| *S. aureus* USA300 (LAC) challenge | | | | | | |
| Mock | 7.20 ± 0.24 | — | — | <100 | 4.0 ± 0.8 | — |
| SpA | 6.81 ± 0.26 | 0.2819 | 0.39 | 476 ± 60 | 3.3 ± 1.0 | 0.5969 |
| SpA-D | 6.34 ± 0.52 | 0.1249 | 0.86 | 358 ± 19 | 2.2 ± 0.6 | 0.0912 |
| SpA-$D_{KKAA}$ | 6.00 ± 0.42 | 0.0189 | 1.20 | 3710 ± 1147 | 1.6 ± 0.6 | 0.0277 |
| $SpA_{KKAA}$ | 3.66 ± 0.76 | 0.0001 | 3.54 | 10200 ± 2476 | 1.2 ± 0.5 | 0.0109 |

[a]Means of staphylococcal load calculated as $\log_{10}$ CFU $g^{-1}$ in homogenized renal tissues 4 days following infection in cohorts of fifteen to twenty BALB/c mice per immunization. Representative of two independent and reproducible animal experiments is shown. Standard error of the means (±SEM) is indicated.
[b]Statistical significance was calculated with the unpaired two-tailed Students t-test and P-values recorded; P-values < 0.05 were deemed significant.
[c]Reduction in bacterial load calculated as $\log_{10}$ CFU $g^{-1}$.
[d]Means of five randomly chosen serum IgG titers were measured prior to staphylococcal infection by ELISA.
[e]Histopathology of hematoxylene-eosin stained, thin sectioned kidneys from ten animals; the average number of abscesses per kidney was recorded and averaged again for the final mean (±SEM).

TABLE 7

Passive immunization of mice with antibodies against protein A.

| [a]Antibody | Staphylococcal load and abscess formation in renal tissue | | | | | |
|---|---|---|---|---|---|---|
| | [b]$\log_{10}$ CFU $g^{-1}$ | [c]P-value | [d]Reduction ($\log_{10}$ CFU $g^{-1}$) | [e]IgG Titer | [f]Number of abscesses | [c]P-value |
| Mock | 7.10 ± 0.14 | — | — | <100 | 4.5 ± 0.8 | — |
| α-SpA-$D_{KKAA}$ | 5.53 ± 0.43 | 0.0016 | 1.57 | 466 ± 114 | 1.9 ± 0.7 | 0.0235 |
| α-$SpA_{KKAA}$ | 5.69 ± 0.34 | 0.0005 | 1.41 | 1575 ± 152 | 1.6 ± 0.5 | 0.0062 |

[a]Affinity purified antibodies were injected into the peritoneal cavity of BALB/c mice at a concentration of 5 mg · $kg^{-1}$ twenty-four hours prior to intravenous challenge with 1 × $10^7$ CFU *S. aureus* Newman.
[b]Means of staphylococcal load calculated as $\log_{10}$ CFU $g^{-1}$ in homogenized renal tissues 4 days following infection in cohorts of fifteen BALB/c mice per immunization. Representative of two independent and reproducible animal experiments is shown. Standard error of the means (±SEM) is indicated.
[c]Statistical significance was calculated with the unpaired two-tailed Students t-test and P-values recorded; P-values < 0.05 were deemed significant.
[d]Reduction in bacterial load calculated as $\log_{10}$ CFU $g^{-1}$.
[e]Means of five randomly chosen serum IgG titers were measured prior to staphylococcal infection by ELISA.
[f]Histopathology of hematoxylene-eosin stained, thin sectioned kidneys from ten animals; the average number of abscesses per kidney was recorded and averaged again for the final mean (±SEM).

Figure 10:
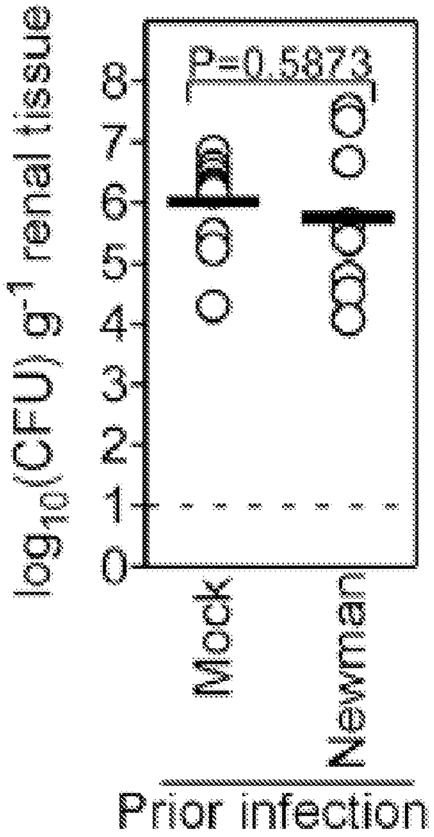
FIG. 10 Staphylococcal infection does not generate protective immunity. BALB/c mice (n=20) were infected with *S. aureus* Newman or mock challenged (PBS) for thirty days and infection cleared with chloramphenicol treatment. Both cohorts of animals were then challenged with *S. aureus* Newman and bacterial load (CFU) in kidney tissue homogenate analyzed following necropsy on day 4.
Figure 11:
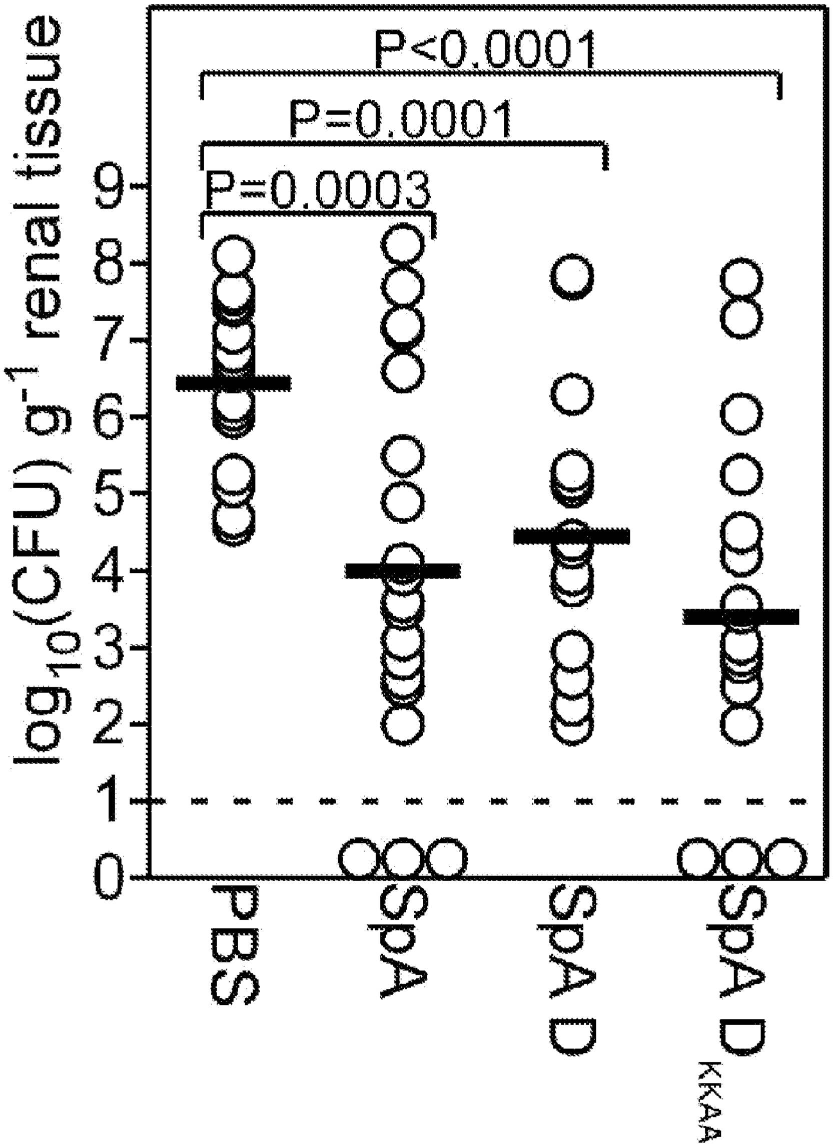
FIG. 11 Comparison of abscess formation in mice treated with PBS, SpA, SpA-D, and SpA-$D_{KKAA}$.
Figures 12A, 12B, 12C:
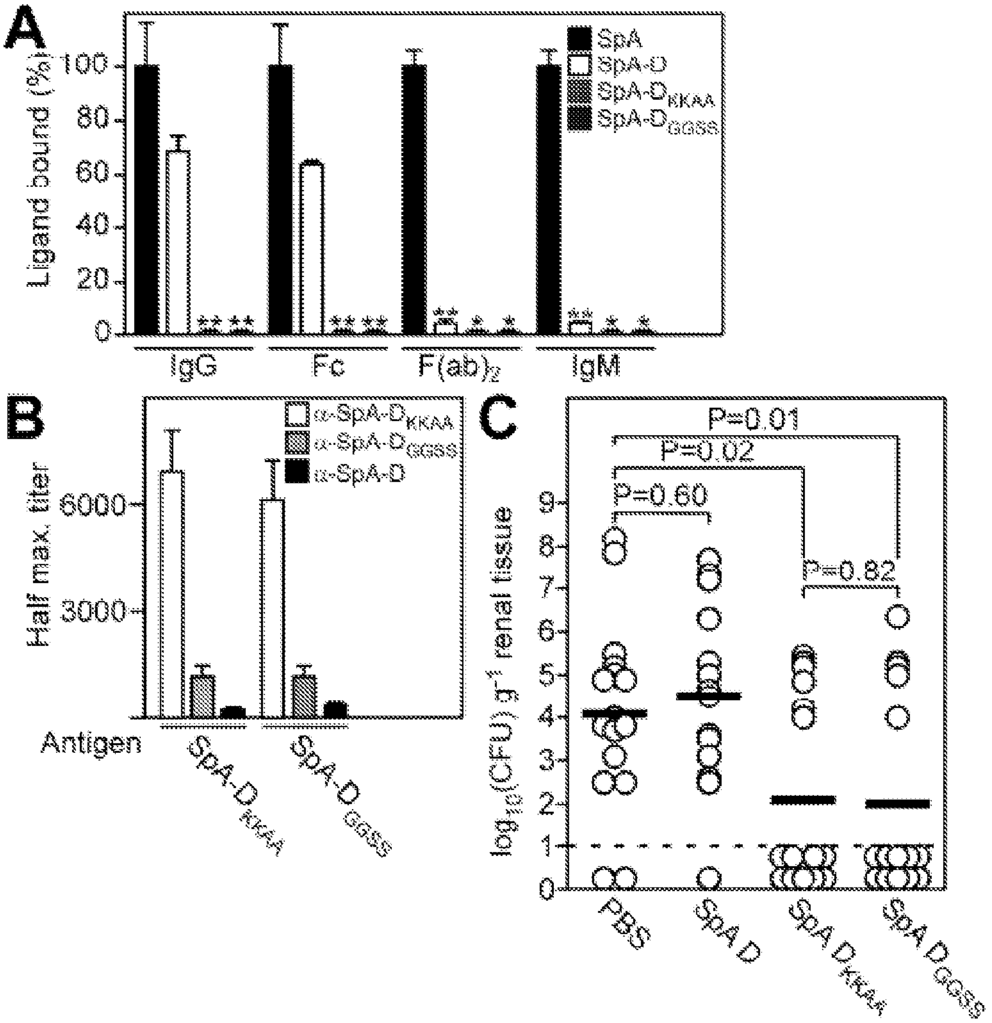
FIGS. 12A-12C (A) ELISA examining the association of immobilized SpA, SpA-D, SpA-DKKAA or SpA-DGGSS with human IgG as well as its Fc or F(ab)2 fragments and IgM. Statistical significance of SpA-DKKAA and SpA-DGGSS binding to each ligand was compared against SpA-D; SpA-D binding was compared against SpA (n=3); * signifies $P<0.05$; ** signifies $P<0.01$. (B) ELISA examining the level of cross-reactive antibodies of hyper-immune sera samples collected from actively immunized mice (n=5) with SpA-D, SpA-DKKAA and SpA-DGGSS. (C) Abscess formation in mice treated with PBS, SpA-D, SpA-$D_{KKAA}$ and SpA-$D_{GGSS}$.

Following infection with virulent *S. aureus*, mice do not develop protective immunity against subsequent infection with the same strain (Burts et al., 2008) (FIG. 10). The average abundance of SpA-$D_{KKAA}$ specific IgG in these animals was determined by dot blot as 0.20 μg $ml^{-1}$ (±0.04) and 0.14 μg $ml^{-1}$ (±0.01) for strains Newman and USA300 LAC, respectively (FIG. 9). The minimal concentration of protein A-specific IgG required for disease protection in $SpA_{KKAA}$ or SpA-$D_{KKAA}$ vaccinated animals (P .0.05 $\log_{10}$ reduction in staphylococcal CFU $g^{-1}$ renal tissue) was calculated as 4.05 μg $ml^1$ (±0.88). Average serum concentration of SpA-specific IgG in adult healthy human volunteers (n=16) was 0.21 μg $ml^{-1}$ (±0.02). Thus, *S. aureus* infections in mice or humans are not associated with immune responses that raise significant levels of neutralizing antibodies directed against protein A, which is likely due to the B cell superantigen attributes of this molecule. In contrast, the average serum concentration of IgG specific for diphtheria toxin in human volunteers, 0.068 μg $ml^1$ (±0.20), was within range for protective immunity against diphtheria (Behring, 1890; Lagergard et al., 1992).

Clinical *S. aureus* isolates express protein A, an essential virulence factor whose B cell surperantigen activity and evasive attributes towards opsono-phagocytic clearance are absolutely required for staphylococcal abscess formation (Palmqvist et al., 2005; Cheng et al., 2009; Silverman and Goodyear, 2006). Protein A can thus be thought of as a toxin, essential for pathogenesis, whose molecular attributes must be neutralized in order to achieve protective immunity. By generating non-toxigenic variants unable to bind Igs via Fcγ or $VH_3$-Fab domains, the inventors measure here for the first time protein A neutralizing immune responses as a correlate for protective immunity against *S. aureus* infection. In contrast to many methicillin-sensitive strains, CA-MRSA isolate USA300 LAC is significantly more virulent (Cheng et al., 2009). For example, immunization of experimental animals with the surface protein IsdB (Kuklin et al., 2006; Stranger-Jones et al., 2006) raises antibodies that confer protection against *S. aureus* Newman (Stranger-Jones et al., 2009) but not against USA300 challenge.

The methods utilized include:

Bacterial Strains and Growth.

*Staphylococcus aureus* strains Newman and USA300 were grown in tryptic soy broth (TSB) at 37° C. *Escherichia coli* strains DH5α and BL21 (DE3) were grown in Luria-Bertani (LB) broth with 100 μg $ml^1$ ampicillin at 37° C.

Rabbit Antibodies.

The coding sequence for SpA was PCR-amplified with two primers, gctgcacatatggcgcaacacgatgaagctcaac (SEQ ID NO:35) and agtggatccttatgcttgagctttgttagcatctgc (SEQ ID NO:36) using *S. aureus* Newman template DNA. SpA-D was PCR-amplified with two primers, aacatatgttcaacaaagatcaa-caaagc (SEQ ID NO:38) and aaggatccagattcgtttaattttttagc (SEQ ID NO:39). The sequence for SpA-$D_{KKAA}$ was mutagenized with two sets of primers catatgttcaacaaagataaaaaaagcgccttctatgaaatc (SEQ ID NO:42) and gatttcatagaaggcgcttttttatctttgttgaacatatg (SEQ ID NO:43) for Q9K, Q10K as well as cttcattcaaagtcttaaagccgccccaagccaaagcactaac (SEQ ID NO:40) and gttagtgctttggcttggggcggctttaagactttgaatgaag (SEQ ID NO:41) for D36A, D37A. The sequence of $SpA_{KKAA}$ was synthesized by Integrated DNA Technologies, Inc. PCR products were cloned into pET-15b generating N-terminal $His_6$ tagged recombinant protein. Plasmids were transformed into BL21 (DE3). Overnight cultures of transformants were diluted 1:100 into fresh media and grown at 37° C. to an $OD_{600}$ 0.5, at which point cultures were induced with 1 mM isopropyl β-D-1-thiogalatopyranoside (IPTG) and grown for an additional three hours. Bacterial cells were sedimented by centrifugation, suspended in column buffer (50 mM Tris-HCl, pH 7.5, 150 mM NaCl) and disrupted with a French pressure cell at 14,000 psi. Lysates were cleared of membrane and insoluble components by ultracentrifugation at 40,000×g. Proteins in the soluble lysate were subjected to nickel-nitrilotriacetic acid (Ni-NTA, Qiagen) affinity chromatography. Proteins were eluted in column buffer containing successively higher concentrations of imidazole (100-500 mM). Protein concentrations were determined by bicinchonic acid (BCA) assay (Thermo Scientific). For antibody generation, rabbits (6 month old New-Zealand white, female, Charles River Laboratories) were immunized with 500 μg protein emulsified in Complete Freund's Adjuvant (Difco) by subscapular injection. For booster immunizations, proteins emulsified in Incomplete Freund's Adjuvant and injected 24 or 48 days following the initial immunization. On day 60, rabbits were bled and serum recovered.

Purified antigen (5 mg protein) was covalently linked to HiTrap NHS-activated HP columns (GE Healthcare). Antigen-matrix was used for affinity chromatography of 10-20 ml of rabbit serum at 4° C. Charged matrix was washed with 50 column volumes of PBS, antibodies eluted with elution buffer (1 M glycine, pH 2.5, 0.5 M NaCl) and immediately neutralized with 1M Tris-HCl, pH 8.5. Purified antibodies were dialyzed overnight against PBS at 4° C.

$F(ab)_2$ Fragments.

Affinity purified antibodies were mixed with 3 mg of pepsin at 37° C. for 30 minutes. The reaction was quenched with 1 M Tris-HCl, pH 8.5 and $F(ab)_2$ fragments were affinity purified with specific antigen-conjugated HiTrap NHS-activated HP columns. Purified antibodies were dialyzed overnight against PBS at 4° C., loaded onto SDS-PAGE gel and visualized with Coomassie Blue staining.

Active and Passive Immunization.

BALB/c mice (3 week old, female, Charles River Laboratories) were immunized with 50 μg protein emulsified in Complete Freund's Adjuvant (Difco) by intramuscular injection. For booster immunizations, proteins were emulsified in Incomplete Freund's Adjuvant and injected 11 days following the initial immunization. On day 20 following immunization, 5 mice were bled to obtain sera for specific antibody titers by enzyme-linked immunosorbent assay (ELISA).

Affinity purified antibodies in PBS were injected at a concentration 5 mg $kg^{-1}$ of experimental animal weight into the peritoneal cavity of BALB/c mice (6 week old, female, Charles River Laboratories) 24 hours prior to challenge with *S. aureus*. Animal blood was collected via periorbital vein puncture. Blood cells were removed with heparinized microhematocrit capillary tubes (Fisher) and Z-gel serum separation micro tubes (Sarstedt) were used to collect and measure antigen specific antibody titers by ELISA.

Mouse Renal Abscess.

Overnight cultures of *S. aureus* Newman or USA300 (LAC) were diluted 1:100 into fresh TSB and grown for 2 hours at 37° C. Staphylococci were sedimented, washed and suspended PBS at $OD_{600}$ of 0.4 (~$1\times10^8$ CFU $ml^{-1}$). Inocula were quantified by spreading sample aliquots on TSA and enumerating colonies formed. BALB/c mice (6 week old, female, Charles River Laboratories) were anesthetized via intraperitoneal injection with 100 mg ml⁻ketamine and 20 mg $ml^{-1}$ xylazine per kilogram of body weight. Mice were infected by retro-obital injection with $1\times10^7$ CFU of *S. aureus* Newman or $5\times10^6$ CFU of *S. aureus* USA300. On day 4 following challenge, mice were killed by $CO_2$ inhalation. Both kidneys were removed, and the staphylococcal load in one organ was analyzed by homogenizing renal tissue with PBS, 1% Triton X-100. Serial dilutions of homogenate were spread on TSA and incubated for colony formation. The remaining organ was examined by histopathology. Briefly, kidneys were fixed in 10% formalin for 24 hours at room temperature. Tissues were embedded in paraffin, thin-sectioned, stained with hematoxylin-eosin, and inspected by light microscopy to enumerate abscess lesions. All mouse experiments were performed in accordance with the institutional guidelines following experimental protocol review and approval by the Institutional Biosafety Committee (IBC) and the Institutional Animal Care and Use Committee (IACUC) at the University of Chicago.

Protein A Binding.

For human IgG binding, Ni-NTA affinity columns were pre-charged with 200 μg of purified proteins (SpA, SpA-D, SpA-$D_{KKAA}$, and SrtA) in column buffer. After washing, 200 μg of human IgG (Sigma) was loaded onto the column. Protein samples were collected from washes and elutions and subjected to SDS-PAGE gel electrophoresis, followed by Coomassie Blue staining. Purified proteins (SpA, $SpA_{KKAA}$, SpA-D and SpA-$D_{KKAA}$) were coated onto MaxiSorp ELISA plates (NUNC) in 0.1M carbonate buffer (pH 9.5) at 1 μg $ml^{-1}$ concentration overnight at 4° C. Plates were next blocked with 5% whole milk followed by incubation with serial dilutions of peroxidase-conjugated human IgG, Fc or $F(ab)_2$ fragments for one hour. Plates were washed and developed using OptEIA ELISA reagents (BD). Reactions were quenched with 1 M phosphoric acid and $A_{450}$ readings were used to calculate half maximal titer and percent binding.

von Willebrand Factor (vWF) Binding Assays.

Purified proteins (SpA, $SpA_{KKAA}$, SpA D and SpA-$D_{KKAA}$) were coated and blocked as described above. Plates were incubated with human vWF at 1 μg $ml^1$ concentration for two hours, then washed and blocked with human IgG for another hour. After washing, plates were incubated with serial dilution of peroxidase-conjugated antibody directed against human vWF for one hour. Plates were washed and developed using OptEIA ELISA reagents (BD). Reactions were quenched with 1 M phosphoric acid and $A_{450}$ readings were used to calculate half maximal titer and percent binding. For inhibition assays, plates were incubated with affinity purified $F(ab)_2$ fragments specific for SpA-$D_{KKAA}$ at 10 $\mu ml^{-1}$ concentration for one hour prior to ligand binding assays.

Splenocyte Apoptosis.

Affinity purified proteins (150 μg of SpA, SpA-D, $SpA_{KKAA}$, and SpA-$D_{KKAA}$) were injected into the peritoneal cavity of BALB/c mice (6 week old, female, Charles River Laboratories). Four hours following injection, animals were killed by $CO_2$ inhalation. Their spleens were removed and homogenized. Cell debris were removed using cell strainer and suspended cells were transferred to ACK lysis buffer (0.15 M $NH_4Cl$, 10 mM $KHCO_3$, 0.1 mM EDTA) to lyse red blood cells. White blood cells were sedimented by centrifugation, suspended in PBS and stained with 1:250 diluted R-PE conjugated anti-CD19 monoclonal antibody (Invitrogen) on ice and in the dark for one hour. Cells were washed with 1% FBS and fixed with 4% formalin overnight at 4° C. The following day, cells were diluted in PBS and analyzed by flow cytometry. The remaining organ was examined for histopathology. Briefly, spleens were fixed in 10% formalin for 24 hours at room temperature. Tissues were embedded in paraffin, thin-sectioned, stained with the Apoptosis detection kit (Millipore), and inspected by light microscopy.

Antibody Quantification.

Sera were collected from healthy human volunteers or BALB/c mice that had been either infected with *S. aureus* Newman or USA300 for 30 days or that had been immunized with SpA-$D_{KKAA}$/$SpA_{KKAA}$ as described above. Human/mouse IgG (Jackson Immunology Laboratory), $SpA_{KKAA}$, and $CRM_{197}$ were blotted onto nitrocellulose membrane. Membranes were blocked with 5% whole milk, followed by incubation with either human or mouse sera. IRDye 700DX conjugated affinity purified anti-human/mouse IgG (Rockland) was used to quantify signal intensities using the Odyssey™ infrared imaging system (Li-cor). Experiments with blood from human volunteers involved protocols that were reviewed, approved and performed under regulatory supervision of The University of Chicago's Institutional Review Board (IRB).

Statistical Analysis.

Two tailed Student's t tests were performed to analyze the statistical significance of renal abscess, ELISA, and B cell superantigen data.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,338,298
U.S. Pat. No. 4,356,170
U.S. Pat. No. 4,367,110
U.S. Pat. No. 4,372,945
U.S. Pat. No. 4,452,901
U.S. Pat. No. 4,474,757
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,684,611
U.S. Pat. No. 4,690,915
U.S. Pat. No. 4,690,915
U.S. Pat. No. 4,748,018
U.S. Pat. No. 4,800,159
U.S. Pat. No. 4,879,236
U.S. Pat. No. 4,952,500
U.S. Pat. No. 5,084,269
U.S. Pat. No. 5,199,942
U.S. Pat. No. 5,221,605
U.S. Pat. No. 5,238,808
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,512,282
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,648,240
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,801,234
U.S. Pat. No. 5,840,846
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,986
U.S. Pat. No. 5,916,776
U.S. Pat. No. 5,922,574
U.S. Pat. No. 5,925,565
U.S. Pat. No. 5,925,565
U.S. Pat. No. 5,928,905
U.S. Pat. No. 5,928,906
U.S. Pat. No. 5,932,451
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,958,895
U.S. Pat. No. 5,981,274
U.S. Pat. No. 5,994,624
U.S. Pat. No. 6,008,341
U.S. Pat. No. 6,288,214
U.S. Pat. No. 6,294,177
U.S. Pat. No. 6,651,655
U.S. Pat. No. 6,656,462
U.S. Pat. No. 6,733,754
U.S. Pat. No. 6,756,361
U.S. Pat. No. 6,770,278
U.S. Pat. No. 6,793,923
U.S. Pat. No. 6,814,971
U.S. Pat. No. 6,936,258
U.S. Patent Appln. 2002/0169288
U.S. Patent Appln. 2003/0153022
Abdallah et al., *Mol. Microbiol.*, 62, 667-679, 2006.
Abdallah et al., *Nat. Rev. Microbiol.*, 5, 883-891, 2007.
Albus et al., *Infect. Immun.*, 59:1008-1014, 1991.
An, *J. Virol.*, 71(3):2292-302, 1997.

Anavi, Sc. thesis from the department of Molecular Microbiology and Biotechnology of the Tel-Aviv University, Israel, 1998.
Andersen et al., *J. Immunol.,* 154, 3359-3372, 1995.
Angel et al., *Cell,* 49:729, 1987b.
Angel et al., *Mol. Cell. Biol.,* 7:2256, 1987a.
Archer, *Clin. Infect. Dis.,* 26, 1179-1181, 1998.
Atchison and Perry, *Cell,* 46:253, 1986.
Atchison and Perry, *Cell,* 48:121, 1987.
Ausubel et al., *In: Current Protocols in Molecular Biology*, John, Wiley & Sons, Inc, New York, 1996.
Baba et al., *J. Bacteriol.* 190:300-310, 2007.
Bae and Schneewind, *Plasmid,* 55:58-63, 2006.
Bae et al., *Proc. Natl. Acad. Sci. USA,* 101, 12312-12317, 2004.
Banerji et al., *Cell,* 27(2 Pt 1):299-308, 1981.
Banerji et al., *Cell,* 33(3):729-740, 1983.
Barany and Merrifield, In: *The Peptides*, Gross and Meienhofer (Eds.), Academic Press, NY, 1-284, 1979.
Behring E A. Über das Zustandekommen der Diphtherie—Immunität bei Thieren. Deutsche Medzinische Wochenschrift, 16:1145-8, 1890.
Bellus, *J. Macromol. Sci. Pure Appl. Chem., A*31(1): 1355-1376, 1994.
Berkhout et al., *Cell,* 59:273-282, 1989.
Birch-Hirschfeld, L. 1934. Über die Agglutination von Staphylokokken durch Bestandteile des Säugetierblutplasmas. Klinische Woschenschrift 13:331.
Bjerketorp et al., *FEMS Microbiol. Lett.,* 234:309-314, 2004.
Blanar et al., *EMBO J.,* 8:1139, 1989.
Bodine and Ley, *EMBO J.,* 6:2997, 1987.
Borrebaeck, In: *Antibody Engineering—A Practical Guide*, W. H. Freeman and Co., 1992.
Boshart et al., *Cell,* 41:521, 1985.
Bosze et al., *EMBO* 1, 5(7):1615-1623, 1986.
Boucher and Corey. *Clin. Infect. Dis.* 46:S334-S349, 2008.
Braddock et al., *Cell,* 58:269, 1989.
Brown et al., *Biochemistry,* 37:4397-4406, 1998.
Bubeck Wardenburg and Schneewind. *J. Exp. Med.* 205:287-294, 2008.
Bubeck-Wardenburg et al., *Infect. Immun.* 74:1040-1044, 2007.
Bubeck-Wardenburg et al., *Proc. Natl. Acad. Sci. USA,* 103: 13831-13836, 2006.
Bulla and Siddiqui, *J. Virol.,* 62:1437, 1986.
Burke et al., *J Inf. Dis.,* 170:1110-1119, 1994.
Burlak et al., *Cell Microbiol.,* 9:1172-1190, 2007.
Burts and Missiakas, *Mol. Microbiol.,* 69:736-46, 2008.
Burts et al., *Proc. Natl. Acad. Sci. USA,* 102:1169-1174, 2005.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Carbonelli et al., *FEMS Microbiol. Lett.,* 177(1):75-82, 1999.
Cedergren et al., *Protein Eng.,* 6:441-448, 1993.
Celander and Haseltine, *J. Virology,* 61:269, 1987.
Celander et al., *J. Virology,* 62:1314, 1988.
Cespedes et al., *J. Infect. Dis.,* 191(3):444-52, 2005.
Champion et al., *Science,* 313:1632-1636, 2006.
Chandler et al., *Cell,* 33:489, 1983.
Chandler et al., *Proc. Natl. Acad. Sci. USA,* 94(8):3596-601, 1997.
Chang et al., *Lancet.,* 362(9381):362-369, 2003.
Chang et al., *Mol. Cell. Biol.,* 9:2153, 1989.
Chatterjee et al., *Proc. Natl. Acad. Sci. USA,* 86:9114, 1989.
Chen and Okayama, *Mol. Cell Biol.,* 7(8):2745-2752, 1987.
Cheng et al., *FASEB J.,* 23:1-12, 2009.
Choi et al., *Cell,* 53:519, 1988.
Cocea, Biotechniques, 23(5):814-816, 1997.
Cohen et al., *J. Cell. Physiol.,* 5:75, 1987.
Cosgrove et al., *Infect. Control Hosp. Epidemiol.* 26:166-174, 2005.
Costa et al., *Mol. Cell. Biol.,* 8:81, 1988.
Cripe et al., *EMBO J.,* 6:3745, 1987.
Culotta and Hamer, *Mol. Cell. Biol.,* 9:1376, 1989.
Dalbey and Widmer, *J. Biol. Chem.,* 260:15925-15931, 1985.
Dandolo et al., *J. Virology,* 47:55-64, 1983.
De Villiers et al., *Nature,* 312(5991):242-246, 1984.
DeBord et al., *Infect. Immun.,* 74:4910-4914, 2006.
DeDent et al., *EMBO J.* 27:2656-2668, 2008.
DeDent et al., *J. Bacteriol.* 189:4473-4484, 2007.
Deisenhofer et al., *Hoppe-Seyh Zeitsch. Physiol. Chem.* 359: 975-985, 1978.
Deisenhofer, *Biochemistry* 20:2361-2370, 1981.
Deschamps et al., *Science,* 230:1174-1177, 1985.
Devereux et al., *Nucl. Acid Res.,* 12:387-395, 1984.
Diep et al., *J. Infect. Dis.,* 193:1495-1503, 2006a.
Diep et al., *Lancet.,* 367:731-739, 2006b.
Dinges et al., *Clin. Microbiol. Rev.,* 13:16-34, 2000.
Duthie and Lorenz, *J. Gen. Microbiol.,* 6:95-107, 1952.
Edbrooke et al., *Mol. Cell. Biol.,* 9:1908, 1989.
Edlund et al., *Science,* 230:912-916, 1985.
Ekstedt and Yotis, *Ann. N.Y. Acad. Sci.,* 80:496-500, 1960.
Emorl and Gaynes, *Clin. Microbiol. Rev.,* 6:428-442, 1993.
EP 0786519
EP 497524
EP 497525
Epitope Mapping Protocols In: *Methods in Molecular Biology*, Vol. 66, Morris (Ed.), 1996.
Fechheimer, et al., *Proc Natl. Acad. Sci. USA,* 84:8463-8467, 1987.
Feng and Holland, *Nature,* 334:6178, 1988.
Field and Smith, *J. Comp. Pathol.,* 55:63, 1945.
Firak and Subramanian, *Mol. Cell. Biol.,* 6:3667, 1986.
Foecking and Hofstetter, *Gene,* 45(1):101-105, 1986.
Fortune et al., *Proc Natl. Acad. Sci. USA,* 102:10676-10681, 2005.
Foster, Nat. Rev. Microbiol., 3:948-958, 2005.
Fournier et al., *Infect. Immun.,* 45:87-93, 1984.
Fraley et al., *Proc. Natl. Acad. Sci. USA,* 76:3348-3352, 1979.
Friedrich et al., *Nature,* 425:535-539, 2003.
Fujita et al., *Cell,* 49:357, 1987.
GB Appln. 2 202 328
Gilles et al., *Cell,* 33:717, 1983.
Gloss et al., *EMBO J.,* 6:3735, 1987.
Godbout et al., *Mol. Cell. Biol.,* 8:1169, 1988.
Gomez et al., *EMBO J.* 26:701-709, 2007.
Gomez et al., *J. Biol. Chem.* 281:20190-20196, 2006.
Gomez et al., *Nature Med.* 10:842-8, 2004.
Goodbourn and Maniatis, *Proc. Natl. Acad. Sci. USA,* 85:1447, 1988.
Goodbourn et al., *Cell,* 45:601, 1986.
Goodyear and Silverman, *J. Exp. Med.,* 197:1125-1139, 2003.
Goodyear and Silverman, *Proc. Nat. Acad. Sci. USA,* 101: 11392-11397, 2004.
Gopal, *Mol. Cell Biol.,* 5:1188-1190, 1985.
Gouda et al., *Biochemistry,* 31(40):9665-72, 1992.
Gouda et al., *Biochemistry,* 37:129-36, 1998.
Graham and Van Der Eb, *Virology,* 52:456-467, 1973.
Graille et al., *Proc. Nat. Acad. Sci. USA* 97:5399-5404, 2000.
Greene et al., *Immunology Today,* 10:272, 1989
Grosschedl and Baltimore, *Cell,* 41:885, 1985.
Guinn et al., *Mol. Microbiol.,* 51:359-370, 2004.

Guss et al., *Eur. J. Biochem.* 138:413-420, 1984.
Harland and Weintraub, *J. Cell Biol.,* 101(3):1094-1099, 1985.
Harlow et al., *Antibodies: A Laboratory Manual*, Cold Spring Harbor Laboratory, Cold Spring Harbor, N.Y., Chapter 8, 1988.
Hartleib et al., *Blood* 96:2149-2156, 2000.
Harvey et al., *Proc. Natl. Acad. Sci. USA,* 83:1084-1088, 1986.
Haslinger and Karin, *Proc. Natl. Acad. Sci. USA,* 82:8572, 1985.
Hauber and Cullen, *J Virology,* 62:673, 1988.
Hen et al., *Nature,* 321:249, 1986.
Hensel et al., *Lymphokine Res.,* 8:347, 1989.
Herr and Clarke, *Cell,* 45:461, 1986.
Hirochika et al., *J. Virol.,* 61:2599, 1987.
Hirsch et al., *Mol. Cell. Biol.,* 10:1959, 1990.
Holbrook et al., *Virology,* 157:211, 1987.
Horlick and Benfield, *Mol. Cell. Biol.,* 9:2396, 1989.
Hsu et al., *Proc. Natl. Acad. Sci. USA,* 100:12420-12425, 2003.
Huang et al., *Cell,* 27:245, 1981.
Hug et al., *Mol. Cell. Biol.,* 8:3065, 1988.
Huston et al., In: *Methods in Enzymology*, Langone (Ed.), Academic Press, NY, 203:46-88, 1991.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc Natl Acad Sci USA,* 85(24):9436-9440, 1988.
Inouye and Inouye, *Nucleic Acids Res.,* 13: 3101-3109, 1985.
Jakobovits et al., *Mol. Cell. Biol.,* 8:2555, 1988.
Jameel and Siddiqui, *Mol. Cell. Biol.,* 6:710, 1986.
Jansson et al., *FEMS Immunol. Med. Microbiol.* 20:69-78 1998.
Jaynes et al., *Mol. Cell. Biol.,* 8:62, 1988.
Jensen, *Acta Path. Microbiol. Scandin.* 44:421-428, 1958.
Johnson et al., *Methods in Enzymol.,* 203:88-99, 1991.
Johnson et al., *Mol. Cell. Biol.,* 9:3393, 1989.
Jones, *Carb. Research,* 340:1097-1106, 2005.
Jonsson et al., *Oral Dis.,* 8(3):130-140, 2002.
Joyce et al., *Carbohydrate Research* 338:903-922 (2003
Kadesch and Berg, *Mol. Cell. Biol.,* 6:2593, 1986.
Kaeppler et al., *Plant Cell Rep.,* 8:415-418, 1990.
Kaneda et al., *Science,* 243:375-378, 1989.
Karin et al., *Mol. Cell. Biol.,* 7:606, 1987.
Katinka et al., *Cell,* 20:393, 1980.
Kato et al, *J. Biol. Chem.,* 266:3361-3364, 1991.
Kawamoto et al., *Mol. Cell. Biol.,* 8:267, 1988.
Kennedy et al., *Proc. Natl. Acad. Sci. USA* 105:1327-1332, 2008.
Kiledjian et al., *Mol. Cell. Biol.,* 8:145, 1988.
Kinoshita, M., N. Kobayashi, S. Nagashima, M. Ishino, S. Otokozawa, K. Mise, A. Sumi, H. Tsutsumi, N. Uehara, N. Watanabe, and M. Endo. 2008. Diversity of staphylocoagulase and identification of novel variants of staphylocoagulase gene in *Staphylococcus aureus*. Microbiol. Immunol.s 52:334-348.
Klamut et al., *Mol. Cell. Biol.,* 10:193, 1990.
Klevens et al., *Clin. Infect. Dis.,* 2008; 47:927-30, 2008.
Klevens et al., *JAMA,* 298:1763-1771, 2007.
Koch et al., *Mol. Cell. Biol.,* 9:303, 1989.
Kohler and Milstein, *Nature* 256:495-497 (1975
Kriegler and Botchan, *In: Eukaryotic Viral Vectors*, Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984a.
Kriegler et al., *Cell,* 53:45, 1988.
Kriegler et al., *In: Cancer Cells 2/Oncogenes and Viral Genes*, Van de Woude et al. eds, Cold Spring Harbor, Cold Spring Harbor Laboratory, 1984b.
Kroh et al., *Proc. Natl. Acad. Sci. USA,* 106:7786-7791, 2009.
Kuhl et al., *Cell,* 50:1057, 1987.
Kuklin et al., *Infect. Immun.,* 74:2215-23, 2006.
Kunz et al., *Nucl. Acids Res.,* 17:1121, 1989.
Kuroda et al., *Lancet.,* 357:1225-1240, 2001.
Kyte and Doolittle, *J. Mol. Biol.,* 157(1):105-132, 1982.
Lagergard et al., *Eur. J. Clin. Microbiol. Infect. Dis.,* 11:341-5, 1992.
Lam et al., *J. Bacteriol.,* 86:87-91, 1963.
Larsen et al., *Proc Natl. Acad. Sci. USA.,* 83:8283, 1986, 1963.
Laspia et al., *Cell,* 59:283, 1989.
Latimer et al., *Mol. Cell. Biol.,* 10:760, 1990.
Lee et al., *Nature,* 294:228, 1981.
Lee et al., *Nucleic Acids Res.,* 12:4191-206, 1984.
Lee, *Trends Microbiol.* 4(4):162-166, 1996.
Levenson et al., *Hum. Gene Ther.,* 9(8):1233-1236, 1998.
Levinson et al., *Nature,* 295:79, 1982.
Lin et al., *Mol. Cell. Biol.,* 10:850, 1990.
Lowy, *New Engl. J. Med.,* 339:520-532, 1998.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.
MacGurn et al., *Mol. Microbiol.,* 57:1653-1663, 2005.
Maira-Litran et al., *Infect. Immun.,* 70:4433-4440, 2002.
Maira-Litran et al., *Vaccine,* 22:872-879, 2004.
Majors and Varmus, *Proc. Natl. Acad. Sci. USA,* 80:5866, 1983.
Markwardt, *Untersuchungen über Hirudin. Naturwissenschaften,* 41:537-538, 1955.
Mazmanian et al., *Mol. Microbiol* 40, 1049-1057, 2001.
Mazmanian et al., *Mol. Microbiol.,* 40(5):1049-1057, 2001.
Mazmanian et al., *Proc. Natl. Acad. Sci. USA,* 97:5510-5515, 2000.
Mazmanian et al., *Science,* 285(5428):760-3, 1999.
McLaughlin et al., *PLoS Pathog.,* 3:e105, 2007.
McNeall et al., *Gene,* 76:81, 1989.
Mernaugh et al., In: *Molecular Methods in Plant Pathology*, Singh et al. (Eds.), CRC Press Inc., Boca Raton, Fla., 359-365, 1995.
Merrifield, *Science,* 232(4748):341-347, 1986.
Miksicek et al., *Cell,* 46:203, 1986.
Mordacq and Linzer, *Genes and Dev.,* 3:760, 1989.
Moreau et al., *Carbohydrate Res.,* 201:285-297, 1990.
Moreau et al., *Nucl. Acids Res.,* 9:6047, 1981.
Moreillon et al., *Infect. Immun.,* 63:4738-4743, 1995.
Moreillon et al., *Infect. Immun.,* 63:4738-4743, 1995.
Mosmann and Coffman, *Ann. Rev. Immunol.,* 7:145-173, 1989.
Muesing et al., *Cell,* 48:691, 1987.
Musher et al., *Medicine* (*Baltimore*), 73:186-208, 1994.
Navarre and Schneewind, *J. Biol. Chem.,* 274:15847-15856, 1999.
Needleman & Wunsch, *J. Mol. Biol.,* 48:443, 1970.
Ng et al., *Nuc. Acids Res.,* 17:601, 1989.

Nicolau and Sene, *Biochim. Biophys. Acta,* 721:185-190, 1982.
Nicolau et al., *Methods Enzymol.,* 149:157-176, 1987.
Novick, *Mol. Microbiol.,* 48:1429-1449, 2003.
O'Brien et al., *Mol. Microbiol.* 44:1033-1044, 2002.
O'Seaghdha et al., *FEBS J.* 273:4831-4841, 2006.
Omirulleh et al., *Plant Mol. Biol.,* 21(3):415-28, 1993.
Ondek et al., *EMBO J.,* 6:1017, 1987.
Ornitz et al., *Mol. Cell. Biol.,* 7:3466, 1987.
Pallen, *Trends Microbiol.,* 10:209-212, 2002.
Palmiter et al., *Nature,* 300:611, 1982.
Palmqvist et al., *Microbes. Infect.,* 7:1501-11, 2005.
Panizzi et al., *J. Biol. Chem.,* 281:1179-1187, 2006.
PCT Appln. PCT/US89/01025
PCT Appln. WO 00/02523
PCT Appln. WO 00/12132
PCT Appln. WO 00/12689
PCT Appln. WO 00/15238
PCT Appln. WO 01/34809
PCT Appln. WO 01/60852
PCT Appln. WO 01/98499
PCT Appln. WO 02/059148
PCT Appln. WO 02/094868
PCT Appln. WO 03/53462
PCT Appln. WO 04/43407
PCT Appln. WO 06/032472
PCT Appln. WO 06/032475
PCT Appln. WO 06/032500
PCT Appln. WO 07/113,222
PCT Appln. WO 07/113,223
PCT Appln. WO 94/09699
PCT Appln. WO 95/06128
PCT Appln. WO 95/08348
PCT Appln. WO 98/57994
Pearson & Lipman, *Proc. Natl. Acad. Sci. USA,* 85:2444, 1988.
Pech et al., *Mol. Cell. Biol.,* 9:396, 1989.
Pelletier and Sonenberg, *Nature,* 334(6180):320-325, 1988.
Perez-Stable and Constantini, *Mol. Cell. Biol.,* 10:1116, 1990.
Phonimdaeng et al., *Mol. Microbiol.,* 4:393-404, 1990.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potrykus et al., *Mol. Gen. Genet.,* 199(2):169-177, 1985.
Pugsley, *Microbiol. Rev.,* 57:50-108, 1993.
Pym et al., *Mol. Microbiol.,* 46; 709-717, 2002.
Pym et al., *Nat. Med.,* 9:533-539, 2003.
Queen and Baltimore, *Cell,* 35:741, 1983.
Quinn et al., *Mol. Cell. Biol.,* 9:4713, 1989.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, 1289-1329, 1990.
Resendez Jr. et al., *Mol. Cell. Biol.,* 8:4579, 1988.
Ripe et al., *Mol. Cell. Biol.,* 9:2224, 1989.
Rippe, et al., *Mol. Cell. Biol.,* 10:689-695, 1990.
Rittling et al., *Nuc. Acids Res.,* 17:1619, 1989.
Roben et al., *J. Immunol.* 154:6437-6445, 1995.
Rosen et al., *Cell,* 41:813, 1988.
Sakai et al., *Genes and Dev.,* 2:1144, 1988.
Salid-Salim et al., *Infect. Control Hosp. Epidemiol.* 24:451-455, 2003.
Sambrook et al., *In: Molecular cloning*, Cold Spring Harbor Laboratory Press, Cold Spring Harbor, N.Y., 2001.
Schaffner et al., *J. Mol. Biol.,* 201:81, 1988.
Schneewind et al., *Cell* 70:267-281, 1992.
Schneewind et al., *EMBO,* 12:4803-4811, 1993.
Schneewind et al., *Science,* 268:103-6, 1995.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Shaw et al., *Microbiology,* 150:217-228, 2004.
Sheagren, *N. Engl. J. Med.* 310:1368-1373, 1984.
Sherman et al., *Mol. Cell. Biol.,* 9:50, 1989.
Shopsin et al., *J. Clin. Microbiol.,* 37:3556-63, 1999.
Sibbald et al., *Microbiol. Mol. Biol. Rev.,* 70:755-788, 2006.
Silverman and Goodyear. *Nat. Rev. Immunol.,* 6:465-75, 2006.
Sjodahl, *Eur. J. Biochem.* 73:343-351, 1977.
Sjoquist et al., *Eur. J. Biochem.* 30:190-194, 1972.
Sleigh and Lockett, *J. EMBO,* 4:3831, 1985.
Smith & Waterman, *Adv. Appl. Math.,* 2:482, 1981.
Smith et al., *Brit. J. Exp. Pathol.,* 28:57, 1947.
Sorensen et al., *Infect. Immun.,* 63:1710-1717, 1995.
Spalholz et al., *Cell,* 42:183, 1985.
Spandau and Lee, *J. Virology,* 62:427, 1988.
Spandidos and Wilkie, *EMBO J.,* 2:1193, 1983.
Stanley et al., *Proc. Natl. Acad. Sci. USA,* 100:13001-13006, 2003.
Stephens and Hentschel, *Biochem. J.,* 248:1, 1987.
Stewart and Young, In: *Solid Phase Peptide Synthesis,* 2d. ed., Pierce Chemical Co., 1984.
Stranger-Jones et al., *Proc. Nat. Acad. Sci. USA,* 103:16942-16947, 2006.
Stuart et al., *Nature,* 317:828, 1985.
Studier et al., *Methods Enzymol.* 185:60-89 1990.
Sullivan and Peterlin, *Mol. Cell. Biol.,* 7:3315, 1987.
Swartzendruber and Lehman, *J. Cell. Physiology,* 85:179, 1975.
Takebe et al., *Mol. Cell. Biol.,* 8:466, 1988.
Tam et al., *J. Am. Chem. Soc.,* 105:6442, 1983.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Thiesen et al., *J. Virology,* 62:614, 1988.
Thomson et al., *J. Immunol.,* 157(2):822-826, 1996.
Tigges et al., *J. Immunol.,* 156(10):3901-3910, 1996.
Tigges et al., *J. Immunol.,* 156(10):3901-3910, 1996.
Ton-That et al., *Proc. Natl. Acad. Sci. USA,* 96(22):12424-9, 1999.
Treisman, *Cell,* 42:889, 1985.
Tronche et al., *Mol. Biol. Med.,* 7:173, 1990.
Trudel and Constantini, *Genes and Dev.,* 6:954, 1987.
Tyndell et al., *Nuc. Acids. Res.,* 9:6231, 1981.
Uhlen et al., *J. Biol. Chem.* 259:1695-1702 and 13628 (Corr.) 1984.
van den Ent and Lowe, *FEBS Lett.,* 579:3837-3841, 2005.
van Wely et al., *FEMS Microbiol. Rev.,* 25:437-454, 2001.
Vannice and Levinson, *J. Virology,* 62:1305, 1988.
Vasseur et al., *Proc Natl. Acad. Sci. USA,* 77:1068, 1980.
Vaughan, et al., *Nat. Biotech.* 16; 535-539, 1998.
Wang and Calame, *Cell,* 47:241, 1986.
Weber et al., *Cell,* 36:983, 1984.
Weinberger et al. *Mol. Cell. Biol.,* 8:988, 1984.
Weiss et al., *J. Antimicrob. Chemother.,* 53(3):480-6, 2004.
Winoto and Baltimore, *Cell,* 59:649, 1989.
Wong et al., *Gene,* 10:87-94, 1980.
Xu et al., *J. Infect. Dis.,* 189:2323-2333, 2004.
Xu et al., *Mol. Microbiol.,* 66(3):787-800, 2007.
Yutzey et al. *Mol. Cell. Biol.,* 9:1397, 1989.

What is claimed is:

1. An isolated polypeptide comprising a variant *Staphylococcus aureus* Protein A (SpA) domain D segment having amino acid substitutions at amino acids corresponding to position 9, 10, 36 and 37 of SEQ ID NO: 2, wherein the substitutions at amino acids corresponding to positions 9 and 10 are with a glycine residue and the substitutions at amino acids corresponding to positions 36 and 37 are with a serine residue.

2. An pharmaceutical composition comprising the isolated polypeptide of claim 1 in a pharmaceutically acceptable formulation.

3. A method for eliciting an immune response against a *Staphylococcus aureus* bacterium in a subject comprising providing to the subject an effective amount of a composition comprising a variant *Staphylococcus aureus* Protein A (SpA) domain D segment having amino acid substitutions at amino acids corresponding to position 9, 10, 36 and 37 of SEQ ID NO: 2, wherein the substitutions at amino acids corresponding to positions 9 and 10 are with a glycine residue and the substitutions at amino acids corresponding to positions 36 and 37 are with a serine residue.

4. The method of claim 3, where the subject is also administered an adjuvant.

5. The method of claim 3, wherein the staphylococcus bacterium is a *S. aureus* bacterium.

6. The method of claim 3, wherein the staphylococcus bacterium is resistant to one or more drug treatments.

7. The method of claim 6, wherein the bacterium is methicillin resistant.

8. The method of claim 3, wherein the composition is administered orally, parenterally, subcutaneously, intramuscularly, or intravenously.

9. The method of claim 3, further comprising administering to the subject a composition comprising a second staphylococcal antigen.

10. The method of claim 3, wherein the subject is human.

11. The method of claim 3, wherein the immune response is a protective immune response.

* * * * *

SEQUENCE LISTING

```
<160> NUMBER OF SEQ ID NOS: 64

<210> SEQ ID NO 1
<211> LENGTH: 150
<212> TYPE: DNA
<213> ORGANISM: Staphylococcus sp.

<400> SEQUENCE: 1

ttcaacaaag atcaacaaag cgccttctat gaaatcttga acatgcctaa cttaaacgaa      60

gcgcaacgta acggcttcat tcaaagtctt aaagacgacc caagccaaag cactaatgtt     120

ttaggtgaag ctaaaaaatt aaacgaatct                                      150


<210> SEQ ID NO 2
<211> LENGTH: 54
<212> TYPE: PRT
<213> ORGANISM: Staphylococcus sp.

<400> SEQUENCE: 2

Gln Gln Asn Asn Phe Asn Lys Asp Gln Gln Ser Ala Phe Tyr Glu Ile
1               5                   10                  15

Leu Asn Met Pro Asn Leu Asn Glu Ala Gln Arg Asn Gly Phe Ile Gln
            20                  25                  30

Ser Leu Lys Asp Asp Pro Ser Gln Ser Thr Asn Val Leu Gly Glu Ala
        35                  40                  45

Lys Lys Leu Asn Glu Ser
    50


<210> SEQ ID NO 3
<211> LENGTH: 51
<212> TYPE: PRT
<213> ORGANISM: Staphylococcus sp.

<400> SEQUENCE: 3

Gln His Asp Glu Ala Gln Gln Asn Ala Phe Tyr Gln Val Leu Asn Met
1               5                   10                  15

Pro Asn Leu Asn Ala Asp Gln Arg Asn Gly Phe Ile Gln Ser Leu Lys
            20                  25                  30

Asp Asp Pro Ser Gln Ser Ala Asn Val Leu Gly Glu Ala Gln Lys Leu
        35                  40                  45

Asn Asp Ser
    50


<210> SEQ ID NO 4
<211> LENGTH: 52
<212> TYPE: PRT
<213> ORGANISM: Staphylococcus sp.

<400> SEQUENCE: 4

Asn Asn Phe Asn Lys Glu Gln Gln Asn Ala Phe Tyr Glu Ile Leu Asn
1               5                   10                  15

Met Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ser Glu Ala Lys Lys
        35                  40                  45

Leu Asn Glu Ser
    50


<210> SEQ ID NO 5
<211> LENGTH: 52
```

<212> TYPE: PRT
<213> ORGANISM: Staphylococcus sp.

<400> SEQUENCE: 5

```
Asn Lys Phe Asn Lys Glu Gln Gln Asn Ala Phe Tyr Glu Ile Leu His
1               5                   10                  15

Leu Pro Asn Leu Thr Glu Glu Gln Arg Asn Gly Phe Ile Gln Ser Leu
            20                  25                  30

Lys Asp Asp Pro Ser Val Ser Lys Glu Ile Leu Ala Glu Ala Lys Lys
        35                  40                  45

Leu Asn Asp Ala
    50
```

<210> SEQ ID NO 6
<211> LENGTH: 52
<212> TYPE: PRT
<213> ORGANISM: Staphylococcus sp.

<400> SEQUENCE: 6

```
Asn Lys Phe Asn Lys Glu Gln Gln Asn Ala Phe Tyr Glu Ile Leu His
1               5                   10                  15

Leu Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ala Glu Ala Lys Lys
        35                  40                  45

Leu Asn Asp Ala
    50
```

<210> SEQ ID NO 7
<211> LENGTH: 52
<212> TYPE: PRT
<213> ORGANISM: Staphylococcus sp.
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 7

```
Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Xaa Xaa Pro Ser Gln Ser Thr Asn Val Leu Gly Glu Ala Lys Lys
        35                  40                  45

Leu Asn Glu Ser
    50
```

<210> SEQ ID NO 8
<211> LENGTH: 52
<212> TYPE: PRT
<213> ORGANISM: Staphylococcus sp.
<220> FEATURE:
<221> NAME/KEY: MISC_FEATURE
<222> LOCATION: (7)..(8)
<223> OTHER INFORMATION: where X is any amino acid other than Q
<220> FEATURE:
<221> NAME/KEY: MISC_FEATURE
<222> LOCATION: (12)..(35)
<223> OTHER INFORMATION: where Y is any amion acid other than D

```
<400> SEQUENCE: 8

Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Tyr Tyr Pro Ser Gln Ser Thr Asn Val Leu Gly Glu Ala Lys Lys
        35                  40                  45

Leu Asn Glu Ser
    50


<210> SEQ ID NO 9
<211> LENGTH: 450
<212> TYPE: PRT
<213> ORGANISM: Staphylococcus sp.

<400> SEQUENCE: 9

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Lys Lys Pro Gly Lys Glu Asp Gly Asn Lys Pro Gly Lys Glu Asp
        275                 280                 285

Gly Asn Lys Pro Gly Lys Glu Asp Asn Lys Lys Pro Gly Lys Glu Asp
    290                 295                 300
```

-continued

```
Gly Asn Lys Pro Gly Lys Glu Asp Asn Asn Lys Pro Gly Lys Glu Asp
305                 310                 315                 320

Gly Asn Lys Pro Gly Lys Glu Asp Asn Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
        355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450


<210> SEQ ID NO 10
<211> LENGTH: 450
<212> TYPE: PRT
<213> ORGANISM: Staphylococcus sp.

<400> SEQUENCE: 10

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220
```

```
Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Lys Lys Pro Gly Lys Glu Asp Gly Asn Lys Pro Gly Lys Glu Asp
        275                 280                 285

Gly Asn Lys Pro Gly Lys Glu Asp Asn Lys Lys Pro Gly Lys Glu Asp
    290                 295                 300

Gly Asn Lys Pro Gly Lys Glu Asp Asn Asn Lys Pro Gly Lys Glu Asp
305                 310                 315                 320

Gly Asn Lys Pro Gly Lys Glu Asp Asn Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
        355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450
```

<210> SEQ ID NO 11
<211> LENGTH: 97
<212> TYPE: PRT
<213> ORGANISM: Staphylococcus sp.

<400> SEQUENCE: 11

```
Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80

Asp Ala Val Gln Glu Gln Asp Gln Gln Leu Ser Asn Asn Phe Gly Leu
                85                  90                  95

Gln
```

<210> SEQ ID NO 12
<211> LENGTH: 102
<212> TYPE: PRT
<213> ORGANISM: Staphylococcus sp.

<400> SEQUENCE: 12

Met Gly Gly Tyr Lys Gly Ile Lys Ala Asp Gly Gly Lys Val Asn Gln
1 5 10 15

Ala Lys Gln Leu Ala Ala Lys Ile Ala Lys Asp Ile Glu Ala Cys Gln
20 25 30

Lys Gln Thr Gln Gln Leu Ala Glu Tyr Ile Glu Gly Ser Asp Trp Glu
35 40 45

Gly Gln Phe Ala Asn Lys Val Lys Asp Val Leu Leu Ile Met Ala Lys
50 55 60

Phe Gln Glu Glu Leu Val Gln Pro Met Ala Asp His Gln Lys Ala Ile
65 70 75 80

Asp Asn Leu Ser Gln Asn Leu Ala Lys Tyr Asp Thr Leu Ser Ile Lys
85 90 95

Gln Gly Leu Asp Arg Val
100

<210> SEQ ID NO 13
<211> LENGTH: 1385
<212> TYPE: PRT
<213> ORGANISM: Staphylococcus sp.

<400> SEQUENCE: 13

Met Leu Asn Arg Glu Asn Lys Thr Ala Ile Thr Arg Lys Gly Met Val
1 5 10 15

Ser Asn Arg Leu Asn Lys Phe Ser Ile Arg Lys Tyr Thr Val Gly Thr
20 25 30

Ala Ser Ile Leu Val Gly Thr Thr Leu Ile Phe Gly Leu Gly Asn Gln
35 40 45

Glu Ala Lys Ala Ala Glu Ser Thr Asn Lys Glu Leu Asn Glu Ala Thr
50 55 60

Thr Ser Ala Ser Asp Asn Gln Ser Ser Asp Lys Val Asp Met Gln Gln
65 70 75 80

Leu Asn Gln Glu Asp Asn Thr Lys Asn Asp Asn Gln Lys Glu Met Val
85 90 95

Ser Ser Gln Gly Asn Glu Thr Thr Ser Asn Gly Asn Lys Ser Ile Glu
100 105 110

Lys Glu Ser Val Gln Ser Thr Thr Gly Asn Lys Val Glu Val Ser Thr
115 120 125

Ala Lys Ser Asp Glu Gln Ala Ser Pro Lys Ser Thr Asn Glu Asp Leu
130 135 140

Asn Thr Lys Gln Thr Ile Ser Asn Gln Glu Gly Leu Gln Pro Asp Leu
145 150 155 160

Leu Glu Asn Lys Ser Val Val Asn Val Gln Pro Thr Asn Glu Glu Asn
165 170 175

Lys Lys Val Asp Ala Lys Thr Glu Ser Thr Thr Leu Asn Val Lys Ser
180 185 190

Asp Ala Ile Lys Ser Asn Ala Glu Thr Leu Val Asp Asn Asn Ser Asn
195 200 205

Ser Asn Asn Glu Asn Asn Ala Asp Ile Ile Leu Pro Lys Ser Thr Ala
210 215 220

Pro Lys Ser Leu Asn Thr Arg Met Arg Met Ala Ala Ile Gln Pro Asn
225 230 235 240

Ser Thr Asp Ser Lys Asn Val Asn Asp Leu Ile Thr Ser Asn Thr Thr
245 250 255

```
Leu Thr Val Val Asp Ala Asp Asn Ser Lys Thr Ile Val Pro Ala Gln
            260                 265                 270

Asp Tyr Leu Ser Leu Lys Ser Gln Ile Thr Val Asp Asp Lys Val Lys
        275                 280                 285

Ser Gly Asp Tyr Phe Thr Ile Lys Tyr Ser Asp Thr Val Gln Val Tyr
    290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Lys Met Gly Ile Asn Tyr Ser Ile Tyr Met Asp Ala Asp Thr Ile Pro
        355                 360                 365

Val Asp Lys Lys Asp Val Pro Phe Ser Val Thr Ile Gly Asn Gln Ile
    370                 375                 380

Thr Thr Thr Thr Ala Asp Ile Thr Tyr Pro Ala Tyr Lys Glu Ala Asp
385                 390                 395                 400

Asn Asn Ser Ile Gly Ser Ala Phe Thr Glu Thr Val Ser His Val Gly
                405                 410                 415

Asn Val Glu Asp Pro Gly Tyr Tyr Asn Gln Val Val Tyr Val Asn Pro
            420                 425                 430

Met Asp Lys Asp Leu Lys Gly Ala Lys Leu Lys Val Glu Ala Tyr His
        435                 440                 445

Pro Lys Tyr Pro Thr Asn Ile Gly Gln Ile Asn Gln Asn Val Thr Asn
    450                 455                 460

Ile Lys Ile Tyr Arg Val Pro Glu Gly Tyr Thr Leu Asn Lys Gly Tyr
465                 470                 475                 480

Asp Val Asn Thr Asn Asp Leu Val Asp Val Thr Asp Glu Phe Lys Asn
                485                 490                 495

Lys Met Thr Tyr Gly Ser Asn Gln Ser Val Asn Leu Asp Phe Gly Asp
            500                 505                 510

Ile Thr Ser Ala Tyr Val Val Met Val Asn Thr Lys Phe Gln Tyr Thr
        515                 520                 525

Asn Ser Glu Ser Pro Thr Leu Val Gln Met Ala Thr Leu Ser Ser Thr
    530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590

Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
    610                 615                 620

Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                645                 650                 655

Asn Gly Leu Ser Ser Val Ile Thr Val Asn Gly Lys Asp Asn Leu Ser
            660                 665                 670
```

```
Ala Asp Leu Gly Ile Tyr Lys Pro Lys Tyr Asn Leu Gly Asp Tyr Val
        675                 680                 685

Trp Glu Asp Thr Asn Lys Asn Gly Ile Gln Asp Gln Asp Glu Lys Gly
    690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                725                 730                 735

Asp Asn Gly Asn Tyr Lys Val Glu Phe Thr Thr Pro Glu Gly Tyr Thr
            740                 745                 750

Pro Thr Thr Val Thr Ser Gly Ser Asp Ile Glu Lys Asp Ser Asn Gly
        755                 760                 765

Leu Thr Thr Thr Gly Val Ile Asn Gly Ala Asp Asn Met Thr Leu Asp
    770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                805                 810                 815

Ser Gly Val Thr Val Thr Leu Lys Asn Glu Asn Gly Glu Val Leu Gln
            820                 825                 830

Thr Thr Lys Thr Asp Lys Asp Gly Lys Tyr Gln Phe Thr Gly Leu Glu
        835                 840                 845

Asn Gly Thr Tyr Lys Val Glu Phe Glu Thr Pro Ser Gly Tyr Thr Pro
    850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                885                 890                 895

Gly Phe Tyr Lys Pro Thr Tyr Asn Leu Gly Asp Tyr Val Trp Glu Asp
            900                 905                 910

Thr Asn Lys Asn Gly Val Gln Asp Lys Asp Glu Lys Gly Ile Ser Gly
        915                 920                 925

Val Thr Val Thr Leu Lys Asp Glu Asn Asp Lys Val Leu Lys Thr Val
    930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                965                 970                 975

Val Thr Ser Gly Asn Asp Thr Glu Lys Asp Ser Asn Gly Leu Thr Thr
            980                 985                 990

Thr Gly Val Ile Lys Asp Ala Asp  Asn Met Thr Leu Asp  Ser Gly Phe
        995                 1000                1005

Tyr Lys  Thr Pro Lys Tyr Ser  Leu Gly Asp Tyr Val  Trp Tyr Asp
    1010                 1015                 1020

Ser Asn  Lys Asp Gly Lys Gln  Asp Ser Thr Glu Lys  Gly Ile Lys
    1025                 1030                 1035

Asp Val  Lys Val Ile Leu Leu  Asn Glu Lys Gly Glu  Val Ile Gly
    1040                 1045                 1050

Thr Thr  Lys Thr Asp Glu Asn  Gly Lys Tyr Arg Phe  Asp Asn Leu
    1055                 1060                 1065

Asp Ser  Gly Lys Tyr Lys Val  Ile Phe Glu Lys Pro  Thr Gly Leu
    1070                 1075                 1080

Thr Gln  Thr Gly Thr Asn Thr  Thr Glu Asp Asp Lys  Asp Ala Asp
```

```
    1085                1090                1095

Gly Gly  Glu Val Asp Val Thr  Ile Thr Asp His Asp  Asp Phe Thr
    1100                1105                1110

Leu Asp  Asn Gly Tyr Tyr Glu  Glu Glu Thr Ser Asp  Ser Asp Ser
    1115                1120                1125

Asp Ser  Asp Ser Asp Ser Asp  Ser Asp Ser Asp Ser  Asp Ser Asp
    1130                1135                1140

Ser Asp  Ser Asp Ser Asp Ser  Asp Ser Asp Ser Asp  Ser Asp Ser
    1145                1150                1155

Asp Ser  Asp Ser Asp Ser Asp  Ser Asp Ser Asp Ser  Asp Ser Asp
    1160                1165                1170

Ser Asp  Ser Asp Ser Asp Ser  Asp Ser Asp Ser Asp  Ser Asp Ser
    1175                1180                1185

Asp Ser  Asp Ser Asp Ser Asp  Ser Asp Ser Asp Ser  Asp Ser Asp
    1190                1195                1200

Ser Asp  Ser Asp Ser Asp Ser  Asp Ser Asp Ser Asp  Ser Asp Ser
    1205                1210                1215

Asp Ser  Asp Ser Asp Ser Asp  Ser Asp Ser Asp Ser  Asp Ser Asp
    1220                1225                1230

Ser Asp  Ser Asp Ser Asp Ser  Asp Ser Asp Ser Asp  Ser Asp Ser
    1235                1240                1245

Asp Ser  Asp Ser Asp Ser Asp  Ser Asp Ser Asp Ser  Asp Ser Asp
    1250                1255                1260

Ser Asp  Ser Asp Ser Asp Ser  Asp Ser Asp Ser Asp  Ser Asp Ser
    1265                1270                1275

Asp Ser  Asp Ser Asp Ser Asp  Ser Asp Ser Asp Ser  Asp Ser Asp
    1280                1285                1290

Ser Asp  Ser Asp Ser Asp Ser  Asp Ser Asp Ser Asp  Ser Asp Ser
    1295                1300                1305

Asp Ser  Asp Ser Asp Ser Asp  Ser Asp Ser Asp Ser  Asp Ser Asp
    1310                1315                1320

Ser Asp  Ala Gly Lys His Thr  Pro Val Lys Pro Met  Ser Thr Thr
    1325                1330                1335

Lys Asp  His His Asn Lys Ala  Lys Ala Leu Pro Glu  Thr Gly Asn
    1340                1345                1350

Glu Asn  Ser Gly Ser Asn Asn  Ala Thr Leu Phe Gly  Gly Leu Phe
    1355                1360                1365

Ala Ala  Leu Gly Ser Leu Leu  Leu Phe Gly Arg Arg  Lys Lys Gln
    1370                1375                1380

Asn Lys
    1385


<210> SEQ ID NO 14
<211> LENGTH: 1141
<212> TYPE: PRT
<213> ORGANISM: Staphylococcus sp.

<400> SEQUENCE: 14

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45
```

-continued

```
Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asp Ser Thr Asn Pro Ile Lys Lys Glu Thr
                85                  90                  95

Asn Thr Asp Ser Gln Pro Glu Ala Lys Glu Glu Ser Thr Thr Ser Ser
            100                 105                 110

Thr Gln Gln Gln Gln Asn Asn Val Thr Ala Thr Thr Glu Thr Lys Pro
        115                 120                 125

Gln Asn Ile Glu Lys Glu Asn Val Lys Pro Ser Thr Asp Lys Thr Ala
    130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
                165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
        195                 200                 205

Pro Lys Glu Pro Val Asn Val Ser Lys Glu Glu Leu Lys Asn Asn Pro
    210                 215                 220

Glu Lys Leu Lys Glu Leu Val Arg Asn Asp Asn Asn Thr Asp Arg Ser
225                 230                 235                 240

Thr Lys Pro Val Ala Thr Ala Pro Thr Ser Val Ala Pro Lys Arg Leu
                245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
        275                 280                 285

Gly Asp Gly Lys Asp Asn Val Ala Ala Ala His Asp Gly Lys Asp Ile
    290                 295                 300

Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
                325                 330                 335

Asp Lys Asn Asp Pro Ile Asp Ile Thr Asp Pro Ser Gly Glu Val Ile
            340                 345                 350

Ala Lys Gly Thr Phe Asp Lys Ala Thr Lys Gln Ile Thr Tyr Thr Phe
        355                 360                 365

Thr Asp Tyr Val Asp Lys Tyr Glu Asp Ile Lys Ala Arg Leu Thr Leu
    370                 375                 380

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val
                405                 410                 415

Asp Tyr Gln Asp Pro Met Val His Gly Asp Ser Asn Ile Gln Ser Ile
            420                 425                 430

Phe Thr Lys Leu Asp Glu Asn Lys Gln Thr Ile Glu Gln Gln Ile Tyr
        435                 440                 445

Val Asn Pro Leu Lys Lys Thr Ala Thr Asn Thr Lys Val Asp Ile Ala
    450                 455                 460

Gly Ser Gln Val Asp Asp Tyr Gly Asn Ile Lys Leu Gly Asn Gly Ser
```

-continued

```
465                 470                 475                 480

Thr Ile Ile Asp Gln Asn Thr Glu Ile Lys Val Tyr Lys Val Asn Pro
                485                 490                 495

Asn Gln Gln Leu Pro Gln Ser Asn Arg Ile Tyr Asp Phe Ser Gln Tyr
            500                 505                 510

Glu Asp Val Thr Ser Gln Phe Asp Asn Lys Lys Ser Phe Ser Asn Asn
        515                 520                 525

Val Ala Thr Leu Asp Phe Gly Asp Ile Asn Ser Ala Tyr Ile Ile Lys
    530                 535                 540

Val Val Ser Lys Tyr Thr Pro Thr Ser Asp Gly Glu Leu Asp Ile Ala
545                 550                 555                 560

Gln Gly Thr Ser Met Arg Thr Thr Asp Lys Tyr Gly Tyr Tyr Asn Tyr
                565                 570                 575

Ala Gly Tyr Ser Asn Phe Ile Val Thr Ser Asn Asp Thr Gly Gly Gly
            580                 585                 590

Asp Gly Thr Val Lys Pro Glu Glu Lys Leu Tyr Lys Ile Gly Asp Tyr
        595                 600                 605

Val Trp Glu Asp Val Asp Lys Asp Gly Val Gln Gly Thr Asp Ser Lys
    610                 615                 620

Glu Lys Pro Met Ala Asn Val Leu Val Thr Leu Thr Tyr Pro Asp Gly
625                 630                 635                 640

Thr Thr Lys Ser Val Arg Thr Asp Ala Asn Gly His Tyr Glu Phe Gly
                645                 650                 655

Gly Leu Lys Asp Gly Glu Thr Tyr Thr Val Lys Phe Glu Thr Pro Ala
            660                 665                 670

Gly Tyr Leu Pro Thr Lys Val Asn Gly Thr Thr Asp Gly Glu Lys Asp
        675                 680                 685

Ser Asn Gly Ser Ser Ile Thr Val Lys Ile Asn Gly Lys Asp Asp Met
    690                 695                 700

Ser Leu Asp Thr Gly Phe Tyr Lys Glu Pro Lys Tyr Asn Leu Gly Asp
705                 710                 715                 720

Tyr Val Trp Glu Asp Thr Asn Lys Asp Gly Ile Gln Asp Ala Asn Glu
                725                 730                 735

Pro Gly Ile Lys Asp Val Lys Val Thr Leu Lys Asp Ser Thr Gly Lys
            740                 745                 750

Val Ile Gly Thr Thr Thr Thr Asp Ala Ser Gly Lys Tyr Lys Phe Thr
        755                 760                 765

Asp Leu Asp Asn Gly Asn Tyr Thr Val Glu Phe Glu Thr Pro Ala Gly
    770                 775                 780

Tyr Thr Pro Thr Val Lys Asn Thr Thr Ala Glu Asp Lys Asp Ser Asn
785                 790                 795                 800

Gly Leu Thr Thr Thr Gly Val Ile Lys Asp Ala Asp Asn Met Thr Leu
                805                 810                 815

Asp Ser Gly Phe Tyr Lys Thr Pro Lys Tyr Ser Leu Gly Asp Tyr Val
            820                 825                 830

Trp Tyr Asp Ser Asn Lys Asp Gly Lys Gln Asp Ser Thr Glu Lys Gly
        835                 840                 845

Ile Lys Asp Val Lys Val Thr Leu Leu Asn Glu Lys Gly Glu Val Ile
    850                 855                 860

Gly Thr Thr Lys Thr Asp Glu Asn Gly Lys Tyr Arg Phe Asp Asn Leu
865                 870                 875                 880

Asp Ser Gly Lys Tyr Lys Val Ile Phe Glu Lys Pro Ala Gly Leu Thr
                885                 890                 895
```

-continued

```
Gln Thr Val Thr Asn Thr Thr Glu Asp Asp Lys Asp Ala Asp Gly Gly
            900                 905                 910

Glu Val Asp Val Thr Ile Thr Asp His Asp Asp Phe Thr Leu Asp Asn
        915                 920                 925

Gly Tyr Phe Glu Glu Asp Thr Ser Asp Ser Asp Ser Asp Ser Asp Ser
    930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser Asp Ser
                965                 970                 975

Asp Ser Asp Ser Asp Ser Asp Ser Asp Ser Asp Ser Asp Ser Asp Ser
            980                 985                 990

Asp Ser Asp Ser Asp Ser Asp Ser  Asp Ser Asp Ser Asp  Ser Asp Ser
        995                 1000                 1005

Asp Ser  Asp Ser Asp Ser Asp  Ser Asp Ser Asp Ser  Asp Ser Asp
    1010                 1015                 1020

Ser Asp  Ser Asp Ser Asp Ser  Asp Ser Asp Ser Asp  Ser Asp Ser
    1025                 1030                 1035

Asp Ser  Asp Ser Asp Ser Asp  Ser Asp Ser Asp Ser  Asp Ser Asp
    1040                 1045                 1050

Ser Asp  Ser Asp Ser Asp Ser  Asp Ser Asp Ser Asp  Ser Asp Ser
    1055                 1060                 1065

Asp Ser  Asp Ser Asp Ser Asp  Ser Asp Ser Asp Ser  Asp Ala Gly
    1070                 1075                 1080

Lys His  Thr Pro Val Lys Pro  Met Ser Thr Thr Lys  Asp His His
    1085                 1090                 1095

Asn Lys  Ala Lys Ala Leu Pro  Glu Thr Gly Ser Glu  Asn Asn Gly
    1100                 1105                 1110

Ser Asn  Asn Ala Thr Leu Phe  Gly Gly Leu Phe Ala  Ala Leu Gly
    1115                 1120                 1125

Ser Leu  Leu Leu Phe Gly Arg  Arg Lys Lys Gln Asn  Lys
    1130                 1135                 1140


<210> SEQ ID NO 15
<211> LENGTH: 350
<212> TYPE: PRT
<213> ORGANISM: Staphylococcus sp.

<400> SEQUENCE: 15

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

Ser Leu Val Tyr Ile Gly Ala Asp Ser Gln Gln Val Asn Ala Ala Thr
        35                  40                  45

Glu Ala Thr Asn Ala Thr Asn Asn Gln Ser Thr Gln Val Ser Gln Ala
    50                  55                  60

Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
                85                  90                  95

Gln Asn Asn Lys Tyr Tyr Phe Gln Thr Val Leu Asn Asn Ala Ser Phe
            100                 105                 110

Trp Lys Glu Tyr Lys Phe Tyr Asn Ala Asn Asn Gln Glu Leu Ala Thr
```

```
        115                 120                 125

Thr Val Val Asn Asp Asn Lys Lys Ala Asp Thr Arg Thr Ile Asn Val
    130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
        195                 200                 205

Thr Lys Pro Val Gln Pro Lys Val Glu Lys Val Lys Pro Thr Val Thr
    210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
                245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
        275                 280                 285

Asn Lys Ser Gln Gln Thr Asn Lys Val Thr Lys His Asn Glu Thr Pro
    290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
                325                 330                 335

Gly Ser Leu Ser Leu Leu Leu Phe Lys Arg Lys Glu Ser Lys
            340                 345                 350


<210> SEQ ID NO 16
<211> LENGTH: 645
<212> TYPE: PRT
<213> ORGANISM: Staphylococcus sp.

<400> SEQUENCE: 16

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Ala Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
    130                 135                 140
```

-continued

```
Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
```

```
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645


<210> SEQ ID NO 17
<211> LENGTH: 80
<212> TYPE: PRT
<213> ORGANISM: Staphylococcus sp.

<400> SEQUENCE: 17

Met Asn Gln His Val Lys Val Thr Phe Asp Phe Thr Asn Tyr Asn Tyr
1               5                   10                  15

Gly Thr Tyr Asp Leu Ala Val Pro Ala Tyr Leu Pro Ile Lys Asn Leu
            20                  25                  30

Ile Ala Leu Val Leu Asp Ser Leu Asp Ile Ser Ile Phe Asp Val Asn
        35                  40                  45

Thr Gln Ile Lys Val Met Thr Lys Gly Gln Leu Leu Val Glu Asn Asp
    50                  55                  60

Arg Leu Ile Asp Tyr Gln Ile Ala Asp Gly Asp Ile Leu Lys Leu Leu
65                  70                  75                  80


<210> SEQ ID NO 18
<211> LENGTH: 877
<212> TYPE: PRT
<213> ORGANISM: Staphylococcus sp.

<400> SEQUENCE: 18

Met Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110

Ala Ser Thr Asn Glu Thr Pro Gln Pro Thr Ala Ile Lys Asn Gln Ala
        115                 120                 125

Thr Ala Ala Lys Met Gln Asp Gln Thr Val Pro Gln Glu Ala Asn Ser
    130                 135                 140

Gln Val Asp Asn Lys Thr Thr Asn Asp Ala Asn Ser Ile Ala Thr Asn
145                 150                 155                 160

Ser Glu Leu Lys Asn Ser Gln Thr Leu Asp Leu Pro Gln Ser Ser Pro
```

```
                165                 170                 175

Gln Thr Ile Ser Asn Ala Gln Gly Thr Ser Lys Pro Ser Val Arg Thr
            180                 185                 190

Arg Ala Val Arg Ser Leu Ala Val Ala Glu Pro Val Val Asn Ala Ala
        195                 200                 205

Asp Ala Lys Gly Thr Asn Val Asn Asp Lys Val Thr Ala Ser Asn Phe
    210                 215                 220

Lys Leu Glu Lys Thr Thr Phe Asp Pro Asn Gln Ser Gly Asn Thr Phe
225                 230                 235                 240

Met Ala Ala Asn Phe Thr Val Thr Asp Lys Val Lys Ser Gly Asp Tyr
                245                 250                 255

Phe Thr Ala Lys Leu Pro Asp Ser Leu Thr Gly Asn Gly Asp Val Asp
            260                 265                 270

Tyr Ser Asn Ser Asn Asn Thr Met Pro Ile Ala Asp Ile Lys Ser Thr
        275                 280                 285

Asn Gly Asp Val Val Ala Lys Ala Thr Tyr Asp Ile Leu Thr Lys Thr
    290                 295                 300

Tyr Thr Phe Val Phe Thr Asp Tyr Val Asn Asn Lys Glu Asn Ile Asn
305                 310                 315                 320

Gly Gln Phe Ser Leu Pro Leu Phe Thr Asp Arg Ala Lys Ala Pro Lys
                325                 330                 335

Ser Gly Thr Tyr Asp Ala Asn Ile Asn Ile Ala Asp Glu Met Phe Asn
            340                 345                 350

Asn Lys Ile Thr Tyr Asn Tyr Ser Ser Pro Ile Ala Gly Ile Asp Lys
        355                 360                 365

Pro Asn Gly Ala Asn Ile Ser Ser Gln Ile Ile Gly Val Asp Thr Ala
    370                 375                 380

Ser Gly Gln Asn Thr Tyr Lys Gln Thr Val Phe Val Asn Pro Lys Gln
385                 390                 395                 400

Arg Val Leu Gly Asn Thr Trp Val Tyr Ile Lys Gly Tyr Gln Asp Lys
                405                 410                 415

Ile Glu Glu Ser Ser Gly Lys Val Ser Ala Thr Asp Thr Lys Leu Arg
            420                 425                 430

Ile Phe Glu Val Asn Asp Thr Ser Lys Leu Ser Asp Ser Tyr Tyr Ala
        435                 440                 445

Asp Pro Asn Asp Ser Asn Leu Lys Glu Val Thr Asp Gln Phe Lys Asn
    450                 455                 460

Arg Ile Tyr Tyr Glu His Pro Asn Val Ala Ser Ile Lys Phe Gly Asp
465                 470                 475                 480

Ile Thr Lys Thr Tyr Val Val Leu Val Glu Gly His Tyr Asp Asn Thr
                485                 490                 495

Gly Lys Asn Leu Lys Thr Gln Val Ile Gln Glu Asn Val Asp Pro Val
            500                 505                 510

Thr Asn Arg Asp Tyr Ser Ile Phe Gly Trp Asn Asn Glu Asn Val Val
        515                 520                 525

Arg Tyr Gly Gly Gly Ser Ala Asp Gly Asp Ser Ala Val Asn Pro Lys
    530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
            580                 585                 590
```

```
Gly Ser Asp Ser Asp Ser Gly Ser Asp Ser Asp Ser Glu Ser Asp Ser
        595                 600                 605

Asp Ser Asp Ser Asp Ser Asp Ser Asp Ser Asp Ser Asp Ser Glu Ser
    610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
                645                 650                 655

Asp Ser Asp Ser Asp Ser Asp Ser Glu Ser Asp Ser Asp Ser Glu Ser
            660                 665                 670

Asp Ser Glu Ser Asp Ser Asp Ser Asp Ser Asp Ser Asp Ser Asp Ser
        675                 680                 685

Asp Ser Asp Ser Asp Ser Asp Ser Asp Ser Asp Ser Asp Ser Asp Ser
    690                 695                 700

Asp Ser Asp Ser Asp Ser Asp Ser Glu Ser Asp Ser Asp Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
        755                 760                 765

Asp Ser Asp Ser Asp Ser Asp Ser Asp Ser Asp Ser Asp Ser Asp Ser
    770                 775                 780

Asp Ser Asp Ser Asp Ser Asp Ser Asp Ser Asp Ser Asp Ser Asp Ser
785                 790                 795                 800

Asp Ser Asp Ser Arg Val Thr Pro Pro Asn Asn Glu Gln Lys Ala Pro
                805                 810                 815

Ser Asn Pro Lys Gly Glu Val Asn His Ser Asn Lys Val Ser Lys Gln
            820                 825                 830

His Lys Thr Asp Ala Leu Pro Glu Thr Gly Asp Lys Ser Glu Asn Thr
        835                 840                 845

Asn Ala Thr Leu Phe Gly Ala Met Met Ala Leu Leu Gly Ser Leu Leu
    850                 855                 860

Leu Phe Arg Lys Arg Lys Gln Asp His Lys Glu Lys Ala
865                 870                 875


<210> SEQ ID NO 19
<211> LENGTH: 227
<212> TYPE: PRT
<213> ORGANISM: Staphylococcus sp.

<400> SEQUENCE: 19

Met Lys Asn Ile Leu Lys Val Phe Asn Thr Thr Ile Leu Ala Leu Ile
1               5                   10                  15

Ile Ile Ile Ala Thr Phe Ser Asn Ser Ala Asn Ala Ala Asp Ser Gly
            20                  25                  30

Thr Leu Asn Tyr Glu Val Tyr Lys Tyr Asn Thr Asn Asp Thr Ser Ile
        35                  40                  45

Ala Asn Asp Tyr Phe Asn Lys Pro Ala Lys Tyr Ile Lys Lys Asn Gly
    50                  55                  60

Lys Leu Tyr Val Gln Ile Thr Val Asn His Ser His Trp Ile Thr Gly
65                  70                  75                  80

Met Ser Ile Glu Gly His Lys Glu Asn Ile Ile Ser Lys Asn Thr Ala
```

```
                85                  90                  95

Lys Asp Glu Arg Thr Ser Glu Phe Glu Val Ser Lys Leu Asn Gly Lys
            100                 105                 110

Ile Asp Gly Lys Ile Asp Val Tyr Ile Asp Glu Lys Val Asn Gly Lys
        115                 120                 125

Pro Phe Lys Tyr Asp His His Tyr Asn Ile Thr Tyr Lys Phe Asn Gly
    130                 135                 140

Pro Thr Asp Val Ala Gly Ala Asn Ala Pro Gly Lys Asp Asp Lys Asn
145                 150                 155                 160

Ser Ala Ser Gly Ser Asp Lys Gly Ser Asp Gly Thr Thr Thr Gly Gln
                165                 170                 175

Ser Glu Ser Asn Ser Ser Asn Lys Asp Lys Val Glu Asn Pro Gln Thr
            180                 185                 190

Asn Ala Gly Thr Pro Ala Tyr Ile Tyr Ala Ile Pro Val Ala Ser Leu
        195                 200                 205

Ala Leu Leu Ile Ala Ile Thr Leu Phe Val Arg Lys Lys Ser Lys Gly
    210                 215                 220

Asn Val Glu
225


<210> SEQ ID NO 20
<211> LENGTH: 635
<212> TYPE: PRT
<213> ORGANISM: Staphylococcus sp.

<400> SEQUENCE: 20

Met Ala Lys Tyr Arg Gly Lys Pro Phe Gln Leu Tyr Val Lys Leu Ser
1               5                   10                  15

Cys Ser Thr Met Met Ala Ser Ser Ile Ile Leu Thr Asn Ile Leu Pro
            20                  25                  30

Tyr Asp Ala Gln Ala Ala Ser Glu Lys Asp Thr Glu Ile Ser Lys Glu
        35                  40                  45

Ile Leu Ser Lys Gln Asp Leu Leu Asp Lys Val Asp Lys Ala Ile Arg
    50                  55                  60

Gln Ile Glu Gln Leu Lys Gln Leu Ser Ala Ser Ser Lys Ala His Tyr
65                  70                  75                  80

Lys Ala Gln Leu Asn Glu Ala Lys Thr Ala Ser Gln Ile Asp Glu Ile
                85                  90                  95

Ile Lys Arg Ala Asn Glu Leu Asp Ser Lys Glu Asn Lys Ser Ser His
            100                 105                 110

Thr Glu Met Asn Gly Gln Ser Asp Ile Asp Ser Lys Leu Asp Gln Leu
        115                 120                 125

Leu Lys Asp Leu Asn Glu Val Ser Ser Asn Val Asp Arg Gly Gln Gln
    130                 135                 140

Ser Gly Glu Asp Asp Leu Asn Ala Met Lys Asn Asp Met Ser Gln Thr
145                 150                 155                 160

Ala Thr Thr Lys Tyr Gly Glu Lys Asp Asp Lys Asn Asp Glu Ala Met
                165                 170                 175

Val Asn Lys Ala Leu Glu Asp Leu Asp His Leu Asn Gln Gln Ile His
            180                 185                 190

Lys Ser Lys Asp Ala Leu Lys Asp Ala Ser Lys Asp Pro Ala Val Ser
        195                 200                 205

Thr Thr Asp Ser Asn His Glu Val Ala Lys Thr Pro Asn Asn Asp Gly
    210                 215                 220
```

-continued

```
Ser Gly His Val Val Leu Asn Lys Phe Leu Ser Asn Glu Glu Asn Gln
225                 230                 235                 240

Ser His Ser Asn Gln Leu Thr Asp Lys Leu Gln Gly Ser Asp Lys Ile
                245                 250                 255

Asn His Ala Met Ile Glu Lys Leu Ala Lys Ser Asn Ala Ser Thr Gln
            260                 265                 270

His Tyr Thr Tyr His Lys Leu Asn Thr Leu Gln Ser Leu Asp Gln Arg
        275                 280                 285

Ile Ala Asn Thr Gln Leu Pro Lys Asn Gln Lys Ser Asp Leu Met Ser
    290                 295                 300

Glu Val Asn Lys Thr Lys Glu Arg Ile Lys Ser Gln Arg Asn Ile Ile
305                 310                 315                 320

Leu Glu Glu Leu Ala Arg Thr Asp Asp Lys Lys Tyr Ala Thr Gln Ser
                325                 330                 335

Ile Leu Glu Ser Ile Phe Asn Lys Asp Glu Ala Asp Lys Ile Leu Lys
            340                 345                 350

Asp Ile Arg Val Asp Gly Lys Thr Asp Gln Gln Ile Ala Asp Gln Ile
        355                 360                 365

Thr Arg His Ile Asp Gln Leu Ser Leu Thr Thr Ser Asp Asp Leu Leu
    370                 375                 380

Thr Ser Leu Ile Asp Gln Ser Gln Asp Lys Ser Leu Leu Ile Ser Gln
385                 390                 395                 400

Ile Leu Gln Thr Lys Leu Gly Lys Ala Glu Ala Asp Lys Leu Ala Lys
                405                 410                 415

Asp Trp Thr Asn Lys Gly Leu Ser Asn Arg Gln Ile Val Asp Gln Leu
            420                 425                 430

Lys Lys His Phe Ala Ser Thr Gly Asp Thr Ser Ser Asp Asp Ile Leu
        435                 440                 445

Lys Ala Ile Leu Asn Asn Ala Lys Asp Lys Lys Gln Ala Ile Glu Thr
    450                 455                 460

Ile Leu Ala Thr Arg Ile Glu Arg Gln Lys Ala Lys Leu Leu Ala Asp
465                 470                 475                 480

Leu Ile Thr Lys Ile Glu Thr Asp Gln Asn Lys Ile Phe Asn Leu Val
                485                 490                 495

Lys Ser Ala Leu Asn Gly Lys Ala Asp Asp Leu Leu Asn Leu Gln Lys
            500                 505                 510

Arg Leu Asn Gln Thr Lys Lys Asp Ile Asp Tyr Ile Leu Ser Pro Ile
        515                 520                 525

Val Asn Arg Pro Ser Leu Leu Asp Arg Leu Asn Lys Asn Gly Lys Thr
    530                 535                 540

Thr Asp Leu Asn Lys Leu Ala Asn Leu Met Asn Gln Gly Ser Asn Leu
545                 550                 555                 560

Leu Asp Ser Ile Pro Asp Ile Pro Thr Pro Lys Pro Glu Lys Thr Leu
                565                 570                 575

Thr Leu Gly Lys Gly Asn Gly Leu Leu Ser Gly Leu Leu Asn Ala Asp
            580                 585                 590

Gly Asn Val Ser Leu Pro Lys Ala Gly Glu Thr Ile Lys Glu His Trp
        595                 600                 605

Leu Pro Ile Ser Val Ile Val Gly Ala Met Gly Val Leu Met Ile Trp
    610                 615                 620

Leu Ser Arg Arg Asn Lys Leu Lys Asn Lys Ala
625                 630                 635
```

<210> SEQ ID NO 21
<211> LENGTH: 953
<212> TYPE: PRT
<213> ORGANISM: Staphylococcus sp.

<400> SEQUENCE: 21

```
Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
            20                  25                  30

Ile Leu Val Gly Thr Thr Leu Ile Phe Gly Leu Ser Gly His Glu Ala
        35                  40                  45

Lys Ala Ala Glu His Thr Asn Gly Glu Leu Asn Gln Ser Lys Asn Glu
    50                  55                  60

Thr Thr Ala Pro Ser Glu Asn Lys Thr Thr Glu Lys Val Asp Ser Arg
65                  70                  75                  80

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Ser Gln Ser Thr Thr Gln Thr Ser Asn
        115                 120                 125

Val Thr Thr Asn Asp Lys Ser Ser Thr Thr Tyr Ser Asn Glu Thr Asp
    130                 135                 140

Lys Ser Asn Leu Thr Gln Ala Lys Asn Val Ser Thr Thr Pro Lys Thr
145                 150                 155                 160

Thr Thr Ile Lys Gln Arg Ala Leu Asn Arg Met Ala Val Asn Thr Val
                165                 170                 175

Ala Ala Pro Gln Gln Gly Thr Asn Val Asn Asp Lys Val His Phe Thr
            180                 185                 190

Asn Ile Asp Ile Ala Ile Asp Lys Gly His Val Asn Lys Thr Thr Gly
        195                 200                 205

Asn Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Lys Thr Asn Thr Thr Thr Tyr Thr Phe Thr Asn Tyr Val
        275                 280                 285

Asp Gln Tyr Thr Asn Val Ser Gly Ser Phe Glu Gln Val Ala Phe Ala
    290                 295                 300

Lys Arg Glu Asn Ala Thr Thr Asp Lys Thr Ala Tyr Lys Met Glu Val
305                 310                 315                 320

Thr Leu Gly Asn Asp Thr Tyr Ser Lys Asp Val Ile Val Asp Tyr Gly
                325                 330                 335

Asn Gln Lys Gly Gln Gln Leu Ile Ser Ser Thr Asn Tyr Ile Asn Asn
            340                 345                 350

Glu Asp Leu Ser Arg Asn Met Thr Val Tyr Val Asn Gln Pro Lys Lys
        355                 360                 365

Thr Tyr Thr Lys Glu Thr Phe Val Thr Asn Leu Thr Gly Tyr Lys Phe
    370                 375                 380
```

-continued

```
Asn Pro Asp Ala Lys Asn Phe Lys Ile Tyr Glu Val Thr Asp Gln Asn
385                 390                 395                 400

Gln Phe Val Asp Ser Phe Thr Pro Asp Thr Ser Lys Leu Lys Asp Val
                405                 410                 415

Thr Gly Gln Phe Asp Val Ile Tyr Ser Asn Asp Asn Lys Thr Ala Thr
            420                 425                 430

Val Asp Leu Leu Asn Gly Gln Ser Ser Ser Asp Lys Gln Tyr Ile Ile
        435                 440                 445

Gln Gln Val Ala Tyr Pro Asp Asn Ser Ser Thr Asp Asn Gly Lys Ile
    450                 455                 460

Asp Tyr Thr Leu Glu Thr Gln Asn Gly Lys Ser Ser Trp Ser Asn Ser
465                 470                 475                 480

Tyr Ser Asn Val Asn Gly Ser Ser Thr Ala Asn Gly Asp Gln Lys Lys
                485                 490                 495

Tyr Asn Leu Gly Asp Tyr Val Trp Glu Asp Thr Asn Lys Asp Gly Lys
            500                 505                 510

Gln Asp Ala Asn Glu Lys Gly Ile Lys Gly Val Tyr Val Ile Leu Lys
        515                 520                 525

Asp Ser Asn Gly Lys Glu Leu Asp Arg Thr Thr Thr Asp Glu Asn Gly
    530                 535                 540

Lys Tyr Gln Phe Thr Gly Leu Ser Asn Gly Thr Tyr Ser Val Glu Phe
545                 550                 555                 560

Ser Thr Pro Ala Gly Tyr Thr Pro Thr Thr Ala Asn Ala Gly Thr Asp
                565                 570                 575

Asp Ala Val Asp Ser Asp Gly Leu Thr Thr Thr Gly Val Ile Lys Asp
            580                 585                 590

Ala Asp Asn Met Thr Leu Asp Ser Gly Phe Tyr Lys Thr Pro Lys Tyr
        595                 600                 605

Ser Leu Gly Asp Tyr Val Trp Tyr Asp Ser Asn Lys Asp Gly Lys Gln
    610                 615                 620

Asp Ser Thr Glu Lys Gly Ile Lys Gly Val Lys Val Thr Leu Gln Asn
625                 630                 635                 640

Glu Lys Gly Glu Val Ile Gly Thr Thr Glu Thr Asp Glu Asn Gly Lys
                645                 650                 655

Tyr Arg Phe Asp Asn Leu Asp Ser Gly Lys Tyr Lys Val Ile Phe Glu
            660                 665                 670

Lys Pro Ala Gly Leu Thr Gln Thr Gly Thr Asn Thr Thr Glu Asp Asp
        675                 680                 685

Lys Asp Ala Asp Gly Gly Glu Val Asp Val Thr Ile Thr Asp His Asp
    690                 695                 700

Asp Phe Thr Leu Asp Asn Gly Tyr Tyr Glu Glu Glu Thr Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
            740                 745                 750

Asp Ser Asp Ser Asp Ser Asp Ser Asp Ser Asp Ser Asp Ser Asp Ser
        755                 760                 765

Asp Ser Asp Ser Glu Ser Asp Ser Asp Ser Asp Ser Asp Ser Asp Ser
    770                 775                 780

Asp Ser Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser Asp Ser
```

```
                805                 810                 815

Asp Ser Asp Ser Asp Ser Asp Asn Asp Ser Asp Ser Asp Ser Asp Ser
            820                 825                 830

Asp Ser Asp Ser Asp Ser Asp Ser Asp Ser Asp Ser Asp Ser Asp Ser
        835                 840                 845

Asp Ser Asp Ser Asp Ser Asp Ser Asp Ser Asp Ser Asp Ser Asp Ser
    850                 855                 860

Asp Ser Asp Ser Asp Ser Asp Ser Asp Ser Asp Ser Asp Ser Asp Ser
865                 870                 875                 880

Asp Ser Asp Ser Asp Ser Asp Ser Asp Ser Asp Ser Asp Ala Gly Lys
                885                 890                 895

His Thr Pro Thr Lys Pro Met Ser Thr Val Lys Asp Gln His Lys Thr
            900                 905                 910

Ala Lys Ala Leu Pro Glu Thr Gly Ser Glu Asn Asn Asn Ser Asn Asn
        915                 920                 925

Gly Thr Leu Phe Gly Gly Leu Phe Ala Ala Leu Gly Ser Leu Leu Leu
    930                 935                 940

Phe Gly Arg Arg Lys Lys Gln Asn Lys
945                 950


<210> SEQ ID NO 22
<211> LENGTH: 989
<212> TYPE: PRT
<213> ORGANISM: Staphylococcus sp.

<400> SEQUENCE: 22

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Asn Thr Asp Ala Ser Asn Lys Asp Val Val Ser Gln Ala Val Asn Pro
        195                 200                 205

Ser Thr Pro Arg Met Arg Ala Phe Ser Leu Ala Ala Val Ala Ala Asp
    210                 215                 220
```

-continued

```
Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
            340                 345                 350

Thr Thr Gly Ile Gly Thr Asn Thr Ala Ser Lys Thr Val Leu Ile Asp
        355                 360                 365

Tyr Glu Lys Tyr Gly Gln Phe His Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
                405                 410                 415

Ile Pro Asn Thr Lys Ser Asn Ala Leu Ile Asp Ala Lys Asn Thr Asp
            420                 425                 430

Ile Lys Val Tyr Arg Val Asp Asn Ala Asn Asp Leu Ser Glu Ser Tyr
        435                 440                 445

Tyr Val Asn Pro Ser Asp Phe Glu Asp Val Thr Asn Gln Val Arg Ile
    450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Val Asn Gly His Ile Asp
                485                 490                 495

Pro Ala Ser Thr Gly Asp Leu Ala Leu Arg Ser Thr Phe Tyr Gly Tyr
            500                 505                 510

Asp Ser Asn Phe Ile Trp Arg Ser Met Ser Trp Asp Asn Glu Val Ala
        515                 520                 525

Phe Asn Asn Gly Ser Gly Ser Gly Asp Gly Ile Asp Lys Pro Val Val
    530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
            580                 585                 590

Ser Ala Ser Asp Ser Asp Ser Ala Ser Asp Ser Asp Ser Ala Ser Asp
        595                 600                 605

Ser Asp Ser Ala Ser Asp Ser Asp Ser Ala Ser Asp Ser Asp Ser Ala
    610                 615                 620

Ser Asp Ser Asp Ser Ala Ser Asp Ser Asp Ser Ala Ser Asp Ser Asp
625                 630                 635                 640

Ser Ala Ser Asp Ser Asp Ser Ala Ser Asp Ser Asp Ser Ala Ser Asp
```

-continued

```
                645                 650                 655

Ser Asp Ser Ala Ser Asp Ser Asp Ser Ala Ser Asp Ser Asp Ser Asp
            660                 665                 670

Ser Asp Ser Asp Ser Asp Ser Asp Ser Asp Ser Asp Ser Asp Ser Asp
        675                 680                 685

Ser Asp Ser Asp Ser Asp Ser Asp Ser Asp Ser Asp Ser Asp Ser Asp
    690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
            740                 745                 750

Ser Asp Ser Asp Ser Asp Ser Asp Ser Asp Ser Asp Ser Asp Ser Asp
        755                 760                 765

Ser Asp Ser Asp Ser Asp Ser Asp Ser Asp Ser Asp Ser Asp Ser Asp
    770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Asp Ser Asp Ser Asp Ser Asp Ser Asp
                805                 810                 815

Ser Asp Ser Asp Ser Ala Ser Asp Ser Asp Ser Asp Ser Asp Ser Glu
            820                 825                 830

Ser Asp Ser Asp Ser Asp Ser Asp Ser Asp Ser Asp Ser Asp Ser Asp
        835                 840                 845

Ser Asp Ser Asp Ser Asp Ser Glu Ser Asp Ser Asp Ser Asp Ser Asp
    850                 855                 860

Ser Asp Ser Glu Ser Asp Ser Asp Ser Asp Ser Asp Ser Asp Ser Asp
865                 870                 875                 880

Ser Ala Ser Asp Ser Asp Ser Gly Ser Asp Ser Asp Ser Ser Ser Asp
                885                 890                 895

Ser Asp Ser Asp Ser Thr Ser Asp Thr Gly Ser Asp Asn Asp Ser Asp
            900                 905                 910

Ser Asp Ser Asn Ser Asp Ser Glu Ser Gly Ser Asn Asn Asn Val Val
        915                 920                 925

Pro Pro Asn Ser Pro Lys Asn Gly Thr Asn Ala Ser Asn Lys Asn Glu
    930                 935                 940

Ala Lys Asp Ser Lys Glu Pro Leu Pro Asp Thr Gly Ser Glu Asp Glu
945                 950                 955                 960

Ala Asn Thr Ser Leu Ile Trp Gly Leu Leu Ala Ser Leu Gly Ser Leu
                965                 970                 975

Leu Leu Phe Arg Arg Lys Lys Glu Asn Lys Asp Lys Lys
            980                 985


<210> SEQ ID NO 23
<211> LENGTH: 584
<212> TYPE: PRT
<213> ORGANISM: Staphylococcus sp.

<400> SEQUENCE: 23

Met Lys Phe Lys Ser Leu Ile Thr Thr Thr Leu Ala Leu Gly Val Leu
1               5                   10                  15

Ala Ser Thr Gly Ala Asn Phe Asn Asn Asn Glu Ala Ser Ala Ala Ala
            20                  25                  30
```

```
Lys Pro Leu Asp Lys Ser Ser Ser Ser Leu His His Gly Tyr Ser Lys
        35                  40                  45

Val His Val Pro Tyr Ala Ile Thr Val Asn Gly Thr Ser Gln Asn Ile
    50                  55                  60

Leu Ser Ser Leu Thr Phe Asn Lys Asn Gln Asn Ile Ser Tyr Lys Asp
65                  70                  75                  80

Leu Glu Asp Arg Val Lys Ser Val Leu Lys Ser Asp Arg Gly Ile Ser
                85                  90                  95

Asp Ile Asp Leu Arg Leu Ser Lys Gln Ala Lys Tyr Thr Val Tyr Phe
            100                 105                 110

Lys Asn Gly Thr Lys Lys Val Ile Asp Leu Lys Ala Gly Ile Tyr Thr
        115                 120                 125

Ala Asp Leu Ile Asn Thr Ser Glu Ile Lys Ala Ile Asn Ile Asn Val
    130                 135                 140

Asp Thr Lys Lys Gln Val Glu Asp Lys Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
        195                 200                 205

Val Asp Leu Arg Leu Ser Lys Gln Ala Lys Tyr Thr Val Asn Phe Lys
    210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
            260                 265                 270

Tyr Ser Ile Asn Leu Asn Gly Thr Ser Thr Asn Ile Leu Ser Asn Leu
        275                 280                 285

Ser Phe Ser Asn Lys Pro Trp Thr Asn Tyr Lys Asn Leu Thr Ser Gln
    290                 295                 300

Ile Lys Ser Val Leu Lys His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Lys Asn Tyr Thr Ala Asn Leu Val
            340                 345                 350

His Ala Lys Asp Val Lys Arg Ile Glu Ile Thr Val Lys Thr Gly Thr
        355                 360                 365

Lys Ala Lys Ala Asp Arg Tyr Val Pro Tyr Thr Ile Ala Val Asn Gly
    370                 375                 380

Thr Ser Thr Pro Ile Leu Ser Asp Leu Lys Phe Thr Gly Asp Pro Arg
385                 390                 395                 400

Val Gly Tyr Lys Asp Ile Ser Lys Lys Val Lys Ser Val Leu Lys His
                405                 410                 415

Asp Arg Gly Ile Gly Glu Arg Glu Leu Lys Tyr Ala Lys Lys Ala Thr
            420                 425                 430

Tyr Thr Val His Phe Lys Asn Gly Thr Lys Lys Val Ile Asn Ile Asn
        435                 440                 445

Ser Asn Ile Ser Gln Leu Asn Leu Leu Tyr Val Gln Asp Ile Lys Lys
```

```
    450                 455                 460

Ile Asp Ile Asp Val Lys Thr Gly Thr Lys Ala Lys Ala Asp Ser Tyr
465                 470                 475                 480

Val Pro Tyr Thr Ile Ala Val Asn Gly Thr Ser Thr Pro Ile Leu Ser
                485                 490                 495

Lys Leu Lys Ile Ser Asn Lys Gln Leu Ile Ser Tyr Lys Tyr Leu Asn
            500                 505                 510

Asp Lys Val Lys Ser Val Leu Lys Ser Glu Arg Gly Ile Ser Asp Leu
        515                 520                 525

Asp Leu Lys Phe Ala Lys Gln Ala Lys Tyr Thr Val Tyr Phe Lys Asn
    530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
                565                 570                 575

Tyr Thr Lys Ser Lys Lys Asn Lys
            580


<210> SEQ ID NO 24
<211> LENGTH: 10419
<212> TYPE: PRT
<213> ORGANISM: Staphylococcus sp.

<400> SEQUENCE: 24

Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
            20                  25                  30

Asn Thr Ser Gln Ala His Ala Ala Glu Thr Asn Gln Pro Ala Ser Val
        35                  40                  45

Val Lys Gln Lys Gln Gln Ser Asn Asn Glu Gln Thr Glu Asn Arg Glu
    50                  55                  60

Ser Gln Val Gln Asn Ser Gln Asn Ser Gln Asn Gly Gln Ser Leu Ser
65                  70                  75                  80

Ala Thr His Glu Asn Glu Gln Pro Asn Ile Ser Gln Ala Asn Leu Val
                85                  90                  95

Asp Gln Lys Val Ala Gln Ser Ser Thr Thr Asn Asp Glu Gln Pro Ala
            100                 105                 110

Ser Gln Asn Val Asn Thr Lys Lys Asp Ser Ala Thr Ala Ala Thr Thr
        115                 120                 125

Gln Pro Asp Lys Glu Gln Ser Lys His Lys Gln Asn Glu Ser Gln Ser
    130                 135                 140

Ala Asn Lys Asn Gly Asn Asp Asn Arg Ala Ala His Val Glu Asn His
145                 150                 155                 160

Glu Ala Asn Val Val Thr Ala Ser Asp Ser Ser Asp Asn Gly Asn Val
                165                 170                 175

Gln His Asp Arg Asn Glu Leu Gln Ala Phe Phe Asp Ala Asn Tyr His
            180                 185                 190

Asp Tyr Arg Phe Ile Asp Arg Glu Asn Ala Asp Ser Gly Thr Phe Asn
        195                 200                 205

Tyr Val Lys Gly Ile Phe Asp Lys Ile Asn Thr Leu Leu Gly Ser Asn
    210                 215                 220

Asp Pro Ile Asn Asn Lys Asp Leu Gln Leu Ala Tyr Lys Glu Leu Glu
225                 230                 235                 240
```

-continued

```
Gln Ala Val Ala Leu Ile Arg Thr Met Pro Gln Arg Gln Gln Thr Ser
                245                 250                 255

Arg Arg Ser Asn Arg Ile Gln Thr Arg Ser Val Glu Ser Arg Ala Ala
            260                 265                 270

Glu Pro Arg Ser Val Ser Asp Tyr Gln Asn Ala Asn Ser Ser Tyr Tyr
        275                 280                 285

Val Glu Asn Ala Asn Asp Gly Ser Gly Tyr Pro Val Gly Thr Tyr Ile
    290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
            340                 345                 350

His Ala Pro His Gln Asn Met Ile Phe Trp Phe Ala Leu Pro Ala Asp
        355                 360                 365

Gln Val Pro Val Gly Arg Thr Asp Phe Val Thr Val Asn Ser Asp Gly
    370                 375                 380

Thr Asn Val Gln Trp Ser His Gly Ala Gly Ala Gly Ala Asn Lys Pro
385                 390                 395                 400

Leu Gln Gln Met Trp Glu Tyr Gly Val Asn Asp Pro His Arg Ser His
                405                 410                 415

Asp Phe Lys Ile Arg Asn Arg Ser Gly Gln Val Ile Tyr Asp Trp Pro
            420                 425                 430

Thr Val His Ile Tyr Ser Leu Glu Asp Leu Ser Arg Ala Ser Asp Tyr
        435                 440                 445

Phe Ser Glu Ala Gly Ala Thr Pro Ala Thr Lys Ala Phe Gly Arg Gln
    450                 455                 460

Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Tyr Ala Ala
            500                 505                 510

Gly Gly Arg Ala Leu Glu Tyr Asn Gln Leu Phe Met Tyr Ser Gln Leu
        515                 520                 525

Tyr Val Glu Ser Thr Gln Asp His Gln Gln Arg Leu Asn Gly Leu Arg
    530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn
                565                 570                 575

Leu Asn Ile Asp Asp Phe Val Asp Asp Pro Leu Ser Tyr Val Lys Thr
            580                 585                 590

Pro Ser Asn Lys Val Leu Gly Phe Tyr Ser Asn Asn Ala Asn Thr Asn
        595                 600                 605

Ala Phe Arg Pro Gly Gly Ala Gln Gln Leu Asn Glu Tyr Gln Leu Ser
    610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Ala Tyr Gly Asn
                645                 650                 655

Ser Glu Thr Leu Val Pro Val Asn Leu Thr Val Leu Pro Glu Ile Gln
```

```
            660                 665                 670

His Asn Ile Lys Phe Phe Lys Asn Asp Asp Thr Gln Asn Ile Ala Glu
        675                 680                 685

Lys Pro Phe Ser Lys Gln Ala Gly His Pro Val Phe Tyr Val Tyr Ala
    690                 695                 700

Gly Asn Gln Gly Asn Ala Ser Val Asn Leu Gly Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
            740                 745                 750

Ser Thr Asn Arg Pro Asn Asn Ala Arg Glu Arg Asn Ile Glu Leu Val
        755                 760                 765

Gly Asn Leu Leu Pro Gly Asp Tyr Phe Gly Thr Ile Arg Phe Gly Arg
    770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
            820                 825                 830

Val Ala Pro Thr Asn Gln Thr Thr Asn Gly Gly Ser Glu Ala Asp Gln
        835                 840                 845

Ile Pro Ser Gly Tyr Thr Ile Leu Ala Thr Gly Thr Pro Asp Gly Val
    850                 855                 860

His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
                885                 890                 895

Ala Ser Asn Met Ser Asn Ala Val Thr Ile Leu Pro Asp Asp Ile Pro
            900                 905                 910

Pro Thr Ile Asn Asn Pro Val Gly Ile Asn Ala Lys Tyr Tyr Arg Gly
        915                 920                 925

Asp Glu Val Asn Phe Thr Met Gly Val Ser Asp Arg His Ser Gly Ile
    930                 935                 940

Lys Asn Thr Thr Ile Thr Thr Leu Pro Asn Gly Trp Thr Ser Asn Leu
945                 950                 955                 960

Thr Lys Ala Asp Lys Asn Asn Gly Ser Leu Ser Ile Thr Gly Arg Val
                965                 970                 975

Ser Met Asn Gln Ala Phe Asn Ser Asp Ile Thr Phe Lys Val Ser Ala
            980                 985                 990

Thr Asp Asn Val Asn Asn Thr Thr  Asn Asp Ser Gln Ser  Lys His Val
        995                 1000                1005

Ser Ile  His Val Gly Lys Ile  Ser Glu Asp Ala His  Pro Ile Val
    1010                1015                1020

Leu Gly  Asn Thr Glu Lys Val  Val Val Val Asn Pro  Thr Ala Val
    1025                1030                1035

Ser Asn  Asp Glu Lys Gln Ser  Ile Ile Thr Ala Phe  Met Asn Lys
    1040                1045                1050

Asn Gln  Asn Ile Arg Gly Tyr  Leu Ala Ser Thr Asp  Pro Val Thr
    1055                1060                1065

Val Asp  Asn Asn Gly Asn Val  Thr Leu His Tyr Arg  Asp Gly Ser
    1070                1075                1080
```

```
Ser Thr  Thr Leu Asp Ala Thr  Asn Val Met Thr Tyr  Glu Pro Val
    1085                 1090                 1095

Val Lys  Pro Glu Tyr Gln Thr  Val Asn Ala Ala Lys  Thr Ala Thr
    1100                 1105                 1110

Val Thr  Ile Ala Lys Gly Gln  Ser Phe Ser Ile Gly  Asp Ile Lys
    1115                 1120                 1125

Gln Tyr  Phe Thr Leu Ser Asn  Gly Gln Pro Ile Pro  Ser Gly Thr
    1130                 1135                 1140

Phe Thr  Asn Ile Thr Ser Asp  Arg Thr Ile Pro Thr  Ala Gln Glu
    1145                 1150                 1155

Val Ser  Gln Met Asn Ala Gly  Thr Gln Leu Tyr His  Ile Thr Ala
    1160                 1165                 1170

Thr Asn  Ala Tyr His Lys Asp  Ser Glu Asp Phe Tyr  Ile Ser Leu
    1175                 1180                 1185

Lys Ile  Ile Asp Val Lys Gln  Pro Glu Gly Asp Gln  Arg Val Tyr
    1190                 1195                 1200

Arg Thr  Ser Thr Tyr Asp Leu  Thr Thr Asp Glu Ile  Ser Lys Val
    1205                 1210                 1215

Lys Gln  Ala Phe Ile Asn Ala  Asn Arg Asp Val Ile  Thr Leu Ala
    1220                 1225                 1230

Glu Gly  Asp Ile Ser Val Thr  Asn Thr Pro Asn Gly  Ala Asn Val
    1235                 1240                 1245

Ser Thr  Ile Thr Val Asn Ile  Asn Lys Gly Arg Leu  Thr Lys Ser
    1250                 1255                 1260

Phe Ala  Ser Asn Leu Ala Asn  Met Asn Phe Leu Arg  Trp Val Asn
    1265                 1270                 1275

Phe Pro  Gln Asp Tyr Thr Val  Thr Trp Thr Asn Ala  Lys Ile Ala
    1280                 1285                 1290

Asn Arg  Pro Thr Asp Gly Gly  Leu Ser Trp Ser Asp  Asp His Lys
    1295                 1300                 1305

Ser Leu  Ile Tyr Arg Tyr Asp  Ala Thr Leu Gly Thr  Gln Ile Thr
    1310                 1315                 1320

Thr Asn  Asp Ile Leu Thr Met  Leu Lys Ala Thr Thr  Thr Val Pro
    1325                 1330                 1335

Gly Leu  Arg Asn Asn Ile Thr  Gly Asn Glu Lys Ser  Gln Ala Glu
    1340                 1345                 1350

Ala Gly  Gly Arg Pro Asn Phe  Arg Thr Thr Gly Tyr  Ser Gln Ser
    1355                 1360                 1365

Asn Ala  Thr Thr Asp Gly Gln  Arg Gln Phe Thr Leu  Asn Gly Gln
    1370                 1375                 1380

Val Ile  Gln Val Leu Asp Ile  Ile Asn Pro Ser Asn  Gly Tyr Gly
    1385                 1390                 1395

Gly Gln  Pro Val Thr Asn Ser  Asn Thr Arg Ala Asn  His Ser Asn
    1400                 1405                 1410

Ser Thr  Val Val Asn Val Asn  Glu Pro Ala Ala Asn  Gly Ala Gly
    1415                 1420                 1425

Ala Phe  Thr Ile Asp His Val  Val Lys Ser Asn Ser  Thr His Asn
    1430                 1435                 1440

Ala Ser  Asp Ala Val Tyr Lys  Ala Gln Leu Tyr Leu  Thr Pro Tyr
    1445                 1450                 1455

Gly Pro  Lys Gln Tyr Val Glu  His Leu Asn Gln Asn  Thr Gly Asn
    1460                 1465                 1470
```

```
Thr Thr  Asp Ala Ile Asn Ile  Tyr Phe Val Pro Ser  Asp Leu Val
    1475                 1480                 1485

Asn Pro  Thr Ile Ser Val Gly  Asn Tyr Thr Asn His  Gln Val Phe
    1490                 1495                 1500

Ser Gly  Glu Thr Phe Thr Asn  Thr Ile Thr Ala Asn  Asp Asn Phe
    1505                 1510                 1515

Gly Val  Gln Ser Val Thr Val  Pro Asn Thr Ser Gln  Ile Thr Gly
    1520                 1525                 1530

Thr Val  Asp Asn Asn His Gln  His Val Ser Ala Thr  Ala Pro Asn
    1535                 1540                 1545

Val Thr  Ser Ala Thr Asn Lys  Thr Ile Asn Leu Leu  Ala Thr Asp
    1550                 1555                 1560

Thr Ser  Gly Asn Thr Ala Thr  Thr Ser Phe Asn Val  Thr Val Lys
    1565                 1570                 1575

Pro Leu  Arg Asp Lys Tyr Arg  Val Gly Thr Ser Ser  Thr Ala Ala
    1580                 1585                 1590

Asn Pro  Val Arg Ile Ala Asn  Ile Ser Asn Asn Ala  Thr Val Ser
    1595                 1600                 1605

Gln Ala  Asp Gln Thr Thr Ile  Ile Asn Ser Leu Thr  Phe Thr Glu
    1610                 1615                 1620

Thr Val  Pro Asn Arg Ser Tyr  Ala Arg Ala Ser Ala  Asn Glu Ile
    1625                 1630                 1635

Thr Ser  Lys Thr Val Ser Asn  Val Ser Arg Thr Gly  Asn Asn Ala
    1640                 1645                 1650

Asn Val  Thr Val Thr Val Thr  Tyr Gln Asp Gly Thr  Thr Ser Thr
    1655                 1660                 1665

Val Thr  Val Pro Val Lys His  Val Ile Pro Glu Ile  Val Ala His
    1670                 1675                 1680

Ser His  Tyr Thr Val Gln Gly  Gln Asp Phe Pro Ala  Gly Asn Gly
    1685                 1690                 1695

Ser Ser  Ala Ser Asp Tyr Phe  Lys Leu Ser Asn Gly  Ser Asp Ile
    1700                 1705                 1710

Ala Asp  Ala Thr Ile Thr Trp  Val Ser Gly Gln Ala  Pro Asn Lys
    1715                 1720                 1725

Asp Asn  Thr Arg Ile Gly Glu  Asp Ile Thr Val Thr  Ala His Ile
    1730                 1735                 1740

Leu Ile  Asp Gly Glu Thr Thr  Pro Ile Thr Lys Thr  Ala Thr Tyr
    1745                 1750                 1755

Lys Val  Val Arg Thr Val Pro  Lys His Val Phe Glu  Thr Ala Arg
    1760                 1765                 1770

Gly Val  Leu Tyr Pro Gly Val  Ser Asp Met Tyr Asp  Ala Lys Gln
    1775                 1780                 1785

Tyr Val  Lys Pro Val Asn Asn  Ser Trp Ser Thr Asn  Ala Gln His
    1790                 1795                 1800

Met Asn  Phe Gln Phe Val Gly  Thr Tyr Gly Pro Asn  Lys Asp Val
    1805                 1810                 1815

Val Gly  Ile Ser Thr Arg Leu  Ile Arg Val Thr Tyr  Asp Asn Arg
    1820                 1825                 1830

Gln Thr  Glu Asp Leu Thr Ile  Leu Ser Lys Val Lys  Pro Asp Pro
    1835                 1840                 1845

Pro Arg  Ile Asp Ala Asn Ser  Val Thr Tyr Lys Ala  Gly Leu Thr
    1850                 1855                 1860

Asn Gln  Glu Ile Lys Val Asn  Asn Val Leu Asn Asn  Ser Ser Val
```

```
    1865                1870                1875

Lys Leu  Phe Lys Ala Asp Asn  Thr Pro Leu Asn Val  Thr Asn Ile
    1880                1885                1890

Thr His  Gly Ser Gly Phe Ser  Ser Val Val Thr Val  Ser Asp Ala
    1895                1900                1905

Leu Pro  Asn Gly Gly Ile Lys  Ala Lys Ser Ser Ile  Ser Met Asn
    1910                1915                1920

Asn Val  Thr Tyr Thr Thr Gln  Asp Glu His Gly Gln  Val Val Thr
    1925                1930                1935

Val Thr  Arg Asn Glu Ser Val  Asp Ser Asn Asp Ser  Ala Thr Val
    1940                1945                1950

Thr Val  Thr Pro Gln Leu Gln  Ala Thr Thr Glu Gly  Ala Val Phe
    1955                1960                1965

Ile Lys  Gly Gly Asp Gly Phe  Asp Phe Gly His Val  Glu Arg Phe
    1970                1975                1980

Ile Gln  Asn Pro Pro His Gly  Ala Thr Val Ala Trp  His Asp Ser
    1985                1990                1995

Pro Asp  Thr Trp Lys Asn Thr  Val Gly Asn Thr His  Lys Thr Ala
    2000                2005                2010

Val Val  Thr Leu Pro Asn Gly  Gln Gly Thr Arg Asn  Val Glu Val
    2015                2020                2025

Pro Val  Lys Val Tyr Pro Val  Ala Asn Ala Lys Ala  Pro Ser Arg
    2030                2035                2040

Asp Val  Lys Gly Gln Asn Leu  Thr Asn Gly Thr Asp  Ala Met Asn
    2045                2050                2055

Tyr Ile  Thr Phe Asp Pro Asn  Thr Asn Thr Asn Gly  Ile Thr Ala
    2060                2065                2070

Ala Trp  Ala Asn Arg Gln Gln  Pro Asn Asn Gln Gln  Ala Gly Val
    2075                2080                2085

Gln His  Leu Asn Val Asp Val  Thr Tyr Pro Gly Ile  Ser Ala Ala
    2090                2095                2100

Lys Arg  Val Pro Val Thr Val  Asn Val Tyr Gln Phe  Glu Phe Pro
    2105                2110                2115

Gln Thr  Thr Tyr Thr Thr Thr  Val Gly Gly Thr Leu  Ala Ser Gly
    2120                2125                2130

Thr Gln  Ala Ser Gly Tyr Ala  His Met Gln Asn Ala  Thr Gly Leu
    2135                2140                2145

Pro Thr  Asp Gly Phe Thr Tyr  Lys Trp Asn Arg Asp  Thr Thr Gly
    2150                2155                2160

Thr Asn  Asp Ala Asn Trp Ser  Ala Met Asn Lys Pro  Asn Val Ala
    2165                2170                2175

Lys Val  Val Asn Ala Lys Tyr  Asp Val Ile Tyr Asn  Gly His Thr
    2180                2185                2190

Phe Ala  Thr Ser Leu Pro Ala  Lys Phe Val Val Lys  Asp Val Gln
    2195                2200                2205

Pro Ala  Lys Pro Thr Val Thr  Glu Thr Ala Ala Gly  Ala Ile Thr
    2210                2215                2220

Ile Ala  Pro Gly Ala Asn Gln  Thr Val Asn Thr His  Ala Gly Asn
    2225                2230                2235

Val Thr  Thr Tyr Ala Asp Lys  Leu Val Ile Lys Arg  Asn Gly Asn
    2240                2245                2250

Val Val  Thr Thr Phe Thr Arg  Arg Asn Asn Thr Ser  Pro Trp Val
    2255                2260                2265
```

```
Lys Glu  Ala Ser Ala Ala Thr  Val Ala Gly Ile Ala  Gly Thr Asn
    2270                 2275                 2280

Asn Gly  Ile Thr Val Ala Ala  Gly Thr Phe Asn Pro  Ala Asp Thr
    2285                 2290                 2295

Ile Gln  Val Val Ala Thr Gln  Gly Ser Gly Glu Thr  Val Ser Asp
    2300                 2305                 2310

Glu Gln  Arg Ser Asp Asp Phe  Thr Val Val Ala Pro  Gln Pro Asn
    2315                 2320                 2325

Gln Ala  Thr Thr Lys Ile Trp  Gln Asn Gly His Ile  Asp Ile Thr
    2330                 2335                 2340

Pro Asn  Asn Pro Ser Gly His  Leu Ile Asn Pro Thr  Gln Ala Met
    2345                 2350                 2355

Asp Ile  Ala Tyr Thr Glu Lys  Val Gly Asn Gly Ala  Glu His Ser
    2360                 2365                 2370

Lys Thr  Ile Asn Val Val Arg  Gly Gln Asn Asn Gln  Trp Thr Ile
    2375                 2380                 2385

Ala Asn  Lys Pro Asp Tyr Val  Thr Leu Asp Ala Gln  Thr Gly Lys
    2390                 2395                 2400

Val Thr  Phe Asn Ala Asn Thr  Ile Lys Pro Asn Ser  Ser Ile Thr
    2405                 2410                 2415

Ile Thr  Pro Lys Ala Gly Thr  Gly His Ser Val Ser  Ser Asn Pro
    2420                 2425                 2430

Ser Thr  Leu Thr Ala Pro Ala  Ala His Thr Val Asn  Thr Thr Glu
    2435                 2440                 2445

Ile Val  Lys Asp Tyr Gly Ser  Asn Val Thr Ala Ala  Glu Ile Asn
    2450                 2455                 2460

Asn Ala  Val Gln Val Ala Asn  Lys Arg Thr Ala Thr  Ile Lys Asn
    2465                 2470                 2475

Gly Thr  Ala Met Pro Thr Asn  Leu Ala Gly Gly Ser  Thr Thr Thr
    2480                 2485                 2490

Ile Pro  Val Thr Val Thr Tyr  Asn Asp Gly Ser Thr  Glu Glu Val
    2495                 2500                 2505

Gln Glu  Ser Ile Phe Thr Lys  Ala Asp Lys Arg Glu  Leu Ile Thr
    2510                 2515                 2520

Ala Lys  Asn His Leu Asp Asp  Pro Val Ser Thr Glu  Gly Lys Lys
    2525                 2530                 2535

Pro Gly  Thr Ile Thr Gln Tyr  Asn Asn Ala Met His  Asn Ala Gln
    2540                 2545                 2550

Gln Gln  Ile Asn Thr Ala Lys  Thr Glu Ala Gln Gln  Val Ile Asn
    2555                 2560                 2565

Asn Glu  Arg Ala Thr Pro Gln  Gln Val Ser Asp Ala  Leu Thr Lys
    2570                 2575                 2580

Val Arg  Ala Ala Gln Thr Lys  Ile Asp Gln Ala Lys  Ala Leu Leu
    2585                 2590                 2595

Gln Asn  Lys Glu Asp Asn Ser  Gln Leu Val Thr Ser  Lys Asn Asn
    2600                 2605                 2610

Leu Gln  Ser Ser Val Asn Gln  Val Pro Ser Thr Ala  Gly Met Thr
    2615                 2620                 2625

Gln Gln  Ser Ile Asp Asn Tyr  Asn Ala Lys Lys Arg  Glu Ala Glu
    2630                 2635                 2640

Thr Glu  Ile Thr Ala Ala Gln  Arg Val Ile Asp Asn  Gly Asp Ala
    2645                 2650                 2655
```

```
Thr Ala  Gln Gln Ile Ser Asp  Glu Lys His Arg Val  Asp Asn Ala
    2660                 2665                 2670

Leu Thr  Ala Leu Asn Gln Ala  Lys His Asp Leu Thr  Ala Asp Thr
    2675                 2680                 2685

His Ala  Leu Glu Gln Ala Val  Gln Gln Leu Asn Arg  Thr Gly Thr
    2690                 2695                 2700

Thr Thr  Gly Lys Lys Pro Ala  Ser Ile Thr Ala Tyr  Asn Asn Ser
    2705                 2710                 2715

Ile Arg  Ala Leu Gln Ser Asp  Leu Thr Ser Ala Lys  Asn Ser Ala
    2720                 2725                 2730

Asn Ala  Ile Ile Gln Lys Pro  Ile Arg Thr Val Gln  Glu Val Gln
    2735                 2740                 2745

Ser Ala  Leu Thr Asn Val Asn  Arg Val Asn Glu Arg  Leu Thr Gln
    2750                 2755                 2760

Ala Ile  Asn Gln Leu Val Pro  Leu Ala Asp Asn Ser  Ala Leu Lys
    2765                 2770                 2775

Thr Ala  Lys Thr Lys Leu Asp  Glu Glu Ile Asn Lys  Ser Val Thr
    2780                 2785                 2790

Thr Asp  Gly Met Thr Gln Ser  Ser Ile Gln Ala Tyr  Glu Asn Ala
    2795                 2800                 2805

Lys Arg  Ala Gly Gln Thr Glu  Ser Thr Asn Ala Gln  Asn Val Ile
    2810                 2815                 2820

Asn Asn  Gly Asp Ala Thr Asp  Gln Gln Ile Ala Ala  Glu Lys Thr
    2825                 2830                 2835

Lys Val  Glu Glu Lys Tyr Asn  Ser Leu Lys Gln Ala  Ile Ala Gly
    2840                 2845                 2850

Leu Thr  Pro Asp Leu Ala Pro  Leu Gln Thr Ala Lys  Thr Gln Leu
    2855                 2860                 2865

Gln Asn  Asp Ile Asp Gln Pro  Thr Ser Thr Thr Gly  Met Thr Ser
    2870                 2875                 2880

Ala Ser  Ile Ala Ala Phe Asn  Glu Lys Leu Ser Ala  Ala Arg Thr
    2885                 2890                 2895

Lys Ile  Gln Glu Ile Asp Arg  Val Leu Ala Ser His  Pro Asp Val
    2900                 2905                 2910

Ala Thr  Ile Arg Gln Asn Val  Thr Ala Ala Asn Ala  Ala Lys Ser
    2915                 2920                 2925

Ala Leu  Asp Gln Ala Arg Asn  Gly Leu Thr Val Asp  Lys Ala Pro
    2930                 2935                 2940

Leu Glu  Asn Ala Lys Asn Gln  Leu Gln His Ser Ile  Asp Thr Gln
    2945                 2950                 2955

Thr Ser  Thr Thr Gly Met Thr  Gln Asp Ser Ile Asn  Ala Tyr Asn
    2960                 2965                 2970

Ala Lys  Leu Thr Ala Ala Arg  Asn Lys Ile Gln Gln  Ile Asn Gln
    2975                 2980                 2985

Val Leu  Ala Gly Ser Pro Thr  Val Glu Gln Ile Asn  Thr Asn Thr
    2990                 2995                 3000

Ser Thr  Ala Asn Gln Ala Lys  Ser Asp Leu Asp His  Ala Arg Gln
    3005                 3010                 3015

Ala Leu  Thr Pro Asp Lys Ala  Pro Leu Gln Thr Ala  Lys Thr Gln
    3020                 3025                 3030

Leu Glu  Gln Ser Ile Asn Gln  Pro Thr Asp Thr Thr  Gly Met Thr
    3035                 3040                 3045

Thr Ala  Ser Leu Asn Ala Tyr  Asn Gln Lys Leu Gln  Ala Ala Arg
```

```
    3050                3055                3060

Gln Lys  Leu Thr Glu Ile Asn  Gln Val Leu Asn Gly  Asn Pro Thr
    3065                3070                3075

Val Gln  Asn Ile Asn Asp Lys  Val Thr Glu Ala Asn  Gln Ala Lys
    3080                3085                3090

Asp Gln  Leu Asn Thr Ala Arg  Gln Gly Leu Thr Leu  Asp Arg Gln
    3095                3100                3105

Pro Ala  Leu Thr Thr Leu His  Gly Ala Ser Asn Leu  Asn Gln Ala
    3110                3115                3120

Gln Gln  Asn Asn Phe Thr Gln  Gln Ile Asn Ala Ala  Gln Asn His
    3125                3130                3135

Ala Ala  Leu Glu Thr Ile Lys  Ser Asn Ile Thr Ala  Leu Asn Thr
    3140                3145                3150

Ala Met  Thr Lys Leu Lys Asp  Ser Val Ala Asp Asn  Asn Thr Ile
    3155                3160                3165

Lys Ser  Asp Gln Asn Tyr Thr  Asp Ala Thr Pro Ala  Asn Lys Gln
    3170                3175                3180

Ala Tyr  Asp Asn Ala Val Asn  Ala Ala Lys Gly Val  Ile Gly Glu
    3185                3190                3195

Thr Thr  Asn Pro Thr Met Asp  Val Asn Thr Val Asn  Gln Lys Ala
    3200                3205                3210

Ala Ser  Val Lys Ser Thr Lys  Asp Ala Leu Asp Gly  Gln Gln Asn
    3215                3220                3225

Leu Gln  Arg Ala Lys Thr Glu  Ala Thr Asn Ala Ile  Thr His Ala
    3230                3235                3240

Ser Asp  Leu Asn Gln Ala Gln  Lys Asn Ala Leu Thr  Gln Gln Val
    3245                3250                3255

Asn Ser  Ala Gln Asn Val Gln  Ala Val Asn Asp Ile  Lys Gln Thr
    3260                3265                3270

Thr Gln  Ser Leu Asn Thr Ala  Met Thr Gly Leu Lys  Arg Gly Val
    3275                3280                3285

Ala Asn  His Asn Gln Val Val  Gln Ser Asp Asn Tyr  Val Asn Ala
    3290                3295                3300

Asp Thr  Asn Lys Lys Asn Asp  Tyr Asn Asn Ala Tyr  Asn His Ala
    3305                3310                3315

Asn Asp  Ile Ile Asn Gly Asn  Ala Gln His Pro Val  Ile Thr Pro
    3320                3325                3330

Ser Asp  Val Asn Asn Ala Leu  Ser Asn Val Thr Ser  Lys Glu His
    3335                3340                3345

Ala Leu  Asn Gly Glu Ala Lys  Leu Asn Ala Ala Lys  Gln Glu Ala
    3350                3355                3360

Asn Thr  Ala Leu Gly His Leu  Asn Asn Leu Asn Asn  Ala Gln Arg
    3365                3370                3375

Gln Asn  Leu Gln Ser Gln Ile  Asn Gly Ala His Gln  Ile Asp Ala
    3380                3385                3390

Val Asn  Thr Ile Lys Gln Asn  Ala Thr Asn Leu Asn  Ser Ala Met
    3395                3400                3405

Gly Asn  Leu Arg Gln Ala Val  Ala Asp Lys Asp Gln  Val Lys Arg
    3410                3415                3420

Thr Glu  Asp Tyr Ala Asp Ala  Asp Thr Ala Lys Gln  Asn Ala Tyr
    3425                3430                3435

Asn Ser  Ala Val Ser Ser Ala  Glu Thr Ile Ile Asn  Gln Thr Thr
    3440                3445                3450
```

-continued

```
Asn Pro  Thr Met Ser Val Asp  Asp Val Asn Arg Ala  Thr Ser Ala
    3455                 3460                 3465

Val Thr  Ser Asn Lys Asn Ala  Leu Asn Gly Tyr Glu  Lys Leu Ala
    3470                 3475                 3480

Gln Ser  Lys Thr Asp Ala Ala  Arg Ala Ile Asp Ala  Leu Pro His
    3485                 3490                 3495

Leu Asn  Asn Ala Gln Lys Ala  Asp Val Lys Ser Lys  Ile Asn Ala
    3500                 3505                 3510

Ala Ser  Asn Ile Ala Gly Val  Asn Thr Val Lys Gln  Gln Gly Thr
    3515                 3520                 3525

Asp Leu  Asn Thr Ala Met Gly  Asn Leu Gln Gly Ala  Ile Asn Asp
    3530                 3535                 3540

Glu Gln  Thr Thr Leu Asn Ser  Gln Asn Tyr Gln Asp  Ala Thr Pro
    3545                 3550                 3555

Ser Lys  Lys Thr Ala Tyr Thr  Asn Ala Val Gln Ala  Ala Lys Asp
    3560                 3565                 3570

Ile Leu  Asn Lys Ser Asn Gly  Gln Asn Lys Thr Lys  Asp Gln Val
    3575                 3580                 3585

Thr Glu  Ala Met Asn Gln Val  Asn Ser Ala Lys Asn  Asn Leu Asp
    3590                 3595                 3600

Gly Thr  Arg Leu Leu Asp Gln  Ala Lys Gln Thr Ala  Lys Gln Gln
    3605                 3610                 3615

Leu Asn  Asn Met Thr His Leu  Thr Thr Ala Gln Lys  Thr Asn Leu
    3620                 3625                 3630

Thr Asn  Gln Ile Asn Ser Gly  Thr Thr Val Ala Gly  Val Gln Thr
    3635                 3640                 3645

Val Gln  Ser Asn Ala Asn Thr  Leu Asp Gln Ala Met  Asn Thr Leu
    3650                 3655                 3660

Arg Gln  Ser Ile Ala Asn Lys  Asp Ala Thr Lys Ala  Ser Glu Asp
    3665                 3670                 3675

Tyr Val  Asp Ala Asn Asn Asp  Lys Gln Thr Ala Tyr  Asn Asn Ala
    3680                 3685                 3690

Val Ala  Ala Ala Glu Thr Ile  Ile Asn Ala Asn Ser  Asn Pro Glu
    3695                 3700                 3705

Met Asn  Pro Ser Thr Ile Thr  Gln Lys Ala Glu Gln  Val Asn Ser
    3710                 3715                 3720

Ser Lys  Thr Ala Leu Asn Gly  Asp Glu Asn Leu Ala  Ala Ala Lys
    3725                 3730                 3735

Gln Asn  Ala Lys Thr Tyr Leu  Asn Thr Leu Thr Ser  Ile Thr Asp
    3740                 3745                 3750

Ala Gln  Lys Asn Asn Leu Ile  Ser Gln Ile Thr Ser  Ala Thr Arg
    3755                 3760                 3765

Val Ser  Gly Val Asp Thr Val  Lys Gln Asn Ala Gln  His Leu Asp
    3770                 3775                 3780

Gln Ala  Met Ala Ser Leu Gln  Asn Gly Ile Asn Asn  Glu Ser Gln
    3785                 3790                 3795

Val Lys  Ser Ser Glu Lys Tyr  Arg Asp Ala Asp Thr  Asn Lys Gln
    3800                 3805                 3810

Gln Glu  Tyr Asp Asn Ala Ile  Thr Ala Ala Lys Ala  Ile Leu Asn
    3815                 3820                 3825

Lys Ser  Thr Gly Pro Asn Thr  Ala Gln Asn Ala Val  Glu Ala Ala
    3830                 3835                 3840
```

-continued

```
Leu Gln  Arg Val Asn Asn Ala  Lys Asp Ala Leu Asn  Gly Asp Ala
    3845                 3850                 3855

Lys Leu  Ile Ala Ala Gln Asn  Ala Ala Lys Gln His  Leu Gly Thr
    3860                 3865                 3870

Leu Thr  His Ile Thr Thr Ala  Gln Arg Asn Asp Leu  Thr Asn Gln
    3875                 3880                 3885

Ile Ser  Gln Ala Thr Asn Leu  Ala Gly Val Glu Ser  Val Lys Gln
    3890                 3895                 3900

Asn Ala  Asn Ser Leu Asp Gly  Ala Met Gly Asn Leu  Gln Thr Ala
    3905                 3910                 3915

Ile Asn  Asp Lys Ser Gly Thr  Leu Ala Ser Gln Asn  Phe Leu Asp
    3920                 3925                 3930

Ala Asp  Glu Gln Lys Arg Asn  Ala Tyr Asn Gln Ala  Val Ser Ala
    3935                 3940                 3945

Ala Glu  Thr Ile Leu Asn Lys  Gln Thr Gly Pro Asn  Thr Ala Lys
    3950                 3955                 3960

Thr Ala  Val Glu Gln Ala Leu  Asn Asn Val Asn Asn  Ala Lys His
    3965                 3970                 3975

Ala Leu  Asn Gly Thr Gln Asn  Leu Asn Asn Ala Lys  Gln Ala Ala
    3980                 3985                 3990

Ile Thr  Ala Ile Asn Gly Ala  Ser Asp Leu Asn Gln  Lys Gln Lys
    3995                 4000                 4005

Asp Ala  Leu Lys Ala Gln Ala  Asn Gly Ala Gln Arg  Val Ser Asn
    4010                 4015                 4020

Ala Gln  Asp Val Gln His Asn  Ala Thr Glu Leu Asn  Thr Ala Met
    4025                 4030                 4035

Gly Thr  Leu Lys His Ala Ile  Ala Asp Lys Thr Asn  Thr Leu Ala
    4040                 4045                 4050

Ser Ser  Lys Tyr Val Asn Ala  Asp Ser Thr Lys Gln  Asn Ala Tyr
    4055                 4060                 4065

Thr Thr  Lys Val Thr Asn Ala  Glu His Ile Ile Ser  Gly Thr Pro
    4070                 4075                 4080

Thr Val  Val Thr Thr Pro Ser  Glu Val Thr Ala Ala  Ala Asn Gln
    4085                 4090                 4095

Val Asn  Ser Ala Lys Gln Glu  Leu Asn Gly Asp Glu  Arg Leu Arg
    4100                 4105                 4110

Glu Ala  Lys Gln Asn Ala Asn  Thr Ala Ile Asp Ala  Leu Thr Gln
    4115                 4120                 4125

Leu Asn  Thr Pro Gln Lys Ala  Lys Leu Lys Glu Gln  Val Gly Gln
    4130                 4135                 4140

Ala Asn  Arg Leu Glu Asp Val  Gln Thr Val Gln Thr  Asn Gly Gln
    4145                 4150                 4155

Ala Leu  Asn Asn Ala Met Lys  Gly Leu Arg Asp Ser  Ile Ala Asn
    4160                 4165                 4170

Glu Thr  Thr Val Lys Thr Ser  Gln Asn Tyr Thr Asp  Ala Ser Pro
    4175                 4180                 4185

Asn Asn  Gln Ser Thr Tyr Asn  Ser Ala Val Ser Asn  Ala Lys Gly
    4190                 4195                 4200

Ile Ile  Asn Gln Thr Asn Asn  Pro Thr Met Asp Thr  Ser Ala Ile
    4205                 4210                 4215

Thr Gln  Ala Thr Thr Gln Val  Asn Asn Ala Lys Asn  Gly Leu Asn
    4220                 4225                 4230

Gly Ala  Glu Asn Leu Arg Asn  Ala Gln Asn Thr Ala  Lys Gln Asn
```

```
    4235                4240                4245

Leu Asn  Thr Leu Ser His Leu  Thr Asn Asn Gln Lys  Ser Ala Ile
    4250                4255                4260

Ser Ser  Gln Ile Asp Arg Ala  Gly His Val Ser Glu  Val Thr Ala
    4265                4270                4275

Thr Lys  Asn Ala Ala Thr Glu  Leu Asn Thr Gln Met  Gly Asn Leu
    4280                4285                4290

Glu Gln  Ala Ile His Asp Gln  Asn Thr Val Lys Gln  Ser Val Lys
    4295                4300                4305

Phe Thr  Asp Ala Asp Lys Ala  Lys Arg Asp Ala Tyr  Thr Asn Ala
    4310                4315                4320

Val Ser  Arg Ala Glu Ala Ile  Leu Asn Lys Thr Gln  Gly Ala Asn
    4325                4330                4335

Thr Ser  Lys Gln Asp Val Glu  Ala Ala Ile Gln Asn  Val Ser Ser
    4340                4345                4350

Ala Lys  Asn Ala Leu Asn Gly  Asp Gln Asn Val Thr  Asn Ala Lys
    4355                4360                4365

Asn Ala  Ala Lys Asn Ala Leu  Asn Asn Leu Thr Ser  Ile Asn Asn
    4370                4375                4380

Ala Gln  Lys Arg Asp Leu Thr  Thr Lys Ile Asp Gln  Ala Thr Thr
    4385                4390                4395

Val Ala  Gly Val Glu Ala Val  Ser Asn Thr Ser Thr  Gln Leu Asn
    4400                4405                4410

Thr Ala  Met Ala Asn Leu Gln  Asn Gly Ile Asn Asp  Lys Thr Asn
    4415                4420                4425

Thr Leu  Ala Ser Glu Asn Tyr  His Asp Ala Asp Ser  Asp Lys Lys
    4430                4435                4440

Thr Ala  Tyr Thr Gln Ala Val  Thr Asn Ala Glu Asn  Ile Leu Asn
    4445                4450                4455

Lys Asn  Ser Gly Ser Asn Leu  Asp Lys Thr Ala Val  Glu Asn Ala
    4460                4465                4470

Leu Ser  Gln Val Ala Asn Ala  Lys Gly Ala Leu Asn  Gly Asn His
    4475                4480                4485

Asn Leu  Glu Gln Ala Lys Ser  Asn Ala Asn Thr Thr  Ile Asn Gly
    4490                4495                4500

Leu Gln  His Leu Thr Thr Ala  Gln Lys Asp Lys Leu  Lys Gln Gln
    4505                4510                4515

Val Gln  Gln Ala Gln Asn Val  Ala Gly Val Asp Thr  Val Lys Ser
    4520                4525                4530

Ser Ala  Asn Thr Leu Asn Gly  Ala Met Gly Thr Leu  Arg Asn Ser
    4535                4540                4545

Ile Gln  Asp Asn Thr Ala Thr  Lys Asn Gly Gln Asn  Tyr Leu Asp
    4550                4555                4560

Ala Thr  Glu Arg Asn Lys Thr  Asn Tyr Asn Asn Ala  Val Asp Ser
    4565                4570                4575

Ala Asn  Gly Val Ile Asn Ala  Thr Ser Asn Pro Asn  Met Asp Ala
    4580                4585                4590

Asn Ala  Ile Asn Gln Ile Ala  Thr Gln Val Thr Ser  Thr Lys Asn
    4595                4600                4605

Ala Leu  Asp Gly Thr His Asn  Leu Thr Gln Ala Lys  Gln Thr Ala
    4610                4615                4620

Thr Asn  Ala Ile Asp Gly Ala  Thr Asn Leu Asn Lys  Ala Gln Lys
    4625                4630                4635
```

Asp Ala Leu Lys Ala Gln Val Thr Ser Ala Gln Arg Val Ala Asn
4640 4645 4650

Val Thr Ser Ile Gln Gln Thr Ala Asn Glu Leu Asn Thr Ala Met
4655 4660 4665

Gly Gln Leu Gln His Gly Ile Asp Asp Glu Asn Ala Thr Lys Gln
4670 4675 4680

Thr Gln Lys Tyr Arg Asp Ala Glu Gln Ser Lys Lys Thr Ala Tyr
4685 4690 4695

Asp Gln Ala Val Ala Ala Ala Lys Ala Ile Leu Asn Lys Gln Thr
4700 4705 4710

Gly Ser Asn Ser Asp Lys Ala Ala Val Asp Arg Ala Leu Gln Gln
4715 4720 4725

Val Thr Ser Thr Lys Asp Ala Leu Asn Gly Asp Ala Lys Leu Ala
4730 4735 4740

Glu Ala Lys Ala Ala Ala Lys Gln Asn Leu Gly Thr Leu Asn His
4745 4750 4755

Ile Thr Asn Ala Gln Arg Thr Asp Leu Glu Gly Gln Ile Asn Gln
4760 4765 4770

Ala Thr Thr Val Asp Gly Val Asn Thr Val Lys Thr Asn Ala Asn
4775 4780 4785

Thr Leu Asp Gly Ala Met Asn Ser Leu Gln Gly Ser Ile Asn Asp
4790 4795 4800

Lys Asp Ala Thr Leu Arg Asn Gln Asn Tyr Leu Asp Ala Asp Glu
4805 4810 4815

Ser Lys Arg Asn Ala Tyr Thr Gln Ala Val Thr Ala Ala Glu Gly
4820 4825 4830

Ile Leu Asn Lys Gln Thr Gly Gly Asn Thr Ser Lys Ala Asp Val
4835 4840 4845

Asp Asn Ala Leu Asn Ala Val Thr Arg Ala Lys Ala Ala Leu Asn
4850 4855 4860

Gly Ala Asp Asn Leu Arg Asn Ala Lys Thr Ser Ala Thr Asn Thr
4865 4870 4875

Ile Asp Gly Leu Pro Asn Leu Thr Gln Leu Gln Lys Asp Asn Leu
4880 4885 4890

Lys His Gln Val Glu Gln Ala Gln Asn Val Ala Gly Val Asn Gly
4895 4900 4905

Val Lys Asp Lys Gly Asn Thr Leu Asn Thr Ala Met Gly Ala Leu
4910 4915 4920

Arg Thr Ser Ile Gln Asn Asp Asn Thr Thr Lys Thr Ser Gln Asn
4925 4930 4935

Tyr Leu Asp Ala Ser Asp Ser Asn Lys Asn Asn Tyr Asn Thr Ala
4940 4945 4950

Val Asn Asn Ala Asn Gly Val Ile Asn Ala Thr Asn Asn Pro Asn
4955 4960 4965

Met Asp Ala Asn Ala Ile Asn Gly Met Ala Asn Gln Val Asn Thr
4970 4975 4980

Thr Lys Ala Ala Leu Asn Gly Ala Gln Asn Leu Ala Gln Ala Lys
4985 4990 4995

Thr Asn Ala Thr Asn Thr Ile Asn Asn Ala His Asp Leu Asn Gln
5000 5005 5010

Lys Gln Lys Asp Ala Leu Lys Thr Gln Val Asn Asn Ala Gln Arg
5015 5020 5025

Val Ser Asp Ala Asn Asn Val Gln His Thr Ala Thr Glu Leu Asn
5030 5035 5040

Ser Ala Met Thr Ala Leu Lys Ala Ala Ile Ala Asp Lys Glu Arg
5045 5050 5055

Thr Lys Ala Ser Gly Asn Tyr Val Asn Ala Asp Gln Glu Lys Arg
5060 5065 5070

Gln Ala Tyr Asp Ser Lys Val Thr Asn Ala Glu Asn Ile Ile Ser
5075 5080 5085

Gly Thr Pro Asn Ala Thr Leu Thr Val Asn Asp Val Asn Ser Ala
5090 5095 5100

Ala Ser Gln Val Asn Ala Ala Lys Thr Ala Leu Asn Gly Asp Asn
5105 5110 5115

Asn Leu Arg Val Ala Lys Glu His Ala Asn Asn Thr Ile Asp Gly
5120 5125 5130

Leu Ala Gln Leu Asn Asn Ala Gln Lys Ala Lys Leu Lys Glu Gln
5135 5140 5145

Val Gln Ser Ala Thr Thr Leu Asp Gly Val Gln Thr Val Lys Asn
5150 5155 5160

Ser Ser Gln Thr Leu Asn Thr Ala Met Lys Gly Leu Arg Asp Ser
5165 5170 5175

Ile Ala Asn Glu Ala Thr Ile Lys Ala Gly Gln Asn Tyr Thr Asp
5180 5185 5190

Ala Ser Pro Asn Asn Arg Asn Glu Tyr Asp Ser Ala Val Thr Ala
5195 5200 5205

Ala Lys Ala Ile Ile Asn Gln Thr Ser Asn Pro Thr Met Glu Pro
5210 5215 5220

Asn Thr Ile Thr Gln Val Thr Ser Gln Val Thr Thr Lys Glu Gln
5225 5230 5235

Ala Leu Asn Gly Ala Arg Asn Leu Ala Gln Ala Lys Thr Thr Ala
5240 5245 5250

Lys Asn Asn Leu Asn Asn Leu Thr Ser Ile Asn Asn Ala Gln Lys
5255 5260 5265

Asp Ala Leu Thr Arg Ser Ile Asp Gly Ala Thr Thr Val Ala Gly
5270 5275 5280

Val Asn Gln Glu Thr Ala Lys Ala Thr Glu Leu Asn Asn Ala Met
5285 5290 5295

His Ser Leu Gln Asn Gly Ile Asn Asp Glu Thr Gln Thr Lys Gln
5300 5305 5310

Thr Gln Lys Tyr Leu Asp Ala Glu Pro Ser Lys Lys Ser Ala Tyr
5315 5320 5325

Asp Gln Ala Val Asn Ala Ala Lys Ala Ile Leu Thr Lys Ala Ser
5330 5335 5340

Gly Gln Asn Val Asp Lys Ala Ala Val Glu Gln Ala Leu Gln Asn
5345 5350 5355

Val Asn Ser Thr Lys Thr Ala Leu Asn Gly Asp Ala Lys Leu Asn
5360 5365 5370

Glu Ala Lys Ala Ala Ala Lys Gln Thr Leu Gly Thr Leu Thr His
5375 5380 5385

Ile Asn Asn Ala Gln Arg Thr Ala Leu Asp Asn Glu Ile Thr Gln
5390 5395 5400

Ala Thr Asn Val Glu Gly Val Asn Thr Val Lys Ala Lys Ala Gln
5405 5410 5415

Gln Leu Asp Gly Ala Met Gly Gln Leu Glu Thr Ser Ile Arg Asp

```
    5420                5425                5430

Lys Asp  Thr Thr Leu Gln Ser  Gln Asn Tyr Gln Asp  Ala Asp Asp
    5435                5440                5445

Ala Lys  Arg Thr Ala Tyr Ser  Gln Ala Val Asn Ala  Ala Ala Thr
    5450                5455                5460

Ile Leu  Asn Lys Thr Ala Gly  Gly Asn Thr Pro Lys  Ala Asp Val
    5465                5470                5475

Glu Arg  Ala Met Gln Ala Val  Thr Gln Ala Asn Thr  Ala Leu Asn
    5480                5485                5490

Gly Ile  Gln Asn Leu Asp Arg  Ala Lys Gln Ala Ala  Asn Thr Ala
    5495                5500                5505

Ile Thr  Asn Ala Ser Asp Leu  Asn Thr Lys Gln Lys  Glu Ala Leu
    5510                5515                5520

Lys Ala  Gln Val Thr Ser Ala  Gly Arg Val Ser Ala  Ala Asn Gly
    5525                5530                5535

Val Glu  His Thr Ala Thr Glu  Leu Asn Thr Ala Met  Thr Ala Leu
    5540                5545                5550

Lys Arg  Ala Ile Ala Asp Lys  Ala Glu Thr Lys Ala  Ser Gly Asn
    5555                5560                5565

Tyr Val  Asn Ala Asp Ala Asn  Lys Arg Gln Ala Tyr  Asp Glu Lys
    5570                5575                5580

Val Thr  Ala Ala Glu Asn Ile  Val Ser Gly Thr Pro  Thr Pro Thr
    5585                5590                5595

Leu Thr  Pro Ala Asp Val Thr  Asn Ala Ala Thr Gln  Val Thr Asn
    5600                5605                5610

Ala Lys  Thr Gln Leu Asn Gly  Asn His Asn Leu Glu  Val Ala Lys
    5615                5620                5625

Gln Asn  Ala Asn Thr Ala Ile  Asp Gly Leu Thr Ser  Leu Asn Gly
    5630                5635                5640

Pro Gln  Lys Ala Lys Leu Lys  Glu Gln Val Gly Gln  Ala Thr Thr
    5645                5650                5655

Leu Pro  Asn Val Gln Thr Val  Arg Asp Asn Ala Gln  Thr Leu Asn
    5660                5665                5670

Thr Ala  Met Lys Gly Leu Arg  Asp Ser Ile Ala Asn  Glu Ala Thr
    5675                5680                5685

Ile Lys  Ala Gly Gln Asn Tyr  Thr Asp Ala Ser Gln  Asn Lys Gln
    5690                5695                5700

Thr Asp  Tyr Asn Ser Ala Val  Thr Ala Ala Lys Ala  Ile Ile Gly
    5705                5710                5715

Gln Thr  Thr Ser Pro Ser Met  Asn Ala Gln Glu Ile  Asn Gln Ala
    5720                5725                5730

Lys Asp  Gln Val Thr Ala Lys  Gln Gln Ala Leu Asn  Gly Gln Glu
    5735                5740                5745

Asn Leu  Arg Thr Ala Gln Thr  Asn Ala Lys Gln His  Leu Asn Gly
    5750                5755                5760

Leu Ser  Asp Leu Thr Asp Ala  Gln Lys Asp Ala Val  Lys Arg Gln
    5765                5770                5775

Ile Glu  Gly Ala Thr His Val  Asn Glu Val Thr Gln  Ala Gln Asn
    5780                5785                5790

Asn Ala  Asp Ala Leu Asn Thr  Ala Met Thr Asn Leu  Lys Asn Gly
    5795                5800                5805

Ile Gln  Asp Gln Asn Thr Ile  Lys Gln Gly Val Asn  Phe Thr Asp
    5810                5815                5820
```

Ala Asp Glu Ala Lys Arg Asn Ala Tyr Thr Asn Ala Val Thr Gln
5825 5830 5835

Ala Glu Gln Ile Leu Asn Lys Ala Gln Gly Pro Asn Thr Ser Lys
5840 5845 5850

Asp Gly Val Glu Thr Ala Leu Glu Asn Val Gln Arg Ala Lys Asn
5855 5860 5865

Glu Leu Asn Gly Asn Gln Asn Val Ala Asn Ala Lys Thr Thr Ala
5870 5875 5880

Lys Asn Ala Leu Asn Asn Leu Thr Ser Ile Asn Asn Ala Gln Lys
5885 5890 5895

Glu Ala Leu Lys Ser Gln Ile Glu Gly Ala Thr Thr Val Ala Gly
5900 5905 5910

Val Asn Gln Val Ser Thr Thr Ala Ser Glu Leu Asn Thr Ala Met
5915 5920 5925

Ser Asn Leu Gln Asn Gly Ile Asn Asp Glu Ala Ala Thr Lys Ala
5930 5935 5940

Ala Gln Lys Tyr Thr Asp Ala Asp Arg Glu Lys Gln Thr Ala Tyr
5945 5950 5955

Asn Asp Ala Val Thr Ala Ala Lys Thr Leu Leu Asp Lys Thr Ala
5960 5965 5970

Gly Ser Asn Asp Asn Lys Ala Ala Val Glu Gln Ala Leu Gln Arg
5975 5980 5985

Val Asn Thr Ala Lys Thr Ala Leu Asn Gly Asp Glu Arg Leu Asn
5990 5995 6000

Glu Ala Lys Asn Thr Ala Lys Gln Gln Val Ala Thr Met Ser His
6005 6010 6015

Leu Thr Asp Ala Gln Lys Ala Asn Leu Thr Ser Gln Ile Glu Ser
6020 6025 6030

Gly Thr Thr Val Ala Gly Val Gln Gly Ile Gln Ala Asn Ala Gly
6035 6040 6045

Thr Leu Asp Gln Ala Met Asn Gln Leu Arg Gln Ser Ile Ala Ser
6050 6055 6060

Lys Asp Ala Thr Lys Ser Ser Glu Asp Tyr Gln Asp Ala Asn Ala
6065 6070 6075

Asp Leu Gln Asn Ala Tyr Asn Asp Ala Val Thr Asn Ala Glu Gly
6080 6085 6090

Ile Ile Ser Ala Thr Asn Asn Pro Glu Met Asn Pro Asp Thr Ile
6095 6100 6105

Asn Gln Lys Ala Ser Gln Val Asn Ser Ala Lys Ser Ala Leu Asn
6110 6115 6120

Gly Asp Glu Lys Leu Ala Ala Ala Lys Gln Thr Ala Lys Ser Asp
6125 6130 6135

Ile Gly Arg Leu Thr Asp Leu Asn Asn Ala Gln Arg Thr Ala Ala
6140 6145 6150

Asn Ala Glu Val Asp Gln Ala Pro Asn Leu Ala Ala Val Thr Ala
6155 6160 6165

Ala Lys Asn Lys Ala Thr Ser Leu Asn Thr Ala Met Gly Asn Leu
6170 6175 6180

Lys His Ala Leu Ala Glu Lys Asp Asn Thr Lys Arg Ser Val Asn
6185 6190 6195

Tyr Thr Asp Ala Asp Gln Pro Lys Gln Gln Ala Tyr Asp Thr Ala
6200 6205 6210

-continued

```
Val Thr Gln Ala Glu Ala Ile Thr Asn Ala Asn Gly Ser Asn Ala
    6215                6220                6225

Asn Glu Thr Gln Val Gln Ala Ala Leu Asn Gln Leu Asn Gln Ala
    6230                6235                6240

Lys Asn Asp Leu Asn Gly Asp Asn Lys Val Ala Gln Ala Lys Glu
    6245                6250                6255

Ser Ala Lys Arg Ala Leu Ala Ser Tyr Ser Asn Leu Asn Asn Ala
    6260                6265                6270

Gln Ser Thr Ala Ala Ile Ser Gln Ile Asp Asn Ala Thr Thr Val
    6275                6280                6285

Ala Gly Val Thr Ala Ala Gln Asn Thr Ala Asn Glu Leu Asn Thr
    6290                6295                6300

Ala Met Gly Gln Leu Gln Asn Gly Ile Asn Asp Gln Asn Thr Val
    6305                6310                6315

Lys Gln Gln Val Asn Phe Thr Asp Ala Asp Gln Gly Lys Lys Asp
    6320                6325                6330

Ala Tyr Thr Asn Ala Val Thr Asn Ala Gln Gly Ile Leu Asp Lys
    6335                6340                6345

Ala His Gly Gln Asn Met Thr Lys Ala Gln Val Glu Ala Ala Leu
    6350                6355                6360

Asn Gln Val Thr Thr Ala Lys Asn Ala Leu Asn Gly Asp Ala Asn
    6365                6370                6375

Val Arg Gln Ala Lys Ser Asp Ala Lys Ala Asn Leu Gly Thr Leu
    6380                6385                6390

Thr His Leu Asn Asn Ala Gln Lys Gln Asp Leu Thr Ser Gln Ile
    6395                6400                6405

Glu Gly Ala Thr Thr Val Asn Gly Val Asn Gly Val Lys Thr Lys
    6410                6415                6420

Ala Gln Asp Leu Asp Gly Ala Met Gln Arg Leu Gln Ser Ala Ile
    6425                6430                6435

Ala Asn Lys Asp Gln Thr Lys Ala Ser Glu Asn Tyr Ile Asp Ala
    6440                6445                6450

Asp Pro Thr Lys Lys Thr Ala Phe Asp Asn Ala Ile Thr Gln Ala
    6455                6460                6465

Glu Ser Tyr Leu Asn Lys Asp His Gly Ala Asn Lys Asp Lys Gln
    6470                6475                6480

Ala Val Glu Gln Ala Ile Gln Ser Val Thr Ser Thr Glu Asn Ala
    6485                6490                6495

Leu Asn Gly Asp Ala Asn Leu Gln Arg Ala Lys Thr Glu Ala Ile
    6500                6505                6510

Gln Ala Ile Asp Asn Leu Thr His Leu Asn Thr Pro Gln Lys Thr
    6515                6520                6525

Ala Leu Lys Gln Gln Val Asn Ala Ala Gln Arg Val Ser Gly Val
    6530                6535                6540

Thr Asp Leu Lys Asn Ser Ala Thr Ser Leu Asn Asn Ala Met Asp
    6545                6550                6555

Gln Leu Lys Gln Ala Ile Ala Asp His Asp Thr Ile Val Ala Ser
    6560                6565                6570

Gly Asn Tyr Thr Asn Ala Ser Pro Asp Lys Gln Gly Ala Tyr Thr
    6575                6580                6585

Asp Ala Tyr Asn Ala Ala Lys Asn Ile Val Asn Gly Ser Pro Asn
    6590                6595                6600

Val Ile Thr Asn Ala Ala Asp Val Thr Ala Ala Thr Gln Arg Val
```

```
    6605                6610                6615

Asn Asn  Ala Glu Thr Gly Leu  Asn Gly Asp Thr Asn  Leu Ala Thr
    6620                6625                6630

Ala Lys  Gln Gln Ala Lys Asp  Ala Leu Arg Gln Met  Thr His Leu
    6635                6640                6645

Ser Asp  Ala Gln Lys Gln Ser  Ile Thr Gly Gln Ile  Asp Ser Ala
    6650                6655                6660

Thr Gln  Val Thr Gly Val Gln  Ser Val Lys Asp Asn  Ala Thr Asn
    6665                6670                6675

Leu Asp  Asn Ala Met Asn Gln  Leu Arg Asn Ser Ile  Ala Asn Lys
    6680                6685                6690

Asp Asp  Val Lys Ala Ser Gln  Pro Tyr Val Asp Ala  Asp Arg Asp
    6695                6700                6705

Lys Gln  Asn Ala Tyr Asn Thr  Ala Val Thr Asn Ala  Glu Asn Ile
    6710                6715                6720

Ile Asn  Ala Thr Ser Gln Pro  Thr Leu Asp Pro Ser  Ala Val Thr
    6725                6730                6735

Gln Ala  Ala Asn Gln Val Ser  Thr Asn Lys Thr Ala  Leu Asn Gly
    6740                6745                6750

Ala Gln  Asn Leu Ala Asn Lys  Lys Gln Glu Thr Thr  Ala Asn Ile
    6755                6760                6765

Asn Gln  Leu Ser His Leu Asn  Asn Ala Gln Lys Gln  Asp Leu Asn
    6770                6775                6780

Thr Gln  Val Thr Asn Ala Pro  Asn Ile Ser Thr Val  Asn Gln Val
    6785                6790                6795

Lys Thr  Lys Ala Glu Gln Leu  Asp Gln Ala Met Glu  Arg Leu Ile
    6800                6805                6810

Asn Gly  Ile Gln Asp Lys Asp  Gln Val Lys Gln Ser  Val Asn Phe
    6815                6820                6825

Thr Asp  Ala Asp Pro Glu Lys  Gln Thr Ala Tyr Asn  Asn Ala Val
    6830                6835                6840

Thr Ala  Ala Glu Asn Ile Ile  Asn Gln Ala Asn Gly  Thr Asn Ala
    6845                6850                6855

Asn Gln  Ser Gln Val Glu Ala  Ala Leu Ser Thr Val  Thr Thr Thr
    6860                6865                6870

Lys Gln  Ala Leu Asn Gly Asp  Arg Lys Val Thr Asp  Ala Lys Asn
    6875                6880                6885

Asn Ala  Asn Gln Thr Leu Ser  Thr Leu Asp Asn Leu  Asn Asn Ala
    6890                6895                6900

Gln Lys  Gly Ala Val Thr Gly  Asn Ile Asn Gln Ala  His Thr Val
    6905                6910                6915

Ala Glu  Val Thr Gln Ala Ile  Gln Thr Ala Gln Glu  Leu Asn Thr
    6920                6925                6930

Ala Met  Gly Asn Leu Lys Asn  Ser Leu Asn Asp Lys  Asp Thr Thr
    6935                6940                6945

Leu Gly  Ser Gln Asn Phe Ala  Asp Ala Asp Pro Glu  Lys Lys Asn
    6950                6955                6960

Ala Tyr  Asn Glu Ala Val His  Asn Ala Glu Asn Ile  Leu Asn Lys
    6965                6970                6975

Ser Thr  Gly Thr Asn Val Pro  Lys Asp Gln Val Glu  Ala Ala Met
    6980                6985                6990

Asn Gln  Val Asn Ala Thr Lys  Ala Ala Leu Asn Gly  Thr Gln Asn
    6995                7000                7005
```

-continued

```
Leu Glu  Lys Ala Lys Gln His  Ala Asn Thr Ala Ile  Asp Gly Leu
    7010                 7015                 7020

Ser His  Leu Thr Asn Ala Gln  Lys Glu Ala Leu Lys  Gln Leu Val
    7025                 7030                 7035

Gln Gln  Ser Thr Thr Val Ala  Glu Ala Gln Gly Asn  Glu Gln Lys
    7040                 7045                 7050

Ala Asn  Asn Val Asp Ala Ala  Met Asp Lys Leu Arg  Gln Ser Ile
    7055                 7060                 7065

Ala Asp  Asn Ala Thr Thr Lys  Gln Asn Gln Asn Tyr  Thr Asp Ala
    7070                 7075                 7080

Ser Gln  Asn Lys Lys Asp Ala  Tyr Asn Asn Ala Val  Thr Thr Ala
    7085                 7090                 7095

Gln Gly  Ile Ile Asp Gln Thr  Thr Ser Pro Thr Leu  Asp Pro Thr
    7100                 7105                 7110

Val Ile  Asn Gln Ala Ala Gly  Gln Val Ser Thr Thr  Lys Asn Ala
    7115                 7120                 7125

Leu Asn  Gly Asn Glu Asn Leu  Glu Ala Ala Lys Gln  Gln Ala Ser
    7130                 7135                 7140

Gln Ser  Leu Gly Ser Leu Asp  Asn Leu Asn Asn Ala  Gln Lys Gln
    7145                 7150                 7155

Thr Val  Thr Asp Gln Ile Asn  Gly Ala His Thr Val  Asp Glu Ala
    7160                 7165                 7170

Asn Gln  Ile Lys Gln Asn Ala  Gln Asn Leu Asn Thr  Ala Met Gly
    7175                 7180                 7185

Asn Leu  Lys Gln Ala Ile Ala  Asp Lys Asp Ala Thr  Lys Ala Thr
    7190                 7195                 7200

Val Asn  Phe Thr Asp Ala Asp  Gln Ala Lys Gln Gln  Ala Tyr Asn
    7205                 7210                 7215

Thr Ala  Val Thr Asn Ala Glu  Asn Ile Ser Lys Ala  Asn Gly Asn
    7220                 7225                 7230

Ala Thr  Gln Ala Glu Val Glu  Gln Ala Ile Lys Gln  Val Asn Ala
    7235                 7240                 7245

Ala Lys  Gln Ala Leu Asn Gly  Asn Ala Asn Val Gln  His Ala Lys
    7250                 7255                 7260

Asp Glu  Ala Thr Ala Leu Ile  Asn Ser Ser Asn Asp  Leu Asn Gln
    7265                 7270                 7275

Ala Gln  Lys Asp Ala Leu Lys  Gln Gln Val Gln Asn  Ala Thr Thr
    7280                 7285                 7290

Val Ala  Gly Val Asn Asn Val  Lys Gln Thr Ala Gln  Glu Leu Asn
    7295                 7300                 7305

Asn Ala  Met Thr Gln Leu Lys  Gln Gly Ile Ala Asp  Lys Glu Gln
    7310                 7315                 7320

Thr Lys  Ala Asp Gly Asn Phe  Val Asn Ala Asp Pro  Asp Lys Gln
    7325                 7330                 7335

Asn Ala  Tyr Asn Gln Ala Val  Ala Lys Ala Glu Ala  Leu Ile Ser
    7340                 7345                 7350

Ala Thr  Pro Asp Val Val Val  Thr Pro Ser Glu Ile  Thr Ala Ala
    7355                 7360                 7365

Leu Asn  Lys Val Thr Gln Ala  Lys Asn Asp Leu Asn  Gly Asn Thr
    7370                 7375                 7380

Asn Leu  Ala Thr Ala Lys Gln  Asn Val Gln His Ala  Ile Asp Gln
    7385                 7390                 7395
```

```
Leu Pro  Asn Leu Asn Gln Ala  Gln Arg Asp Glu Tyr  Ser Lys Gln
    7400                 7405                 7410

Ile Thr  Gln Ala Thr Leu Val  Pro Asn Val Asn Ala  Ile Gln Gln
    7415                 7420                 7425

Ala Ala  Thr Thr Leu Asn Asp  Ala Met Thr Gln Leu  Lys Gln Gly
    7430                 7435                 7440

Ile Ala  Asn Lys Ala Gln Ile  Lys Gly Ser Glu Asn  Tyr His Asp
    7445                 7450                 7455

Ala Asp  Thr Asp Lys Gln Thr  Ala Tyr Asp Asn Ala  Val Thr Lys
    7460                 7465                 7470

Ala Glu  Glu Leu Leu Lys Gln  Thr Thr Asn Pro Thr  Met Asp Pro
    7475                 7480                 7485

Asn Thr  Ile Gln Gln Ala Leu  Thr Lys Val Asn Asp  Thr Asn Gln
    7490                 7495                 7500

Ala Leu  Asn Gly Asn Gln Lys  Leu Ala Asp Ala Lys  Gln Asp Ala
    7505                 7510                 7515

Lys Thr  Thr Leu Gly Thr Leu  Asp His Leu Asn Asp  Ala Gln Lys
    7520                 7525                 7530

Gln Ala  Leu Thr Thr Gln Val  Glu Gln Ala Pro Asp  Ile Ala Thr
    7535                 7540                 7545

Val Asn  Asn Val Lys Gln Asn  Ala Gln Asn Leu Asn  Asn Ala Met
    7550                 7555                 7560

Thr Asn  Leu Asn Asn Ala Leu  Gln Asp Lys Thr Glu  Thr Leu Asn
    7565                 7570                 7575

Ser Ile  Asn Phe Thr Asp Ala  Asp Gln Ala Lys Lys  Asp Ala Tyr
    7580                 7585                 7590

Thr Asn  Ala Val Ser His Ala  Glu Gly Ile Leu Ser  Lys Ala Asn
    7595                 7600                 7605

Gly Ser  Asn Ala Ser Gln Thr  Glu Val Glu Gln Ala  Met Gln Arg
    7610                 7615                 7620

Val Asn  Glu Ala Lys Gln Ala  Leu Asn Gly Asn Asp  Asn Val Gln
    7625                 7630                 7635

Arg Ala  Lys Asp Ala Ala Lys  Gln Val Ile Thr Asn  Ala Asn Asp
    7640                 7645                 7650

Leu Asn  Gln Ala Gln Lys Asp  Ala Leu Lys Gln Gln  Val Asp Ala
    7655                 7660                 7665

Ala Gln  Thr Val Ala Asn Val  Asn Thr Ile Lys Gln  Thr Ala Gln
    7670                 7675                 7680

Asp Leu  Asn Gln Ala Met Thr  Gln Leu Lys Gln Gly  Ile Ala Asp
    7685                 7690                 7695

Lys Asp  Gln Thr Lys Ala Asn  Gly Asn Phe Val Asn  Ala Asp Thr
    7700                 7705                 7710

Asp Lys  Gln Asn Ala Tyr Asn  Asn Ala Val Ala His  Ala Glu Gln
    7715                 7720                 7725

Ile Ile  Ser Gly Thr Pro Asn  Ala Asn Val Asp Pro  Gln Gln Val
    7730                 7735                 7740

Ala Gln  Ala Leu Gln Gln Val  Asn Gln Ala Lys Gly  Asp Leu Asn
    7745                 7750                 7755

Gly Asn  His Asn Leu Gln Val  Ala Lys Asp Asn Ala  Asn Thr Ala
    7760                 7765                 7770

Ile Asp  Gln Leu Pro Asn Leu  Asn Gln Pro Gln Lys  Thr Ala Leu
    7775                 7780                 7785

Lys Asp  Gln Val Ser His Ala  Glu Leu Val Thr Gly  Val Asn Ala
```

7790 7795 7800

Ile Lys Gln Asn Ala Asp Ala Leu Asn Asn Ala Met Gly Thr Leu
7805 7810 7815

Lys Gln Gln Ile Gln Ala Asn Ser Gln Val Pro Gln Ser Val Asp
7820 7825 7830

Phe Thr Gln Ala Asp Gln Asp Lys Gln Gln Ala Tyr Asn Asn Ala
7835 7840 7845

Ala Asn Gln Ala Gln Gln Ile Ala Asn Gly Ile Pro Thr Pro Val
7850 7855 7860

Leu Thr Pro Asp Thr Val Thr Gln Ala Val Thr Thr Met Asn Gln
7865 7870 7875

Ala Lys Asp Ala Leu Asn Gly Asp Glu Lys Leu Ala Gln Ala Lys
7880 7885 7890

Gln Glu Ala Leu Ala Asn Leu Asp Thr Leu Arg Asp Leu Asn Gln
7895 7900 7905

Pro Gln Arg Asp Ala Leu Arg Asn Gln Ile Asn Gln Ala Gln Ala
7910 7915 7920

Leu Ala Thr Val Glu Gln Thr Lys Gln Asn Ala Gln Asn Val Asn
7925 7930 7935

Thr Ala Met Ser Asn Leu Lys Gln Gly Ile Ala Asn Lys Asp Thr
7940 7945 7950

Val Lys Ala Ser Glu Asn Tyr His Asp Ala Asp Ala Asp Lys Gln
7955 7960 7965

Thr Ala Tyr Thr Asn Ala Val Ser Gln Ala Glu Gly Ile Ile Asn
7970 7975 7980

Gln Thr Thr Asn Pro Thr Leu Asn Pro Asp Glu Ile Thr Arg Ala
7985 7990 7995

Leu Thr Gln Val Thr Asp Ala Lys Asn Gly Leu Asn Gly Glu Ala
8000 8005 8010

Lys Leu Ala Thr Glu Lys Gln Asn Ala Lys Asp Ala Val Ser Gly
8015 8020 8025

Met Thr His Leu Asn Asp Ala Gln Lys Gln Ala Leu Lys Gly Gln
8030 8035 8040

Ile Asp Gln Ser Pro Glu Ile Ala Thr Val Asn Gln Val Lys Gln
8045 8050 8055

Thr Ala Thr Ser Leu Asp Gln Ala Met Asp Gln Leu Ser Gln Ala
8060 8065 8070

Ile Asn Asp Lys Ala Gln Thr Leu Ala Asp Gly Asn Tyr Leu Asn
8075 8080 8085

Ala Asp Pro Asp Lys Gln Asn Ala Tyr Lys Gln Ala Val Ala Lys
8090 8095 8100

Ala Glu Ala Leu Leu Asn Lys Gln Ser Gly Thr Asn Glu Val Gln
8105 8110 8115

Ala Gln Val Glu Ser Ile Thr Asn Glu Val Asn Ala Ala Lys Gln
8120 8125 8130

Ala Leu Asn Gly Asn Asp Asn Leu Ala Asn Ala Lys Gln Gln Ala
8135 8140 8145

Lys Gln Gln Leu Ala Asn Leu Thr His Leu Asn Asp Ala Gln Lys
8150 8155 8160

Gln Ser Phe Glu Ser Gln Ile Thr Gln Ala Pro Leu Val Thr Asp
8165 8170 8175

Val Thr Thr Ile Asn Gln Lys Ala Gln Thr Leu Asp His Ala Met
8180 8185 8190

```
Glu Leu Leu Arg Asn Ser Val Ala Asp Asn Gln Thr Thr Leu Ala
    8195                8200                8205

Ser Glu Asp Tyr His Asp Ala Thr Ala Gln Arg Gln Asn Asp Tyr
    8210                8215                8220

Asn Gln Ala Val Thr Ala Ala Asn Asn Ile Ile Asn Gln Thr Thr
    8225                8230                8235

Ser Pro Thr Met Asn Pro Asp Asp Val Asn Gly Ala Thr Thr Gln
    8240                8245                8250

Val Asn Asn Thr Lys Val Ala Leu Asp Gly Asp Glu Asn Leu Ala
    8255                8260                8265

Ala Ala Lys Gln Gln Ala Asn Asn Arg Leu Asp Gln Leu Asp His
    8270                8275                8280

Leu Asn Asn Ala Gln Lys Gln Gln Leu Gln Ser Gln Ile Thr Gln
    8285                8290                8295

Ser Ser Asp Ile Ala Ala Val Asn Gly His Lys Gln Thr Ala Glu
    8300                8305                8310

Ser Leu Asn Thr Ala Met Gly Asn Leu Ile Asn Ala Ile Ala Asp
    8315                8320                8325

His Gln Ala Val Glu Gln Arg Gly Asn Phe Ile Asn Ala Asp Thr
    8330                8335                8340

Asp Lys Gln Thr Ala Tyr Asn Thr Ala Val Asn Glu Ala Ala Ala
    8345                8350                8355

Met Ile Asn Lys Gln Thr Gly Gln Asn Ala Asn Gln Thr Glu Val
    8360                8365                8370

Glu Gln Ala Ile Thr Lys Val Gln Thr Thr Leu Gln Ala Leu Asn
    8375                8380                8385

Gly Asp His Asn Leu Gln Val Ala Lys Thr Asn Ala Thr Gln Ala
    8390                8395                8400

Ile Asp Ala Leu Thr Ser Leu Asn Asp Pro Gln Lys Thr Ala Leu
    8405                8410                8415

Lys Asp Gln Val Thr Ala Ala Thr Leu Val Thr Ala Val His Gln
    8420                8425                8430

Ile Glu Gln Asn Ala Asn Thr Leu Asn Gln Ala Met His Gly Leu
    8435                8440                8445

Arg Gln Ser Ile Gln Asp Asn Ala Ala Thr Lys Ala Asn Ser Lys
    8450                8455                8460

Tyr Ile Asn Glu Asp Gln Pro Glu Gln Gln Asn Tyr Asp Gln Ala
    8465                8470                8475

Val Gln Ala Ala Asn Asn Ile Ile Asn Glu Gln Thr Ala Thr Leu
    8480                8485                8490

Asp Asn Asn Ala Ile Asn Gln Ala Ala Thr Thr Val Asn Thr Thr
    8495                8500                8505

Lys Ala Ala Leu His Gly Asp Val Lys Leu Gln Asn Asp Lys Asp
    8510                8515                8520

His Ala Lys Gln Thr Val Ser Gln Leu Ala His Leu Asn Asn Ala
    8525                8530                8535

Gln Lys His Met Glu Asp Thr Leu Ile Asp Ser Glu Thr Thr Arg
    8540                8545                8550

Thr Ala Val Lys Gln Asp Leu Thr Glu Ala Gln Ala Leu Asp Gln
    8555                8560                8565

Leu Met Asp Ala Leu Gln Gln Ser Ile Ala Asp Lys Asp Ala Thr
    8570                8575                8580
```

```
Arg Ala  Ser Ser Ala Tyr Val  Asn Ala Glu Pro Asn  Lys Lys Gln
    8585                 8590                 8595

Ser Tyr  Asp Glu Ala Val Gln  Asn Ala Glu Ser Ile  Ile Ala Gly
    8600                 8605                 8610

Leu Asn  Asn Pro Thr Ile Asn  Lys Gly Asn Val Ser  Ser Ala Thr
    8615                 8620                 8625

Gln Ala  Val Ile Ser Ser Lys  Asn Ala Leu Asp Gly  Val Glu Arg
    8630                 8635                 8640

Leu Ala  Gln Asp Lys Gln Thr  Ala Gly Asn Ser Leu  Asn His Leu
    8645                 8650                 8655

Asp Gln  Leu Thr Pro Ala Gln  Gln Gln Ala Leu Glu  Asn Gln Ile
    8660                 8665                 8670

Asn Asn  Ala Thr Thr Arg Gly  Glu Val Ala Gln Lys  Leu Thr Glu
    8675                 8680                 8685

Ala Gln  Ala Leu Asn Gln Ala  Met Glu Ala Leu Arg  Asn Ser Ile
    8690                 8695                 8700

Gln Asp  Gln Gln Gln Thr Glu  Ala Gly Ser Lys Phe  Ile Asn Glu
    8705                 8710                 8715

Asp Lys  Pro Gln Lys Asp Ala  Tyr Gln Ala Ala Val  Gln Asn Ala
    8720                 8725                 8730

Lys Asp  Leu Ile Asn Gln Thr  Asn Asn Pro Thr Leu  Asp Lys Ala
    8735                 8740                 8745

Gln Val  Glu Gln Leu Thr Gln  Ala Val Asn Gln Ala  Lys Asp Asn
    8750                 8755                 8760

Leu His  Gly Asp Gln Lys Leu  Ala Asp Asp Lys Gln  His Ala Val
    8765                 8770                 8775

Thr Asp  Leu Asn Gln Leu Asn  Gly Leu Asn Asn Pro  Gln Arg Gln
    8780                 8785                 8790

Ala Leu  Glu Ser Gln Ile Asn  Asn Ala Ala Thr Arg  Gly Glu Val
    8795                 8800                 8805

Ala Gln  Lys Leu Ala Glu Ala  Lys Ala Leu Asp Gln  Ala Met Gln
    8810                 8815                 8820

Ala Leu  Arg Asn Ser Ile Gln  Asp Gln Gln Gln Thr  Glu Ser Gly
    8825                 8830                 8835

Ser Lys  Phe Ile Asn Glu Asp  Lys Pro Gln Lys Asp  Ala Tyr Gln
    8840                 8845                 8850

Ala Ala  Val Gln Asn Ala Lys  Asp Leu Ile Asn Gln  Thr Gly Asn
    8855                 8860                 8865

Pro Thr  Leu Asp Lys Ser Gln  Val Glu Gln Leu Thr  Gln Ala Val
    8870                 8875                 8880

Thr Thr  Ala Lys Asp Asn Leu  His Gly Asp Gln Lys  Leu Ala Arg
    8885                 8890                 8895

Asp Gln  Gln Gln Ala Val Thr  Thr Val Asn Ala Leu  Pro Asn Leu
    8900                 8905                 8910

Asn His  Ala Gln Gln Gln Ala  Leu Thr Asp Ala Ile  Asn Ala Ala
    8915                 8920                 8925

Pro Thr  Arg Thr Glu Val Ala  Gln His Val Gln Thr  Ala Thr Glu
    8930                 8935                 8940

Leu Asp  His Ala Met Glu Thr  Leu Lys Asn Lys Val  Asp Gln Val
    8945                 8950                 8955

Asn Thr  Asp Lys Ala Gln Pro  Asn Tyr Thr Glu Ala  Ser Thr Asp
    8960                 8965                 8970

Lys Lys  Glu Ala Val Asp Gln  Ala Leu Gln Ala Ala  Glu Ser Ile
```

-continued

```
    8975                8980                8985

Thr Asp  Pro Thr Asn Gly Ser  Asn Ala Asn Lys Asp  Ala Val Asp
    8990                8995                9000

Gln Val  Leu Thr Lys Leu Gln  Glu Lys Glu Asn Glu  Leu Asn Gly
    9005                9010                9015

Asn Glu  Arg Val Ala Glu Ala  Lys Thr Gln Ala Lys  Gln Thr Ile
    9020                9025                9030

Asp Gln  Leu Thr His Leu Asn  Ala Asp Gln Ile Ala  Thr Ala Lys
    9035                9040                9045

Gln Asn  Ile Asp Gln Ala Thr  Lys Leu Gln Pro Ile  Ala Glu Leu
    9050                9055                9060

Val Asp  Gln Ala Thr Gln Leu  Asn Gln Ser Met Asp  Gln Leu Gln
    9065                9070                9075

Gln Ala  Val Asn Glu His Ala  Asn Val Glu Gln Thr  Val Asp Tyr
    9080                9085                9090

Thr Gln  Ala Asp Ser Asp Lys  Gln Asn Ala Tyr Lys  Gln Ala Ile
    9095                9100                9105

Ala Asp  Ala Glu Asn Val Leu  Lys Gln Asn Ala Asn  Lys Gln Gln
    9110                9115                9120

Val Asp  Gln Ala Leu Gln Asn  Ile Leu Asn Ala Lys  Gln Ala Leu
    9125                9130                9135

Asn Gly  Asp Glu Arg Val Ala  Leu Ala Lys Thr Asn  Gly Lys His
    9140                9145                9150

Asp Ile  Asp Gln Leu Asn Ala  Leu Asn Asn Ala Gln  Gln Asp Gly
    9155                9160                9165

Phe Lys  Gly Arg Ile Asp Gln  Ser Asn Asp Leu Asn  Gln Ile Gln
    9170                9175                9180

Gln Ile  Val Asp Glu Ala Lys  Ala Leu Asn Arg Ala  Met Asp Gln
    9185                9190                9195

Leu Ser  Gln Glu Ile Thr Asp  Asn Glu Gly Arg Thr  Lys Gly Ser
    9200                9205                9210

Thr Asn  Tyr Val Asn Ala Asp  Thr Gln Val Lys Gln  Val Tyr Asp
    9215                9220                9225

Glu Thr  Val Asp Lys Ala Lys  Gln Ala Leu Asp Lys  Ser Thr Gly
    9230                9235                9240

Gln Asn  Leu Thr Ala Lys Gln  Val Ile Lys Leu Asn  Asp Ala Val
    9245                9250                9255

Thr Ala  Ala Lys Lys Ala Leu  Asn Gly Glu Glu Arg  Leu Asn Asn
    9260                9265                9270

Arg Lys  Ala Glu Ala Leu Gln  Arg Leu Asp Gln Leu  Thr His Leu
    9275                9280                9285

Asn Asn  Ala Gln Arg Gln Leu  Ala Ile Gln Gln Ile  Asn Asn Ala
    9290                9295                9300

Glu Thr  Leu Asn Lys Ala Ser  Arg Ala Ile Asn Arg  Ala Thr Lys
    9305                9310                9315

Leu Asp  Asn Ala Met Gly Ala  Val Gln Gln Tyr Ile  Asp Glu Gln
    9320                9325                9330

His Leu  Gly Val Ile Ser Ser  Thr Asn Tyr Ile Asn  Ala Asp Asp
    9335                9340                9345

Asn Leu  Lys Ala Asn Tyr Asp  Asn Ala Ile Ala Asn  Ala Ala His
    9350                9355                9360

Glu Leu  Asp Lys Val Gln Gly  Asn Ala Ile Ala Lys  Ala Glu Ala
    9365                9370                9375
```

```
Glu Gln  Leu Lys Gln Asn Ile  Ile Asp Ala Gln Asn  Ala Leu Asn
    9380                 9385                 9390

Gly Asp  Gln Asn Leu Ala Asn  Ala Lys Asp Lys Ala  Asn Ala Phe
    9395                 9400                 9405

Val Asn  Ser Leu Asn Gly Leu  Asn Gln Gln Gln Gln  Asp Leu Ala
    9410                 9415                 9420

His Lys  Ala Ile Asn Asn Ala  Asp Thr Val Ser Asp  Val Thr Asp
    9425                 9430                 9435

Ile Val  Asn Asn Gln Ile Asp  Leu Asn Asp Ala Met  Glu Thr Leu
    9440                 9445                 9450

Lys His  Leu Val Asp Asn Glu  Ile Pro Asn Ala Glu  Gln Thr Val
    9455                 9460                 9465

Asn Tyr  Gln Asn Ala Asp Asp  Asn Ala Lys Thr Asn  Phe Asp Asp
    9470                 9475                 9480

Ala Lys  Arg Leu Ala Asn Thr  Leu Leu Asn Ser Asp  Asn Thr Asn
    9485                 9490                 9495

Val Asn  Asp Ile Asn Gly Ala  Ile Gln Ala Val Asn  Asp Ala Ile
    9500                 9505                 9510

His Asn  Leu Asn Gly Asp Gln  Arg Leu Gln Asp Ala  Lys Asp Lys
    9515                 9520                 9525

Ala Ile  Gln Ser Ile Asn Gln  Ala Leu Ala Asn Lys  Leu Lys Glu
    9530                 9535                 9540

Ile Glu  Ala Ser Asn Ala Thr  Asp Gln Asp Lys Leu  Ile Ala Lys
    9545                 9550                 9555

Asn Lys  Ala Glu Glu Leu Ala  Asn Ser Ile Ile Asn  Asn Ile Asn
    9560                 9565                 9570

Lys Ala  Thr Ser Asn Gln Ala  Val Ser Gln Val Gln  Thr Ala Gly
    9575                 9580                 9585

Asn His  Ala Ile Glu Gln Val  His Ala Asn Glu Ile  Pro Lys Ala
    9590                 9595                 9600

Lys Ile  Asp Ala Asn Lys Asp  Val Asp Lys Gln Val  Gln Ala Leu
    9605                 9610                 9615

Ile Asp  Glu Ile Asp Arg Asn  Pro Asn Leu Thr Asp  Lys Glu Lys
    9620                 9625                 9630

Gln Ala  Leu Lys Asp Arg Ile  Asn Gln Ile Leu Gln  Gln Gly His
    9635                 9640                 9645

Asn Gly  Ile Asn Asn Ala Met  Thr Lys Glu Glu Ile  Glu Gln Ala
    9650                 9655                 9660

Lys Ala  Gln Leu Ala Gln Ala  Leu Gln Asp Ile Lys  Asp Leu Val
    9665                 9670                 9675

Lys Ala  Lys Glu Asp Ala Lys  Gln Asp Val Asp Lys  Gln Val Gln
    9680                 9685                 9690

Ala Leu  Ile Asp Glu Ile Asp  Gln Asn Pro Asn Leu  Thr Asp Lys
    9695                 9700                 9705

Glu Lys  Gln Ala Leu Lys Tyr  Arg Ile Asn Gln Ile  Leu Gln Gln
    9710                 9715                 9720

Gly His  Asn Asp Ile Asn Asn  Ala Leu Thr Lys Glu  Glu Ile Glu
    9725                 9730                 9735

Gln Ala  Lys Ala Gln Leu Ala  Gln Ala Leu Gln Asp  Ile Lys Asp
    9740                 9745                 9750

Leu Val  Lys Ala Lys Glu Asp  Ala Lys Asn Ala Ile  Lys Ala Leu
    9755                 9760                 9765
```

```
Ala Asn Ala Lys Arg Asp Gln Ile Asn Ser Asn Pro Asp Leu Thr
    9770                9775                9780

Pro Glu Gln Lys Ala Lys Ala Leu Lys Glu Ile Asp Glu Ala Glu
    9785                9790                9795

Lys Arg Ala Leu Gln Asn Val Glu Asn Ala Gln Thr Ile Asp Gln
    9800                9805                9810

Leu Asn Arg Gly Leu Asn Leu Gly Leu Asp Asp Ile Arg Asn Thr
    9815                9820                9825

His Val Trp Glu Val Asp Glu Gln Pro Ala Val Asn Glu Ile Phe
    9830                9835                9840

Glu Ala Thr Pro Glu Gln Ile Leu Val Asn Gly Glu Leu Ile Val
    9845                9850                9855

His Arg Asp Asp Ile Ile Thr Glu Gln Asp Ile Leu Ala His Ile
    9860                9865                9870

Asn Leu Ile Asp Gln Leu Ser Ala Glu Val Ile Asp Thr Pro Ser
    9875                9880                9885

Thr Ala Thr Ile Ser Asp Ser Leu Thr Ala Lys Val Glu Val Thr
    9890                9895                9900

Leu Leu Asp Gly Ser Lys Val Ile Val Asn Val Pro Val Lys Val
    9905                9910                9915

Val Glu Lys Glu Leu Ser Val Val Lys Gln Gln Ala Ile Glu Ser
    9920                9925                9930

Ile Glu Asn Ala Ala Gln Gln Lys Ile Asn Glu Ile Asn Asn Ser
    9935                9940                9945

Val Thr Leu Thr Leu Glu Gln Lys Glu Ala Ala Ile Ala Glu Val
    9950                9955                9960

Asn Lys Leu Lys Gln Gln Ala Ile Asp His Val Asn Asn Ala Pro
    9965                9970                9975

Asp Val His Ser Val Glu Glu Ile Gln Gln Gln Glu Gln Ala His
    9980                9985                9990

Ile Glu Gln Phe Asn Pro Glu Gln Phe Thr Ile Glu Gln Ala Lys
    9995                10000               10005

Ser Asn Ala Ile Lys Ser Ile Glu Asp Ala Ile Gln His Met Ile
    10010               10015               10020

Asp Glu Ile Lys Ala Arg Thr Asp Leu Thr Asp Lys Glu Lys Gln
    10025               10030               10035

Glu Ala Ile Ala Lys Leu Asn Gln Leu Lys Glu Gln Ala Ile Gln
    10040               10045               10050

Ala Ile Gln Arg Ala Gln Ser Ile Asp Glu Ile Ser Glu Gln Leu
    10055               10060               10065

Glu Gln Phe Lys Ala Gln Met Lys Ala Ala Asn Pro Thr Ala Lys
    10070               10075               10080

Glu Leu Ala Lys Arg Lys Gln Glu Ala Ile Ser Arg Ile Lys Asp
    10085               10090               10095

Phe Ser Asn Glu Lys Ile Asn Ser Ile Arg Asn Ser Glu Ile Gly
    10100               10105               10110

Thr Ala Asp Glu Lys Gln Ala Ala Met Asn Gln Ile Asn Glu Ile
    10115               10120               10125

Val Leu Glu Thr Ile Arg Asp Ile Asn Asn Ala His Thr Leu Gln
    10130               10135               10140

Gln Val Glu Ala Ala Leu Asn Asn Gly Ile Ala Arg Ile Ser Ala
    10145               10150               10155

Val Gln Ile Val Thr Ser Asp Arg Ala Lys Gln Ser Ser Ser Thr
```

```
    10160               10165               10170

Gly Asn   Glu Ser Asn Ser His   Leu Thr Ile Gly Tyr   Gly Thr Ala
    10175               10180               10185

Asn His   Pro Phe Asn Ser Ser   Thr Ile Gly His Lys   Lys Lys Leu
    10190               10195               10200

Asp Glu   Asp Asp Asp Ile Asp   Pro Leu His Met Arg   His Phe Ser
    10205               10210               10215

Asn Asn   Phe Gly Asn Val Ile   Lys Asn Ala Ile Gly   Val Val Gly
    10220               10225               10230

Ile Ser   Gly Leu Leu Ala Ser   Phe Trp Phe Phe Ile   Ala Lys Arg
    10235               10240               10245

Arg Arg   Lys Glu Asp Glu Glu   Glu Glu Leu Glu Ile   Arg Asp Asn
    10250               10255               10260

Asn Lys   Asp Ser Ile Lys Glu   Thr Leu Asp Asp Thr   Lys His Leu
    10265               10270               10275

Pro Leu   Leu Phe Ala Lys Arg   Arg Arg Lys Glu Asp   Glu Glu Asp
    10280               10285               10290

Val Thr   Val Glu Glu Lys Asp   Ser Leu Asn Asn Gly   Glu Ser Leu
    10295               10300               10305

Asp Lys   Val Lys His Thr Pro   Phe Phe Leu Pro Lys   Arg Arg Arg
    10310               10315               10320

Lys Glu   Asp Glu Glu Asp Val   Glu Val Thr Asn Glu   Asn Thr Asp
    10325               10330               10335

Glu Lys   Val Leu Lys Asp Asn   Glu His Ser Pro Leu   Leu Phe Ala
    10340               10345               10350

Lys Arg   Arg Lys Asp Lys Glu   Glu Asp Val Glu Thr   Thr Thr Ser
    10355               10360               10365

Ile Glu   Ser Lys Asp Glu Asp   Val Pro Leu Leu Leu   Ala Lys Lys
    10370               10375               10380

Lys Asn   Gln Lys Asp Asn Gln   Ser Lys Asp Lys Lys   Ser Ala Ser
    10385               10390               10395

Lys Asn   Thr Ser Lys Lys Val   Ala Ala Lys Lys Lys   Lys Lys Lys
    10400               10405               10410

Ala Lys   Lys Asn Lys Lys
    10415


<210> SEQ ID NO 25
<211> LENGTH: 340
<212> TYPE: PRT
<213> ORGANISM: Staphylococcus sp.

<400> SEQUENCE: 25

Met Lys Lys Lys Leu Leu Val Leu Thr Met Ser Thr Leu Phe Ala Thr
1               5                   10                  15

Gln Ile Met Asn Ser Asn His Ala Lys Ala Ser Val Thr Glu Ser Val
            20                  25                  30

Asp Lys Lys Phe Val Val Pro Glu Ser Gly Ile Asn Lys Ile Ile Pro
        35                  40                  45

Ala Tyr Asp Glu Phe Lys Asn Ser Pro Lys Val Asn Val Ser Asn Leu
    50                  55                  60

Thr Asp Asn Lys Asn Phe Val Ala Ser Glu Asp Lys Leu Asn Lys Ile
65                  70                  75                  80

Ala Asp Ser Ser Ala Ala Ser Lys Ile Val Asp Lys Asn Phe Val Val
                85                  90                  95
```

-continued

```
Pro Glu Ser Lys Leu Gly Asn Ile Val Pro Glu Tyr Lys Glu Ile Asn
            100                 105                 110

Asn Arg Val Asn Val Ala Thr Asn Asn Pro Ala Ser Gln Gln Val Asp
        115                 120                 125

Lys His Phe Val Ala Lys Gly Pro Glu Val Asn Arg Phe Ile Thr Gln
    130                 135                 140

Asn Lys Val Asn His His Phe Ile Thr Thr Gln Thr His Tyr Lys Lys
145                 150                 155                 160

Val Ile Thr Ser Tyr Lys Ser Thr His Val His Lys His Val Asn His
                165                 170                 175

Ala Lys Asp Ser Ile Asn Lys His Phe Ile Val Lys Pro Ser Glu Ser
            180                 185                 190

Pro Arg Tyr Thr His Pro Ser Gln Ser Leu Ile Ile Lys His His Phe
        195                 200                 205

Ala Val Pro Gly Tyr His Ala His Lys Phe Val Thr Pro Gly His Ala
    210                 215                 220

Ser Ile Lys Ile Asn His Phe Cys Val Val Pro Gln Ile Asn Ser Phe
225                 230                 235                 240

Lys Val Ile Pro Pro Tyr Gly His Asn Ser His Arg Met His Val Pro
                245                 250                 255

Ser Phe Gln Asn Asn Thr Thr Ala Thr His Gln Asn Ala Lys Val Asn
            260                 265                 270

Lys Ala Tyr Asp Tyr Lys Tyr Phe Tyr Ser Tyr Lys Val Val Lys Gly
        275                 280                 285

Val Lys Lys Tyr Phe Ser Phe Ser Gln Ser Asn Gly Tyr Lys Ile Gly
    290                 295                 300

Lys Pro Ser Leu Asn Ile Lys Asn Val Asn Tyr Gln Tyr Ala Val Pro
305                 310                 315                 320

Ser Tyr Ser Pro Thr His Tyr Val Pro Glu Phe Lys Gly Ser Leu Pro
                325                 330                 335

Ala Pro Arg Val
            340


<210> SEQ ID NO 26
<211> LENGTH: 130
<212> TYPE: PRT
<213> ORGANISM: Staphylococcus sp.

<400> SEQUENCE: 26

Met Asn Phe Asn Asp Ile Glu Thr Met Val Lys Ser Lys Phe Lys Asp
1               5                   10                  15

Ile Lys Lys His Ala Glu Glu Ile Ala His Glu Ile Glu Val Arg Ser
            20                  25                  30

Gly Tyr Leu Arg Lys Ala Glu Gln Tyr Lys Arg Leu Glu Phe Asn Leu
        35                  40                  45

Ser Phe Ala Leu Asp Asp Ile Glu Ser Thr Ala Lys Asp Val Gln Thr
    50                  55                  60

Ala Lys Ser Ser Ala Asn Lys Asp Ser Val Thr Val Lys Gly Lys Ala
65                  70                  75                  80

Pro Asn Thr Leu Tyr Ile Glu Lys Arg Asn Leu Met Lys Gln Lys Leu
                85                  90                  95

Glu Met Leu Gly Glu Asp Ile Asp Lys Asn Lys Glu Ser Leu Gln Lys
            100                 105                 110

Ala Lys Glu Ile Ala Gly Glu Lys Ala Ser Glu Tyr Phe Asn Lys Ala
        115                 120                 125
```

```
Met Asn
    130


<210> SEQ ID NO 27
<211> LENGTH: 636
<212> TYPE: PRT
<213> ORGANISM: Staphylococcus sp.

<400> SEQUENCE: 27

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Gly Lys Ser Gln Val Asn Ala Gly Ser Lys Asn Gly Thr Leu Ile
        35                  40                  45

Asp Ser Arg Tyr Leu Asn Ser Ala Leu Tyr Tyr Leu Glu Asp Tyr Ile
    50                  55                  60

Ile Tyr Ala Ile Gly Leu Thr Asn Lys Tyr Glu Tyr Gly Asp Asn Ile
65                  70                  75                  80

Tyr Lys Glu Ala Lys Asp Arg Leu Leu Glu Lys Val Leu Arg Glu Asp
                85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
        115                 120                 125

Ala Asn Phe His Lys Tyr Asn Leu Glu Glu Leu Ser Met Lys Glu Tyr
    130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300

Thr Val Lys Lys Tyr Gly Glu Thr Glu Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Glu Thr Thr Gln Pro
            340                 345                 350

Val Ala Gln Pro Leu Val Lys Ile Pro Gln Gly Thr Ile Thr Gly Glu
```

-continued

```
        355                 360                 365

Ile Val Lys Gly Pro Glu Tyr Pro Thr Met Glu Asn Lys Thr Val Gln
    370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
                405                 410                 415

Leu Glu Gly Leu Glu Gly Ser Ser Ser Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser Gln Tyr Gly
    450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr His Ala Asn Gly Gln Val Ser Tyr Gly Ala Arg Pro Thr Tyr
        515                 520                 525

Lys Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Gly Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asn Gly Gln Val Ser Tyr Gly Ala Arg Pro Thr
        595                 600                 605

Tyr Lys Lys Pro Ser Lys Thr Asn Ala Tyr Asn Val Thr Thr His Ala
    610                 615                 620

Asp Gly Thr Ala Thr Tyr Gly Pro Arg Val Thr Lys
625                 630                 635


<210> SEQ ID NO 28
<211> LENGTH: 745
<212> TYPE: PRT
<213> ORGANISM: Staphylococcus sp.

<400> SEQUENCE: 28

Ala Glu Gln His Thr Pro Met Lys Ala His Ala Val Thr Thr Ile Asp
1               5                   10                  15

Lys Ala Thr Thr Asp Lys Gln Gln Val Pro Pro Thr Lys Glu Ala Ala
            20                  25                  30

His His Ser Gly Lys Glu Ala Ala Thr Asn Val Ser Ala Ser Ala Gln
        35                  40                  45

Gly Thr Ala Asp Asp Thr Asn Ser Lys Val Thr Ser Asn Ala Pro Ser
    50                  55                  60

Asn Lys Pro Ser Thr Val Val Ser Thr Lys Val Asn Glu Thr Arg Asp
65                  70                  75                  80

Val Asp Thr Gln Gln Ala Ser Thr Gln Lys Pro Thr His Thr Ala Thr
                85                  90                  95
```

```
Phe Lys Leu Ser Asn Ala Lys Thr Ala Ser Leu Ser Pro Arg Met Phe
            100                 105                 110

Ala Ala Asn Ala Pro Gln Thr Thr Thr His Lys Ile Leu His Thr Asn
        115                 120                 125

Asp Ile His Gly Arg Leu Ala Glu Glu Lys Gly Arg Val Ile Gly Met
    130                 135                 140

Ala Lys Leu Lys Thr Val Lys Glu Gln Glu Lys Pro Asp Leu Met Leu
145                 150                 155                 160

Asp Ala Gly Asp Ala Phe Gln Gly Leu Pro Leu Ser Asn Gln Ser Lys
                165                 170                 175

Gly Glu Glu Met Ala Lys Ala Met Asn Ala Val Gly Tyr Asp Ala Met
            180                 185                 190

Ala Val Gly Asn His Glu Phe Asp Phe Gly Tyr Asp Gln Leu Lys Lys
        195                 200                 205

Leu Glu Gly Met Leu Asp Phe Pro Met Leu Ser Thr Asn Val Tyr Lys
    210                 215                 220

Asp Gly Lys Arg Ala Phe Lys Pro Ser Thr Ile Val Thr Lys Asn Gly
225                 230                 235                 240

Ile Arg Tyr Gly Ile Ile Gly Val Thr Thr Pro Glu Thr Lys Thr Lys
                245                 250                 255

Thr Arg Pro Glu Gly Ile Lys Gly Val Glu Phe Arg Asp Pro Leu Gln
            260                 265                 270

Ser Val Thr Ala Glu Met Met Arg Ile Tyr Lys Asp Val Asp Thr Phe
        275                 280                 285

Val Val Ile Ser His Leu Gly Ile Asp Pro Ser Thr Gln Glu Thr Trp
    290                 295                 300

Arg Gly Asp Tyr Leu Val Lys Gln Leu Ser Gln Asn Pro Gln Leu Lys
305                 310                 315                 320

Lys Arg Ile Thr Val Ile Asp Gly His Ser His Thr Val Leu Gln Asn
                325                 330                 335

Gly Gln Ile Tyr Asn Asn Asp Ala Leu Ala Gln Thr Gly Thr Ala Leu
            340                 345                 350

Ala Asn Ile Gly Lys Ile Thr Phe Asn Tyr Arg Asn Gly Glu Val Ser
        355                 360                 365

Asn Ile Lys Pro Ser Leu Ile Asn Val Lys Asp Val Glu Asn Val Thr
    370                 375                 380

Pro Asn Lys Ala Leu Ala Glu Gln Ile Asn Gln Ala Asp Gln Thr Phe
385                 390                 395                 400

Arg Ala Gln Thr Ala Glu Val Ile Ile Pro Asn Asn Thr Ile Asp Phe
                405                 410                 415

Lys Gly Glu Arg Asp Asp Val Arg Thr Arg Glu Thr Asn Leu Gly Asn
            420                 425                 430

Ala Ile Ala Asp Ala Met Glu Ala Tyr Gly Val Lys Asn Phe Ser Lys
        435                 440                 445

Lys Thr Asp Phe Ala Val Thr Asn Gly Gly Gly Ile Arg Ala Ser Ile
    450                 455                 460

Ala Lys Gly Lys Val Thr Arg Tyr Asp Leu Ile Ser Val Leu Pro Phe
465                 470                 475                 480

Gly Asn Thr Ile Ala Gln Ile Asp Val Lys Gly Ser Asp Val Trp Thr
                485                 490                 495

Ala Phe Glu His Ser Leu Gly Ala Pro Thr Thr Gln Lys Asp Gly Lys
            500                 505                 510

Thr Val Leu Thr Ala Asn Gly Gly Leu Leu His Ile Ser Asp Ser Ile
```

```
        515                 520                 525

Arg Val Tyr Tyr Asp Ile Asn Lys Pro Ser Gly Lys Arg Ile Asn Ala
    530                 535                 540

Ile Gln Ile Leu Asn Lys Glu Thr Gly Lys Phe Glu Asn Ile Asp Leu
545                 550                 555                 560

Lys Arg Val Tyr His Val Thr Met Asn Asp Phe Thr Ala Ser Gly Gly
                565                 570                 575

Asp Gly Tyr Ser Met Phe Gly Gly Pro Arg Glu Glu Gly Ile Ser Leu
            580                 585                 590

Asp Gln Val Leu Ala Ser Tyr Leu Lys Thr Ala Asn Leu Ala Lys Tyr
        595                 600                 605

Asp Thr Thr Glu Pro Gln Arg Met Leu Leu Gly Lys Pro Ala Val Ser
    610                 615                 620

Glu Gln Pro Ala Lys Gly Gln Gln Gly Ser Lys Gly Ser Lys Ser Gly
625                 630                 635                 640

Lys Asp Thr Gln Pro Ile Gly Asp Asp Lys Val Met Asp Pro Ala Lys
                645                 650                 655

Lys Pro Ala Pro Gly Lys Val Val Leu Leu Leu Ala His Arg Gly Thr
            660                 665                 670

Val Ser Ser Gly Thr Glu Gly Ser Gly Arg Thr Ile Glu Gly Ala Thr
        675                 680                 685

Val Ser Ser Lys Ser Gly Lys Gln Leu Ala Arg Met Ser Val Pro Lys
    690                 695                 700

Gly Ser Ala His Glu Lys Gln Leu Pro Lys Thr Gly Thr Asn Gln Ser
705                 710                 715                 720

Ser Ser Pro Glu Ala Met Phe Val Leu Leu Ala Gly Ile Gly Leu Ile
                725                 730                 735

Ala Thr Val Arg Arg Arg Lys Ala Ser
            740                 745


<210> SEQ ID NO 29
<211> LENGTH: 628
<212> TYPE: PRT
<213> ORGANISM: Staphylococcus sp.

<400> SEQUENCE: 29

Met Ser Asp Arg Phe Ile Lys Phe Asn Asp Glu Gln Leu Asp Ala Lys
1               5                   10                  15

Gln Val Met Met Leu Gln Asp Leu Ala Arg Leu Leu Leu Lys Asn Glu
            20                  25                  30

Gln Thr Gln Val Lys Ile Gln Lys Phe Pro Tyr Tyr Asn Pro Val Gln
        35                  40                  45

Asn Val Leu Ile Thr Ser Trp Phe Trp Ser His Arg Pro Ser His Ile
    50                  55                  60

Glu Met Ala Gly Leu Lys Thr Asp Val Met Leu Ala Ala Tyr Gly Tyr
65                  70                  75                  80

His Met Met Asp Val Gln Ile Val Asn Glu Val Val Gln Asp Lys Thr
                85                  90                  95

Phe Lys His Pro Lys Phe Tyr Gln Gln Leu Phe Lys Leu Leu Glu Asp
            100                 105                 110

Met Arg Val Leu Asn Ser Ile Lys Val Glu Arg Pro Ser Thr Ala Lys
        115                 120                 125

Leu Ile Asp Leu Arg Leu Asp Thr Arg Ile Ser Tyr Thr Glu Ser Gln
    130                 135                 140
```

-continued

```
Ile Lys Val Tyr Arg Thr Lys Thr Gln Tyr Thr Asp Leu Leu Phe Leu
145                 150                 155                 160

Tyr Leu Glu His Ala Phe Leu Ser Gln Asp Phe Phe Asp Ile Pro Ser
                165                 170                 175

Ile His Ser Asp Leu Asp Asp Ile Leu Val Asn Met Phe Leu Tyr Leu
            180                 185                 190

Pro Asn Phe Phe Gln Asn Gln Asn Ser Glu Asp Asn Met Tyr Leu Ala
        195                 200                 205

Gln Arg Ile Met Tyr Gln Val Asp Asp Ile Leu Lys Glu Asp Met Leu
    210                 215                 220

Asn Glu Tyr Tyr Tyr Leu Pro Lys Thr Leu Tyr Asn Thr Leu Ala Ser
225                 230                 235                 240

Pro Glu Phe Asp Asp Leu Lys Arg Thr Asp Ala Ser Gln Val Asp Gly
                245                 250                 255

Gln Asp Asp Thr Ser Glu Asp Asp Asp Asn Glu Ser Glu Lys Ala Asp
            260                 265                 270

Ser Lys Ser Ala Asp Ser Glu Ser Lys Gly Gly Ala Tyr Leu Glu Met
        275                 280                 285

Glu Leu His Glu Gly Gln Asn Ser Glu Thr Leu Gly Asn Asp Glu Ala
    290                 295                 300

Arg Glu Gly Asp Ala Thr Asp Asp Met Thr Asp Met Met Thr Lys Lys
305                 310                 315                 320

Gly Lys Gly Ser Asn Asp Thr Leu Asn Arg Glu Glu Gly Asp Ala Val
                325                 330                 335

Gly Gln Ser Gln Ala Phe Gln Leu Asp Gly Val Asn Lys Asn Val Glu
            340                 345                 350

Ile Lys Trp Gln Ile Pro Glu Ile Glu Pro Gln Tyr Val Leu Glu Tyr
        355                 360                 365

Gln Glu Ser Lys Gln Asp Val Gln Tyr Glu Ile Lys Asp Leu Ile Gln
    370                 375                 380

Ile Ile Lys Lys Thr Ile Glu Arg Glu Gln Arg Asp Ala Arg Phe Asn
385                 390                 395                 400

Leu Thr Lys Gly Arg Leu Gln Lys Asp Leu Ile Asn Trp Phe Ile Asp
                405                 410                 415

Asp Gln Tyr Lys Leu Phe Tyr Lys Lys Gln Asp Leu Ser Lys Ser Phe
            420                 425                 430

Asp Ala Thr Phe Thr Leu Leu Ile Asp Ala Ser Ala Ser Met His Asp
        435                 440                 445

Lys Met Ala Glu Thr Lys Lys Gly Val Val Leu Phe His Glu Thr Leu
    450                 455                 460

Lys Ala Leu Asn Ile Lys His Glu Ile Leu Ser Phe Ser Glu Asp Ala
465                 470                 475                 480

Phe Asp Ser Asp Glu His Ala Gln Pro Asn Ile Ile Asn Glu Ile Ile
                485                 490                 495

Asn Tyr Asp Tyr Ser Thr Phe Glu Lys Asp Gly Pro Arg Ile Met Ala
            500                 505                 510

Leu Glu Pro Gln Asp Asp Asn Arg Asp Gly Val Ala Ile Arg Val Ala
        515                 520                 525

Ser Glu Arg Leu Met Arg Arg Asn Gln His Gln Arg Phe Leu Ile Val
    530                 535                 540

Phe Ser Asp Gly Glu Pro Ser Ala Phe Asn Tyr Ser Gln Asp Gly Ile
545                 550                 555                 560

Ile Asp Thr Tyr Glu Ala Val Glu Met Ser Arg Lys Phe Gly Ile Glu
```

```
                565                 570                 575

Val Phe Asn Val Phe Leu Ser Gln Asp Pro Ile Thr Glu Asp Val Glu
            580                 585                 590

Gln Thr Ile His Asn Ile Tyr Gly Gln Tyr Ala Ile Phe Val Glu Gly
        595                 600                 605

Val Ala His Leu Pro Gly His Leu Ser Pro Leu Leu Lys Lys Leu Leu
    610                 615                 620

Leu Lys Ser Leu
625


<210> SEQ ID NO 30
<211> LENGTH: 154
<212> TYPE: PRT
<213> ORGANISM: Staphylococcus sp.

<400> SEQUENCE: 30

Ala Glu Ile Asn Lys Gln Thr Thr Ser Gln Gly Val Thr Thr Glu Lys
1               5                   10                  15

Asn Asn Gly Ile Ala Val Leu Glu Gln Asp Val Ile Thr Pro Thr Val
            20                  25                  30

Lys Pro Gln Ala Lys Gln Asp Ile Ile Gln Ala Val Thr Thr Arg Lys
        35                  40                  45

Gln Gln Ile Lys Lys Ser Asn Ala Ser Leu Gln Asp Glu Lys Asp Val
    50                  55                  60

Ala Asn Asp Lys Ile Gly Lys Ile Glu Thr Lys Ala Ile Lys Asp Ile
65                  70                  75                  80

Asp Ala Ala Thr Thr Asn Ala Gln Val Glu Ala Ile Lys Thr Lys Ala
                85                  90                  95

Ile Asn Asp Ile Asn Gln Thr Thr Pro Ala Thr Thr Ala Lys Ala Ala
            100                 105                 110

Ala Leu Glu Glu Phe Asp Glu Val Val Gln Ala Gln Ile Asp Gln Ala
        115                 120                 125

Pro Leu Asn Pro Asp Thr Thr Asn Glu Glu Val Ala Glu Ala Ile Glu
    130                 135                 140

Arg Ile Asn Ala Ala Lys Val Ser Gly Val
145                 150


<210> SEQ ID NO 31
<211> LENGTH: 584
<212> TYPE: PRT
<213> ORGANISM: Staphylococcus sp.

<400> SEQUENCE: 31

Met Lys Phe Lys Ser Leu Ile Thr Thr Thr Leu Ala Leu Gly Val Leu
1               5                   10                  15

Ala Ser Thr Gly Ala Asn Phe Asn Asn Asn Glu Ala Ser Ala Ala Ala
            20                  25                  30

Lys Pro Leu Asp Lys Ser Ser Ser Ser Leu His His Gly Tyr Ser Lys
        35                  40                  45

Val His Val Pro Tyr Ala Ile Thr Val Asn Gly Thr Ser Gln Asn Ile
    50                  55                  60

Leu Ser Ser Leu Thr Phe Asn Lys Asn Gln Asn Ile Ser Tyr Lys Asp
65                  70                  75                  80

Leu Glu Asp Arg Val Lys Ser Val Leu Lys Ser Asp Arg Gly Ile Ser
                85                  90                  95

Asp Ile Asp Leu Arg Leu Ser Lys Gln Ala Lys Tyr Thr Val Tyr Phe
```

-continued

```
            100                 105                 110

Lys Asn Gly Thr Lys Lys Val Ile Asp Leu Lys Ala Gly Ile Tyr Thr
        115                 120                 125

Ala Asp Leu Ile Asn Thr Ser Glu Ile Lys Ala Ile Asn Ile Asn Val
    130                 135                 140

Asp Thr Lys Lys Gln Val Glu Asp Lys Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
        195                 200                 205

Val Asp Leu Arg Leu Ser Lys Gln Ala Lys Tyr Thr Val Asn Phe Lys
    210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
            260                 265                 270

Tyr Ser Ile Asn Leu Asn Gly Thr Ser Thr Asn Ile Leu Ser Asn Leu
        275                 280                 285

Ser Phe Ser Asn Lys Pro Trp Thr Asn Tyr Lys Asn Leu Thr Ser Gln
    290                 295                 300

Ile Lys Ser Val Leu Lys His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Lys Asn Tyr Thr Ala Asn Leu Val
            340                 345                 350

His Ala Lys Asp Val Lys Arg Ile Glu Ile Thr Val Lys Thr Gly Thr
        355                 360                 365

Lys Ala Lys Ala Asp Arg Tyr Val Pro Tyr Thr Ile Ala Val Asn Gly
    370                 375                 380

Thr Ser Thr Pro Ile Leu Ser Asp Leu Lys Phe Thr Gly Asp Pro Arg
385                 390                 395                 400

Val Gly Tyr Lys Asp Ile Ser Lys Lys Val Lys Ser Val Leu Lys His
                405                 410                 415

Asp Arg Gly Ile Gly Glu Arg Glu Leu Lys Tyr Ala Lys Lys Ala Thr
            420                 425                 430

Tyr Thr Val His Phe Lys Asn Gly Thr Lys Lys Val Ile Asn Ile Asn
        435                 440                 445

Ser Asn Ile Ser Gln Leu Asn Leu Leu Tyr Val Gln Asp Ile Lys Lys
    450                 455                 460

Ile Asp Ile Asp Val Lys Thr Gly Thr Lys Ala Lys Ala Asp Ser Tyr
465                 470                 475                 480

Val Pro Tyr Thr Ile Ala Val Asn Gly Thr Ser Thr Pro Ile Leu Ser
                485                 490                 495

Lys Leu Lys Ile Ser Asn Lys Gln Leu Ile Ser Tyr Lys Tyr Leu Asn
            500                 505                 510

Asp Lys Val Lys Ser Val Leu Lys Ser Glu Arg Gly Ile Ser Asp Leu
        515                 520                 525
```

-continued

```
Asp Leu Lys Phe Ala Lys Gln Ala Lys Tyr Thr Val Tyr Phe Lys Asn
    530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
                565                 570                 575

Tyr Thr Lys Ser Lys Lys Asn Lys
            580


<210> SEQ ID NO 32
<211> LENGTH: 508
<212> TYPE: PRT
<213> ORGANISM: Staphylococcus sp.

<400> SEQUENCE: 32

Met Lys Asn Lys Leu Leu Val Leu Ser Leu Gly Ala Leu Cys Val Ser
1               5                   10                  15

Gln Ile Trp Glu Ser Asn Arg Ala Ser Ala Val Val Ser Gly Glu Lys
            20                  25                  30

Asn Pro Tyr Val Ser Glu Ser Leu Lys Leu Thr Asn Asn Lys Asn Lys
        35                  40                  45

Ser Arg Thr Val Glu Glu Tyr Lys Lys Ser Leu Asp Asp Leu Ile Trp
    50                  55                  60

Ser Phe Pro Asn Leu Asp Asn Glu Arg Phe Asp Asn Pro Glu Tyr Lys
65                  70                  75                  80

Glu Ala Met Lys Lys Tyr Gln Gln Arg Phe Met Ala Glu Asp Glu Ala
                85                  90                  95

Leu Lys Lys Phe Phe Ser Glu Glu Lys Lys Ile Lys Asn Gly Asn Thr
            100                 105                 110

Asp Asn Leu Asp Tyr Leu Gly Leu Ser His Glu Arg Tyr Glu Ser Val
        115                 120                 125

Phe Asn Thr Leu Lys Lys Gln Ser Glu Glu Phe Leu Lys Glu Ile Glu
    130                 135                 140

Asp Ile Lys Lys Asp Asn Pro Glu Leu Lys Asp Phe Asn Glu Glu Glu
145                 150                 155                 160

Gln Leu Lys Cys Asp Leu Glu Leu Asn Lys Leu Glu Asn Gln Ile Leu
                165                 170                 175

Met Leu Gly Lys Thr Phe Tyr Gln Asn Tyr Arg Asp Asp Val Glu Ser
            180                 185                 190

Leu Tyr Ser Lys Leu Asp Leu Ile Met Gly Tyr Lys Asp Glu Glu Arg
        195                 200                 205

Ala Asn Lys Lys Ala Val Asn Lys Arg Met Leu Glu Asn Lys Lys Glu
    210                 215                 220

Asp Leu Glu Thr Ile Ile Asp Glu Phe Phe Ser Asp Ile Asp Lys Thr
225                 230                 235                 240

Arg Pro Asn Asn Ile Pro Val Leu Glu Asp Glu Lys Gln Glu Glu Lys
                245                 250                 255

Asn His Lys Asn Met Ala Gln Leu Lys Ser Asp Thr Glu Ala Ala Lys
            260                 265                 270

Ser Asp Glu Ser Lys Arg Ser Lys Arg Ser Lys Arg Ser Leu Asn Thr
        275                 280                 285

Gln Asn His Lys Pro Ala Ser Gln Glu Val Ser Glu Gln Gln Lys Ala
    290                 295                 300

Glu Tyr Asp Lys Arg Ala Glu Glu Arg Lys Ala Arg Phe Leu Asp Asn
```

305 310 315 320

Gln Lys Ile Lys Lys Thr Pro Val Val Ser Leu Glu Tyr Asp Phe Glu
325 330 335

His Lys Gln Arg Ile Asp Asn Glu Asn Asp Lys Lys Leu Val Val Ser
340 345 350

Ala Pro Thr Lys Lys Pro Thr Ser Pro Thr Thr Tyr Thr Glu Thr Thr
355 360 365

Thr Gln Val Pro Met Pro Thr Val Glu Arg Gln Thr Gln Gln Gln Ile
370 375 380

Ile Tyr Asn Ala Pro Lys Gln Leu Ala Gly Leu Asn Gly Glu Ser His
385 390 395 400

Asp Phe Thr Thr Thr His Gln Ser Pro Thr Thr Ser Asn His Thr His
405 410 415

Asn Asn Val Val Glu Phe Glu Glu Thr Ser Ala Leu Pro Gly Arg Lys
420 425 430

Ser Gly Ser Leu Val Gly Ile Ser Gln Ile Asp Ser Ser His Leu Thr
435 440 445

Glu Arg Glu Lys Arg Val Ile Lys Arg Glu His Val Arg Glu Ala Gln
450 455 460

Lys Leu Val Asp Asn Tyr Lys Asp Thr His Ser Tyr Lys Asp Arg Ile
465 470 475 480

Asn Ala Gln Gln Lys Val Asn Thr Leu Ser Glu Gly His Gln Lys Arg
485 490 495

Phe Asn Lys Gln Ile Asn Lys Val Tyr Asn Gly Lys
500 505

<210> SEQ ID NO 33
<211> LENGTH: 520
<212> TYPE: PRT
<213> ORGANISM: Staphylococcus sp.

<400> SEQUENCE: 33

Met Leu Thr Leu Gln Ile His Thr Gly Gly Ile Asn Leu Lys Lys Lys
1 5 10 15

Asn Ile Tyr Ser Ile Arg Lys Leu Gly Val Gly Ile Ala Ser Val Thr
20 25 30

Leu Gly Thr Leu Leu Ile Ser Gly Gly Val Thr Pro Ala Ala Asn Ala
35 40 45

Ala Gln His Asp Glu Ala Gln Gln Asn Ala Phe Tyr Gln Val Leu Asn
50 55 60

Met Pro Asn Leu Asn Ala Asp Gln Arg Asn Gly Phe Ile Gln Ser Leu
65 70 75 80

Lys Asp Asp Pro Ser Gln Ser Ala Asn Val Leu Gly Glu Ala Gln Lys
85 90 95

Leu Asn Asp Ser Gln Ala Pro Lys Ala Asp Ala Gln Gln Asn Asn Phe
100 105 110

Asn Lys Asp Gln Gln Ser Ala Phe Tyr Glu Ile Leu Asn Met Pro Asn
115 120 125

Leu Asn Glu Ala Gln Arg Asn Gly Phe Ile Gln Ser Leu Lys Asp Asp
130 135 140

Pro Ser Gln Ser Thr Asn Val Leu Gly Glu Ala Lys Lys Leu Asn Glu
145 150 155 160

Ser Gln Ala Pro Lys Ala Asp Asn Asn Phe Asn Lys Glu Gln Gln Asn
165 170 175

```
Ala Phe Tyr Glu Ile Leu Asn Met Pro Asn Leu Asn Glu Glu Gln Arg
            180                 185                 190

Asn Gly Phe Ile Gln Ser Leu Lys Asp Asp Pro Ser Gln Ser Ala Asn
        195                 200                 205

Leu Leu Ser Glu Ala Lys Lys Leu Asn Glu Ser Gln Ala Pro Lys Ala
    210                 215                 220

Asp Asn Lys Phe Asn Lys Glu Gln Gln Asn Ala Phe Tyr Glu Ile Leu
225                 230                 235                 240

His Leu Pro Asn Leu Asn Glu Glu Gln Arg Asn Gly Phe Ile Gln Ser
                245                 250                 255

Leu Lys Asp Asp Pro Ser Gln Ser Ala Asn Leu Leu Ala Glu Ala Lys
            260                 265                 270

Lys Leu Asn Asp Ala Gln Ala Pro Lys Ala Asp Asn Lys Phe Asn Lys
        275                 280                 285

Glu Gln Gln Asn Ala Phe Tyr Glu Ile Leu His Leu Pro Asn Leu Thr
    290                 295                 300

Glu Glu Gln Arg Asn Gly Phe Ile Gln Ser Leu Lys Asp Asp Pro Ser
305                 310                 315                 320

Val Ser Lys Glu Ile Leu Ala Glu Ala Lys Lys Leu Asn Asp Ala Gln
                325                 330                 335

Ala Pro Lys Glu Glu Asp Asn Asn Lys Pro Gly Lys Glu Asp Gly Asn
            340                 345                 350

Lys Pro Gly Lys Glu Asp Asn Asn Lys Pro Gly Lys Glu Asp Asn Lys
        355                 360                 365

Lys Pro Gly Lys Glu Asp Asn Asn Lys Pro Gly Lys Glu Asp Asn Asn
    370                 375                 380

Lys Pro Gly Lys Glu Asp Gly Asn Lys Pro Gly Lys Glu Asp Asn Lys
385                 390                 395                 400

Lys Pro Gly Lys Glu Asp Asn Asn Lys Pro Gly Lys Glu Asp Gly Asn
                405                 410                 415

Lys Pro Gly Lys Glu Asp Gly Asn Gly Val His Val Val Lys Pro Gly
            420                 425                 430

Asp Thr Val Asn Asp Ile Ala Lys Ala Asn Gly Thr Thr Ala Asp Lys
        435                 440                 445

Ile Ala Ala Asp Asn Lys Leu Ala Asp Lys Asn Met Ile Lys Pro Gly
    450                 455                 460

Gln Glu Leu Val Val Asp Lys Lys Gln Pro Ala Asn His Ala Asp Ala
465                 470                 475                 480

Asn Lys Ala Gln Ala Leu Pro Glu Thr Gly Glu Glu Asn Pro Phe Ile
                485                 490                 495

Gly Thr Thr Val Phe Gly Gly Leu Ser Leu Ala Leu Gly Ala Ala Leu
            500                 505                 510

Leu Ala Gly Arg Arg Arg Glu Leu
        515                 520
```

<210> SEQ ID NO 34
<211> LENGTH: 291
<212> TYPE: PRT
<213> ORGANISM: Staphylococcus sp.

<400> SEQUENCE: 34

```
Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30
```

```
Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 35
<211> LENGTH: 34
<212> TYPE: DNA
<213> ORGANISM: Staphylococcus sp.

<400> SEQUENCE: 35

gctgcacata tggcgcaaca cgatgaagct caac                                34


<210> SEQ ID NO 36
<211> LENGTH: 30
<212> TYPE: DNA
<213> ORGANISM: Staphylococcus sp.

<400> SEQUENCE: 36

agtggatcct tatgctttgt tagcatctgc                                     30


<210> SEQ ID NO 37
<211> LENGTH: 19
<212> TYPE: PRT
<213> ORGANISM: Staphylococcus sp.

<400> SEQUENCE: 37
```

Met Gly Ser Ser His His His His His His Ser Ser Gly Leu Val Pro
1 5 10 15

Arg Gly Ser

<210> SEQ ID NO 38
<211> LENGTH: 29
<212> TYPE: DNA
<213> ORGANISM: Staphylococcus sp.

<400> SEQUENCE: 38
aacatatgtt caacaaagat caacaaagc 29

<210> SEQ ID NO 39
<211> LENGTH: 29
<212> TYPE: DNA
<213> ORGANISM: Staphylococcus sp.

<400> SEQUENCE: 39
aaggatccag attcgtttaa ttttttagc 29

<210> SEQ ID NO 40
<211> LENGTH: 43
<212> TYPE: DNA
<213> ORGANISM: Staphylococcus sp.

<400> SEQUENCE: 40
cttcattcaa agtcttaaag ccgccccaag ccaaagcact aac 43

<210> SEQ ID NO 41
<211> LENGTH: 43
<212> TYPE: DNA
<213> ORGANISM: Staphylococcus sp.

<400> SEQUENCE: 41
gttagtgctt tggcttgggg cggctttaag actttgaatg aag 43

<210> SEQ ID NO 42
<211> LENGTH: 42
<212> TYPE: DNA
<213> ORGANISM: Staphylococcus sp.

<400> SEQUENCE: 42
catatgttca acaaagataa aaaaagcgcc ttctatgaaa tc 42

<210> SEQ ID NO 43
<211> LENGTH: 42
<212> TYPE: DNA
<213> ORGANISM: Staphylococcus sp.

<400> SEQUENCE: 43
gatttcatag aaggcgcttt ttttatcttt gttgaacata tg 42

<210> SEQ ID NO 44
<211> LENGTH: 42
<212> TYPE: DNA
<213> ORGANISM: Staphylococcus sp.

<400> SEQUENCE: 44
catatgttca acaaagatgg aggaagcgcc ttctatgaaa tc 42

<210> SEQ ID NO 45
<211> LENGTH: 42
<212> TYPE: DNA
<213> ORGANISM: Staphylococcus sp.

<400> SEQUENCE: 45
gatttcatag aaggcgcttc ctccatcttt gttgaacata tg 42

<210> SEQ ID NO 46
<211> LENGTH: 52
<212> TYPE: DNA
<213> ORGANISM: Staphylococcus sp.

<400> SEQUENCE: 46
ggggacaagt ttgtacaaaa aagcaggctg atgactaagt tgaaaaaaga ag 52

<210> SEQ ID NO 47
<211> LENGTH: 28
<212> TYPE: DNA
<213> ORGANISM: Staphylococcus sp.

<400> SEQUENCE: 47
aaggatcccc tccaaaatgt aattgccc 28

<210> SEQ ID NO 48
<211> LENGTH: 30
<212> TYPE: DNA
<213> ORGANISM: Staphylococcus sp.

<400> SEQUENCE: 48
aaggatccgt ttgtaactct atccaaagac 30

<210> SEQ ID NO 49
<211> LENGTH: 49
<212> TYPE: DNA
<213> ORGANISM: Staphylococcus sp.

<400> SEQUENCE: 49
ggggaccact ttgtacaaga aagctgggtg acacctattg cacgattcg 49

<210> SEQ ID NO 50
<211> LENGTH: 50
<212> TYPE: DNA
<213> ORGANISM: Staphylococcus sp.

<400> SEQUENCE: 50
ggggacaagt ttgtacaaaa aagcaggctc agatagcgat tcagattcag 50

<210> SEQ ID NO 51
<211> LENGTH: 31
<212> TYPE: DNA
<213> ORGANISM: Staphylococcus sp.

<400> SEQUENCE: 51
aaggatccct gtattttctc cttaattttc c 31

<210> SEQ ID NO 52
<211> LENGTH: 30
<212> TYPE: DNA
<213> ORGANISM: Staphylococcus sp.

<400> SEQUENCE: 52
aaggatccca tggctgcaaa gcaaataatg 30

<210> SEQ ID NO 53
<211> LENGTH: 51
<212> TYPE: DNA
<213> ORGANISM: Staphylococcus sp.

<400> SEQUENCE: 53
ggggaccact ttgtacaaga aagctgggtg ccctggtgta acaaatttat g 51

<210> SEQ ID NO 54
<211> LENGTH: 37
<212> TYPE: DNA
<213> ORGANISM: Staphylococcus sp.

<400> SEQUENCE: 54
gaaggatccg tttattctag ttaatatata gttaatg 37

<210> SEQ ID NO 55
<211> LENGTH: 33
<212> TYPE: DNA
<213> ORGANISM: Staphylococcus sp.

<400> SEQUENCE: 55
gaactgcagc tgtatgtctt tggatagagt tac 33

<210> SEQ ID NO 56
<211> LENGTH: 33
<212> TYPE: DNA
<213> ORGANISM: Staphylococcus sp.

<400> SEQUENCE: 56
gaaggatccg gtggcttttt tacttggatt ttc 33

<210> SEQ ID NO 57
<211> LENGTH: 33
<212> TYPE: DNA
<213> ORGANISM: Staphylococcus sp.

<400> SEQUENCE: 57
gaactgcagc gacaaactca ttatttgctt tgc 33

<210> SEQ ID NO 58
<211> LENGTH: 27
<212> TYPE: DNA
<213> ORGANISM: Staphylococcus sp.

<400> SEQUENCE: 58
gaactcgagt ctagcttatt tacatgg 27

<210> SEQ ID NO 59
<211> LENGTH: 45
<212> TYPE: DNA
<213> ORGANISM: Staphylococcus sp.

<400> SEQUENCE: 59
gaactcgaga tagaaggcag aatagtaaca aaggattata gtggg 45

<210> SEQ ID NO 60
<211> LENGTH: 27
<212> TYPE: DNA

<213> ORGANISM: Staphylococcus sp.

<400> SEQUENCE: 60
gtaggatcct gggatagagt tacaaac 27

<210> SEQ ID NO 61
<211> LENGTH: 34
<212> TYPE: DNA
<213> ORGANISM: Staphylococcus sp.

<400> SEQUENCE: 61
gaactcgagg cattatgtgt atcacaaatt tggg 34

<210> SEQ ID NO 62
<211> LENGTH: 43
<212> TYPE: DNA
<213> ORGANISM: Staphylococcus sp.

<400> SEQUENCE: 62
gaactcgaga tagaaggcag agtggtttct ggggagaaga atc 43

<210> SEQ ID NO 63
<211> LENGTH: 33
<212> TYPE: DNA
<213> ORGANISM: Staphylococcus sp.

<400> SEQUENCE: 63
gaactcgagg cagccatgca ttaattattt gcc 33

<210> SEQ ID NO 64
<211> LENGTH: 677
<212> TYPE: PRT
<213> ORGANISM: Staphylococcus sp.

<400> SEQUENCE: 64

```
Met Lys Ser Asn Leu Arg Tyr Gly Ile Arg Lys His Lys Leu Gly Ala
1               5                   10                  15

Ala Ser Val Phe Leu Gly Thr Met Ile Val Val Gly Met Gly Gln Glu
            20                  25                  30

Lys Glu Ala Ala Ala Ser Glu Gln Asn Asn Thr Thr Val Glu Glu Ser
        35                  40                  45

Gly Ser Ser Ala Thr Glu Ser Lys Ala Ser Glu Thr Gln Thr Thr Thr
    50                  55                  60

Asn Asn Val Asn Thr Ile Asp Glu Thr Gln Ser Tyr Ser Ala Thr Ser
65                  70                  75                  80

Thr Glu Gln Pro Ser Gln Ser Thr Gln Val Thr Thr Glu Glu Ala Pro
                85                  90                  95

Lys Thr Val Gln Ala Pro Lys Val Glu Thr Ser Arg Val Asp Leu Pro
            100                 105                 110

Ser Glu Lys Val Ala Asp Lys Glu Thr Thr Gly Thr Gln Val Asp Ile
        115                 120                 125

Ala Gln Pro Ser Asn Val Ser Glu Ile Lys Pro Arg Met Lys Arg Ser
    130                 135                 140

Thr Asp Val Thr Ala Val Ala Glu Lys Glu Val Val Glu Glu Thr Lys
145                 150                 155                 160

Ala Thr Gly Thr Asp Val Thr Asn Lys Val Glu Val Glu Glu Gly Ser
                165                 170                 175

Glu Ile Val Gly His Lys Gln Asp Thr Asn Val Val Asn Pro His Asn
            180                 185                 190
```

```
Ala Glu Arg Val Thr Leu Lys Tyr Lys Trp Lys Phe Gly Glu Gly Ile
        195                 200                 205

Lys Ala Gly Asp Tyr Phe Asp Phe Thr Leu Ser Asp Asn Val Glu Thr
    210                 215                 220

His Gly Ile Ser Thr Leu Arg Lys Val Pro Glu Ile Lys Ser Thr Asp
225                 230                 235                 240

Gly Gln Val Met Ala Thr Gly Glu Ile Ile Gly Glu Arg Lys Val Arg
                245                 250                 255

Tyr Thr Phe Lys Glu Tyr Val Gln Glu Lys Lys Asp Leu Thr Ala Glu
            260                 265                 270

Leu Ser Leu Asn Leu Phe Ile Asp Pro Thr Thr Val Thr Gln Lys Gly
        275                 280                 285

Asn Gln Asn Val Glu Val Lys Leu Gly Glu Thr Thr Val Ser Lys Ile
    290                 295                 300

Phe Asn Ile Gln Tyr Leu Gly Gly Val Arg Asp Asn Trp Gly Val Thr
305                 310                 315                 320

Ala Asn Gly Arg Ile Asp Thr Leu Asn Lys Val Asp Gly Lys Phe Ser
                325                 330                 335

His Phe Ala Tyr Met Lys Pro Asn Asn Gln Ser Leu Ser Ser Val Thr
            340                 345                 350

Val Thr Gly Gln Val Thr Lys Gly Asn Lys Pro Gly Val Asn Asn Pro
        355                 360                 365

Thr Val Lys Val Tyr Lys His Ile Gly Ser Asp Asp Leu Ala Glu Ser
    370                 375                 380

Val Tyr Ala Lys Leu Asp Asp Val Ser Lys Phe Glu Asp Val Thr Asp
385                 390                 395                 400

Asn Met Ser Leu Asp Phe Asp Thr Asn Gly Gly Tyr Ser Leu Asn Phe
                405                 410                 415

Asn Asn Leu Asp Gln Ser Lys Asn Tyr Val Ile Lys Tyr Glu Gly Tyr
            420                 425                 430

Tyr Asp Ser Asn Ala Ser Asn Leu Glu Phe Gln Thr His Leu Phe Gly
        435                 440                 445

Tyr Tyr Asn Tyr Tyr Tyr Thr Ser Asn Leu Thr Trp Lys Asn Gly Val
    450                 455                 460

Ala Phe Tyr Ser Asn Asn Ala Gln Gly Asp Gly Lys Asp Lys Leu Lys
465                 470                 475                 480

Glu Pro Ile Ile Glu His Ser Thr Pro Ile Glu Leu Glu Phe Lys Ser
                485                 490                 495

Glu Pro Pro Val Glu Lys His Glu Leu Thr Gly Thr Ile Glu Glu Ser
            500                 505                 510

Asn Asp Ser Lys Pro Ile Asp Phe Glu Tyr His Thr Ala Val Glu Gly
        515                 520                 525

Ala Glu Gly His Ala Glu Gly Thr Ile Glu Thr Glu Glu Asp Ser Ile
    530                 535                 540

His Val Asp Phe Glu Glu Ser Thr His Glu Asn Ser Lys His His Ala
545                 550                 555                 560

Asp Val Val Glu Tyr Glu Glu Asp Thr Asn Pro Gly Gly Gly Gln Val
                565                 570                 575

Thr Thr Glu Ser Asn Leu Val Glu Phe Asp Glu Asp Ser Thr Lys Gly
            580                 585                 590

Ile Val Thr Gly Ala Val Ser Asp His Thr Thr Ile Glu Asp Thr Lys
        595                 600                 605
```

-continued

```
Glu Tyr Thr Thr Glu Ser Asn Leu Ile Glu Leu Val Asp Glu Leu Pro
    610                 615                 620

Glu Glu His Gly Gln Ala Gln Gly Pro Ile Glu Glu Ile Thr Glu Asn
625                 630                 635                 640

Asn His His Ile Ser His Ser Gly Leu Gly Thr Glu Asn Gly His Gly
                645                 650                 655

Asn Tyr Gly Val Ile Glu Glu Ile Glu Glu Asn Ser His Val Asp Ile
            660                 665                 670

Lys Ser Glu Leu Gly
        675
```